(12) United States Patent
Cox et al.

(10) Patent No.: US 7,759,070 B2
(45) Date of Patent: Jul. 20, 2010

(54) CONSERVED INNER CORE LIPOPOLYSACCHARIDE EPITOPES AS MULTI-SPECIES VACCINE CANDIDATES

(75) Inventors: Andrew D. Cox, Ottawa (CA); James C. Richards, Ottawa (CA)

(73) Assignee: National Research Council of Canada, Ottawa, Ontario (CA)

(*) Notice: Subject to any disclaimer, the term of this patent is extended or adjusted under 35 U.S.C. 154(b) by 409 days.

(21) Appl. No.: 11/569,093

(22) PCT Filed: May 16, 2005

(86) PCT No.: PCT/CA2005/000745

§ 371 (c)(1),
(2), (4) Date: Nov. 14, 2006

(87) PCT Pub. No.: WO2005/111196

PCT Pub. Date: Nov. 24, 2005

(65) Prior Publication Data

US 2008/0008723 A1 Jan. 10, 2008

Related U.S. Application Data

(60) Provisional application No. 60/571,489, filed on May 17, 2004.

(30) Foreign Application Priority Data

May 14, 2004 (CA) ..................... 2467329

(51) Int. Cl.
*A61K 8/73* (2006.01)
*A61K 31/715* (2006.01)
*G01N 33/53* (2006.01)

(52) U.S. Cl. .............. 435/7.1; 424/70.13; 514/54
(58) Field of Classification Search .............. None
See application file for complete search history.

(56) References Cited

FOREIGN PATENT DOCUMENTS

| CA | 2477068 | 8/2003 |
|---|---|---|
| WO | 0036419 A1 | 6/2000 |
| WO | 0216440 A2 | 2/2002 |

OTHER PUBLICATIONS

Plotkin (Vaccines WB Saunders Co. p. 571, 1988).*
St Michael F. et al: "Structural Analysis of the Lipopolysaccharide of Pasteurella Mutocida Sstrain VP161: Identification of Both Kdo-P and Kdo-Kdo Species In The Lipopolysaccharide"vol. 340, No. 1, Jan. 17, 2005, pp. 59-68.
Jean R. Brisson et al: "The Core oligosaccharide component from mannheimia (Pasteurela) Haemolytica Serotyp A1 Lipopolysaccharide ContainsL-Glycero-D-Manno and D-Manno-Heptoses: Analysis Of The Structure And Conformation By High-Resolution NMR Spectroscopy" vol. 80, Jan. 1, 2002 pp. 949-963.
Tullius et al., "The IbgAB gene cluster of Haemophilus ducreyi encodes a beta-1, 4-galactosyltransferase and an alpha-1,6-DD-heptosyltransferase involved in lipooligosaccharide biosynthesis", Infect. Immun, Jun. 2002, vol. 70, No. 6, pp. 2853-2861.
St. Michael et al., "Structural analysis of the lipopolysaccharide of Pasteurella multocida genome strain Pm70 and identification of the putative lipopolysaccharide glycosyltransferases", Glycobiology, Nov. 2004, vol. 15, No. 4, pp. 323-333.
St. Michael et al., "Structural analysis of the lipopolysaccharide derived core oligosaccharides of Actinobacillus pleuropneumoniae serotypes 1, 2, 5a and the genom strain 5b", Carboydr. Res., Aug. 2004, vol. 339, No. 11, pp. 1973-1984.
International Application No. PCT/CA2005/000745, International Search Report dated Sep. 6, 2005.

* cited by examiner

*Primary Examiner*—Mark Navarro
(74) *Attorney, Agent, or Firm*—David L. Conn; Borden Ladner Gervais LLP

(57) ABSTRACT

A conserved inner-core oligosaccharide epitope expressed on the lipopolysaccharide (LPS) of a range of disease causing pathogenic bacterial isolates, including *Actinobacillus pleuropneumoniae* (Ap), *Mannheimia haemolytica* (Mh) and *Pasteurella multocida* (Pm), is disclosed. Construction of a mutant bacterial strain exclusively expressing the conserved inner core OS epitope as a terminally exposed structure has allowed the identification, production and isolation of an inner core LPS which is common to all three organisms. Further provided are associated vaccines, antibodies raised against the conserved LPS inner core and glycoconjugates comprising the LPS inner core linked to an immunogenic carrier.

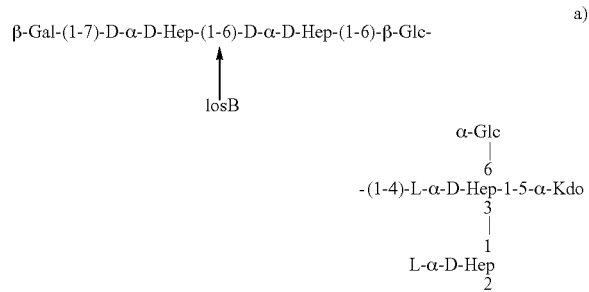

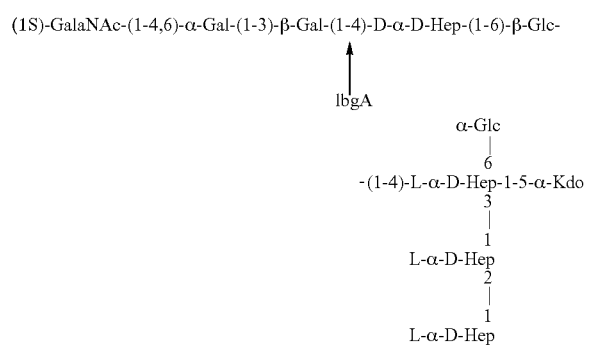

24 Claims, 58 Drawing Sheets

Figure 1:
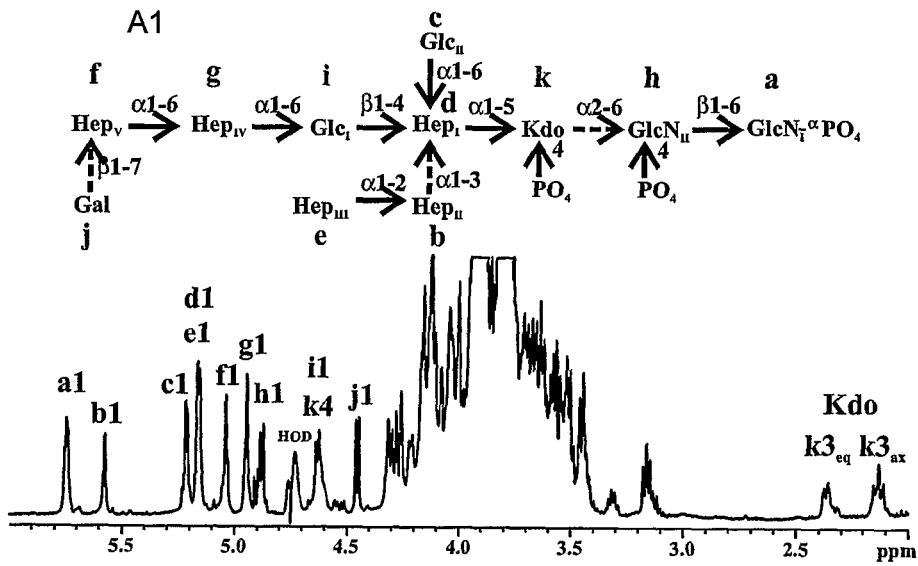

Fig. 23 (above) & Fig. 24 (below)
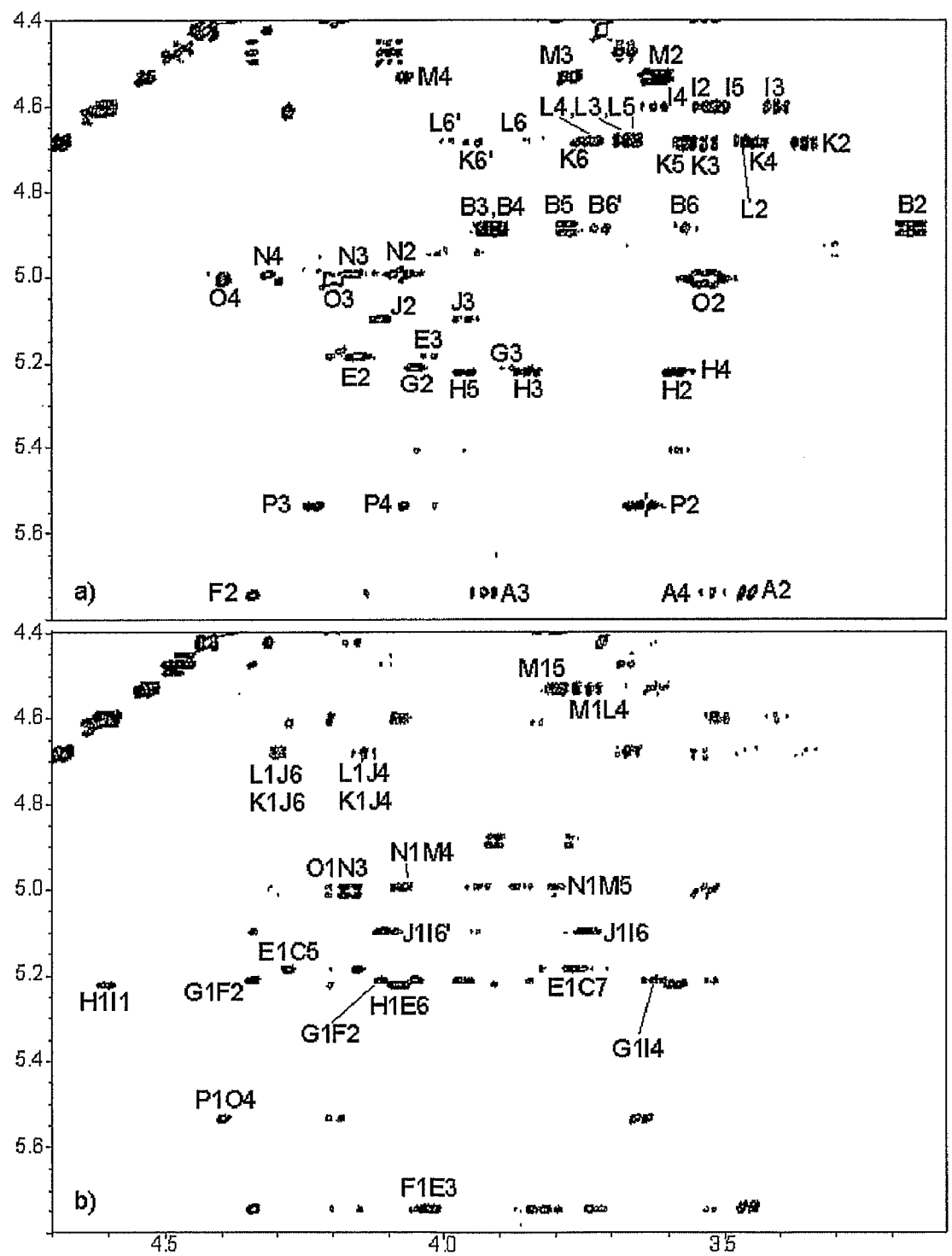

Fig. 36
A
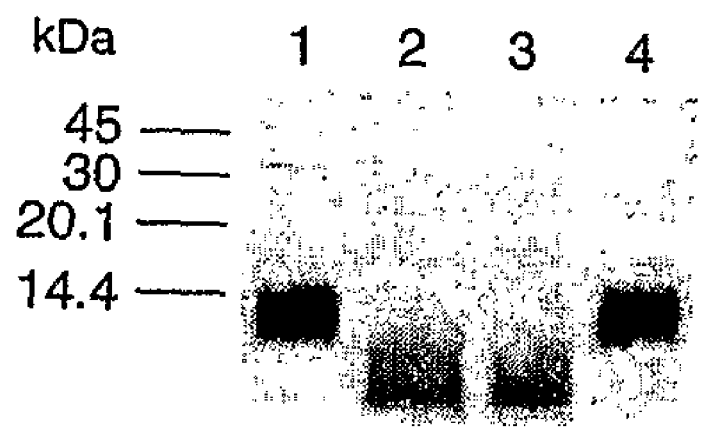
B
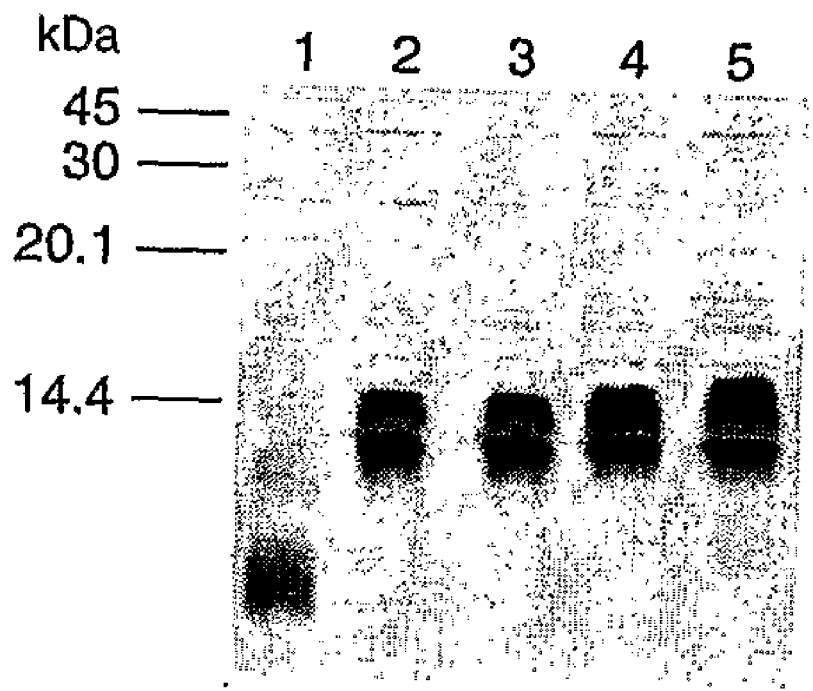

Fig. 37
a)
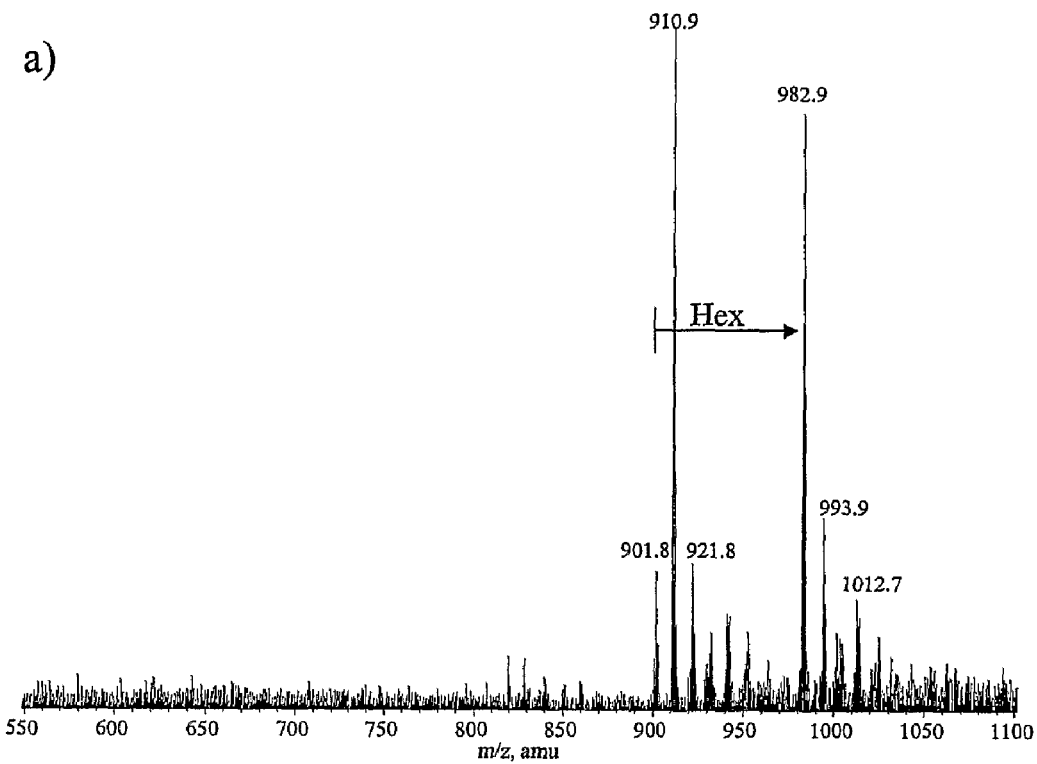
b)
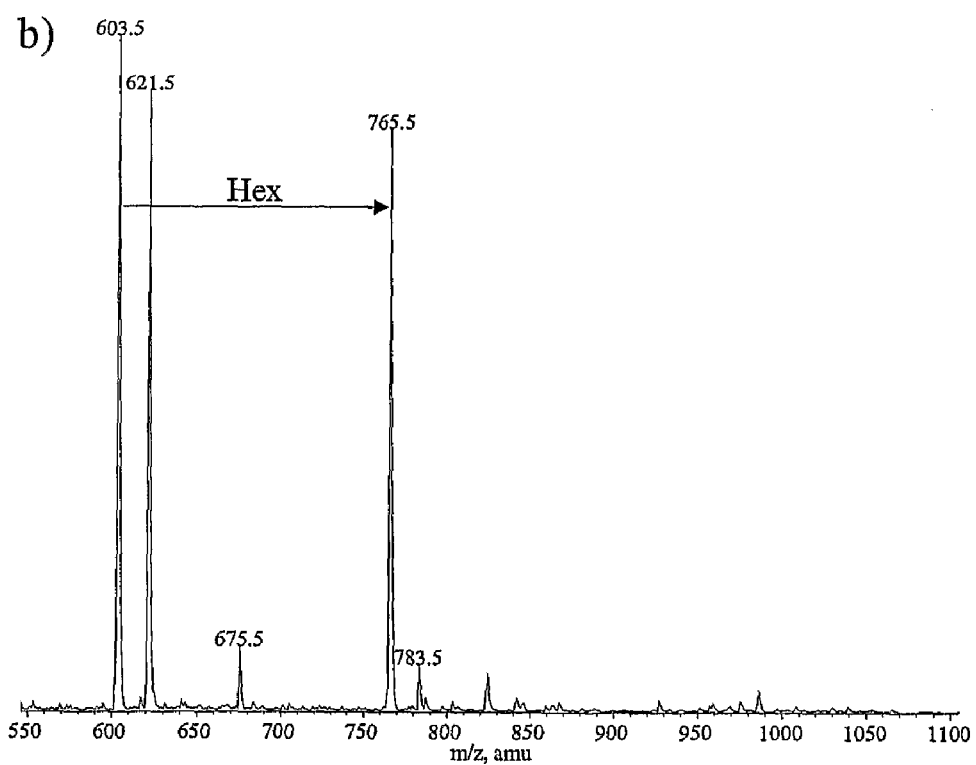

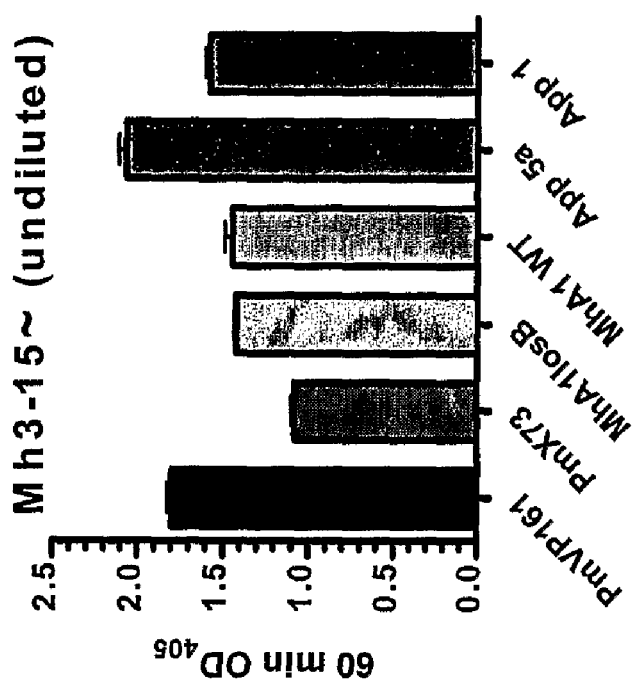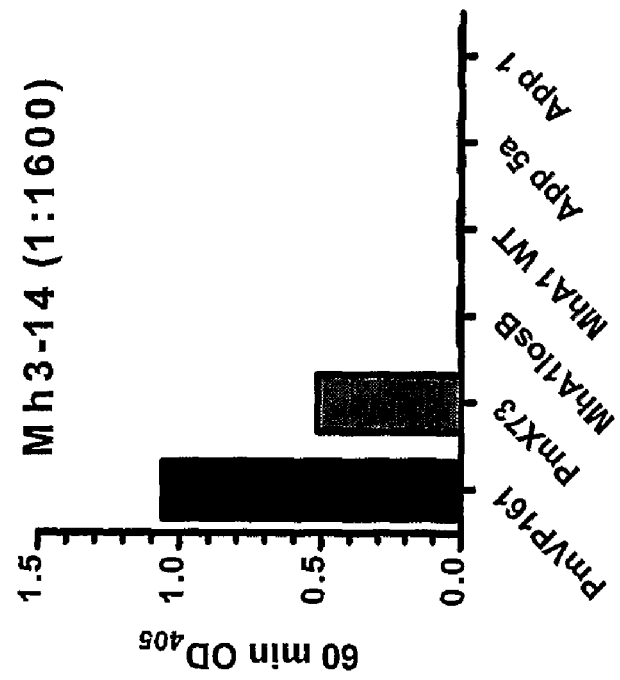
Fig. 48

Fig. 51.
a)
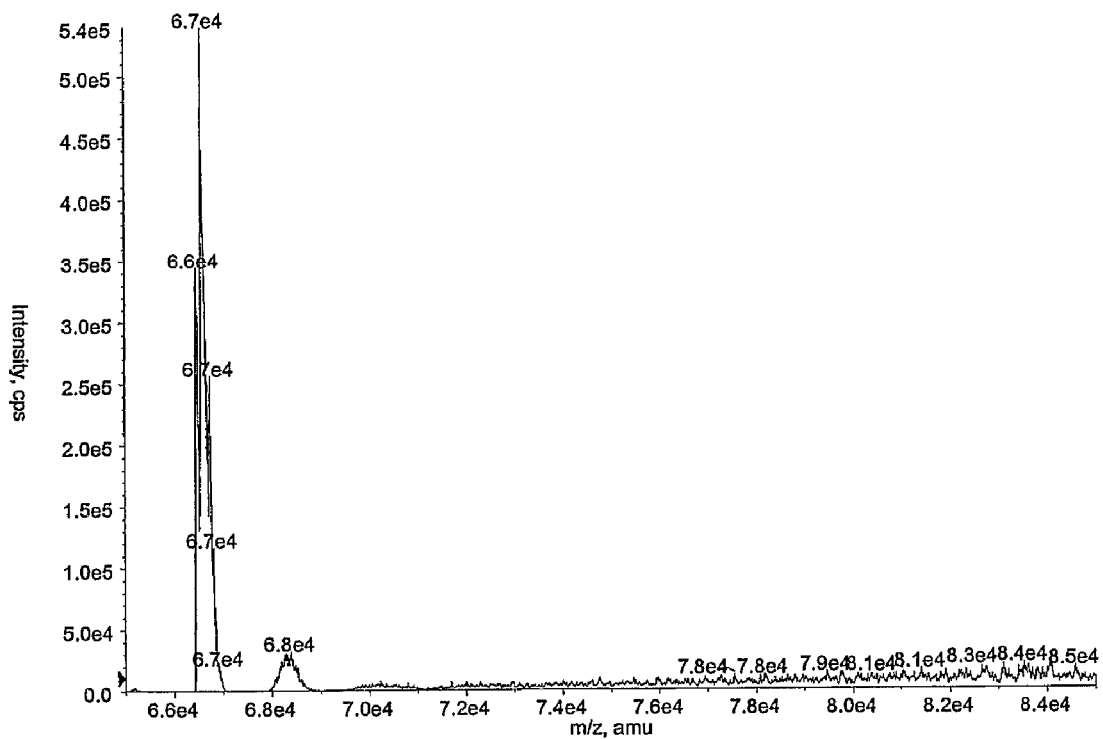
b)
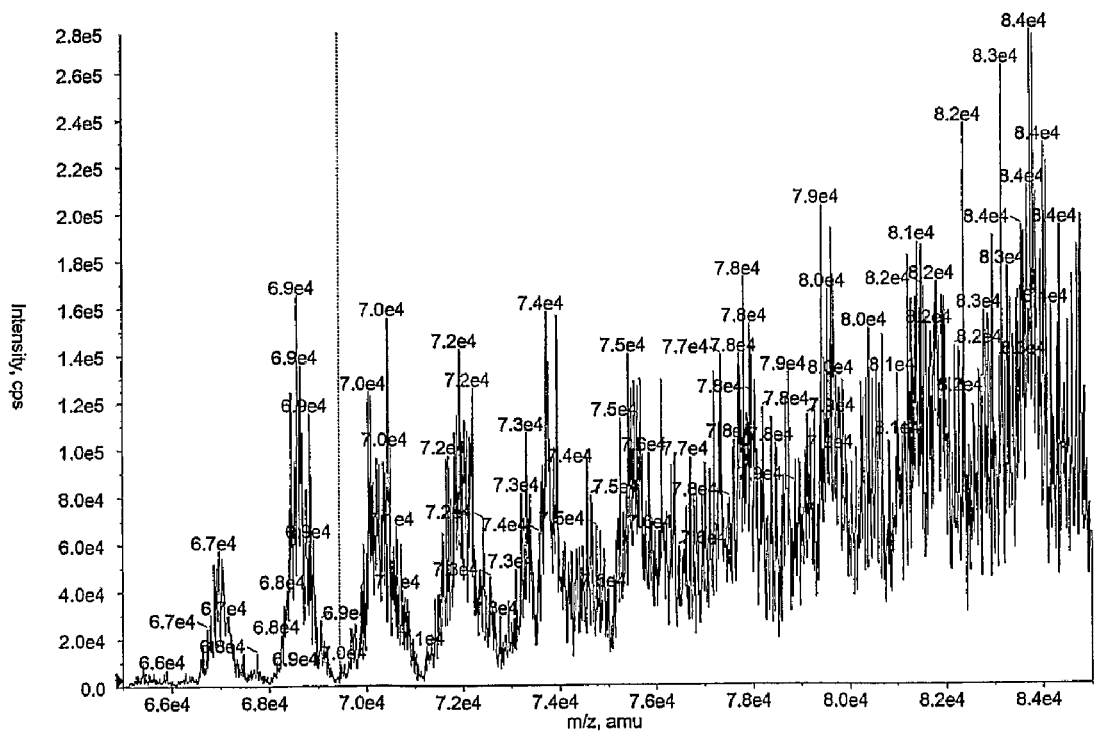

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Forward primer for waaQPM amplification; has
      BamHI site for cloning.

<400> SEQUENCE: 1
gagtaggatc ctgaaacatg ttccc                                            25

<210> SEQ ID NO 2
```

```
<211> LENGTH: 27
<212> TYPE: DNA
<213> ORGANISM: Artificial Sequence
<220> FEATURE:
<223> OTHER INFORMATION: Reverse primer for waaQPM amplification, has
      SalI site for cloning.

<400> SEQUENCE: 2
ggttgggtcg accaagccac attactg                                       27

<210> SEQ ID NO 3
<211> LENGTH: 32
<212> TYPE: DNA
<213> ORGANISM: Artificial Sequence
<220> FEATURE:
<223> OTHER INFORMATION: losB-kpn primer

<400> SEQUENCE: 3
atatggtacc tatcagcggt agagattcta ac                                 32

<210> SEQ ID NO 4
<211> LENGTH: 37
<212> TYPE: DNA
<213> ORGANISM: Artificial Sequence
<220> FEATURE:
<223> OTHER INFORMATION: losB-xba primer

<400> SEQUENCE: 4
tgctctagac cgaacctgca ccaaaaagat ttaacgc                            37

<210> SEQ ID NO 5
<211> LENGTH: 30
<212> TYPE: DNA
<213> ORGANISM: Artificial Sequence
<220> FEATURE:
<223> OTHER INFORMATION: primer that corresponds to sequence within the
      losB structural gene

<400> SEQUENCE: 5
ccgctgcgag agataagtgg atactttatc                                    30

<210> SEQ ID NO 6
<211> LENGTH: 34
<212> TYPE: DNA
<213> ORGANISM: Artificial Sequence
<220> FEATURE:
<223> OTHER INFORMATION: primer that corresponds to sequence within the
      losB structural gene

<400> SEQUENCE: 6
gacattggga tctttattta gatttcaaac cgac                               34
```

CONSERVED INNER CORE LIPOPOLYSACCHARIDE EPITOPES AS MULTI-SPECIES VACCINE CANDIDATES

FIELD OF THE INVENTION

The invention is directed at veterinary bacterial pathogens lipopolysaccharide (LPS), comprising one or more epitopes of the inner-core oligosaccharide portion of the LPS. The invention identifies conserved epitopes that are expressed on the LPS of bacterial veterinary pathogens across a range of disease causing isolates including but not necessarily limited to *Actinobacillus pleuropneumoniae* (Ap), *Mannheimia haemolytica* (Mh) and *Pasteurella multocida* (Pm).

BACKGROUND OF THE INVENTION

Bacterial pathogens are a significant cause of economic loss in commercial farm operations as well as a health issue in a wide range of animal populations, including humans.

Three of the most common bacterial pathogens involved in veterinary diseases are *Mannheimia* (*Pasteurella*) *haemolytica* (Mh), *Actinobacillus pleuropneumoniae* (Ap) and *Pasteurella multocida* (Pm). MA is primarily a bovine and ovine pathogen, Ap is a porcine pathogen and Pm is a multi-species pathogen including poultry, cattle and swine, and is also the causative agent of dog and cat bite infections in humans. Taken together they cause diseases resulting in major economic losses to the animal farming industry.

Current practice involves using bacterins or crudely modified live strains as vaccines. Such approaches are not entirely satisfactory as effectiveness can be inadequate and there is a significant incidence of adverse effects.

There is currently no single vaccine available to provide cross-species protection against infections caused by these three species, Mh, Ap and Pm. It would be useful to have a vaccine against the pathogenic bacteria of concern. Vaccine approaches to combat diseases caused by Mh are still mainly based on bacterins and live attenuated strains. More recent versions of live vaccines incorporate secreted or extracted Mh antigens such as neuraminidase, leukotoxin, sialoglycoprotease, outer membrane and uncharacterised proteins. Leukotoxin has traditionally been the main sub-unit vaccine candidate, although immunization with a mutant strain expressing non-toxic leukotoxin was still partially virulent in a calf challenge model and leukotoxin in combination with capsular polysaccharide was unable to produce a protective immune response. In contrast, LPS has been shown to stabilize leukolytic activity and so a conjugate vaccine based on LPS and detoxified leukotoxin may offer promise [Li, J., and K. D. Clinkenbeard. 1999. Infect. Immun. 67: 2920-2927].

Current vaccine approaches to combat diseases caused by Ap are based on live attenuated strains as they contain the highly labile Apx toxins, which induce neutralizing antibodies required for protection. These Apx toxins form the basis for the major sub-unit vaccine against Ap but only seem to induce partial clinical protection. Adhesins including the core OS of LPS have been proposed as improved vaccine candidates [Van Overbeke I., et al. 2003. J. Vet. Med. B. Infect. Dis. Vet. Public Health. 50: 289-293]. Current vaccines to prevent Pm disease in pigs consist of toxoids and somatic antigens such as capsules and outer membrane proteins. Pm was first shown by Pasteur to induce fowl cholera in chickens and current strategies for protection against this disease utilize an attenuated Pm strain. In general however, this strategy is severely limited as the immune response remains serotype-restricted and fails to provide cross-protection against other serotypes. The LPS of Pm has however been shown to play a partial role in the immunity to infection.

Considerable evidence has accumulated indicating that LPS from each of these organisms may be a good candidate for subunit vaccine design. LPS has been shown to be both visible and a major antigenic determinant on the surface of Mh and mAbs raised to A1 LPS facilitated phagocytosis but not complement mediated killing in vitro [Wilson, C. F., et al. 1992. Vet. Microbiol. 31: 161-168].

In Pm ribosome-LPS vaccines protected chickens against fowl cholera disease from homologous Pm strains [Phillips, M., and R. B. Rimler. 1984. Am. J. Vet. Res. 45: 1785-1789]. Additionally, immunization with a LPS-protein complex provided 100% protection to mice when challenged with a homologous strain yet when separated the individual components of the complex afforded no protection. MAbs raised to LPS from Pm only afforded partial protection in a mouse model and although they were opsonophagocytic, were not bactericidal in the presence of complement. However in another study a mAb to Pm LPS completely protected mice against homologous challenge and was bactericidal [Wijew-ardana, T. G., et al. 1990. J. Med. Microbiol. 33: 217-222]. An anti-idiotype vaccine mimicking LPS from type A was protective in a mouse model when challenge was with homologous organisms.

In Ap, the LPS and more specifically the core region of the LPS has been implicated in the adhesive abilities of the bacterium. A conjugate vaccine of BSA linked to Ap serotype 1 LPS was protective against mice following homologous but not heterologous challenge and conjugates of both smooth and rough Ap LPS from serotype 5 and 1 suggested that the carbohydrate portion of the cell wall of Ap plays a significant role in the porcine immune response [Fenwick, B., and B. I. Osburn. 1986. Infect. Immun. 54: 583-586].

In this context the veterinary organisms of interest contain surface exposed carbohydrate moieties that can be considered as vaccine candidates. These carbohydrate moieties include LPS and capsular polysaccharides. Capsular polysaccharides are repeating units of several carbohydrate residues directly linked to the bacterial surface whereas LPS consists of three regions, a lipid A region that links the LPS molecule to the bacterial surface via fatty acid residues, a relatively conserved core oligosaccharide region which links the lipid A region to the third region, the variable polysaccharide antigen (O-antigen). The heterogeneity of the capsular and O-antigenic polysaccharides from strain to strain would ordinarily preclude them as economically viable vaccine candidates due to their ability to provide coverage only to homologous strains. Recent advances in molecular genetics, molecular structure analysis and immunochemistry have provided powerful tools, which have allowed us to identify carbohydrate structures as candidate vaccine antigens.

Lipopolysaccharide (LPS) is an essential and characteristic surface-exposed antigen of Mh, Ap and Pm. (As discussed above, the terms lipopolysaccharide and LPS as used herein encompass short chain lipopolysaccharide and lipooligosaccharide (LOS)). Pm strains express heterogeneous populations of low-molecular-weight LPS, which can exhibit extensive antigenic diversity among multiple oligosaccharide epitopes, whereas strains of Mh and Ap produce both low-molecular-weight LPS and traditional LPS molecules with O-antigenic polymers. The LPS carbohydrate structures of Mh, Ap and Pm described by the Applicant herein can provide a source of protective antigens when they are presented to the host immune system in an appropriate fashion, for example, as a protein-conjugate. LPS proved useful as a vaccine candidate in Applicant's study because unexpectedly surface expressed carbohydrate antigens were identified which possess oligosaccharide epitopes that are genetically and physiologically stable, that are conserved across the range of strains, and that are accessible to host clearance mechanisms across the three species Mh, Ap or Pm.

The carbohydrate regions of Mh, Ap and Pm LPS molecules provide targets for recognition by host immune responses. Determination of structure is crucial to understanding the biology of Mh, Ap and Pm LPS and its role in bacterial virulence. Mh, Ap and Pm LPS comprises a heterogeneous mixture of molecules consisting of a variable oligosaccharide moiety and a membrane anchoring-Lipid A component and in the case of some strains of Mh and Ap a polymeric O-antigen. Based on the experiments described herein, a structural model was developed for Mh, Ap and Pm LPS consisting of a conserved tetra-heptosyl-di-glucosyl inner-core moiety, which is attached via a phosphorylated ketodeoxyoctonoate residue (Kdo) to a lipid A component and which has been found to be conserved and present in every strain so far examined.

From the structural analyses it was clear that the maximum structure absolutely conserved across the three species was that illustrated in Structure I below.

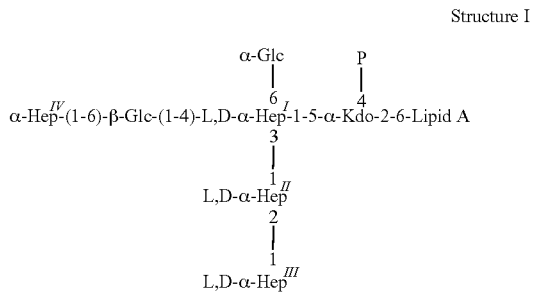

Structure I where Kdo is 3-deoxy-D-manno-2-octulosonic acid, Hep is heptose, Glc is glucose, P is phosphate and Lipid A is detoxified.

In order to utilize an antigen for vaccine development, four essential criteria must be fulfilled. That is the immunogenic epitope of the candidate antigen must be:

i) genetically stable;

ii) conserved in all clinically relevant strains across the species iii) accessible (in vitro and in vivo) to host immune mechanisms; and, iv) able to induce protective antibodies in vivo.

This invention has identified a conserved LPS carbohydrate epitope that has been shown to satisfy the majority of these criteria.

i) Genetic stability: The genes involved in the biosynthesis of the conserved inner core oligosaccharide have been identified in the genome strains of the three bacterial species, (two Pm strains, one Mh strain and two Ap strains). Genes involved in the different outer core variations exhibited by these bacterial species have been found to be variably present, and these data have been corroborated with structural data on these genome strains and additional strains of each bacterial species. However, both structural and genetic analyses (see Table A) have indicated that the inner core structure is structurally conserved due to the consistent presence of the genes known to be responsible for inner core biosynthesis.

TABLE A

Glycosyltransferases of the conserved inner core LPS of the veterinary pathogens

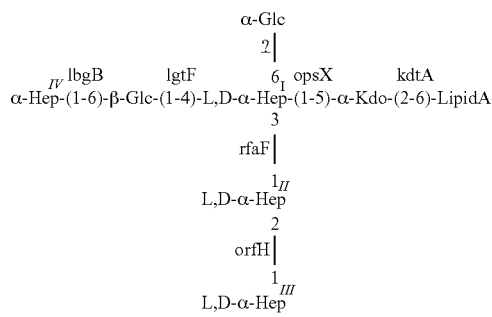

Conserved inner core glycosyltransferases in the veterinary pathogen genome strains

| Gene | Pm-3480 | Pm70 | Ap_1 | Ap_5 | Mh |
|---|---|---|---|---|---|
| kdtA | Contig49 $e^{-155}$* | PM1305 $e^{-155}$ | Contig25 $e^{-129}$ | ap93i1204 $e^{-128}$ | Contig164 $e^{-126}$ |
| opsX | Contig49 $e^{-145}$ | PM1302 $e^{-152}$ | Contig24 $e^{-111}$ | ap93i0300 $e^{-108}$ | Contig165 $e^{-116}$ |
| rfaF | Contig68 $e^{-165}$ | PM1844 $e^{-165}$ | Contig25 $e^{-153}$ | ap93i0451 $e^{-154}$ | Contig81 $e^{-155}$ |
| orfH | Contig28 $e^{-132}$ | PM1294 $e^{-132}$ | Contig24 $e^{-83}$ | ap93i0686 $e^{-120}$ | Contig109 $e^{-132}$ |
| lgtF | Contig49 $e^{-110}$ | PM1306 $e^{-110}$ | Contig24 $e^{-110}$ | ap93i0684 $e^{-114}$ | Contig109 $e^{-116}$ |
| lbgB | Contig59 $e^{-inf}$ | PM1144 $e^{-inf}$ | Contig29 $e^{-98}$ | ap93i1369 $e^{-98}$ | Contig147 $e^{-89}$ |

*e-values based on Blasting veterinary pathogen genomes with inner core LPS glycosyltransferases from *Haemophilus influenzae* strain KW-20 (Rd), except lbgB where PM1144 from Pm70 genome was used.

Genome data obtained from: Baylor College of Medicine, Houston (Mh); Department of Microbiology and Immunology, Laboratory for Genomics and Bioinformatics, Oklahoma University Health Sciences Center (Pm-3480 and Ap1); Institute for Biological Sciences, National Research Council, Ottawa, Canada (Ap5); Computational Biology Centre, University of Minnesota (Pm70).

ii) Structural conservation: In every strain investigated by Applicant to date this tetra-heptosyl-di-glucosyl moiety has been contained within the following structural element (Structure II):

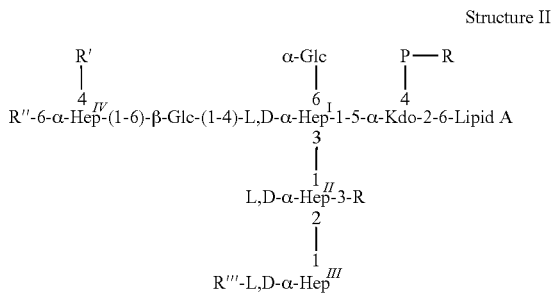

Structure II where: —R is H or phosphoethanolamine (PEtn), P is phosphate, R' and R" are H or oligosaccharide chain extensions, preferably not including β-D-Galp-(1-7)-D-α-D-Hepp-(1-6), and R'" is a variable O-antigen in Ap, Kdo is 3-deoxy-D-manno-2-octulosonic acid and Lipid A is detoxified.

instead of the Kdo-P or Kdo-P-PEtn moiety, the presence of the second Kdo residue is concomitant with the loss of the inner core α-Glc residue. Outer core variation has been observed both within and between the three species of interest. In Ap serotype 1 the outer core extension has been completely structurally characterised by NMR and shown to contain the rarely encountered open-chain N-acetylgalactosamine structure terminal to the oligosaccharide extension of (1S)-GalaNAc-(1-4,6)-α-Gal-(1-3)-β-Gal. This structure has also been inferred from mass spectrometry in serotypes 9 and 11 also. In Ap serotype 2 the $Hep^{IV}$ residue was found to be di-substituted at the 4-position with a β-Glc residue and at the 6-position with a D, D-α-$Hep^V$ residue. In Ap serotype 5 only the D, D-α-$Hep^V$ residue is substituting $Hep^{IV}$. A similar outer core extension to that found for Ap serotype 5 is observed in Mh, where the second D, D-α-$Hep^{V}$ residue is itself substituted at the 7-position with a β-Gal residue. In Pm, studies on two serotype 1 strains, VP161 and X73 revealed an unusual outer core extension wherein the $Hep^{IV}$ residue was symmetrically substituted at both the 4- and 6-positions with β-Gal residues that themselves were mono-substituted with phosphocholine moieties at the 3-positions, or elaborated in addition to the phosphocholine residues, phosphoethanolamine residues at the 6-positions of the β-Gal residues (X73). Another study on the genome sequenced strain Pm70 revealed di-substitution of the $Hep^{IV}$ residue at the 4- and 6-positions once again. The 4-position was substituted by a β-glucose residue and at the 6-position with the unusual pentasaccharide α-GalNAc-(1-3)-β-GalNAc-(1-3)-α-Gal-(1-4)-β-Gal-(1-4)-β-Glc.

TABLE B

Structure of conserved and variable regions in the core oligosaccharides of the LPS from the veterinary pathogens *Mannheimia haemolytica* (Mh), *Actinobacillus pleuropneumoniae* (Ap) and *Pasteurella multocida* (Pm).

| Species | Strain/ Serotype | R' | R" | R |
|---|---|---|---|---|
| Mh | A1 | H | β-D-Galp-(1-7)-D-α-D-$Hep^{V}$p-(1- | H |
| | A8 | H | D-α-D-$Hep^{V}$p-(1- | H |
| | SH1217 | H | β-D-Galp-(1-7)-D-α-D-$Hep^{V}$p-(1- | H |
| Ap | 1 | (1S)-GalaNAc-(1-4,6)-α-D-Gal-(1-3)-β-D-Gal-(1- | H | H |
| | 2 | β-D-Glc-(1- | D-α-D-$Hep^{V}$-(1- | H |
| | 5a | H | D-α-D-$Hep^{V}$-(1- | H |
| | 5b | H | D-α-D-$Hep^{V}$-(1- | H |
| Pm* | Pm70 | β-D-Glc-(1- | α-D-GalpNAc-(1-3)-β-D-GalpNAc-(1-3)-α-D-Gal-(1-4)-β-D-Gal-(1-4)-β-D-Glc-(1- | PEtn |
| | VP161 | PCho-3-β-D-Gal-(1- | PCho-3-β-D-Gal-(1- | H |
| | X73 | (PEtn-6)-PCho-3-β-D-Gal-(1- | (PEtn-6)-PCho-3-β-D-Gal-(1- | H |

For Pm the heptose residue, $Hep^{IV}$ is of the L-α-D configuration. Also in Pm, the α-glucose residue at the 6-position of $Hep^{I}$, is absent in a minority of glycoforms, concomitant with a structural difference at the Kdo residue, when instead of P-R at the 4-position of Kdo there is a second Kdo residue.

The first heptose residue ($Hep^{I}$) is the only heptose residue from which core oligosaccharide extension has been shown to occur in all three species, Ap, Mh and Pm. Outer core extension elongates further from the $Hep^{IV}$ residue. No core oligosaccharide extension has been observed from $Hep^{II}$ or $Hep^{III}$ in any species. O-antigen extension in Ap serotype 5 was found to occur from the $Hep^{III}$ residue [St. Michael, F. et. al. 2004, Carbohydr. Res., 339: 1973-1984], the location of O-antigen attachment to the core OS has not been shown in Mh. No antigenic polymeric repeating units have been observed in Pm. Four genes have been shown to be involved in O-antigen biosynthesis in Ap serotype 1, including rfbP and rfbU, mutants of which result in Ap strains without O-antigen [Labrie, J. et al. 2002, J. Endotox. Res., 8: 27-38]. The inner core of all three species can be further substituted with a phosphoethanolamine residue, either at the 3-position of the $Hep^{II}$ residue in Pm strain Pm70, or at the Kdo-P residue in all species Ap, Mh, and Pm. In Pm, a minor population of LPS glycoforms have been shown to elaborate two Kdo residues iii) Accessibility: Since this inner core structure is consistently expressed in these three species it was important to ascertain if epitopes of this inner core structure were accessible and conformationally conserved regardless of the variability in outer core, O-antigen and other cell surface structures. To achieve this the conserved structure needed to be elaborated as a terminal structure and to that end glycosyltransferases were targeted that would expose this structure. The availability of the complete genome sequence of Pm strain Pm70 in conjunction with thorough knowledge of this strains LPS structure (see Example 3), facilitated tentative identification of the glycosyltransferases responsible for the biosynthesis of the Pm70 LPS structure. Other genome sequences are also evolving for a second Pm strain (P-3480), two Ap strains (serotypes 1 and 5) and one Mh strain (serotype A1), and a Bioinformatics approach was utilised in order to identify target genes for mutagenesis. Mh strain A1 was selected for mutagenesis studies, as the amount of O-antigen present in this organism is low compared to Ap and therefore should not interfere with subsequent immunological studies. As illustrated below, candidate glycosyltransferases were identified in both a) Mh strain A1 and b) Ap serotype 1.

a)

b)

A homologue of the *H. ducreyi* lbgA galactosyltransferase gene [Tullius, M. V. et al 2002, Infect. Immun. 70: 2853-2861] had been identified in Ap located between two genes that were found to be involved in core oligosaccharide biosynthesis by mini-Tn10 transposon mutagenesis [Galarneau, C. et al 2000, Pathogenesis, 1: 253-264]. The adjacent gene in Ap, lbgB showed considerable homology to a D-glycero-D-manno-heptosyltransferase from *Haemophilus ducreyi*. Blast analysis of the Mh genome sequence (Baylor College, Houston) with the lbgB gene sequence from Ap, revealed two adjacent homologues to the D-glycero-D-manno-heptosyltransferase in the Mh genome sequence. The best lbgB homologue identified was postulated to be the D-glycero-D-manno-heptosyltransferase responsible for the addition of the first D-glycero-D-manno-heptose residue ($Hep^{IV}$) in the extension from the first L-glycero-D-manno-heptose residue ($Hep^{I}$), and we therefore postulated that the second homologue, which we termed losB, was the D-glycero-D-manno-heptosyltransferase responsible for the addition of the second D-glycero-D-manno-heptose residue ($Hep^{V}$).

Utilising standard molecular biological techniques, this gene was mutated and the resulting LPS derived from the mutant strain was structurally characterised to show that the targeted conserved inner core structure had been obtained (see Example 7). MAbs and pAbs were raised to this inner core LPS structure in order to examine the degree of conservation and accessibility of this structure across a range of strains of these veterinary pathogens. Polyclonal sera were obtained that were cross-reactive with both LPS and whole cells of each of the three species, Mh, Ap and Pm. Four mAbs (G3, G8, E8 and D8) were obtained from one fusion that were specific for an inner core conformation as it is presented on whole cells of Mh. Three mAbs (3-4, 3-5 and 3-16) were obtained from a subsequent fusion that were capable of cross-reacting with LPS from all of the strains of interest from Ap, Pm and Mh thus establishing the potential of a conserved cross-reactive LPS epitope shared between these three significant veterinary pathogens. Ascites fluid was raised from four of these mAbs (G3, G8, 3-5 and 3-16) and examined by whole cell ELISA which, revealed that the LPS epitopes recognised by these mAbs were accessible on the whole cells, thus demonstrating that the conserved inner core epitopes are accessible on the cell surface. Furthermore, mAbs G3 and G8 facilitated passive protection in a mouse model of Mh infection, illustrating accessibility to this inner core structure in vivo.

iv) Functional antibodies: Polyclonal sera containing antibodies cross-reactive with LPS of the species of interest, and mAbs G8 and G3 were able to facilitate complement-mediated lysis of Mh cells. Passive protection studies were performed in the well established mouse model of Mh infection, which revealed that provision of mAbs (G3 and G8) specific for this conserved inner core LPS structure in Mh were able to protect against disease. Finally a conjugate vaccine was produced linking the conserved carbohydrate structure to the carrier protein HSA, and mouse sera raised following immunization with this conjugate was found to be cross-reactive with LPS and whole cells from the three species of interest.

SUMMARY OF THE INVENTION

The invention provides vaccines, vaccine components, and uses thereof suitable for providing immunity involving B-cell activating molecules derived from veterinary bacterial pathogens lipopolysaccharide (LPS), said molecules comprising one or more epitopes of the inner-core oligosaccharide portion of the lipopolysaccharide. The disclosure herein identifies and characterizes epitopes that are expressed on the LPS of bacterial veterinary pathogens across a range of disease causing isolates including but not necessarily limited to *Actinobacillus pleuropneumoniae* (Ap), *Mannheimia haemolytica* (Mh) and *Pasteurella multocida* (Pm). There is identified herein a defined sub-unit antigen suitable for use in the manufacture of vaccines. Antigens that are vaccine candidates are preferably displayed on the surface of the bacteria, in its natural state, so that the immune response to the vaccine antigen can subsequently target the live organism.

We have found and produced an inner core LPS which is common to all three organisms. LPS has been shown to play a role in the immunity to each of these veterinary pathogens and if the LPS antigen is conformationally conserved the immune response would likely recognise homologous and heterologous strains and indeed species.

Structural analysis data suggested that all these veterinary pathogens shared a common and conserved inner core OS structure. It was decided therefore to explore the potential of a LPS-based vaccine.

A first step in this process was the construction of a mutant strain expressing exclusively the conserved inner core OS epitope as a terminally exposed structure. This study has generated a mutant in the α-1,6-D-glycero-D-manno-heptosyltransferase gene from Mh strain A1 in order to present the conserved inner core epitope as a terminally exposed moiety.

MAbs and pAbs were raised to this inner core LPS structure in order to examine the degree of conservation and accessibility of this structure across a range of strains of these veterinary pathogens. Three mAbs were obtained that were capable of cross-reacting with LPS from all of the strains of interest from Ap, Pm and Mh thus establishing the potential of a conserved cross-reactive LPS epitope shared between these three significant veterinary pathogens.

Whole cell ELISA analyses revealed that these LPS epitopes were recognised by the mAbs on the whole cells, thus demonstrating that the inner core epitopes are accessible on the cell surface. Mabs, which recognised the inner core oligosaccharide were able to facilitate complement-mediated bactericidal lysis of the Mh cells. Passive protection studies were performed in the well established mouse model of Mh infection, which revealed that provision of mAbs specific for this conserved inner core LPS structure were able to protect against disease. Finally a conjugate vaccine was produced linking the conserved carbohydrate structure to the carrier protein HSA, and mouse sera raised following immunization with this conjugate was found to be cross-reactive with the three species of interest.

In one aspect, the invention provides a lipopolysaccharide moiety comprising a conserved di-glucosyl-tetra-heptosyl inner-core free of variable outer core oligosaccharide chain extensions.

In another aspect, the invention provides a lipopolysaccharide moiety comprising a di-glucosyl-tetra-heptosyl inner-core moiety having the following structure II:

Structure II $$\begin{array}{ccc} R' & \alpha\text{-Glc} & P\text{---}R \\ | & | & | \\ 4 & 6 & 4 \end{array}$$
$$R''\text{-6-}\alpha\text{-Hep}^{IV}\text{-(1-6)-}\beta\text{-Glc-(1-4)-L,D-}\alpha\text{-Hep}^{I}\text{-1-5-}\alpha\text{-Kdo-2-6-Lipid A}$$
$$\begin{array}{c} 3 \\ | \\ 1 \\ L,D\text{-}\alpha\text{-Hep}^{II}\text{-3-R} \\ 2 \\ | \\ 1 \\ R'''\text{-L,D-}\alpha\text{-Hep}^{III} \end{array}$$

where: —R is H or phosphoethanolamine (PEtn), P is phosphate, R' and R" are H or oligosaccharide chain extensions, preferably not including β-D-Galp-(1-7)-D-α-D-Hepp-(1-6), and R''' is a variable O-antigen in Ap, Kdo is 3-deoxy-D-manno-2-octulosonic acid and Lipid A is detoxified.

In another aspect, the invention provides an immunogenic composition for conferring protection in an animal host against a disease caused by Mh, Ap or Pm, comprising either of the lipopolysaccharide moieties described above.

In another aspect, the invention provides a use of at least one gene in the LPS biosynthetic pathway for the production of lipopolysaccharide in Mh, Ap or Pm, to obtain a mutant strain comprising either of the lipopolysaccharide moieties described above.

In another aspect, the invention provides a use of at least one immunogenic epitope to elicit a functional cross-reactive antibody against Mh, Ap or Pm, wherein the epitope comprises either of the lipopolysaccharide moieties described above.

In another aspect, the invention provides a functional antibody which is cross-reactive against Mh, Ap or Pm, and which is elicited by either of the lipopolysaccharide moieties described above.

In another aspect, the invention provides a method for the production of a functional cross-reactive antibody against Mh, Ap or Pm, which comprises: (a) generating antibodies to either of the lipopolysaccharide moieties described above, (b) testing such antibodies against a plurality of Mh, Ap and Pm strains, and (c) selecting those antibodies which are cross-reactive.

In another aspect, the invention provides a method of immunizing a host against disease caused by infection with Mh, Ap or Pm, which comprises administering to the host an immunoeffective amount of the immunogenic composition described above.

The following conserved inner core LPS structure has been identified in Ap, Mh and Pm. This structure is useful as a vaccine candidate that provides broad coverage to all strains. The unexpected finding that all three species elaborate this identical structural unit, allows the preparation of multi-species vaccines based on this one conserved structure.

$$\begin{array}{ccc} R' & \alpha\text{-Glc} & P\text{---}R \\ | & | & | \\ 4 & 6 & 4 \end{array}$$
$$R''\text{-6-}\alpha\text{-Hep}^{IV}\text{-(1-6)-}\beta\text{-Glc-(1-4)-L,D-}\alpha\text{-Hep}^{I}\text{-1-5-}\alpha\text{-Kdo-2-6-Lipid A}$$
$$\begin{array}{c} 3 \\ | \\ 1 \\ L,D\text{-}\alpha\text{-Hep}^{II}\text{-3-R} \\ 2 \\ | \\ 1 \\ R'''\text{-L,D-}\alpha\text{-Hep}^{III} \end{array}$$

Where: —R is H or phosphoethanolamine (PEtn), P is phosphate, R' and R" are H or oligosaccharide chain extensions, preferably not including β-D-Galp-(1-7)-D-α-D-Hepp-(1-6), and R''' is a variable O-antigen in Ap, Kdo is 3-deoxy-D-manno-2-octulosonic acid and Lipid A is detoxified.

The structural analyses performed to characterize these conserved structures in each species are detailed in Examples 1, Mh; 2, Ap and 3-5, Pm. Example 1 describes the structural analysis of the serotype A1 LPS of *Pasteurella haemolytica*. Example 2 describes the structural analysis of the LPS from several serotypes of Ap whereby the structural relatedness of the inner core molecules of Mh and Ap was first identified. Example 3 describes the structural analysis of the LPS from the genome strain of Pm whereby the structural conservation of the inner core molecules of all three species was first identified. Example 4 describes the structural analysis of the LP of Pm strain VP161. Example 5 describes the structural analysis of the core oligosaccharide of Pm strain X73. Example 6 describes identification of the orfH gene, the Hep III to Hep II heptosyltransferase of Pm. Example 7 describes production of a D-glycero-D-manno-heptosyltransferase mutant of *Mannheimia haemolytica* displaying a veterinary pathogen specific conserved LPS structure and development and cross-reactivity of antibodies to this LPS structure. Example 8 describes the production and investigation of a glycoconjugate vaccine utilising the conserved inner core LPS molecule as the carbohydrate moiety. Example 9 describes the bactericidal assay data obtained using inner core specific monoclonal antibodies and polyclonal sera. Example 10 describes the passive protection experiment data obtained using inner core specific monoclonal antibodies. Taken together these examples indicate that these inner-core lipopolysaccharide epitopes are vaccine candidates for the prevention of diseases caused by bacterial species with LPS molecules that contain this inner core structure.

Vaccines comprised of capsular polysaccharides are effective at preventing human disease caused by the homologous encapsulated bacteria. These carbohydrate antigens are often poorly immunogenic in humans due to a lack of T-cell dependent response. However, by conjugating the specific polysaccharide antigen to a suitable protein carrier, the immunogenicity of the carbohydrate antigen can be greatly enhanced over the polysaccharide alone. Glycoconjugate vaccines based on the specific capsular polysaccharide of type b *H. influenzae* (Hib), and type c *Neisseria meningitidis* e.g. ProHiBit, MenC, have already proven successful in the control of invasive Hib and meningococcal diseases.

The general strategy is to conjugate the conserved inner core LPS molecule in an appropriate manner to a suitable carrier molecule in order to elicit the desired immune response following immunization of the host.

An immunogenic carrier protein is preferably selected from the group consisting of tetanus toxin/toxoid, diphtheria toxin/toxoid ($CRM_{197}$), detoxified *P. aeruginosa* toxin A, cholera toxin/toxoid, pertussis toxin/toxoid, *Clostridium perfringens* exotoxins/toxoid, hepatitis B surface antigen, hepatitis B core antigen, rotavirus VP 7 protein, respiratory syncytial virus F and G proteins or other suitable carrier.

An adjuvant is preferably selected from the group consisting of Freund's adjuvant, alum and Ribi or any other pharmaceutically acceptable adjuvant.

In an embodiment of the invention there is provided a method of inducing or increasing immunity in an animal, fish or bird against a bacterial pathogen comprising administering a conserved inner core LPS molecule. In some instances the bacterial pathogen will be a variety of *Mannheimia, Actinobacillus*, or *Pasteurella*. In some instances the bacterial pathogen will be a veterinary organism of interest. Administration may be by any suitable route, including injection, application to a mucous membrane, transdermal application, oral (preferably suitably coated), etc. In some instances the inner core LPS molecule will be linked or associated with a suitable carrier molecule. In some instances a suitable adjuvant will also be used. In some instances the inner core LPS will be co-administered with an antibacterial drug or another immune stimulation. In some instances the conserved inner core LPS molecule will be the inner core LPS of structure I. In some instances the conserved inner core LPS molecule will be the inner core LPS of structure II without one or both R and $R^1$ as defined therein. In some instances the conserved inner core LPS will be at least one of the following:

a) b) c) d) e) f)

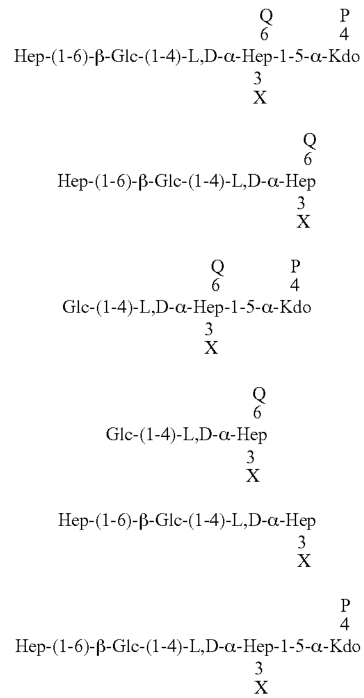

wherein:

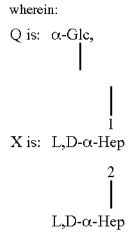

and P is phosphate.

In some instances the conserved inner core LPS will be a variant of one or more molecules a-f, above or of one of the generic structures disclosed (with or without R and $R^1$) wherein one or more terminal sugars appears as an isomer or has been modified to preserve it in a particular isomeric form.

In an embodiment of the invention there are provided the antigenic LPS-derived oligosaccharides described above free from covalent bonds to other oligosaccharides.

In an embodiment of the invention there is provided a method of making a vaccine comprising linking a conserved inner core LPS molecule or a portion and/or variant thereof to an immunogenic carrier protein. In some instances an adjuvant may be provided together with the LPS molecule-carrier protein.

DESCRIPTION OF THE FIGURES

FIG. 1 shows a proton NMR spectrum at 600 MHz of the core oligosaccharide component from *M. haemolytica* serotype A1 LPS in $D_2O$ (300 K, pH 3). The HOD resonance is at 4.756 ppm. Resonances in the anomeric region up from 4.4 ppm are labelled along with the Kdo methylene resonances. The determined structure designated as A1 and nomenclature for the residues are also shown. Heterogeneity due to partial truncation of the backbone oligosaccharide is indicated by dotted arrows at linkage sites. In the text the minor component for f due to heterogeneity is indicated by f'. Hep$_I$, Hep$_{II}$ and Hep$_{III}$ are D-D-heptoses. Other residues have the D-configuration.

Figure 2:
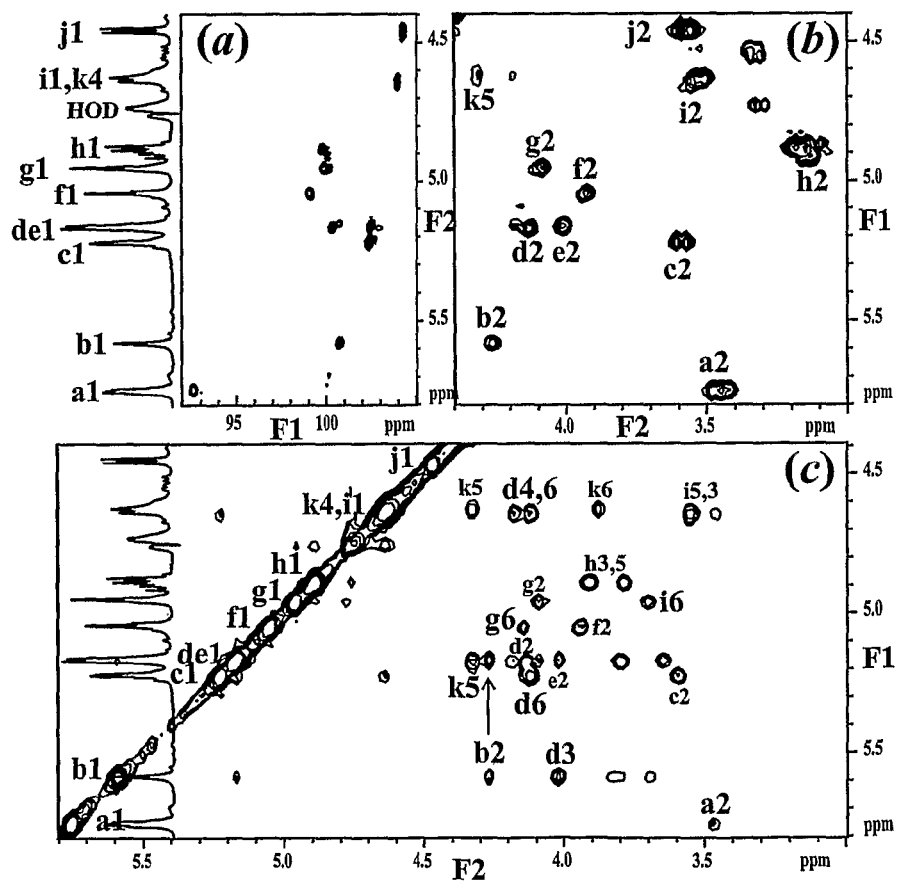

FIG. 2 shows 2D NMR experiments for A1 showing the HMQC spectrum of the anomeric region (a) and the COSY (b) and NOESY (c) spectra of the anomeric and ring region. The arrow indicates the position of the b2 resonance observed near k5.

Figure 3:
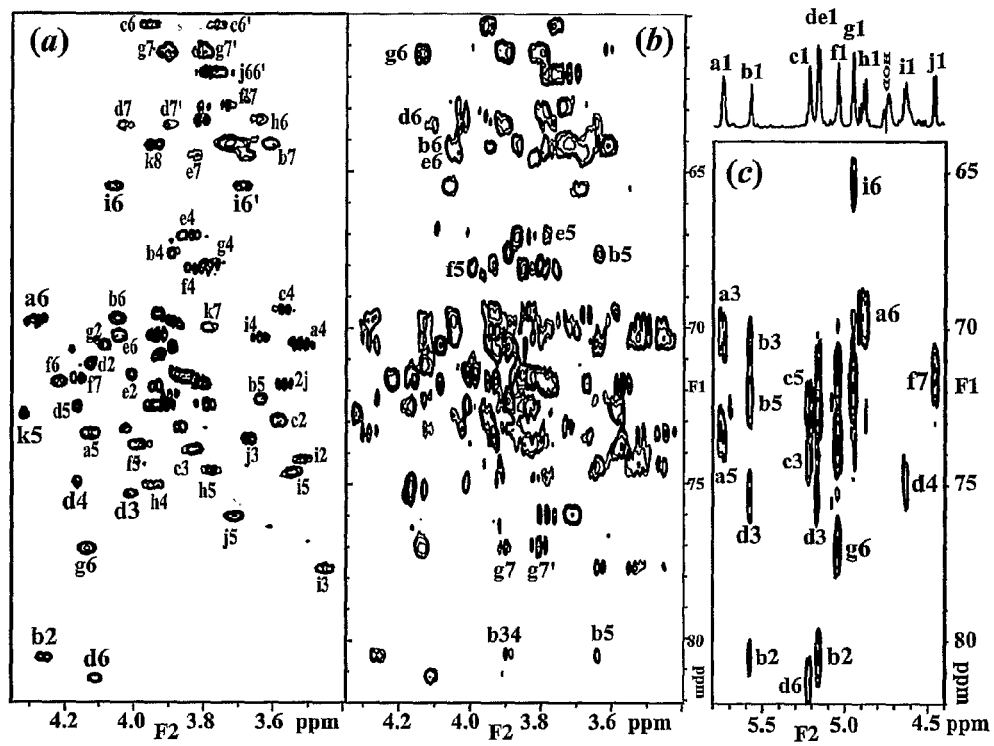

FIG. 3 show selected plots from the heteronuclear $^1$H—$^{13}$C 2D NMR spectra of A1. (a) In the HMQC spectrum of the ring region some assignments are labelled where possible. (b) In the HMQC-TOSCY spectrum, the C7-H7s-C6-H6, C4-H4-C5-H5 TOCSY correlations and those for b2 are labelled. (c) In the HMBC spectrum, the H1-C1-O1-Cx interglycosidic correlations are shown for the anomeric proton resonances along with their intra-residue correlations.

Figure 4:
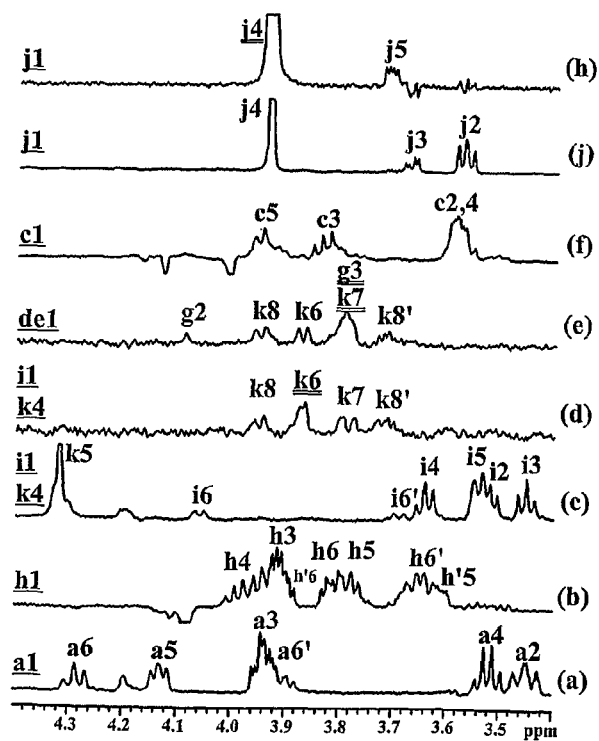

FIG. 4 shows 1D selective experiments for assignment of the non-heptose residues in A1. (a) 1D TOCSY (a1, 180 ms); (b) 1D TOCSY (h1, 180 ms); (c) 1D TOCSY (i1 k4, 180 ms); (d) 1D NOESY-TOCSY (i1 k4, 400 ms; k6 180 ms); (e) 1D NOESY-TOCSY (de1, 400 ms; g3 k7, 180 ms); (f) 1D TOCSY (c1, 180 ms); (g) 1D TOCSY j1, 180 ms); and (h) 1D TOCSY-NOESY (j1, 180 ms; j4,400 ms). Minor components for f and h due to heterogeneity are indicated by f' and h' respectively. The resonance for the first selective step is underlined and the one for the second selection step is doubly underlined, where applicable. Selected resonances in the anomeric region are indicated on the left of the spectra.

Figure 5:
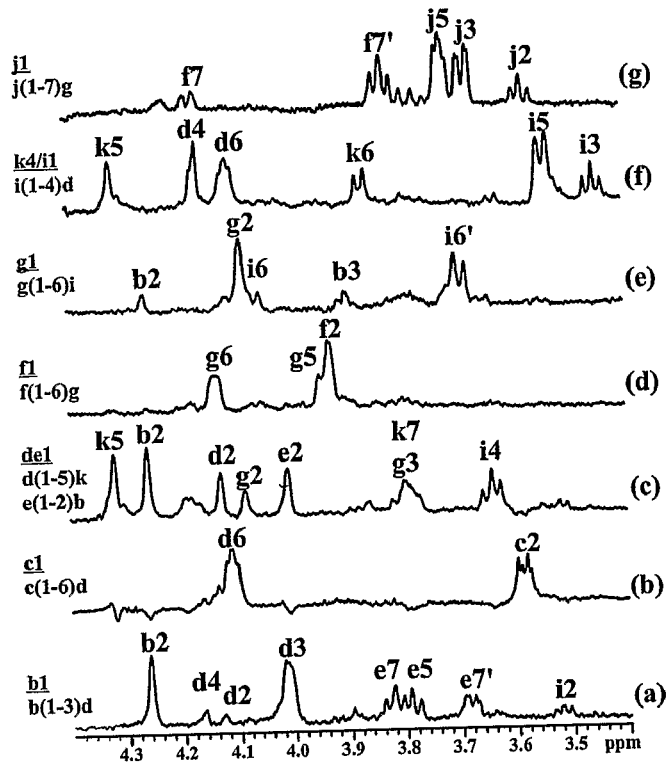

FIG. 5 shows 1D selective experiments to detect dipolar interactions in A1. 1D NOESY spectra of the resonances in the anomeric region with a 200 ms mixing time for b1, c1, de1, f1, g1, i1/k4 and a 1D ROESY (f1, 500 ms) for j1 in (a)-(g), respectively. The selected anomeric resonances are indicated on the left of the spectra.

Figure 6:
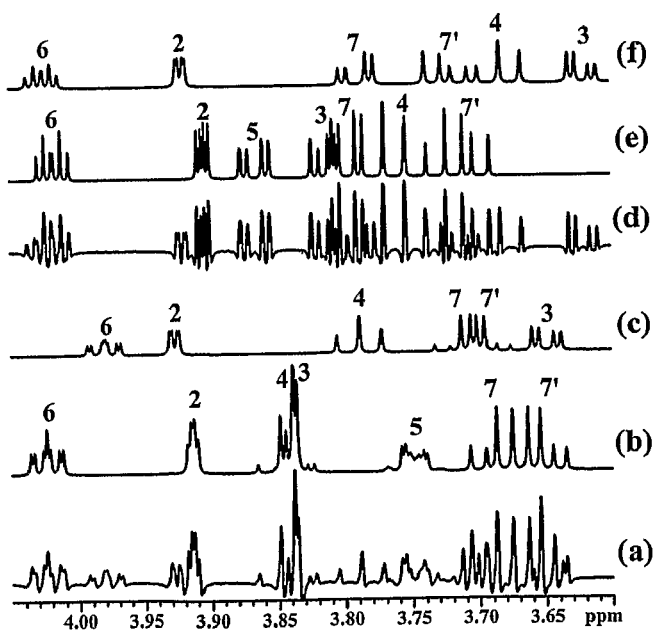

FIG. 6 shows proton spectra of heptose monosaccharides. Resolution enhanced spectrum of D-L-heptose at 600 MHz in D$_2$O, 300 K (a) and its enhanced spectrum for the α (b) and β forms (c). Resolution enhanced spectrum of D-D-heptose at 600 MHz in D$_2$O, 300 K (d) and its spin simulated spectra for the α (e) and β forms (f). The anomerics and the H-5β resonances are not shown. Note that strong coupling for the H-3, H-4 and virtual coupling for H-5 resonances are reproduced correctly for (b).

Figure 7:
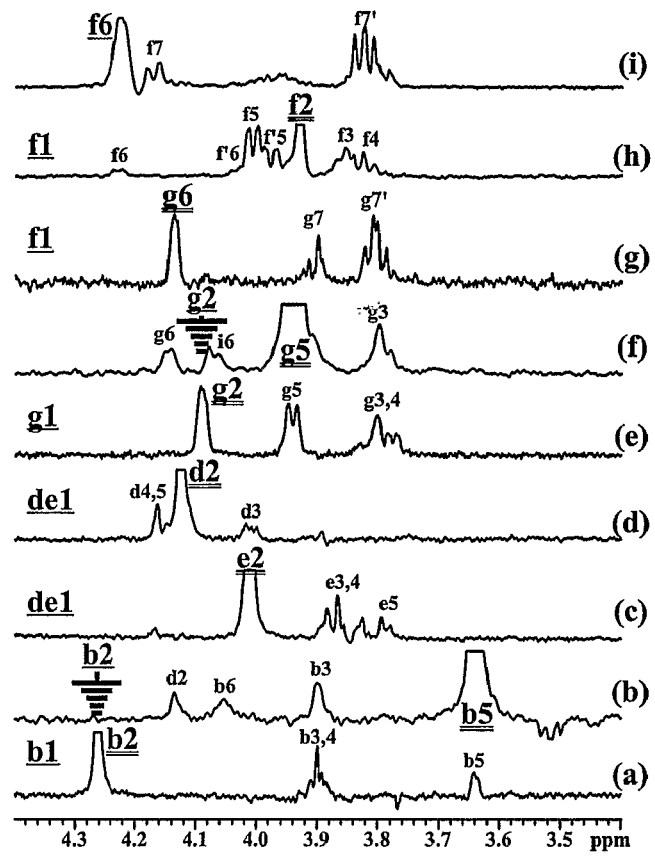

FIG. 7 shows 1D selective experiments for assignment of the heptose residues in A1. (a) 1D TOCSY-TOCSY (b1, 75 ms; b2, 75 ms) to detect b3, b4 and b5; (b) 1D TOCSY-NOESY (b2, 150 ms; b5, 400 ms) to detect the b5-b6 and b5-b3 NOEs. Note also the strong b5-d2 NOE due to the b(1-3)d linkage; (c) 1d TOCSY-TOCSY (de1, 75 ms; e2, 75 ms) to detect e3, e4 and e5; (d) 1D TOCSY-TOCSY (de1, 75 ms; d2, 75 ms) to detect d3, d4 and d5; (e) 1d TOCSY-TOCSY (g1, 90 ms; g2, 150 ms) to detect g3 to g5; (f) 1D TOCSY-NOESY (g2, 150 ms; g5, 400 ms) showing the g5-g6 and g5-g3 NOEs and g5-i6 NOE in accord with the g(1-6)I linkage; (g) 1D NOESY-TOCSY (f1, 400 ms; g6, 180 ms) to detect the g7 resonances from the f1-g6interglycosidic NOE in accordance with the f(1-6)g linkage; (h) 1D TOCSY-TOCSY (f1, 90 ms; f2, 150 ms) for detection of f and f resonances up to H-6. Note the clear multiplet pattern for f5 and f'5; (i) 1D TOCSY (f6, 40 ms) to detect the f7 resonances only due to the short spin lock time. The resonance for the first selective step is underlined and the one for the second selective step is doubly underlined, where applicable. Selected resonances in the anomeric region are indicated on the left of the spectra.

Figure 8:
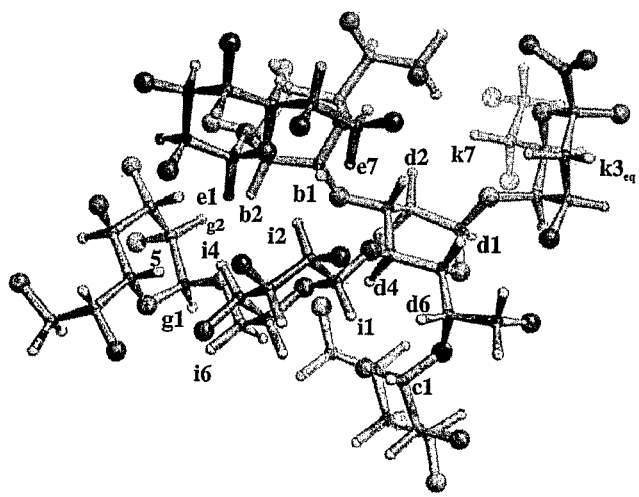

FIG. 8 shows a molecular model of a minimum-energy conformer obtained from a MMC calculation of the inner core heptasaccharide of A1. Oxygens are depicted as the larger spheres and hydroxyl protons are removed. Relevant protons are labelled. Note the close proximity of the e-b branch to the g-i branch and the close proximity of the exocyclic chain of residue e to the anomeric proton of residue b consistent with the long range NOEs observed. Also, note the differences in orientation of the exocyclic chain between L-D-heptose (residues d, b, e) and D-D-heptose (residue g).

Figure 9:
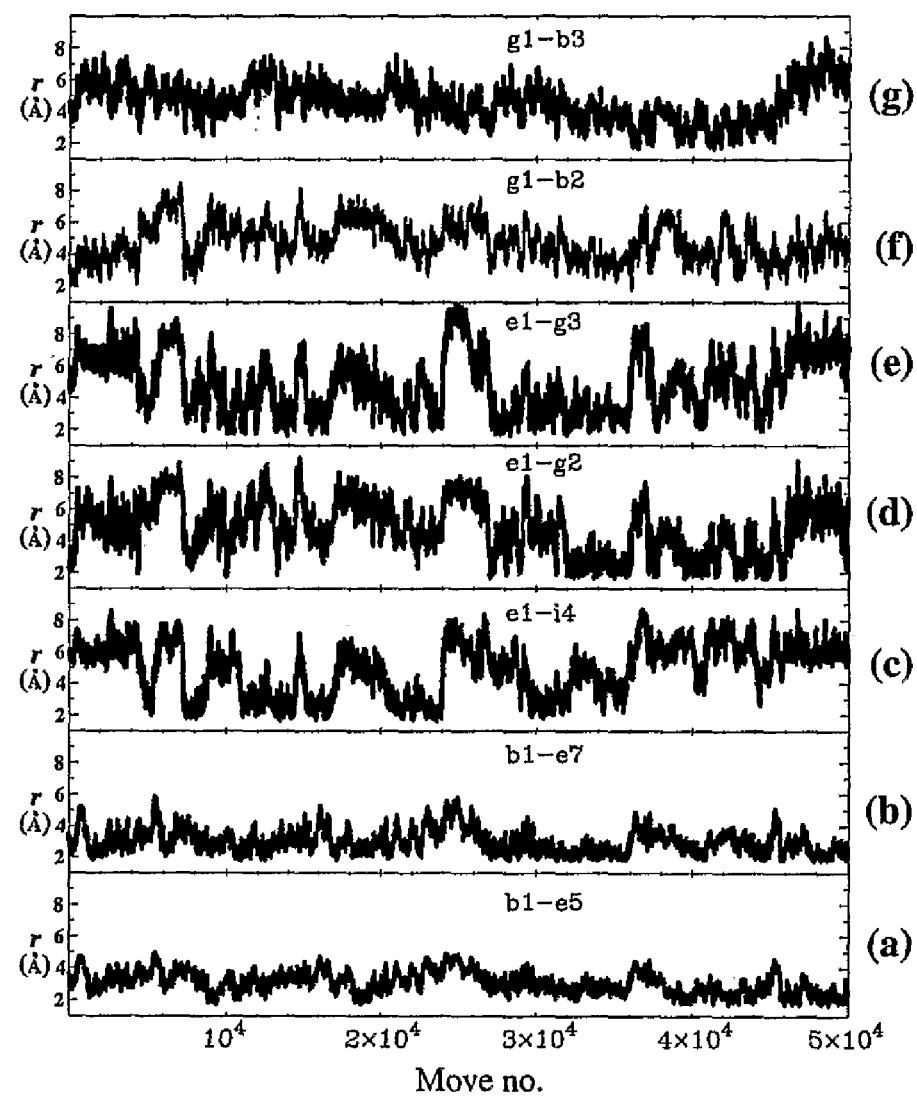

FIG. 9 shows the variation of inter-proton distances® vs. macro move as a MMC calculation of the inner core heptasaccharide of A1 for b1-e5, b1-e7, e1-14, e1-g2, g1-b2, g1-b3 in (a)-(g) respectively. Occurrences of inter-proton distances in the 2-4 Å range are consistent with the observed long range b-e, e-i and e-g NOEs.

Figure 10:
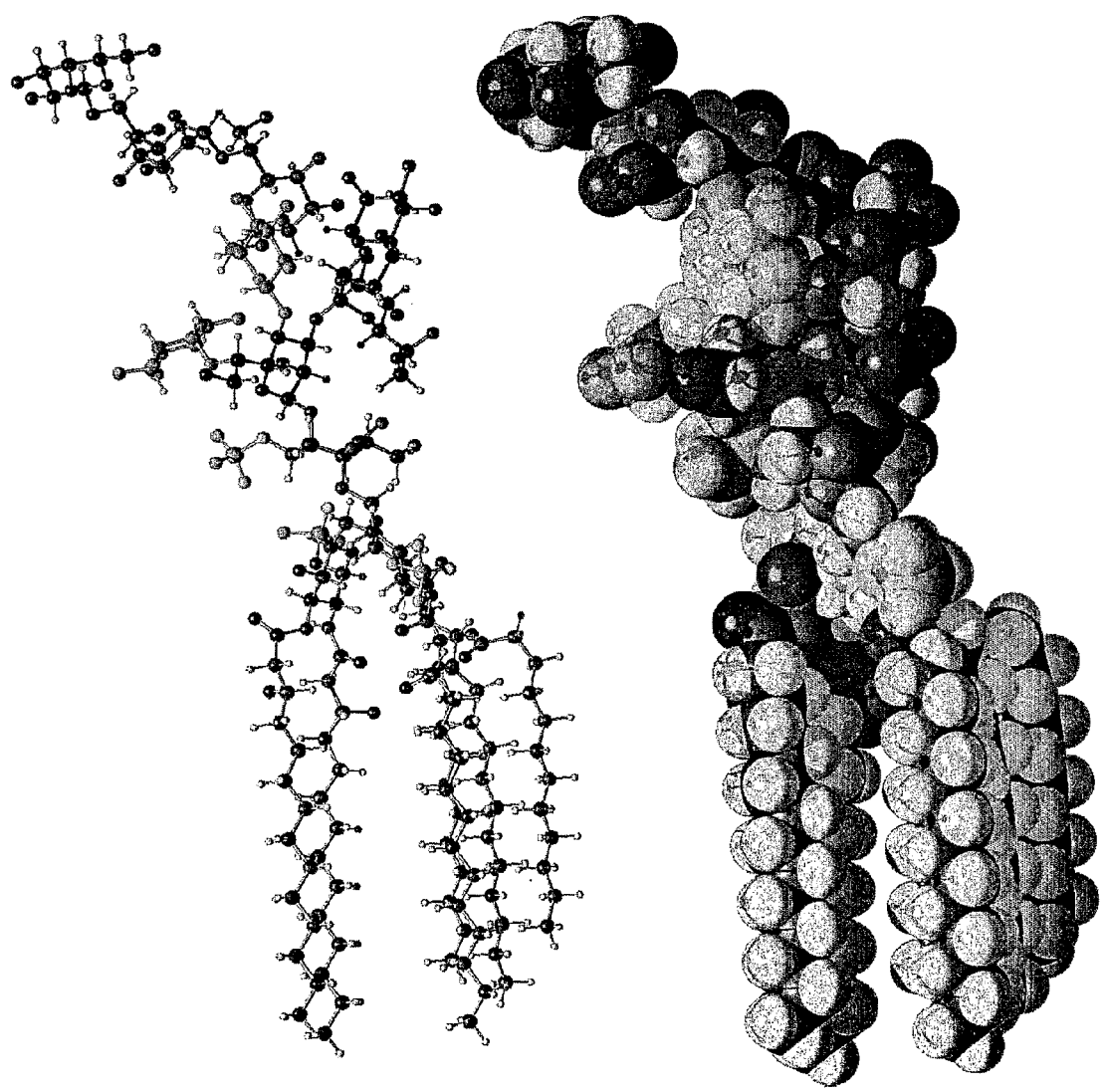

FIG. 10 show a molecular model of the LPS of *M. haemolytica* A1 constructed using a lipid A having the fatty acyl substitution patterns reported for LPS from *H. influenzae*. The lipid A moiety is coloured with Kdo in grey, heptoses in red or purple, glucose in green and galactose in blue. The PO$_4$ groups are yellow. Hydroxyl protons have been removed.

Figure 11:
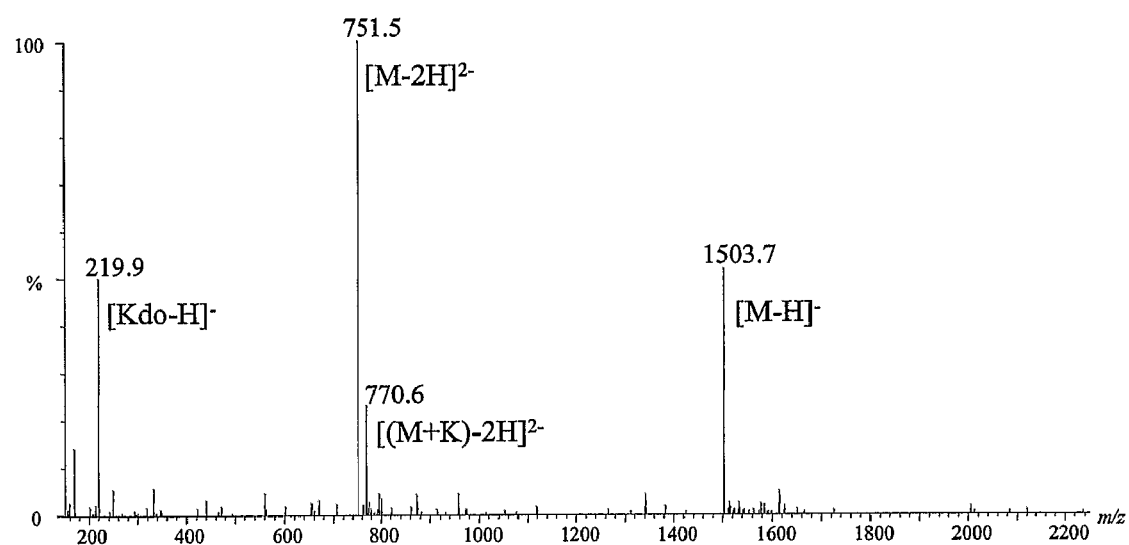

FIG. 11. Negative ion electrospray mass spectrum of Ap serotype 5a core OS.

Figure 12:
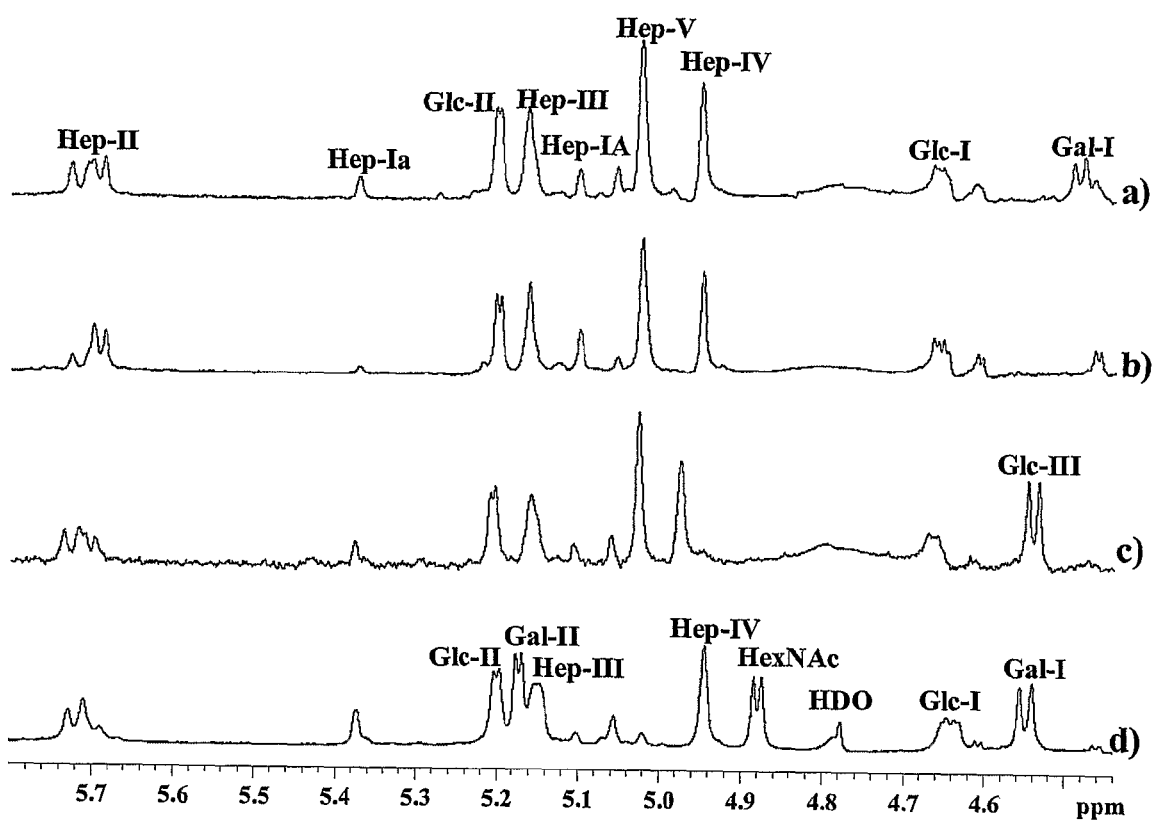

FIG. 12. Anomeric regions of the $^1$H-NMR spectra of the core OS from Ap serotypes a) 5a; b) 5b; c) 2; d) 1. The spectra were recorded in D$_2$O at pH 7.0 and 25° C.

Figure 13:
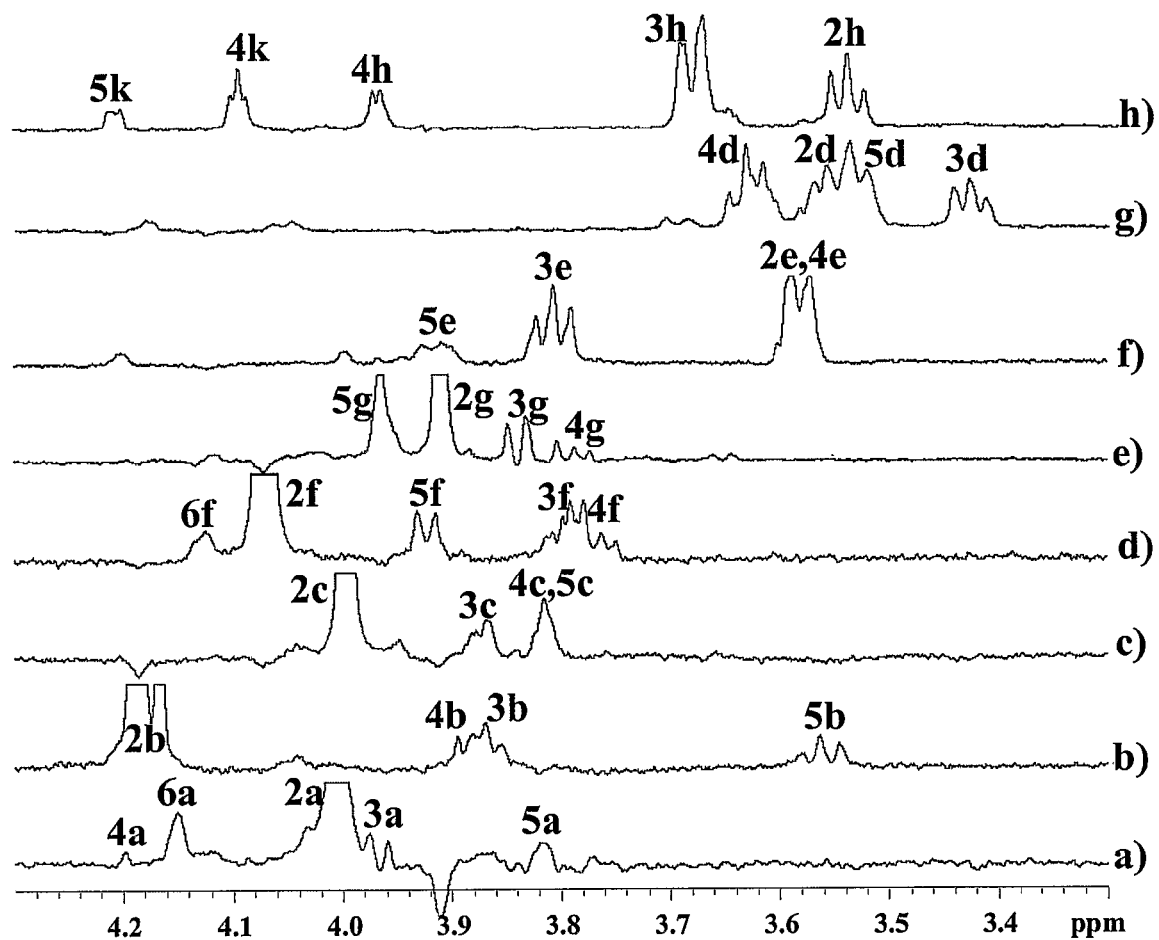

FIG. 13. Ring regions of the selective 1D-TOCSY NMR spectra of the core OS from Ap serotype 5a residues a) Hep I; b) Hep II; c) Hep III; d) Hep IV; e) Hep V; f) Glc II; g) Glc I; h) Gal I. Letter designations for each residue are as indicated in Example 2, Table 2. The spectra were recorded in D$_2$O at pH 7.0 and 25° C. with mixing times of 150 ms for the heptose residues and 90 ms for the hexose residues.

Figure 14:
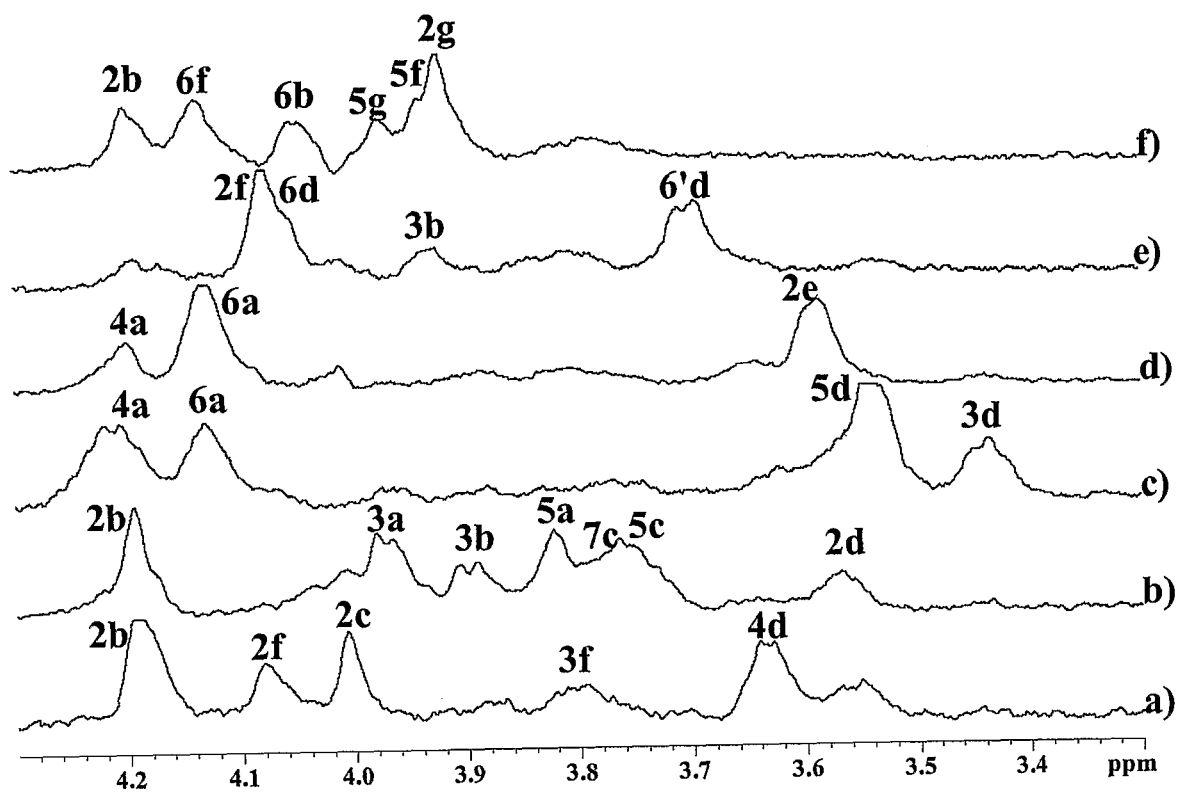

FIG. 14. Ring regions of the selective 1D-NOESY NMR spectra of the core OS from Ap serotype 5a residues a) Hep III; b) Hep II; c) Glc I; d) Glc II; e) Hep IV; f) Hep V. Letter designations for each residue are as indicated in Example 2, Table 2. The spectra were recorded in D$_2$O at pH 7.0 and 25° C. with a mixing time of 400 ms.

Figure 15:
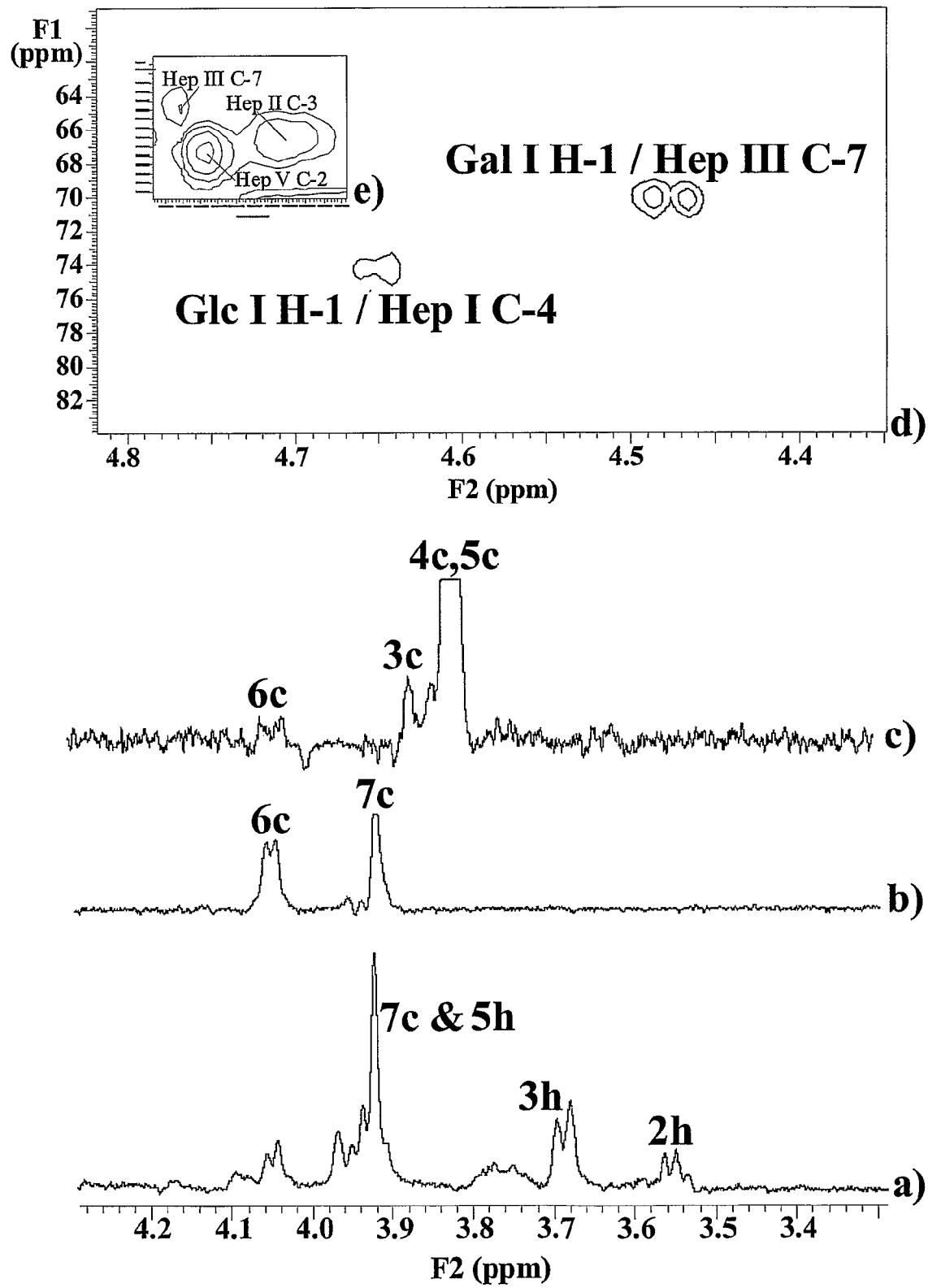

FIG. 15. Determination of the location of the O-chain Gal I residue of the core OS from Ap serotype 5a. a) 1D-NOESY NMR spectrum from the anomeric $^1$H-resonance of Gal I; b) 1D-NOESY-TOCSY spectrum from the anomeric $^1$H-resonance of Gal I residue in the NOESY step and from the H-7 $^1$H-resonance of the Hep III residue in the TOCSY step; c) 1D-TOCSY-NOESY spectrum from the anomeric $^1$H-resonance of Hep III residue in the TOCSY step and from the H-4/H-5 $^1$H-resonances of the Hep III residue in the NOESY step. d) Region of the $^{13}$C—$^1$H-HMBC NMR spectrum indicating the HMBC from the anomeric $^1$H-resonances of Gal I and Glc I. e) Region of the $^{13}$C—$^1$H-HSQC NMR spectrum indicating the $^{13}$C-cross-peaks from the H-7 $^1$H-resonance of Hep III, the H-2 $^1$H-resonance of Hep V and the H-3 $^1$H-resonance of Hep II. The spectra were recorded in D$_2$O at pH 7.0 and 25° C.

Figure 16:
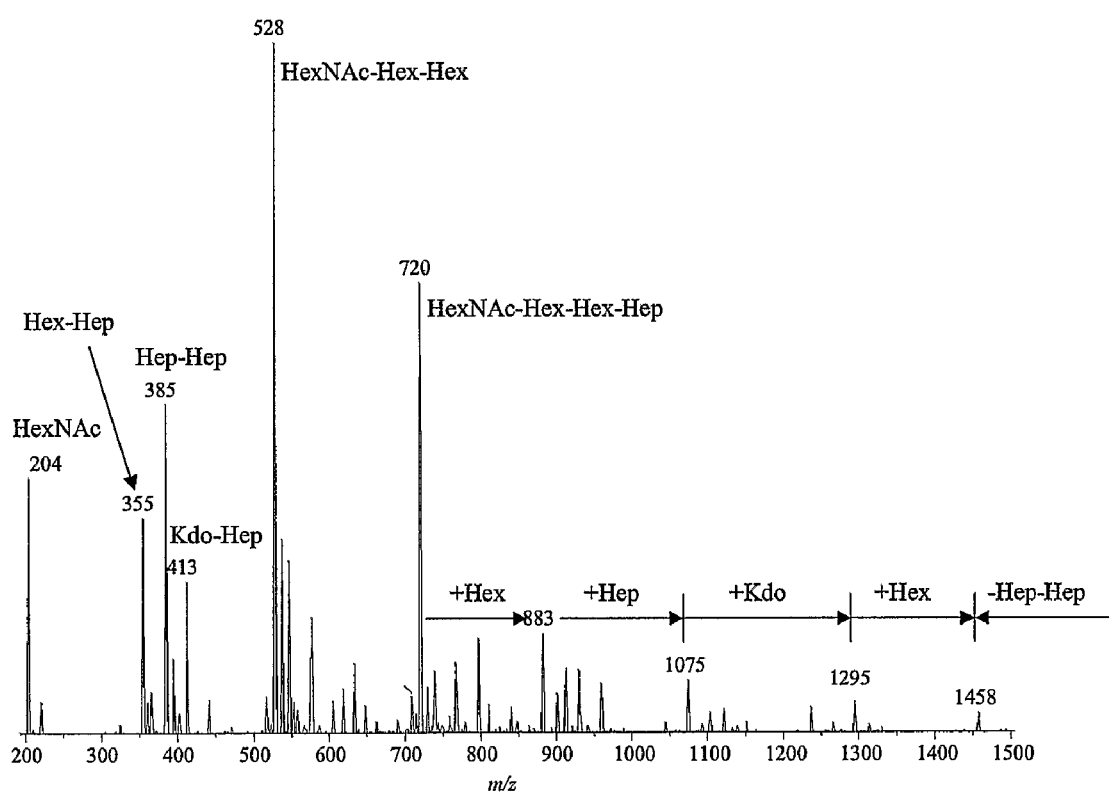

FIG. 16. Positive ion capillary electrophoresis-electrospray mass spectrum of the core OS from Ap serotype 1. Product ion spectrum from m/z 930$^{2+}$.

Figure 17:
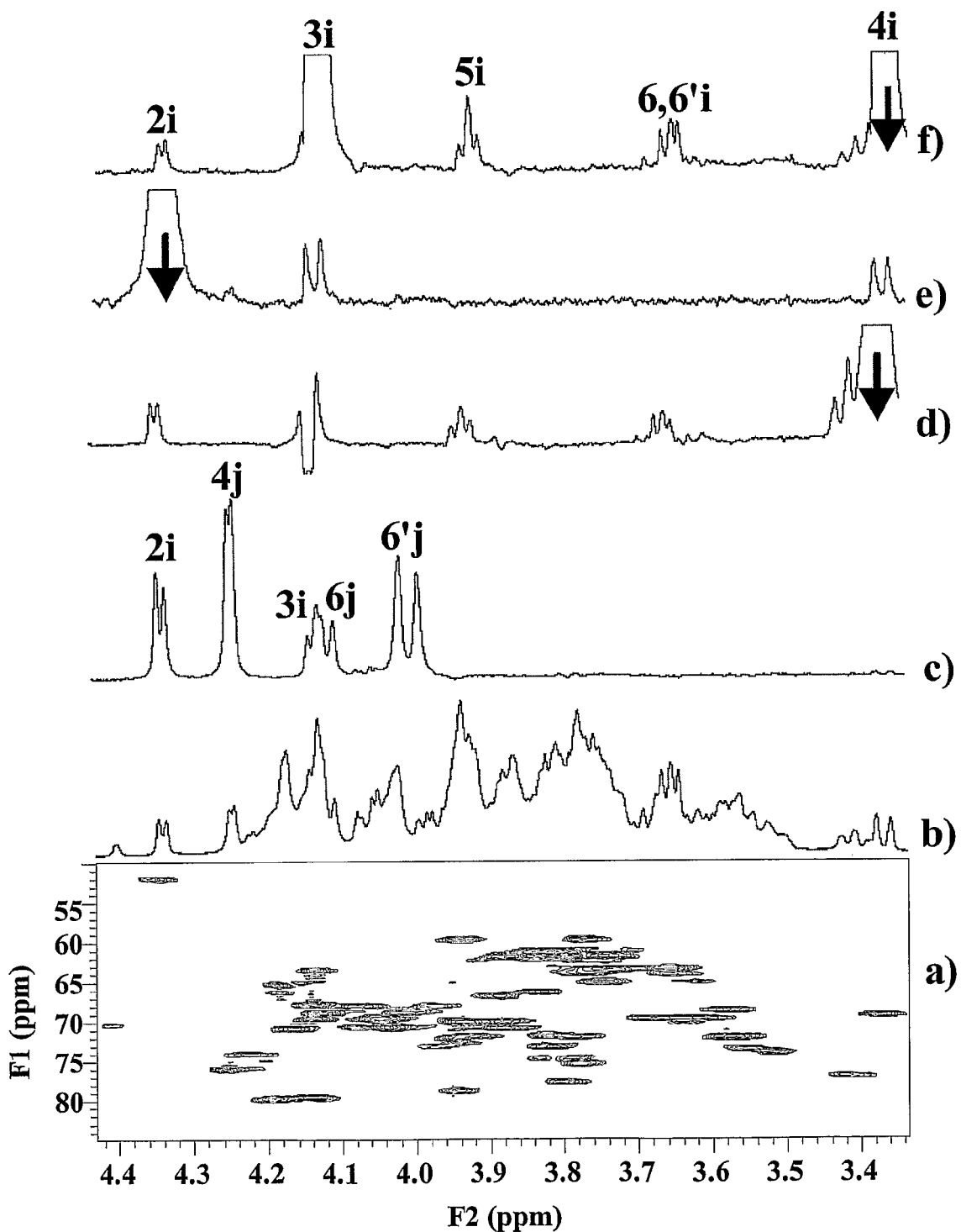

FIG. 17. Identification of the open-chain N-acetylgalactosamine residue of the core OS from Ap serotype 1. a) Ring region of the 2D-$^{13}$C—$^1$H-HSQC NMR spectrum of the core OS from Ap serotype 1. b) Ring region of the $^1$H-NMR spectrum of the core OS from Ap serotype 1. c) 1-D NOESY spectrum from the H-1 $^1$H-resonance of the GalNAc residue. d) 1-D TOCSY spectrum from the H-4 $^1$H-resonance of the GalNAc residue. e) 1-D NOESY spectrum from the H-2 $^1$H-resonance of the GalNAc residue. f) 1-D NOESY spectrum from the H-4 $^1$H-resonance of the HexNAc residue. The spectra were recorded in D$_2$O at pH 7.0 and 25° C. The assignments of the resonances are as indicated (i, GalNAc; j, Gal II).

Figure 18:
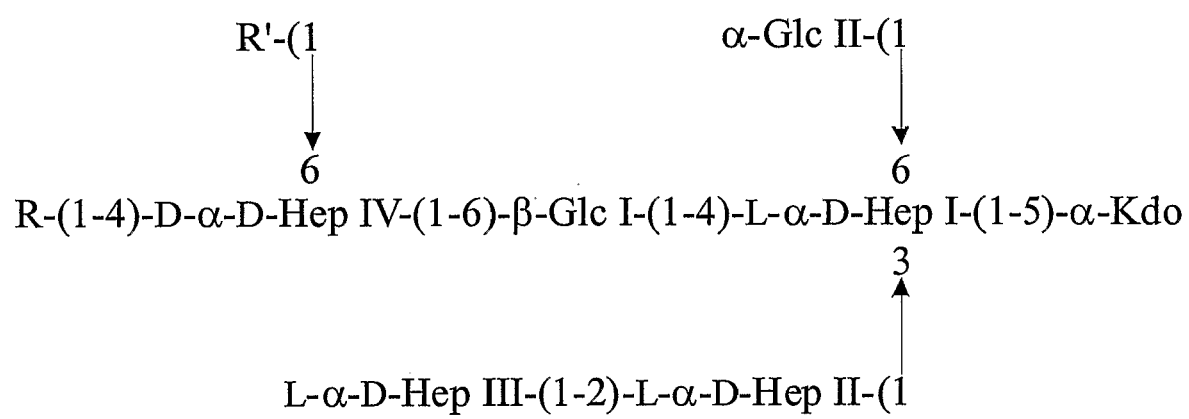

FIG. 18. Structural representation of an embodiment of the core oligosaccharides from Ap serotypes 1, 2, 5a and 5b. For serotype 1; R is α-GaloNAc-(1-4,6)-β-Gal II-(1-3)-β-Gal I, and R' is H where o indicates open-chain configuration. For serotype 2; R is β-Glc III, and R' is D-α-D-Hep V. For serotypes 5a and 5b; R is H and R' is D-α-D-Hep V.

Figure 19:
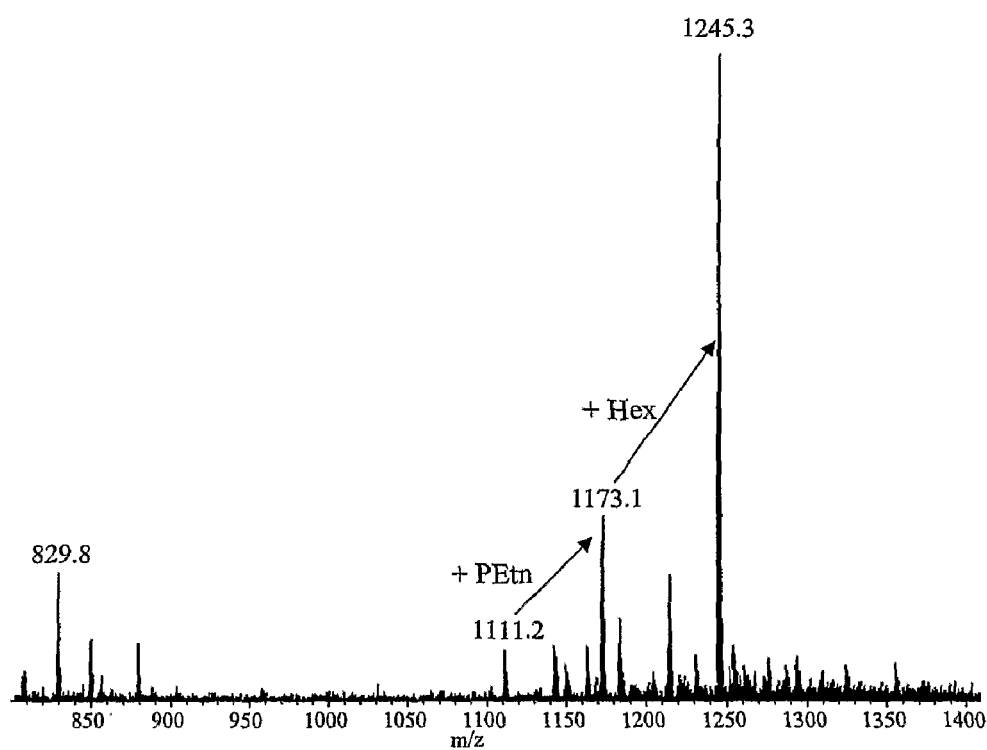

FIG. 19. Negative ion electrospray mass spectrum of *Pasteurella multocida* strain Pm70 core OS.

Figure 20:
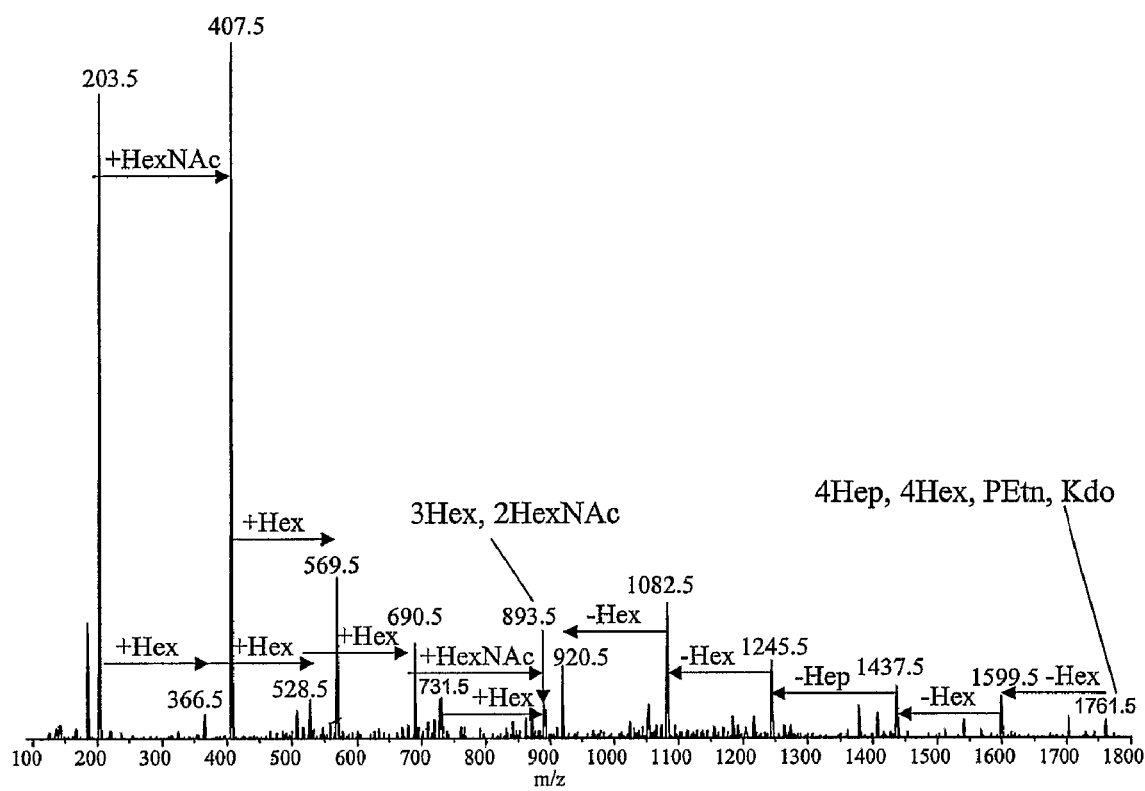

FIG. 20. Positive ion capillary electrophoresis-electrospray mass spectrum of *Pasteurella multocida* strain Pm70 core OS MS/MS of m/z 1246.5$^{2+}$.

Figure 21:
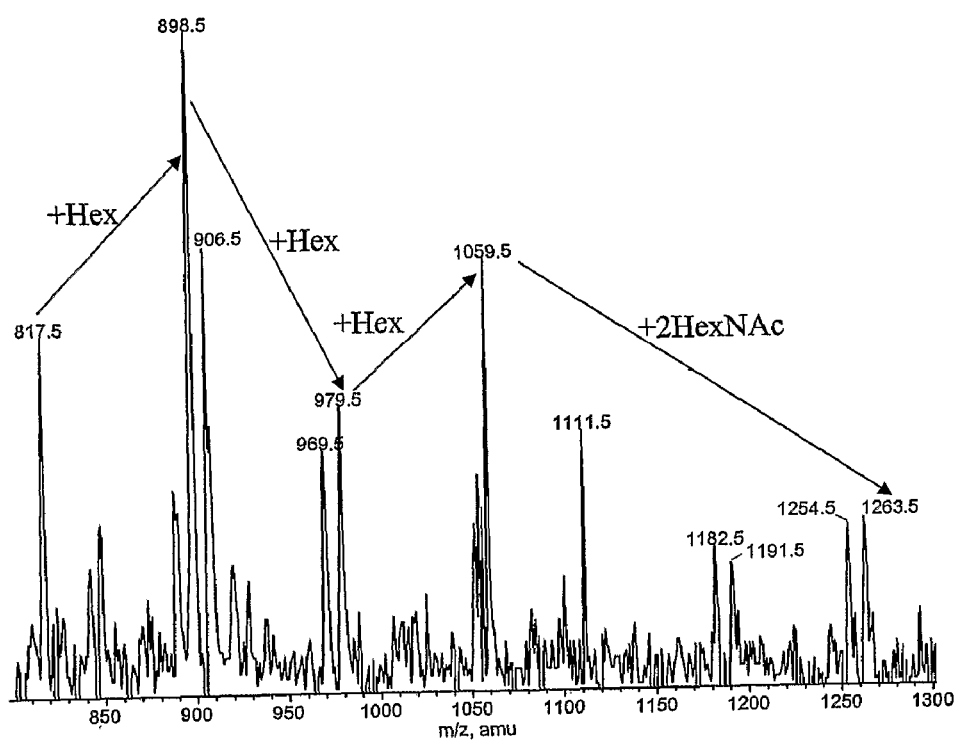

FIG. 21. Positive ion capillary electrophoresis-electrospray mass spectrum of *Pasteurella multocida* strain Pm70 core OS precursor ion scan of m/z 316$^+$.

Figure 22:
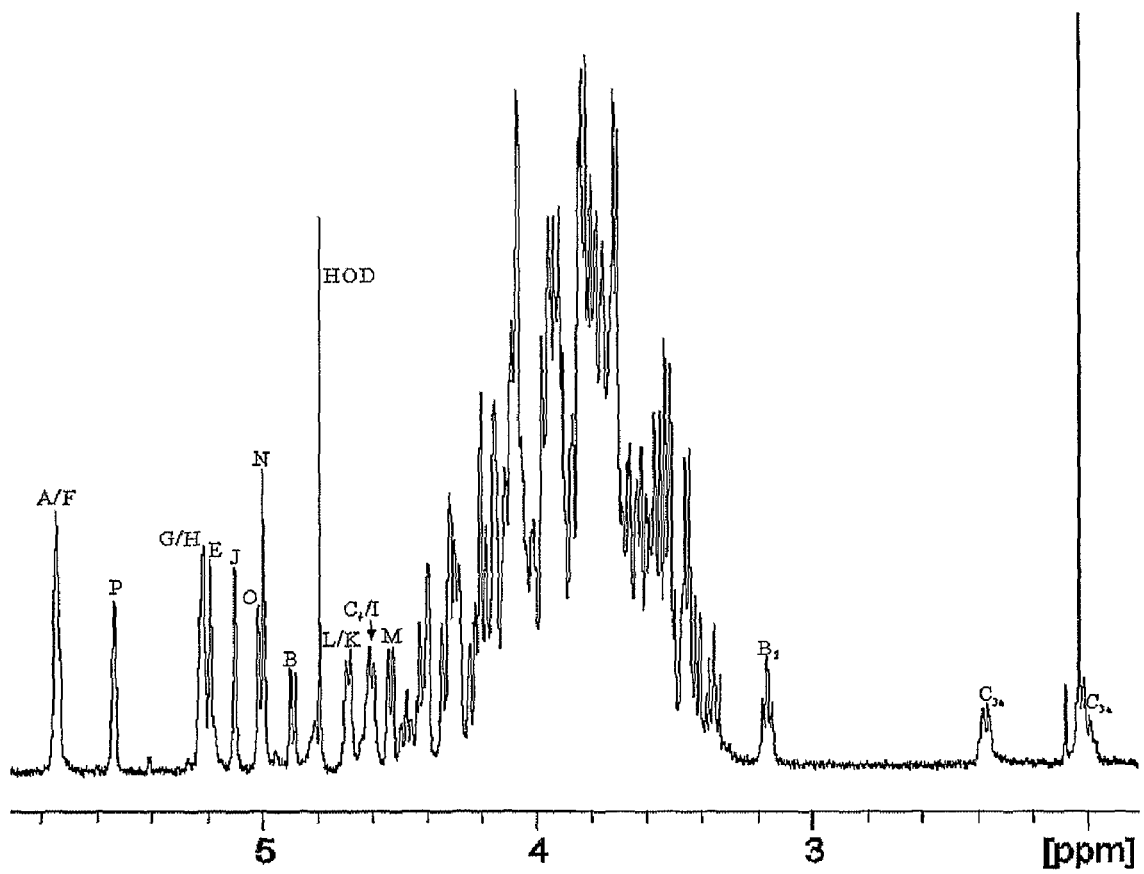

FIG. 22. Anomeric region of the $^1$H-NMR spectra of the fully deacylated LPS from *Pasteurella multocida* strain Pm70. The spectrum was recorded in D$_2$O at pH 7.0 and 25° C. Residues are labelled as in Example 3 Table 2.

FIG. 23. Portion of the anomeric region of the TOCSY spectrum from the core OS from *Pasteurella multocida* strain Pm70. The spectrum was recorded in D$_2$O at 25° C.

FIG. 24. Portion of the anomeric region of the NOESY spectrum from the core OS from *Pasteurella multocida* strain Pm70. The spectrum was recorded in D$_2$O at 25° C.

Figure 25:
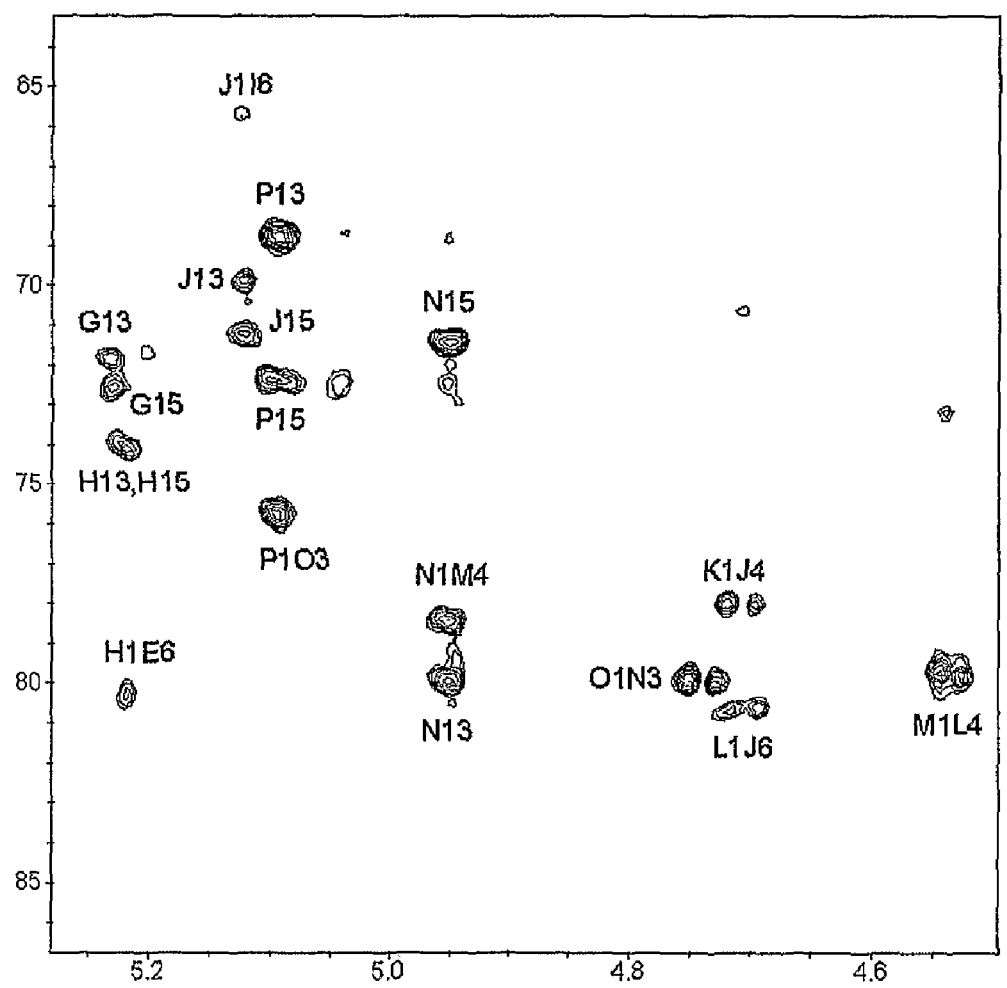

FIG. 25. Anomeric region of the $^1$H—$^{13}$C HMBC NMR spectrum of the core OS from *Pasteurella multocida* strain Pm70. Inset is the region of the spectrum showing the diagnostic signals for the N-acetyl-amino sugars. The spectrum was recorded in D$_2$O at pH 7.0 and 25° C.

Figure 26:
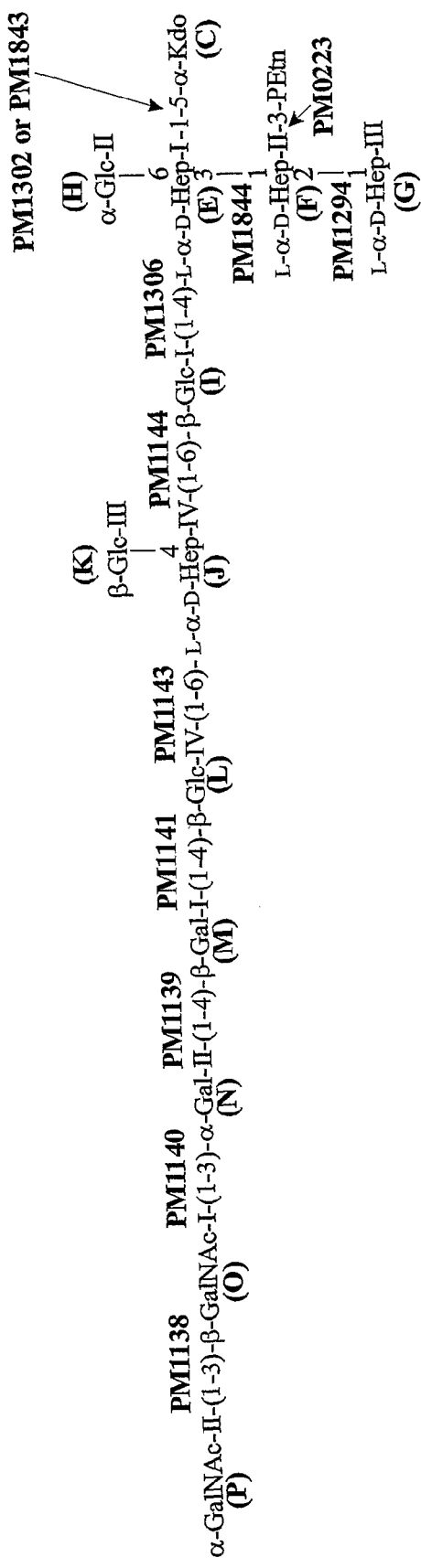

FIG. 26. Structure of the core oligosaccharide of *Pasteurella multocida* strain Pm70 with the putative glycosyltransferases indicated.

FIG. 27 Negative ion capillary electrophoresis-electrospray mass spectra of the LPS-OH from Pm strain VP161. a) Product ion spectrum from m/z 992$^{3-}$, b) Product ion spectrum from m/z 999$^{3-}$, c) Product ion spectrum from m/z 1040$^{3-}$.

FIG. 28 Positive ion capillary electrophoresis-electrospray mass spectra of the core OS from Pm strain VP161. a) Product ion spectrum from m/z 903$^{2+}$, b) Product ion spectrum from m/z 984$^{2+}$, c) Product ion spectrum from m/z 424$^{2+}$ utilising a high orifice voltage.

Figure 29:
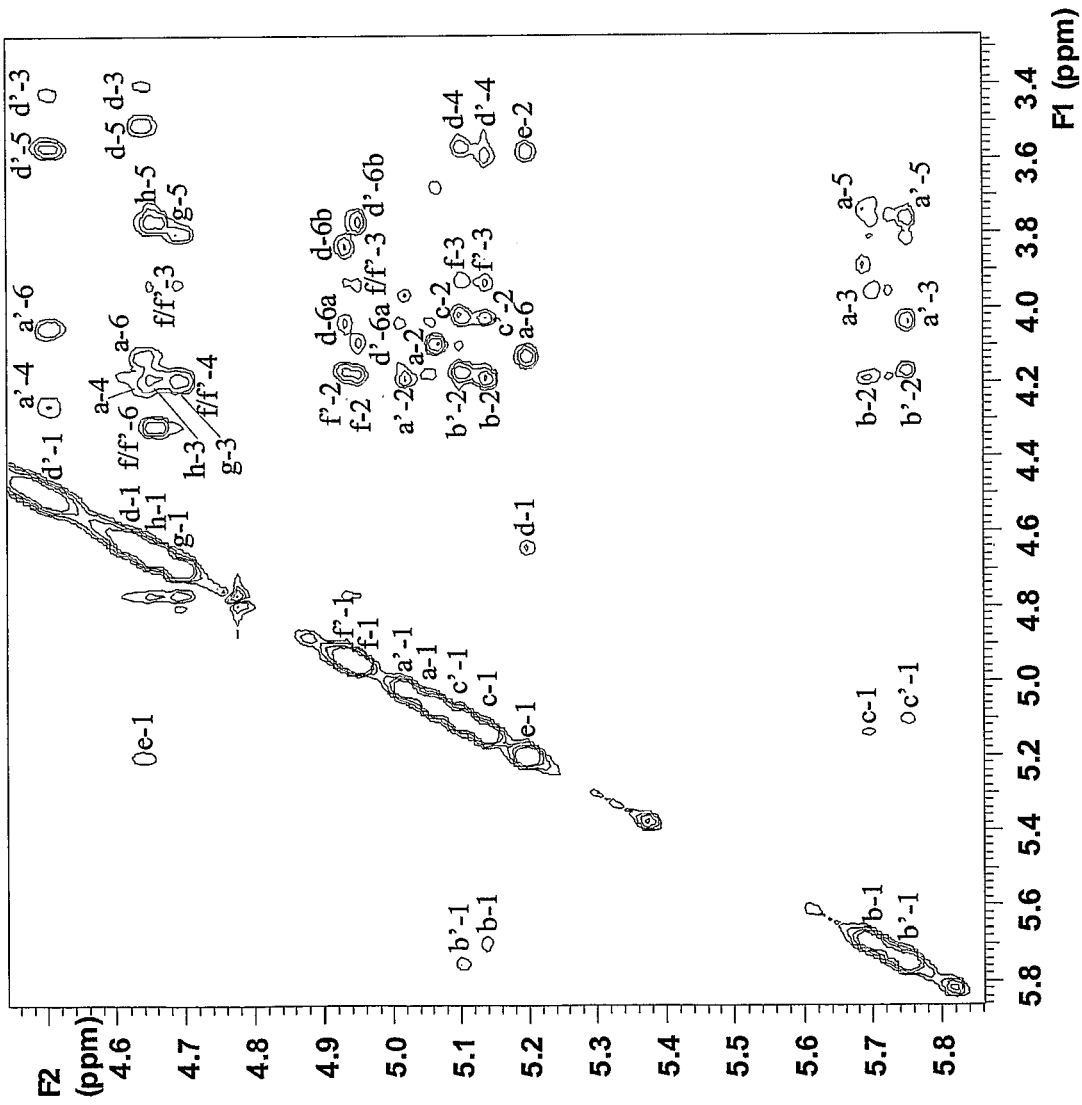

FIG. 29 Region of the 2D-NOESY NMR spectrum of the core OS from Pm strain VP161. Letter designations for each residue are as indicated in Example 4, Table 2. The spectrum was recorded in D$_2$O at pH 7.0 and 25° C. with a mixing time of 400 ms.

Figure 30:
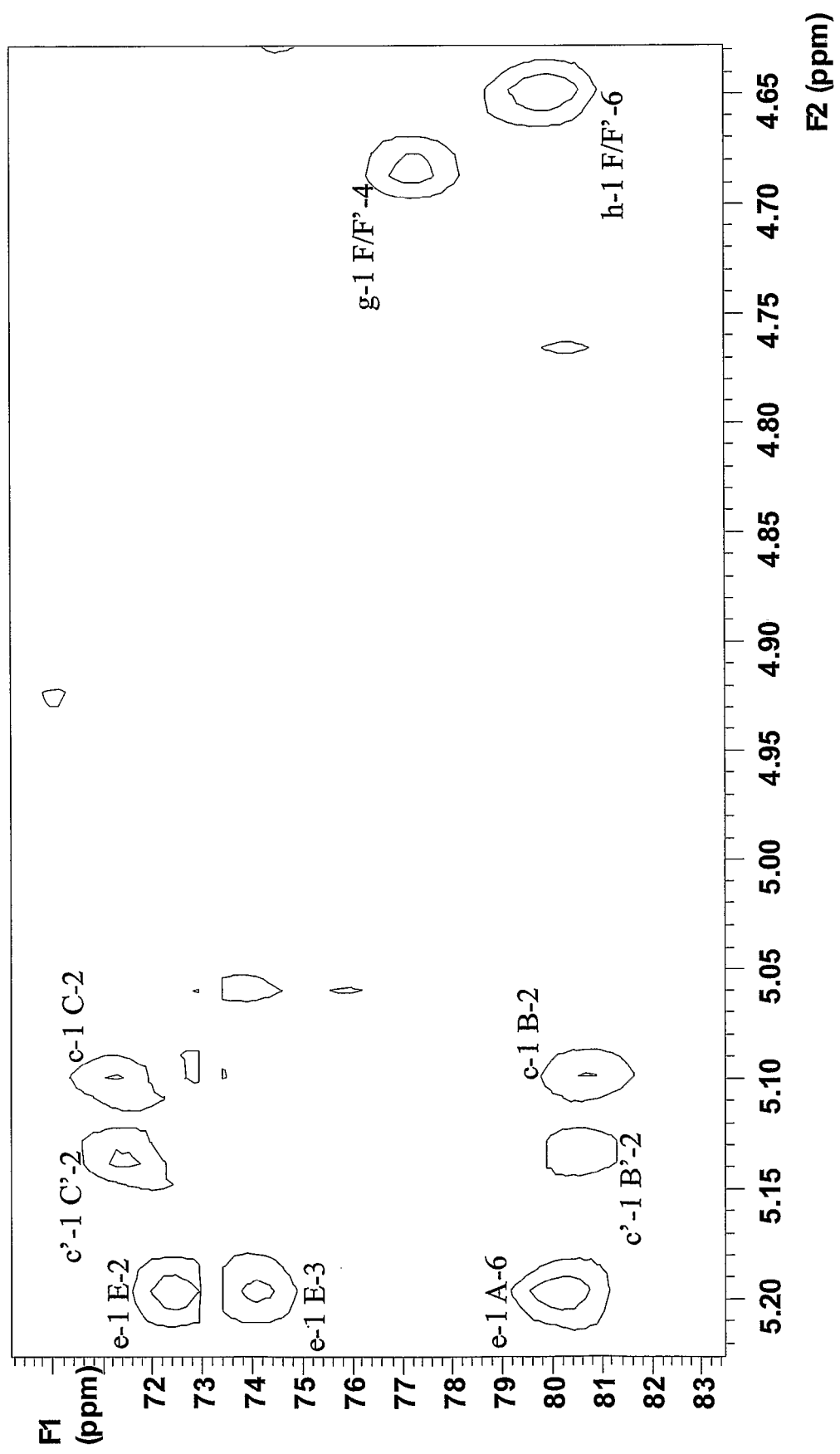

FIG. 30. Region of the 2D-$^{13}$C—$^1$H-HMBC NMR spectrum of the core OS from Pm strain VP161 showing correlations between anomeric $^1$H-resonances (lower case letters) and ring $^{13}$C-resonances (upper case letters). The spectrum was recorded in D$_2$O at pH 7.0 and 25° C.

Figure 31:
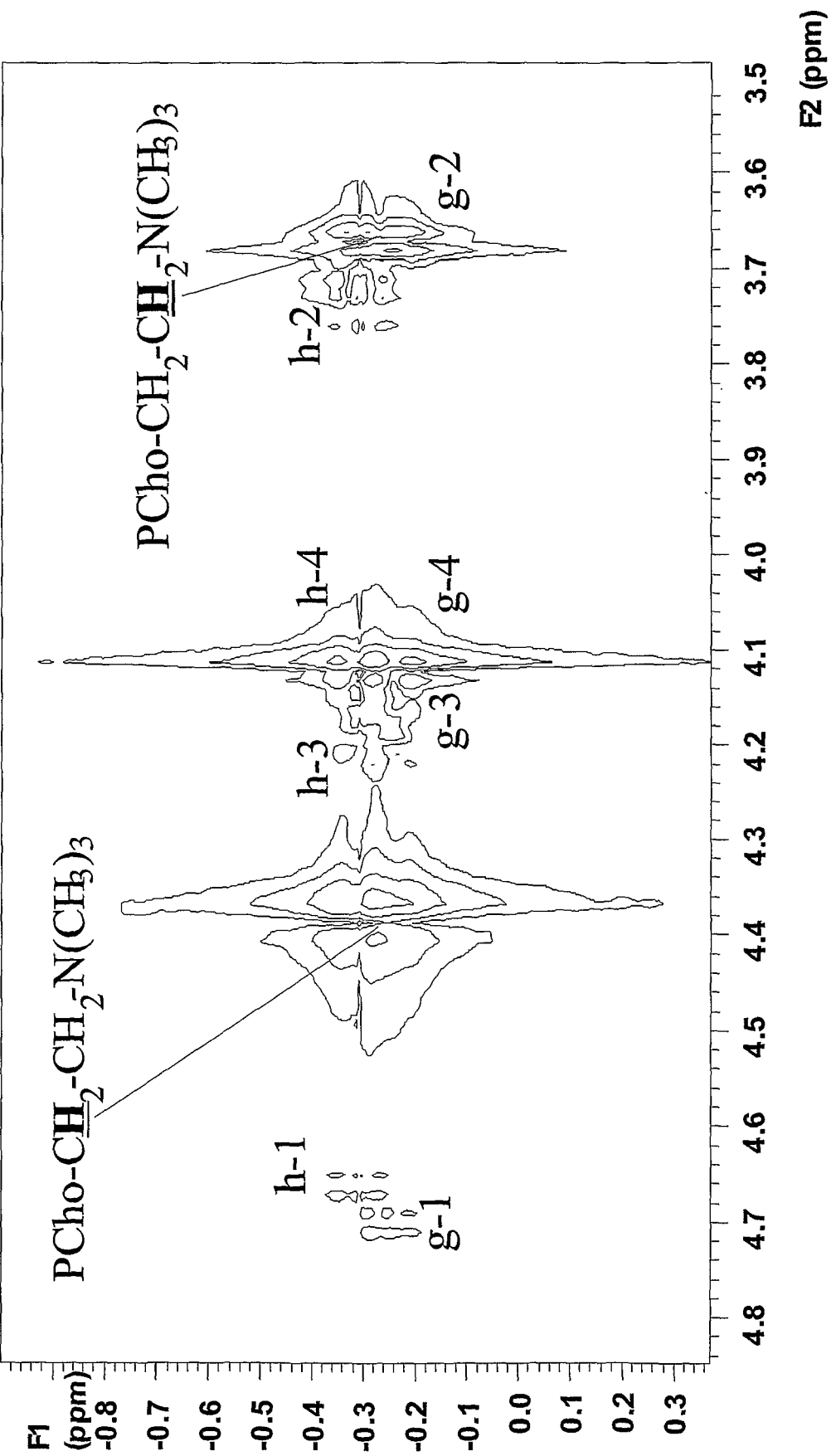

FIG. 31 Region of the 2D-$^{31}$P—$^1$H-HSQC-TOCSY NMR spectrum of the core OS from Pm strain VP161 showing correlations between the $^{31}$P-resonances (x-axis) and $^1$H-resonances (y-axis) for the galactose residues labelled g-1 to g-4 & h-1 to h-4 and the choline resonances. The spectrum was recorded in D$_2$O at pH 7.0 and 25° C.

Figure 32:
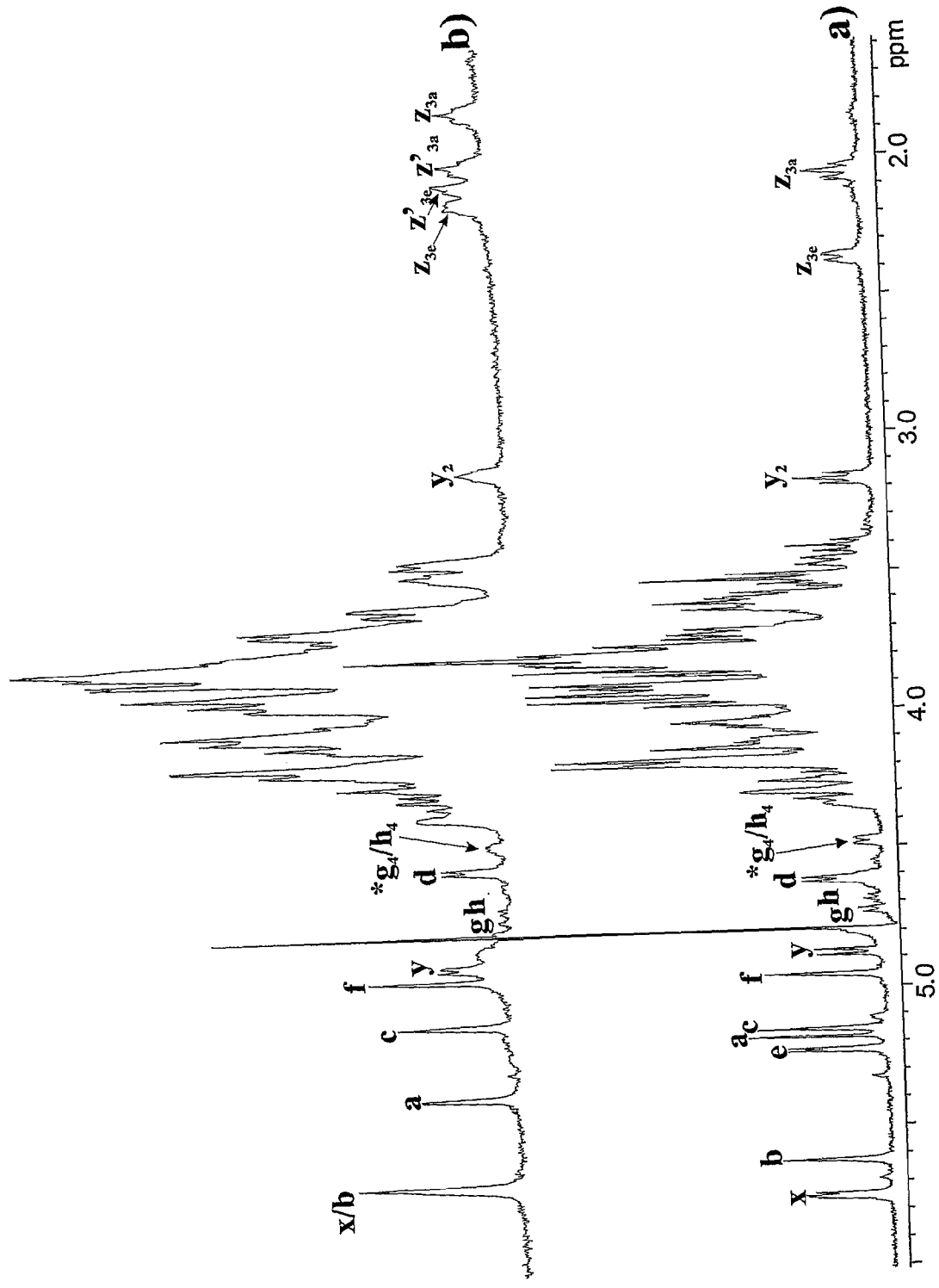

FIG. 32 $^1$H-NMR spectra of the fully deacylated LPS from Pm strain VP161; a) Glycoform containing one Kdo residue; b) Glycoform containing two Kdo residues. The spectra were recorded in D$_2$O at pH 7.0 and 25° C. Letter designations for each residue are as indicated in Example 4, Table 2. *Low field shifts for the H-4 proton resonances of Gal I (g) and Gal II (h) are due to hydrolysis and migration of PCho residues during KOH treatment.

Figure 33A:
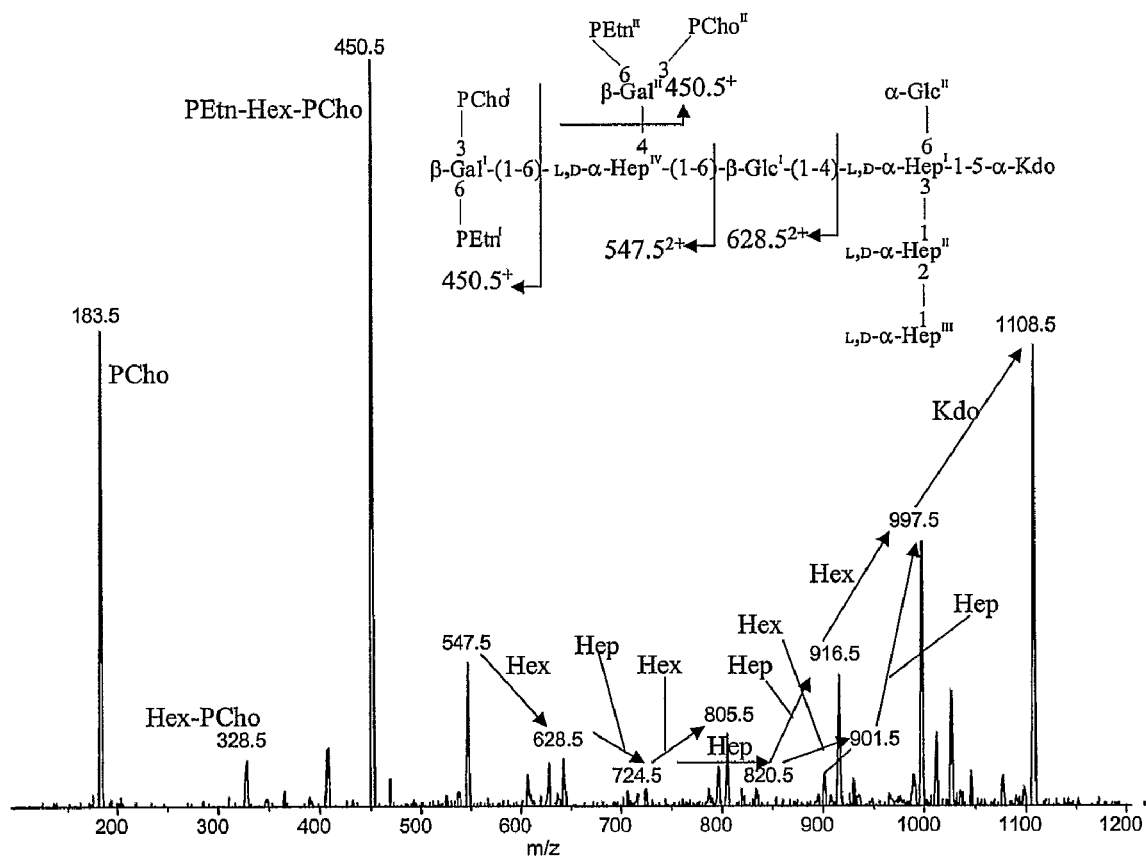
Figure 33B:
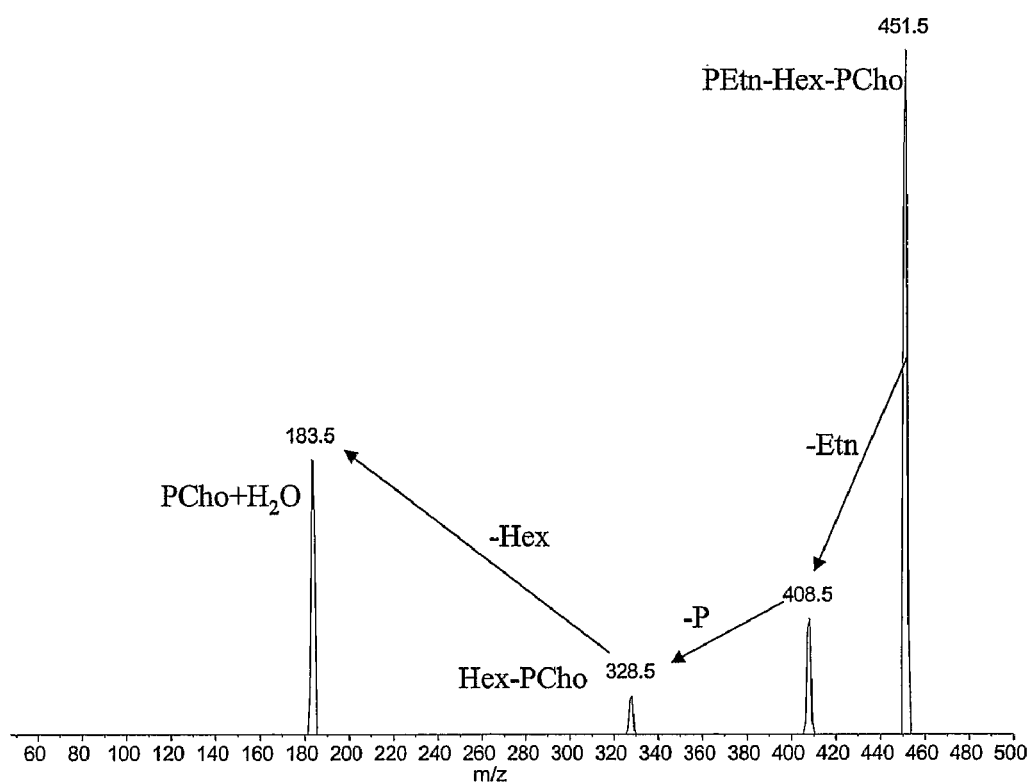

FIG. 33 Positive ion capillary electrophoresis-electrospray mass spectra of the core OS from Pm strain X73. a) Product ion spectrum from m/z 1108$^{2+}$, b) Product ion spectrum from m/z 451.5$^+$ utilising a high orifice voltage.

Figure 34:
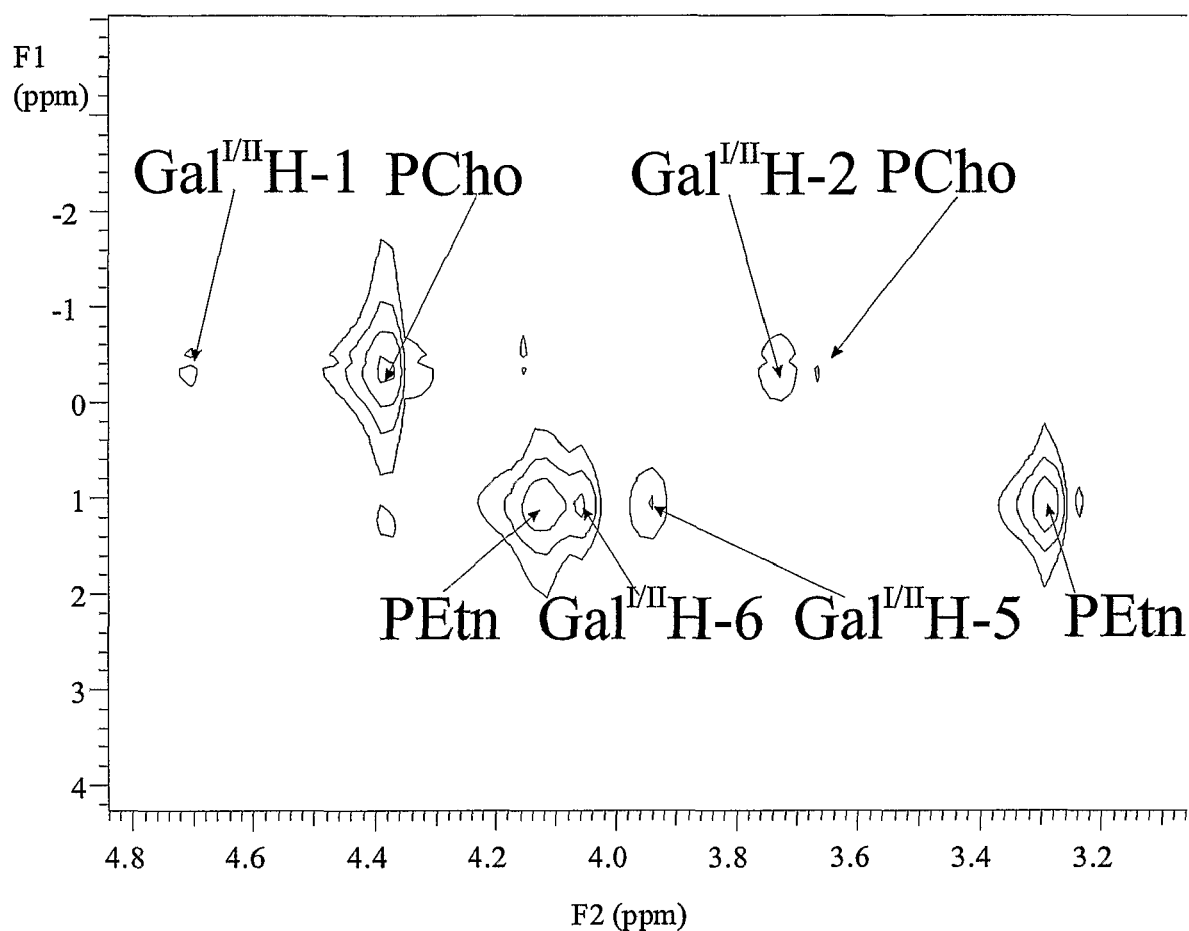

FIG. 34 Region of the 2D-$^{31}$P—$^1$H-HMQC-TOCSY NMR spectrum of the core OS from Pm strain X73 showing correlations between the $^{31}$P-resonances (x-axis) and $^1$H-resonances with a mixing time optimised at 10 Hz for the $^{31}$P—$^1$H coupling between PEtn and the galactose residues. The spectrum was recorded in D$_2$O at pH 7.0 and 25° C.

Figure 35:
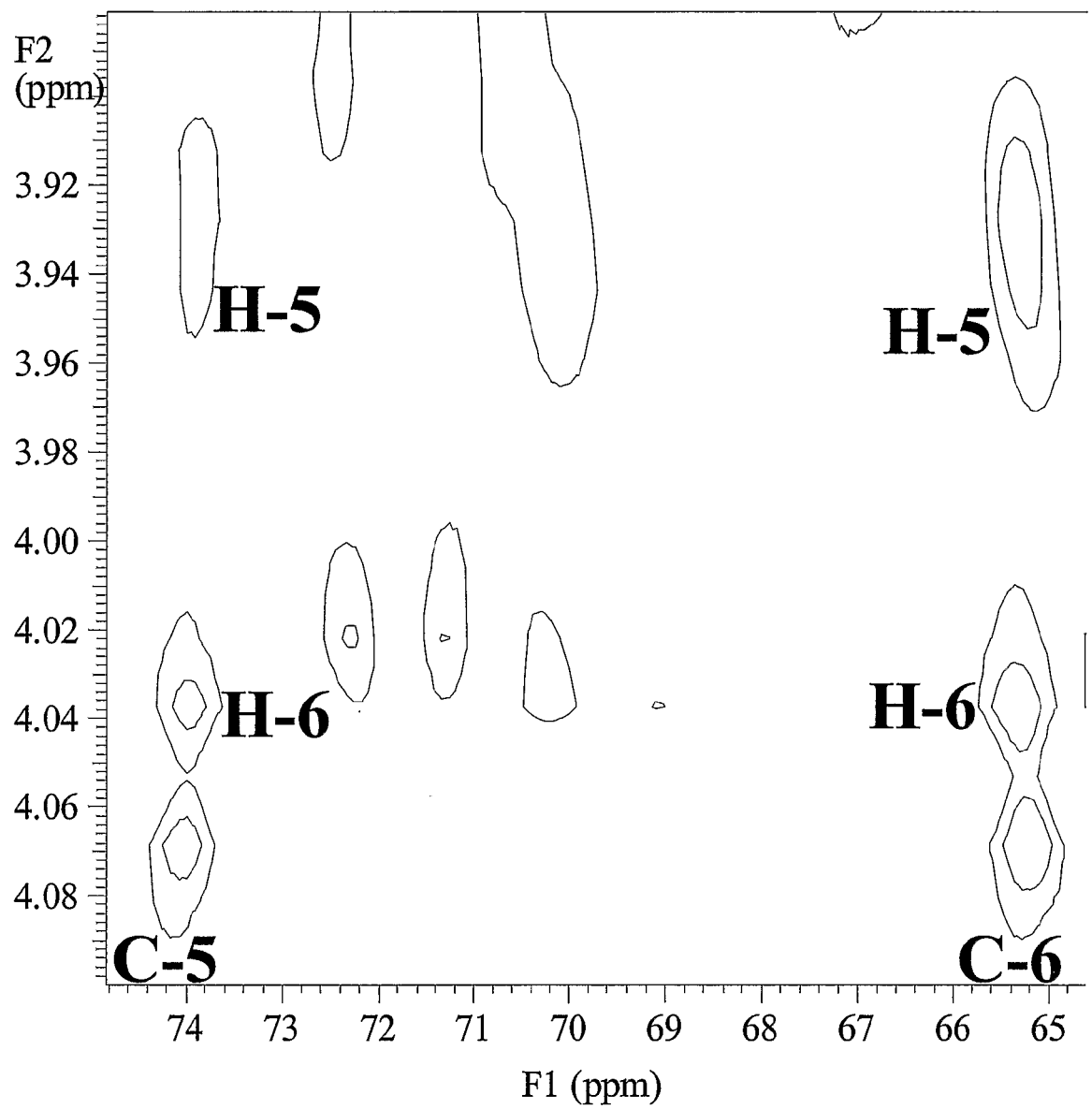

FIG. 35 Region of the 2D-$^{13}$C-$^1$H-HSQC-TOCSY NMR spectrum of the core OS from Pm strain X73 showing correlations between the $^{13}$C-resonances (y-axis) and $^1$H-resonances indicating the correlations between the C-5, C-6, H-5 and H-6 resonances of the galactose residues. The spectrum was recorded in D$_2$O at pH 7.0 and 25° C.

FIG. 36. Analysis of *P. multocida* LPS by SDS-PAGE and silver staining of whole cell lysates. (A) Comparison of *P. multocida* LPS profiles from wild-type VP161 (lane 1); heptosyltransferase mutant AL251 (lane 2); control strain AL438 (AL251 containing vector plasmid pAL99) (lane 3) and the complemented mutant strain AL298 (lane 4).

(B) Comparison of LPS profiles of *P. multocida* heptosyltransferase mutant AL251 (lane 1); wild-type VP161 (lane 2) and *P. multocida* wild-type revertants isolated from three different chickens inoculated with AL251 (lanes 3, 4 and 5).

FIG. 37 Negative ion capillary electrophoresis electrospray mass spectra of *P. multocida* core OS. (A) Doubly charged region of core OS from parent strain VP161; (B) Singly charged region of core OS from mutant strain AL251.

Figure 38:
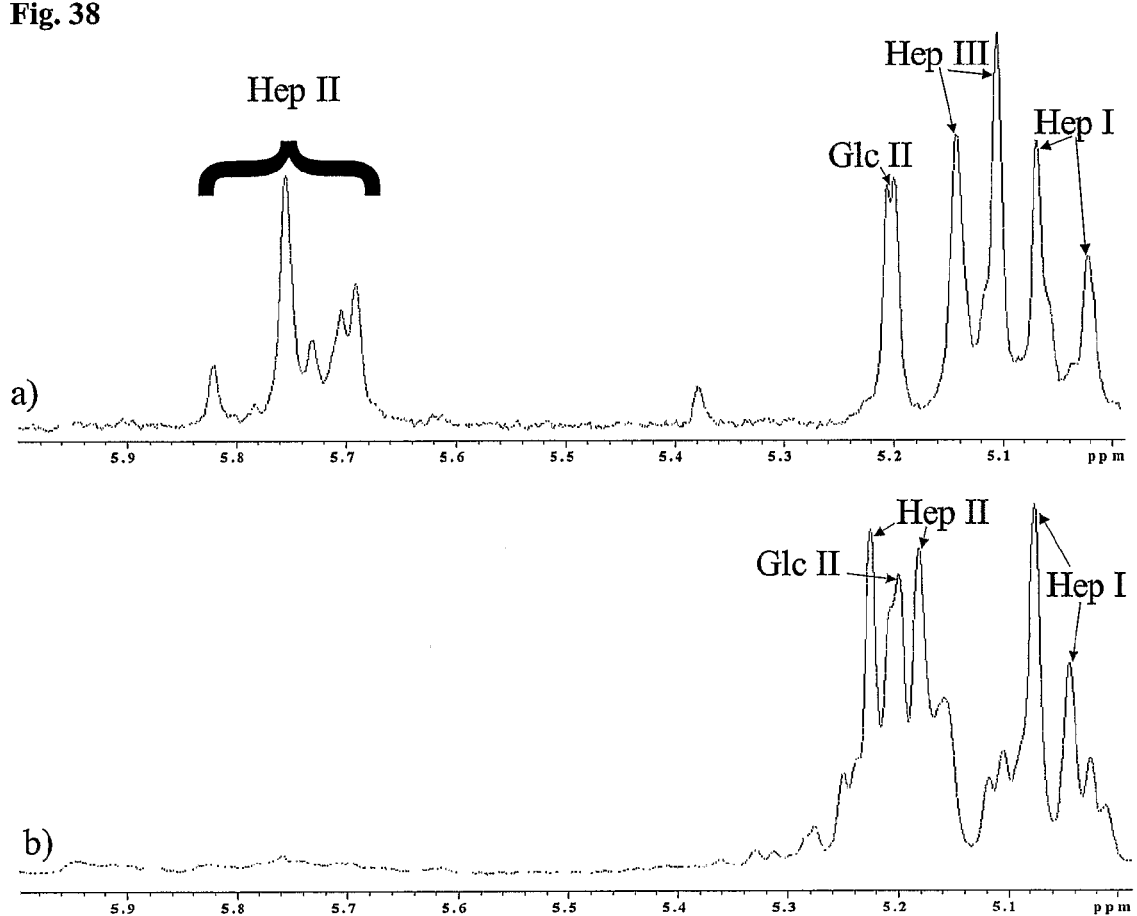

FIG. 38 Region of the $^1$H-NMR spectrum of the core OS derived from the LPS of (A) *P. multocida* parent strain VP161 and (B) *P. multocida* mutant strain AL251. The spectra were recorded at 25° C. and referenced against internal acetone at 2.225 ppm.

Figure 39:
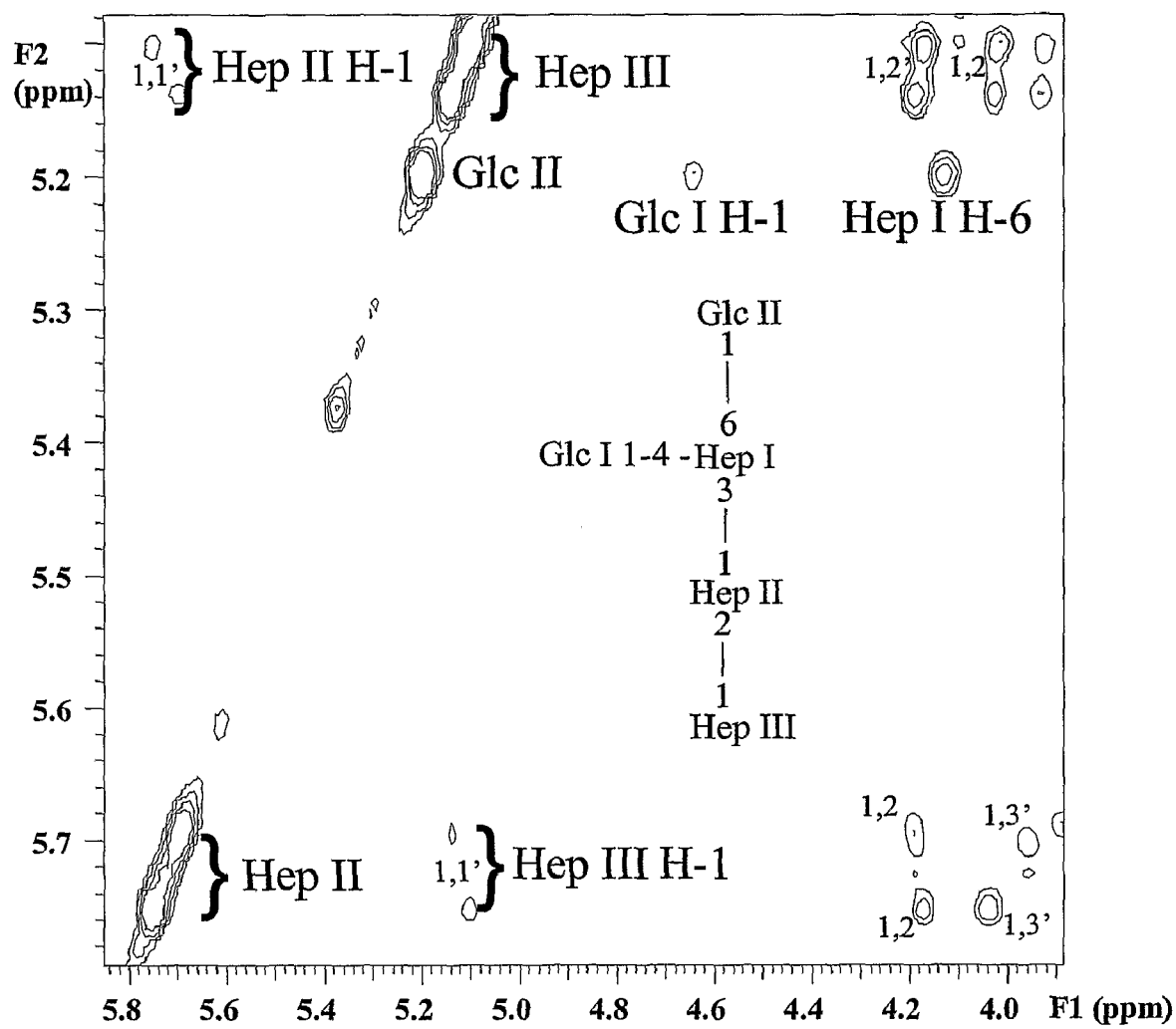

FIG. 39 Region of the NOESY spectrum of *P. multocida* VP161 core OS. NOE connectivities are as indicated. Inset; structure of the inner core OS from VP161. The spectrum was recorded at 25° C. and referenced against internal acetone at 2.225 ppm.

Figure 40:
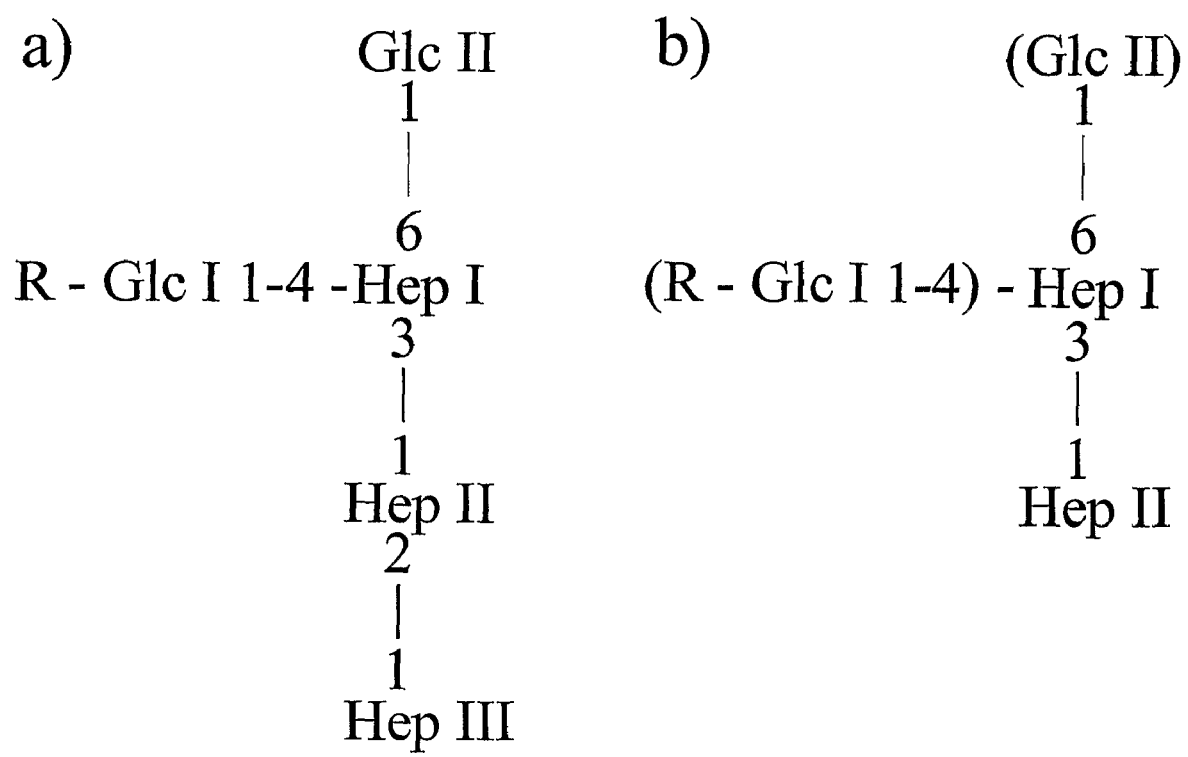

FIG. 40 Proposed structures of inner core LPS of *P. multocida* from (A) parent strain VP161 and (B) mutant strain AL251, where R is oligosaccharide chain extension beyond Glc.

Figure 41:
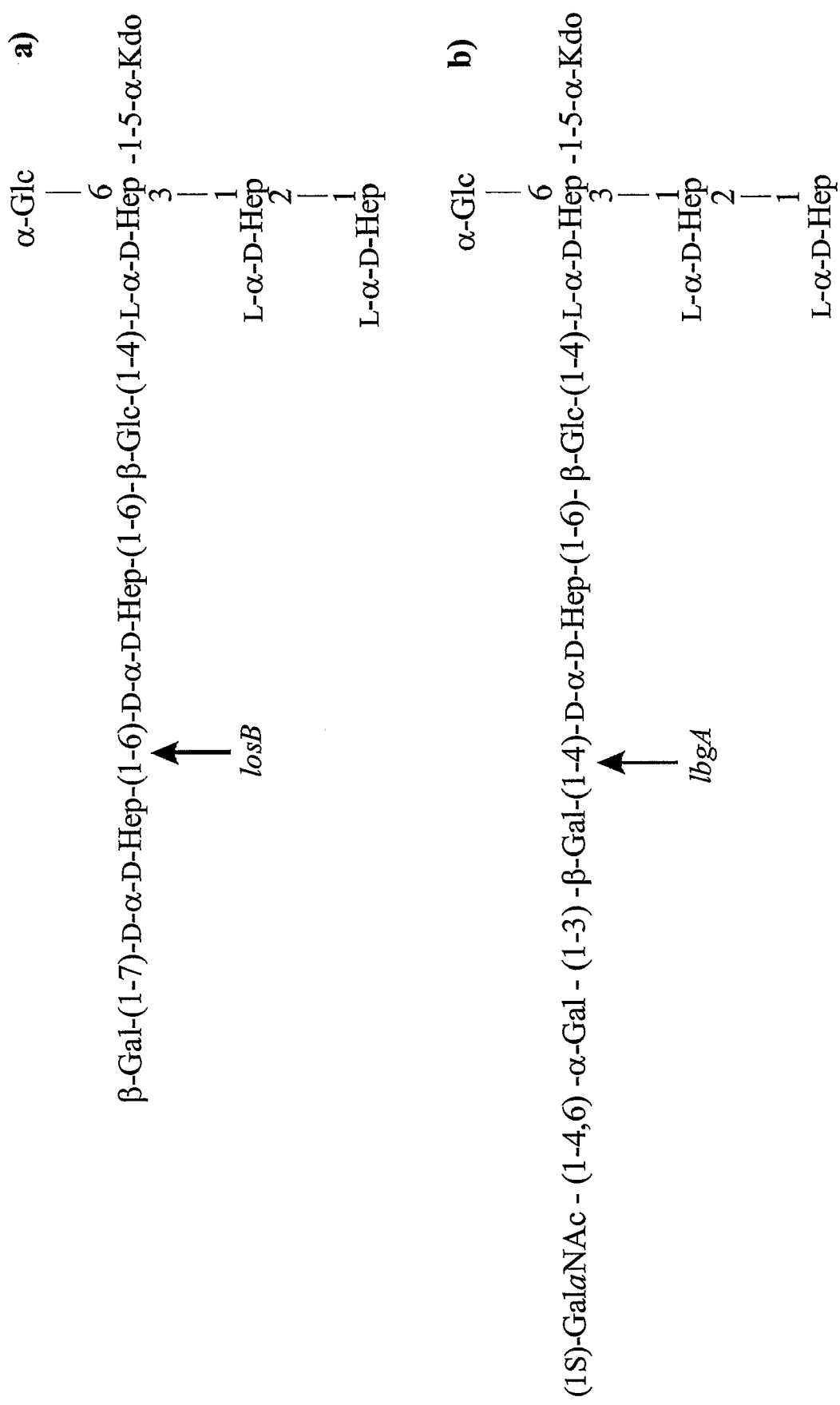

FIG. 41 Structural representation of the core oligosaccharides from the strains a) *Mannheimia haemolytica* strain A1, b) *Actinobacillus pleuropneumoniae* serotype 1. The glycosyltransferase responsible for the first stage in outer core decoration are indicated.

Figure 42A:
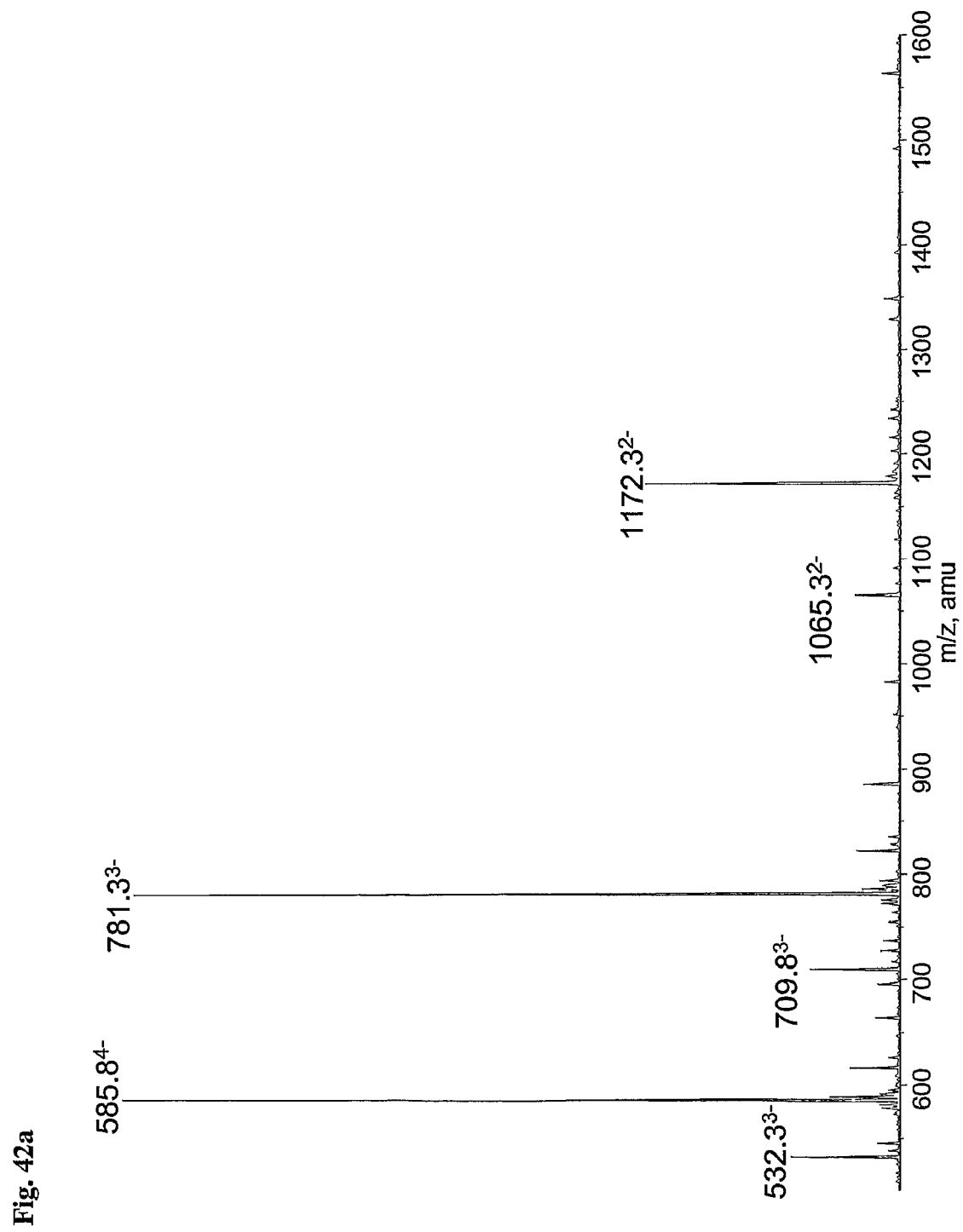
Figure 42B:
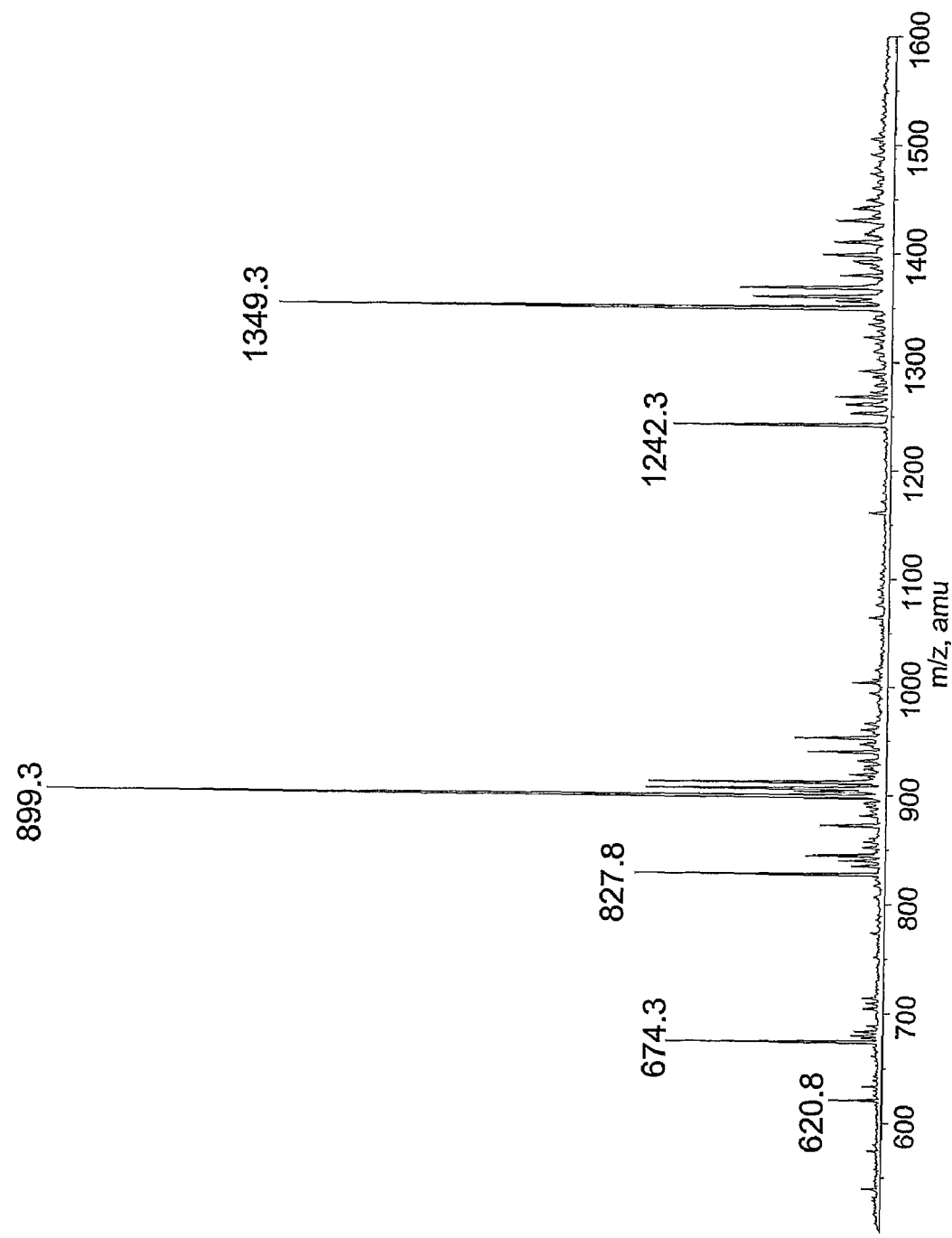

FIG. 42 Negative ion capillary electrophoresis-electrospray ionisation mass spectrum of a) the O-deacylated LPS from *Mannheimia haenzolytica* mutant strain losB and b) the O-deacylated LPS from *Mannheimia haemolytica* mutant strain losB complemented in trans with pNF 2176AAlosB containing the losB gene.

Figure 43:
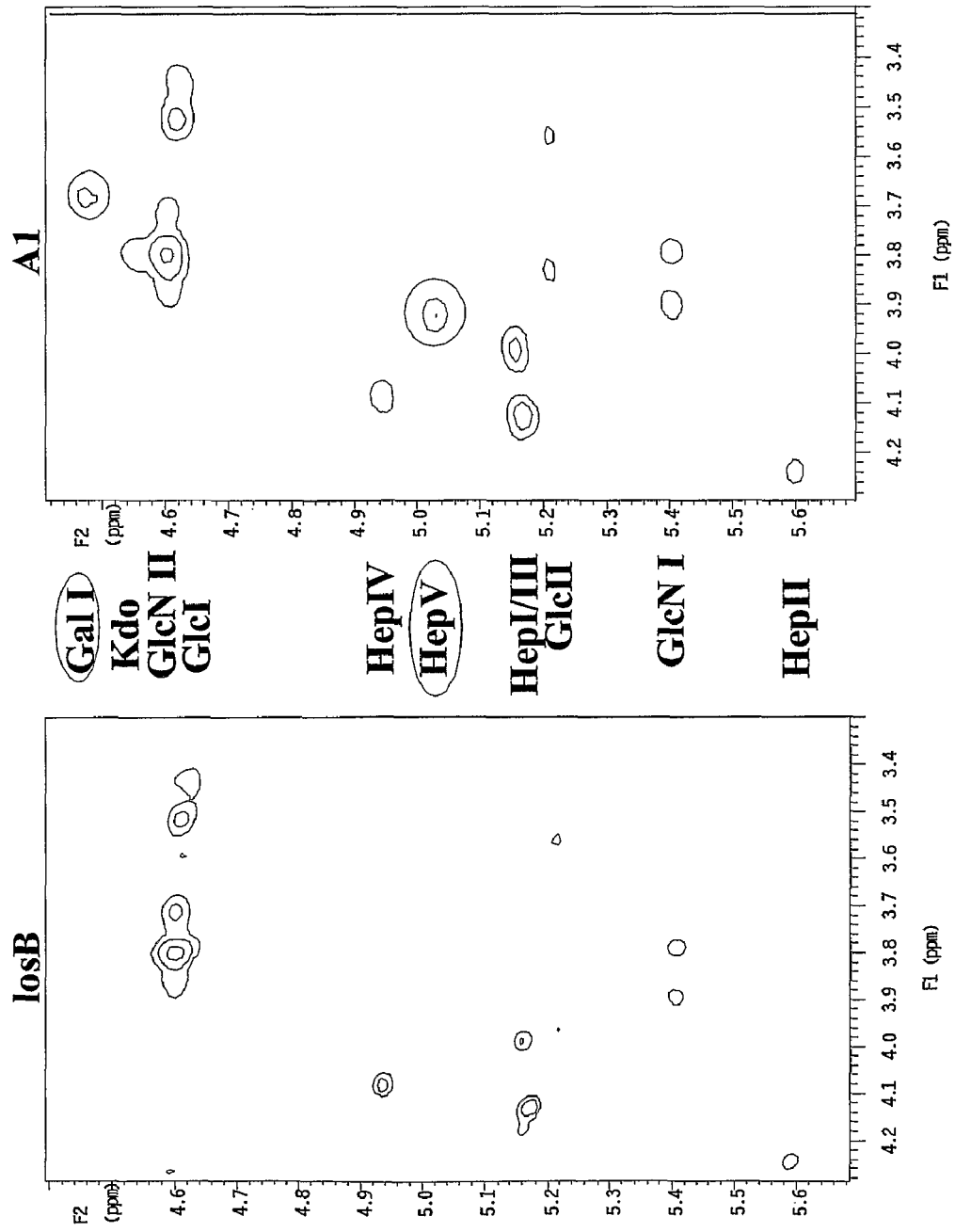

FIG. 43 Regions of the 2D-TOCSY NMR spectra of the completely deacylated LPS from wild type *Mannheimia haemolytica* strain A1 and mutant strain losB. Designations for each residue are as indicated with the outer core residues absent from the losB mutant strain circled. The spectrum was recorded in D$_2$O at pH 7.0 and 25° C. with a mixing time of 400 ms.

Figure 44:
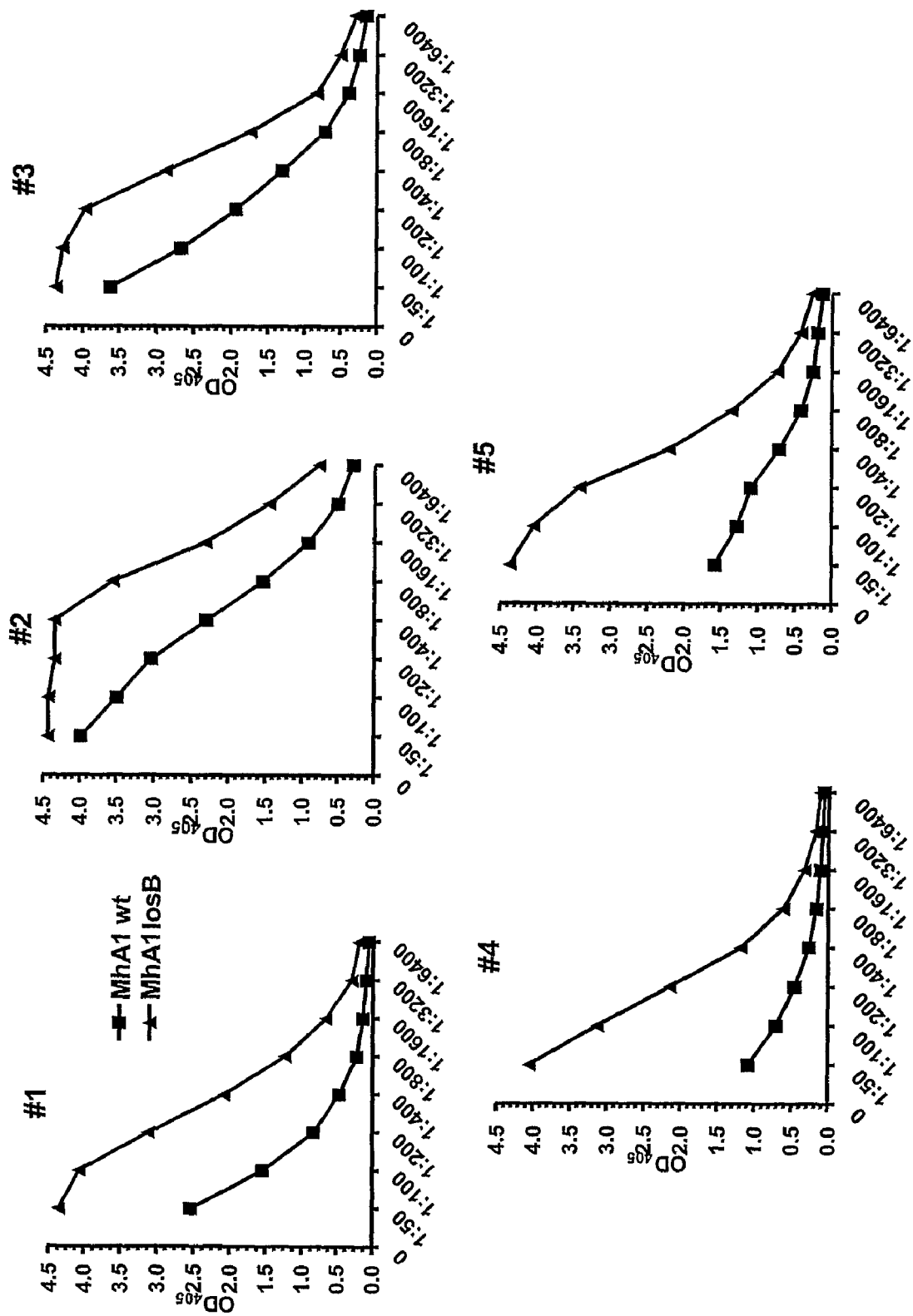

FIG. 44 ELISA (OD$_{405}$) of D42 polyclonal sera from mice # 1-5 against purified LPS from strains Ah losB (▲) and wt (■). Mouse designations as indicated in the figure. All sera dilutions are as indicated.

Figure 45:
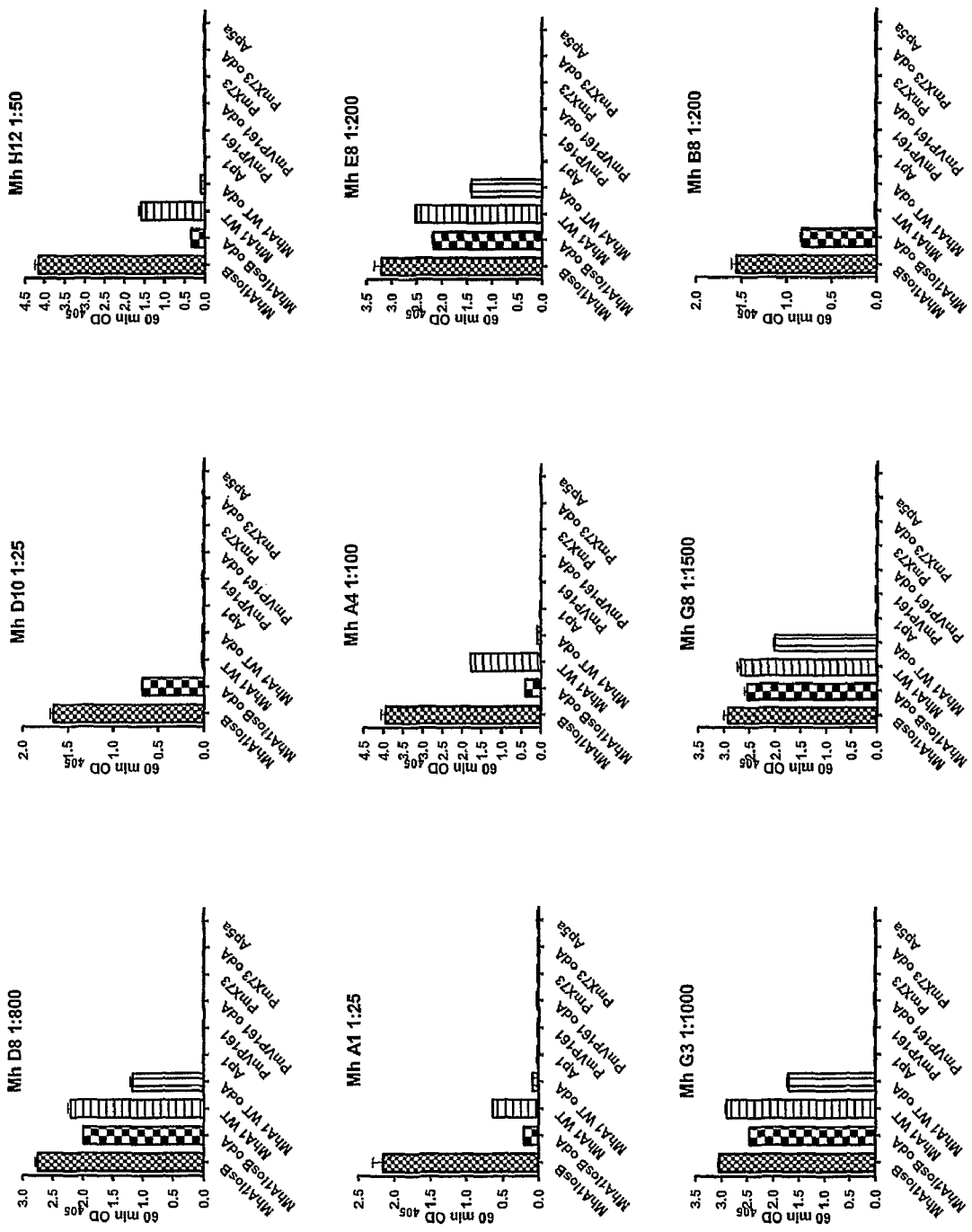

FIG. 45 ELISA (OD$_{405}$) of nine inner core LPS mAbs against LPS from strains Mh losB and wt, App serotypes 1 and 5a and Pm strains VP161 and X73 and LPS-OH from the Mh and Pm strains. mAb designations and dilutions as indicated in the figure.

Figure 46:
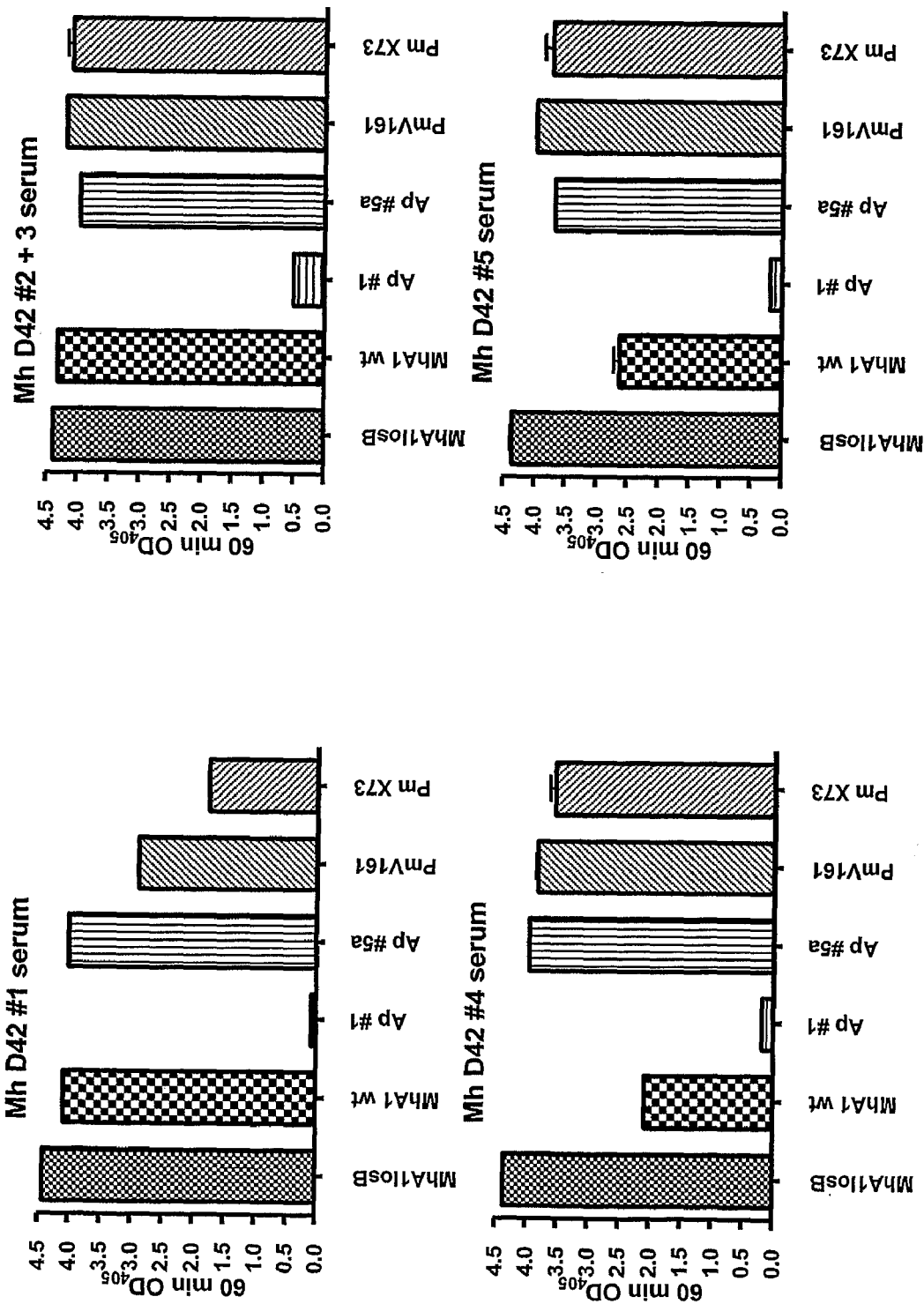

FIG. 46 ELISA (OD$_{405}$) of D42 polyclonal sera from mouse # 1, mice # 2+3, mouse # 4 and mouse # 5 against LPS from strains Mh losB and wt, App serotypes 1 and 5a and Pm strains VP161 and X73. Mouse designations and as indicated in the figure. All sera were used at a 1:50 dilution.

Figure 47:
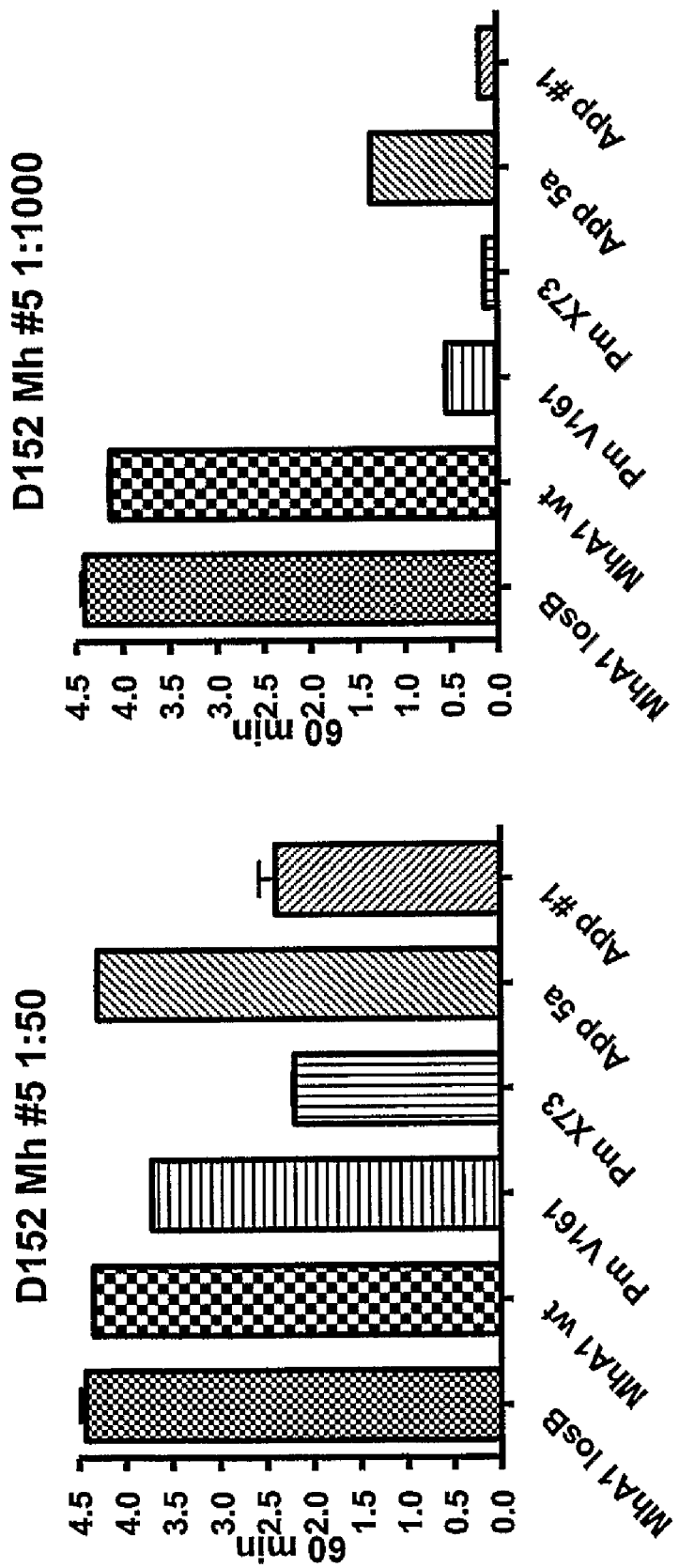

FIG. 47 ELISA (OD$_{405}$) of D152 polyclonal sera from mouse # 5 against LPS from strains Mh losB and wt, App serotypes 1 and 5a and Pm strains VP161 and X73. Dilutions as indicated in the figure.

FIG. 48 ELISA (OD$_{405}$) of spent supernatants from two representative inner core LPS mAbs against LPS from strains Mh losB and wt, Ap serotypes 1 and 5a and Pm strains VP161 and X73. MAb designations and dilutions as indicated in the figure.

Figure 49:
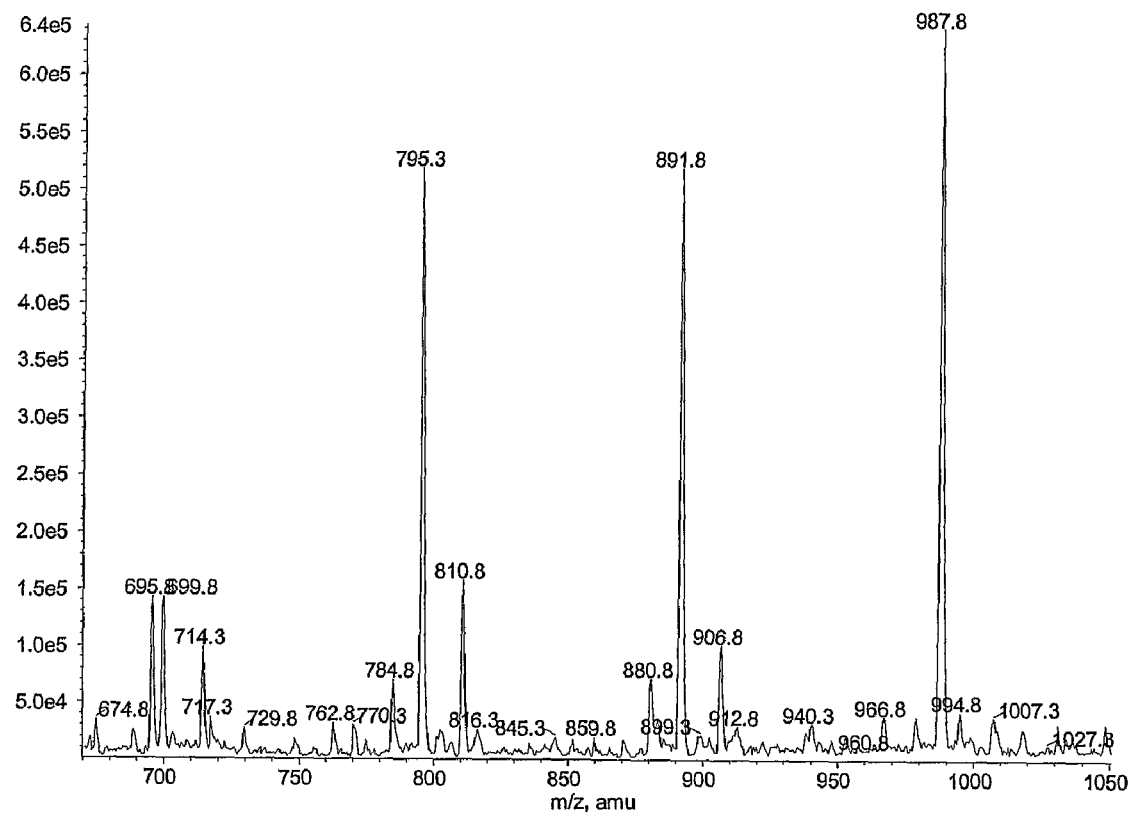

FIG. 49 Negative ion capillary electrophoresis electrospray mass spectra of Mh losB KOH treated LPS.

Figure 50:
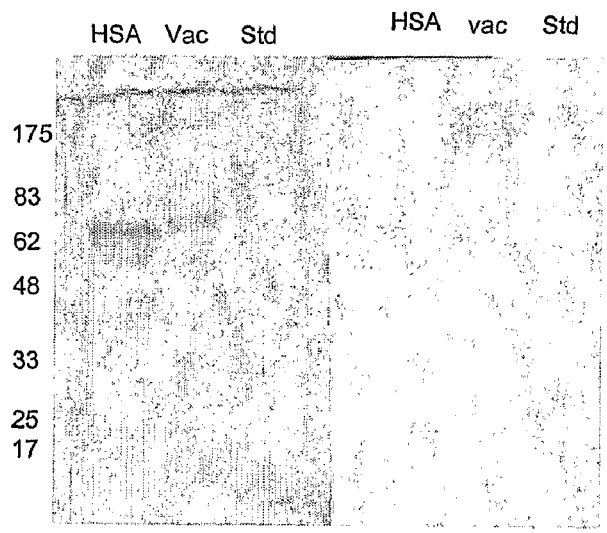

FIG. 50 SDS-PAGE and Western blot analysis of MhlosB-HSA conjugate. Run on a 12.5% SDS-PAGE gel and blotted and screened with carbohydrate specific mAb G8 used at a dilution of 1:10$^6$.

FIG. 51 CE-ES-MS analysis of a) HSA; b) HSA-MhlosB glycoconjugate.

Figure 52:
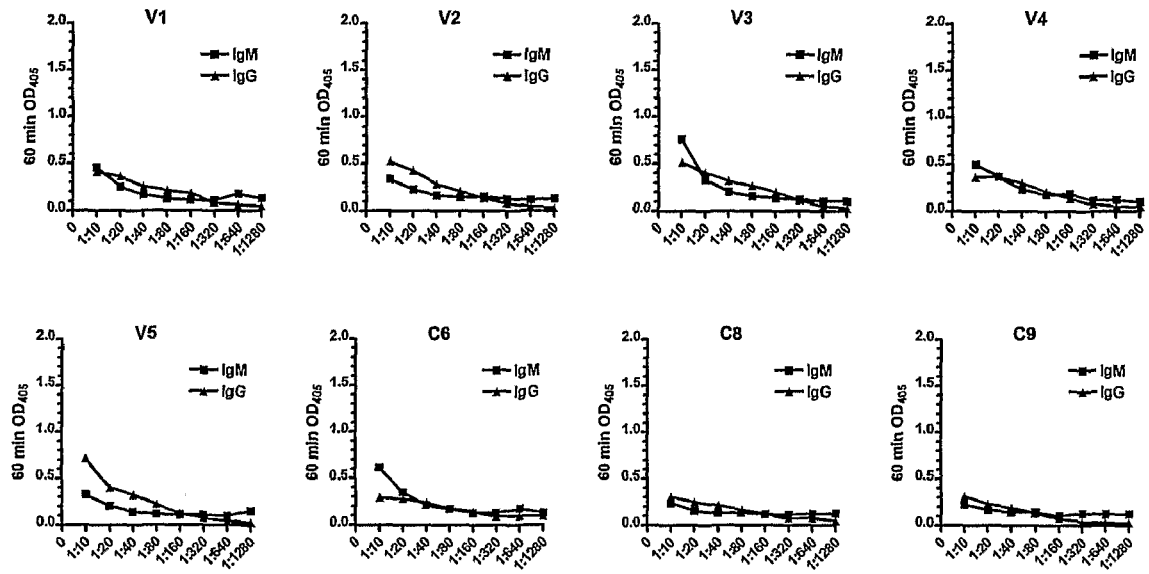

FIG. 52. ELISA (OD$_{405}$) of D23 polyclonal sera from vaccinated mice # V1-V5 and control mice C6, C8 and C9 against purified LPS from strain Mh losB, screening for IgG response (▲) and IgM response (■). Mouse designations as indicated in the figure. All sera dilutions are as indicated.

Figure 53:
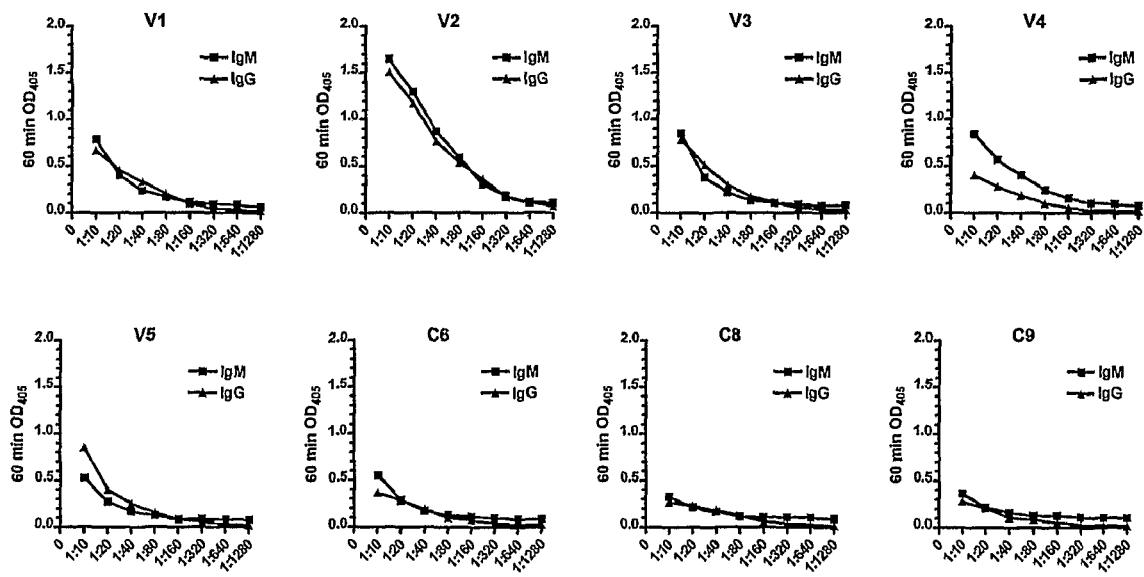

FIG. 53. ELISA (OD$_{405}$) of D45 polyclonal sera from vaccinated mice # V1-V5 and control mice C6, C8 and C9 against purified LPS from strain Mh losB, screening for IgG response (▲) and IgM response (■). Mouse designations as indicated in the figure. All sera dilutions are as indicated.

Figure 54:
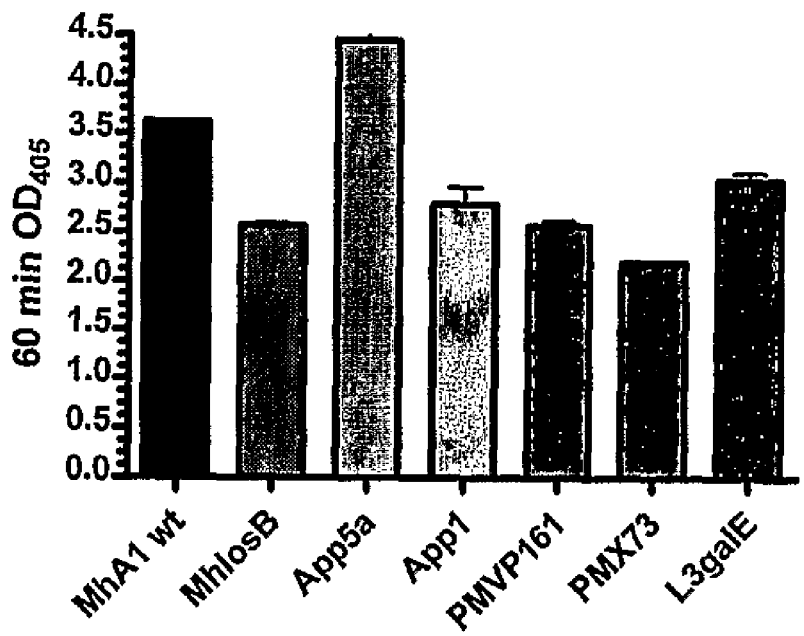

FIG. 54. ELISA (OD$_{405}$) of polyclonal sera V2 (1:25 diln) against LPS from strains Mh losB and wt, Ap serotypes 1 and 5a and Pm strains VP161 and X73.

Figure 55:
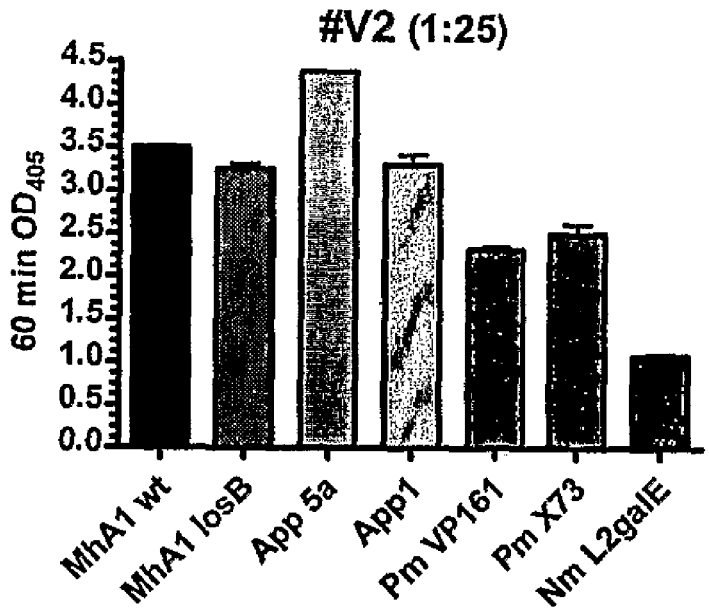

FIG. 55. ELISA (OD$_{405}$) of polyclonal sera V2 (1:25 diln) against whole cells from strains Mh losB and wt, Ap serotypes 1 and 5a and Pm strains VP161 and X73.

Figure 56:
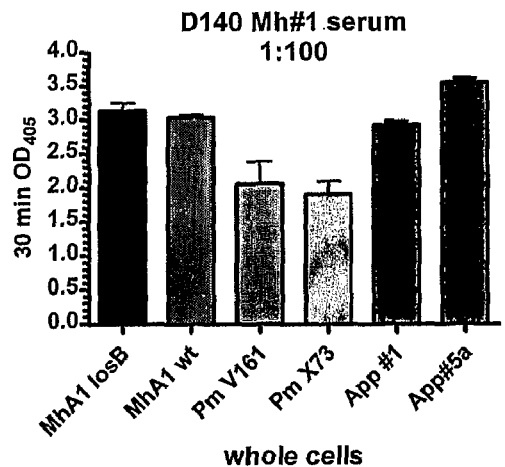

FIG. 56. ELISA (OD$_{405}$) of polyclonal sera Mh #1 (1:100 diln) against whole cells from strains Mh losB and wt, Ap serotypes 1 and 5a and Pm strains VP161 and X73.

Figure 57:
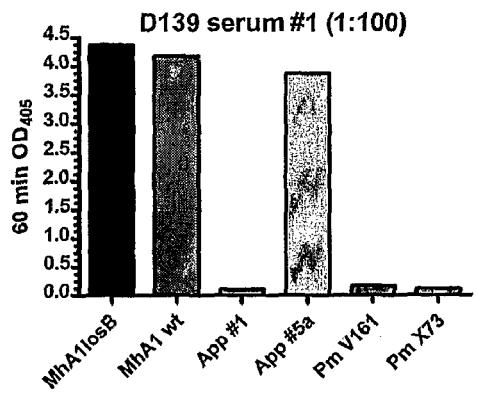

FIG. 57. ELISA (OD$_{405}$) of polyclonal sera Mh #1 (1:100 diln) against LPS from strains Mh losB and wt, Ap serotypes 1 and 5 a and Pm strains VP161 and X73.

Figure 58:
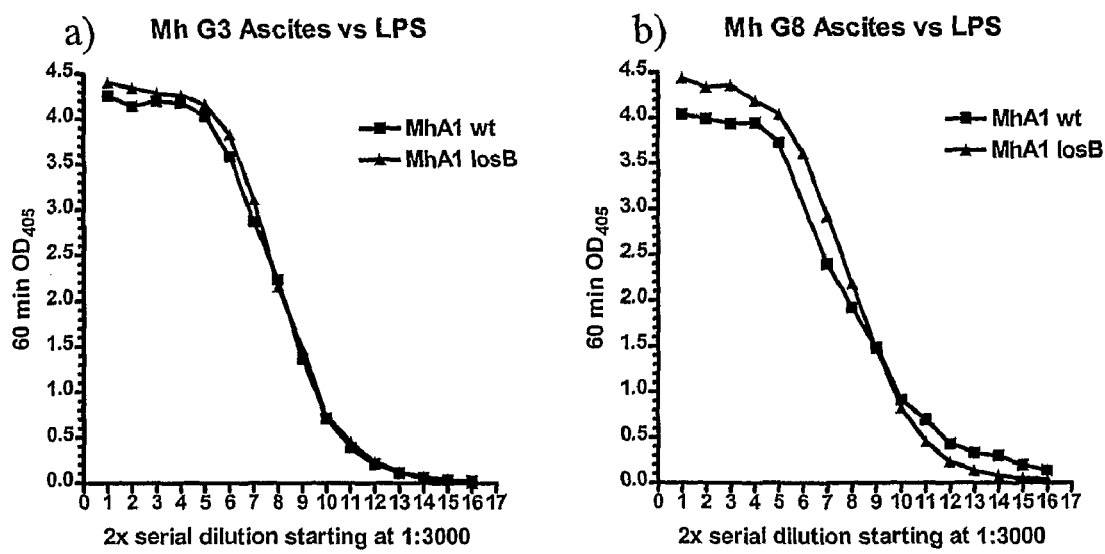

FIG. 58. ELISA (OD$_{405}$) of ascites fluid from a) mAb G3 and b) mAb G8 against LPS from strains Mh losB and wt.

Figure 59:
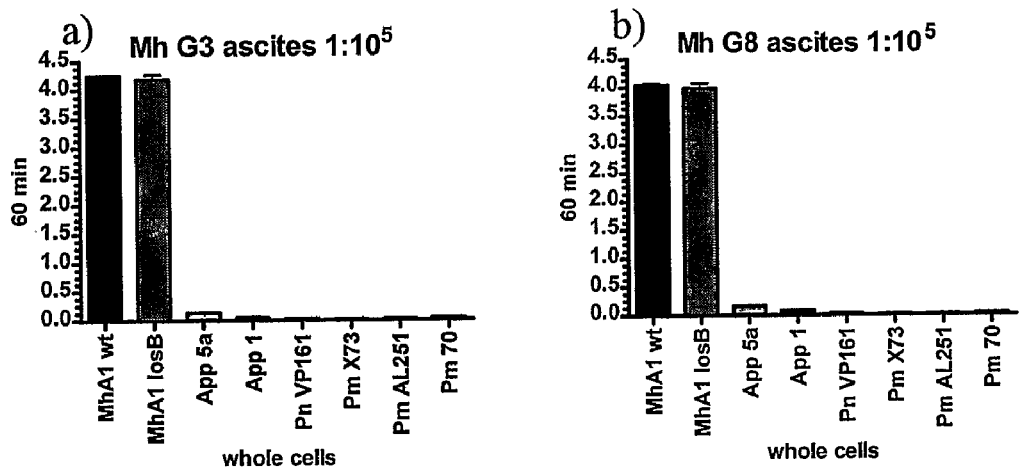

FIG. 59. ELISA (OD$_{405}$) of ascites fluid from a) mAb G3 and b) mAb G8 against whole cells from strains Mh losB and wt; Ap serotypes 1 and 5a; Pm strains VP161, X73 and Pm70.

Figure 60:
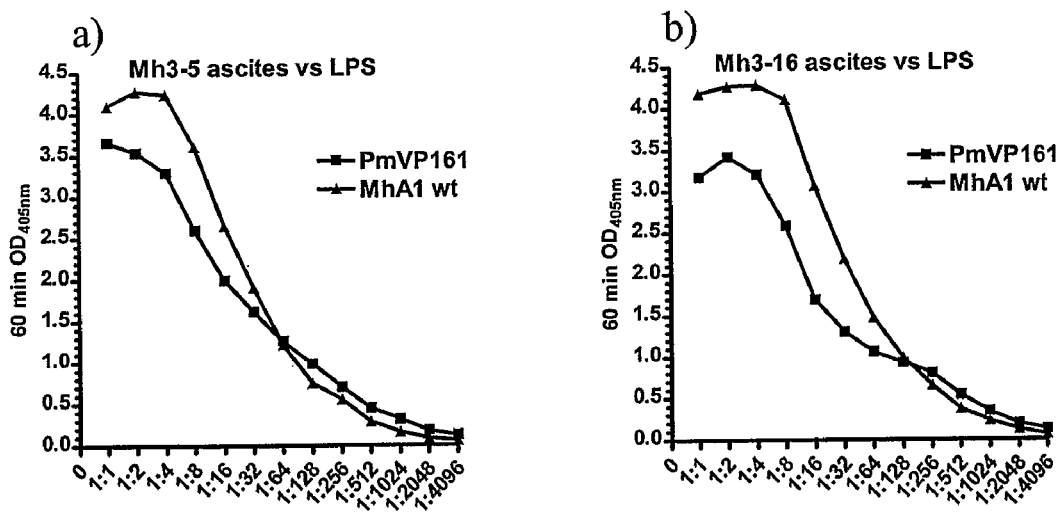

FIG. 60. ELISA (OD$_{405}$) of ascites fluid from a) mAb 3-5 and b) mAb 3-16 against LPS from strains Mh wt and Pm strain VP161.

Figure 61:
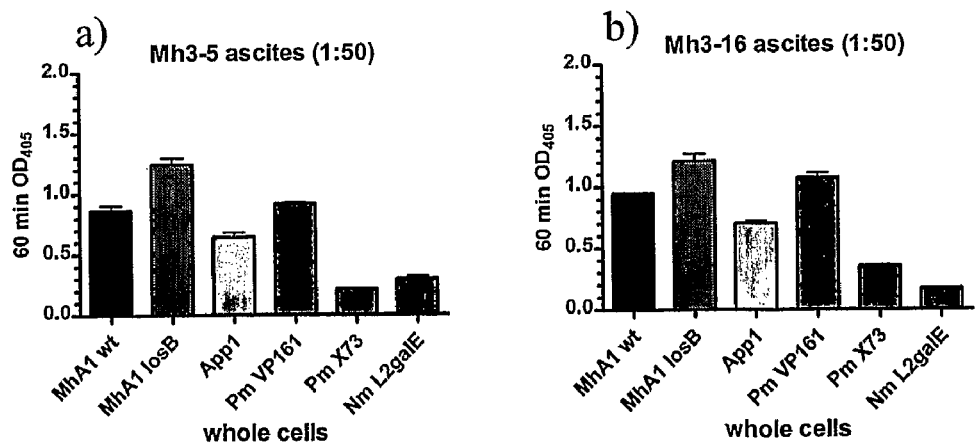

FIG. 61. ELISA (OD$_{405}$) of ascites fluid from a) mAb 3-5 and b) mAb 3-16 against whole cells from strains Mh wt and losB, Ap serotype 1 and Pm strain VP161 and X73 and *Neisseria meninigitidis* strain L2 galE.

Figure 62:
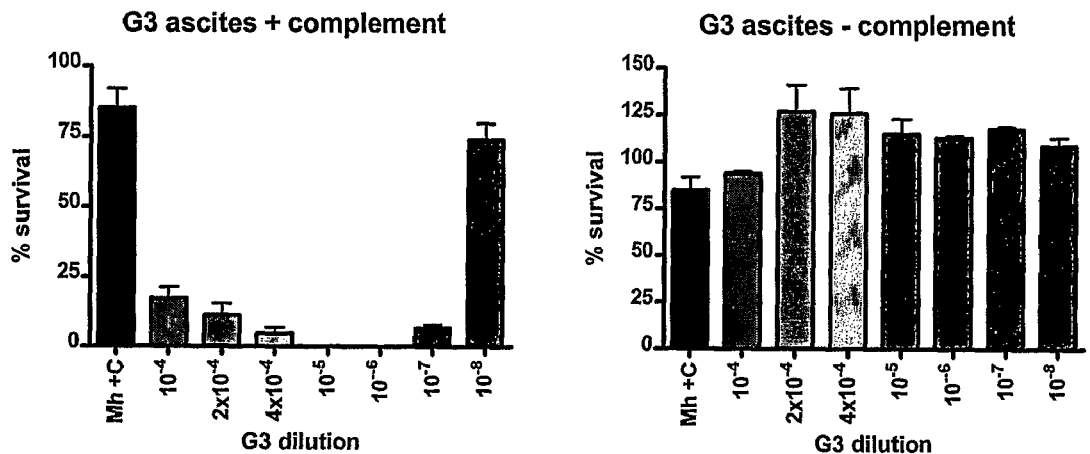

FIG. 62. Serum bactericidal assay with dilutions of immune sera from mAb G3 and the corresponding complement deficient controls; where % survival=[Mean #CFU T30 test/Mean # CFU T30 Mh alone]×100%.

Figure 63:
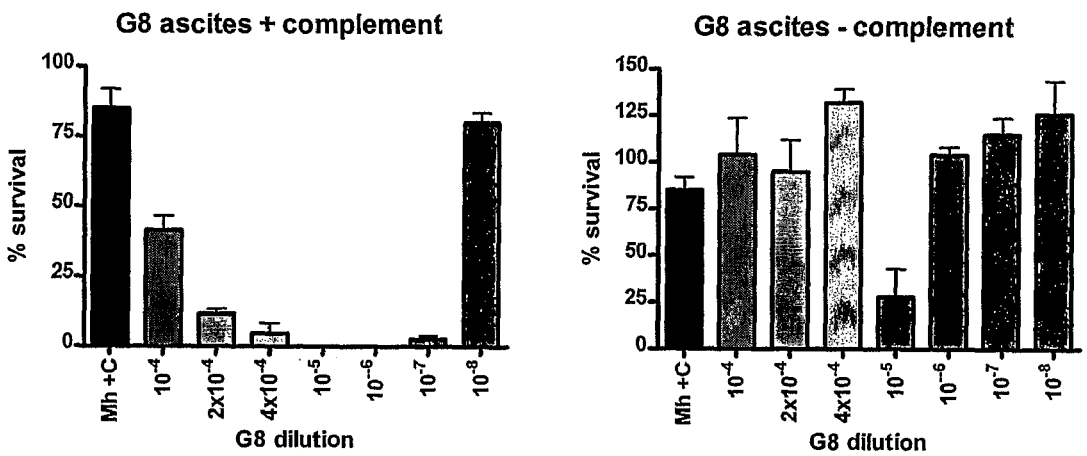

FIG. 63. Serum bactericidal assay with dilutions of immune sera from mAb G8 and the corresponding complement deficient controls; where % survival=[Mean #CFU T30 test/Mean # CFU T30 Mh alone]×100%.

Figure 64:
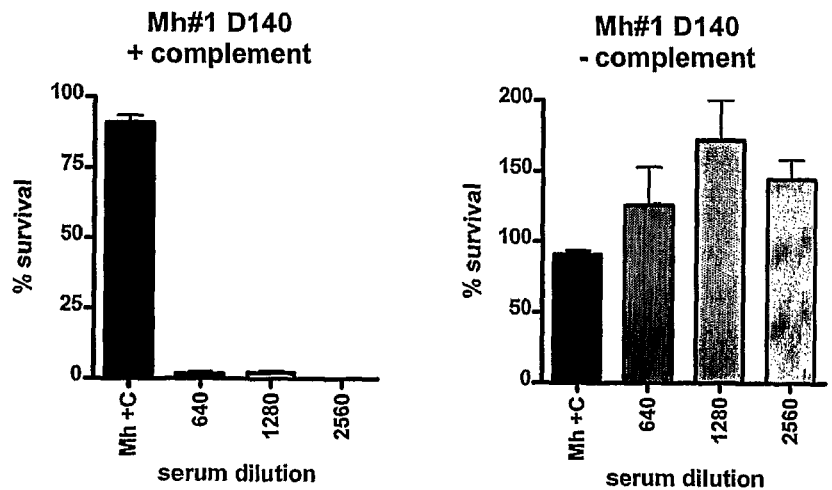

FIG. 64. Serum bactericidal assay with dilutions of polyclonal sera from Mh losB whole cell immunised mouse (Mh #1 D140) and the corresponding complement deficient controls; where % survival=[Mean #CFU T30 test/Mean # CFU T30 Mh alone]×100%.

Figure 65:
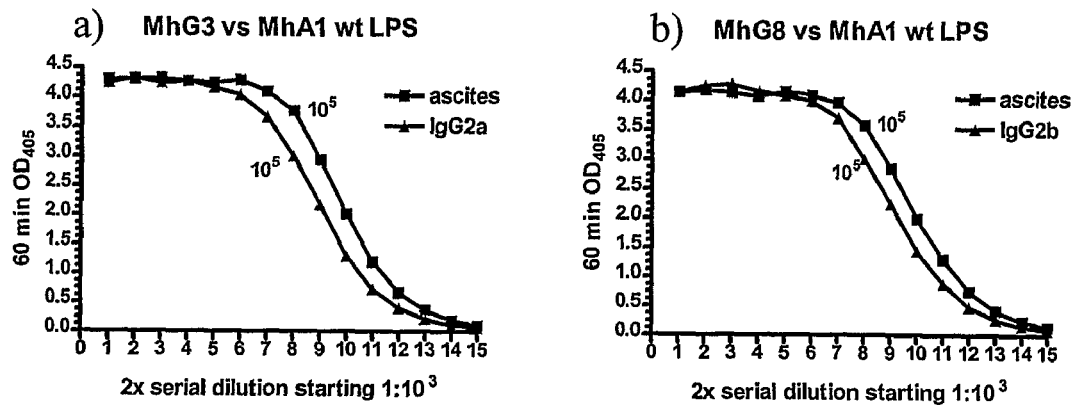

FIG. 65. Protein A column purification of a) mAb G3 and b) mAbG8 ascites fluid as measured by ELISA (OD$_{405}$) of ascites fluid pre and post column against LPS from Mh wt strain.

Figure 66:
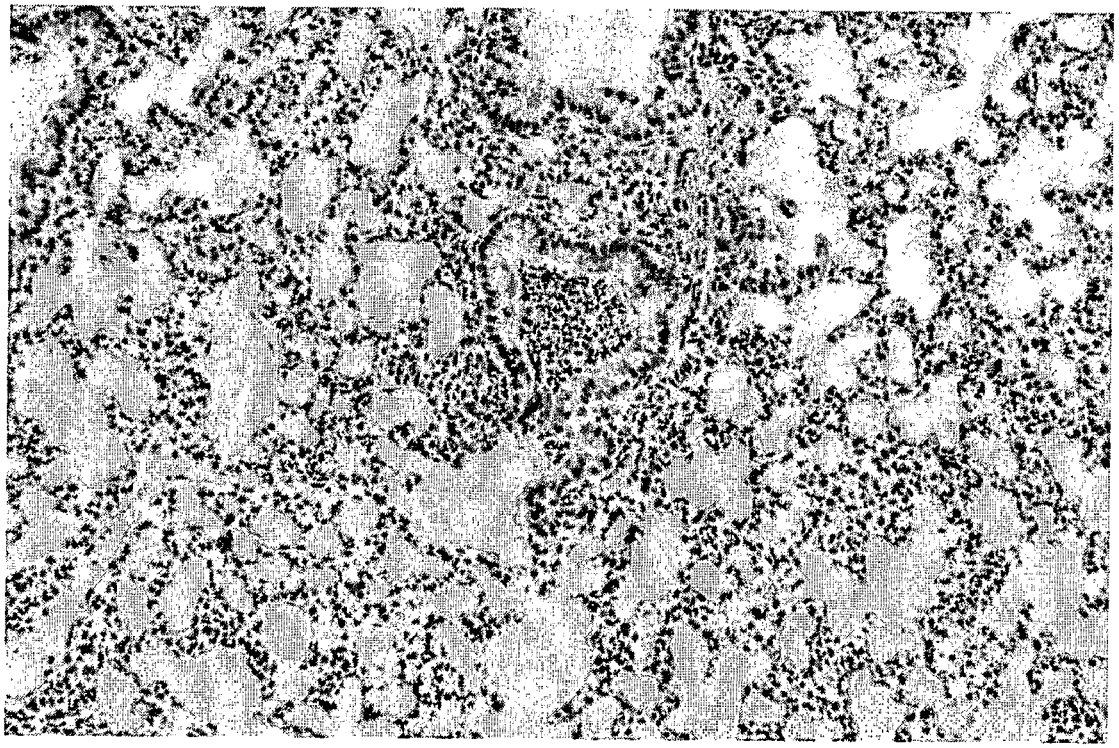

FIG. 66. Lung from a Group B mouse killed at dpi 3 showing the presence of moderate numbers of neutrophils in the lumen of a medium-sized bronchus.

Figure 67:
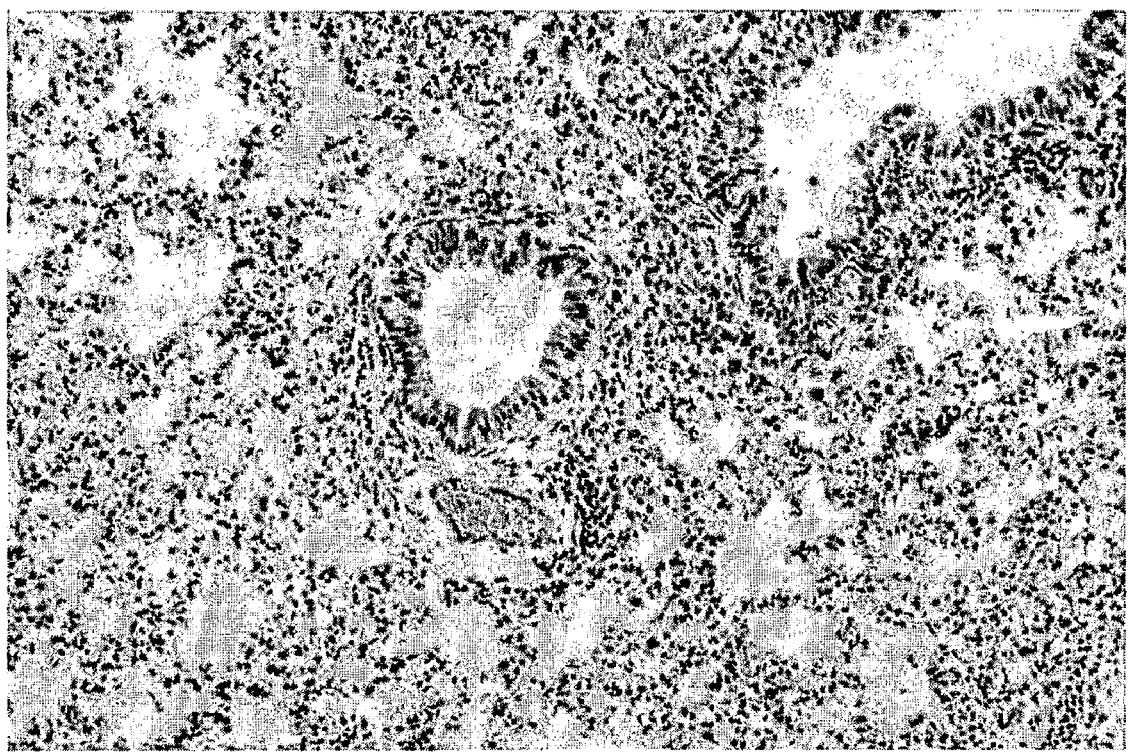

FIG. 67. Lung from a Group C mouse killed at dpi 3 showing the resolution of bronchopneumonia with the presence of small numbers of lymphoid cells in some areas.

DETAILED DESCRIPTION OF THE INVENTION

Example 1

This Example forms the basis of a publication in Can. J. Chem. 80, 1715 (2002). Investigation of *M. haemolytica* serotype A1. Analysis of the LPS of *M. haemolytica* serotype A1 revealed Hex$_3$Hep$_5$Kdo as the major core oligosaccharide component. This was determined by 1D 1H NMR and FAB-MS analysis of the oligosaccharide fraction obtained following mild acid hydrolysis (1% HOAc, 100° C., 3 h) of the LPS sample. The core oligosaccharide was found to contain D-glucose, D-galactose, L-D-heptose, and DD-heptose in a molar ratio of 2:1:3:2 in the major fraction as determined by GLC-MS analysis of their alditol acetate and 2-butyl glycoside derivatives. The D-Gal residue was found to be a terminal non-reducing moiety from methylation analysis and was absent in the minor component of the core oligosaccharide fraction, that had the composition of Hex$_2$Hep$_5$Kdo. The occurrence of Kdo in the LPS was established by calorimetric analysis.

Treatment of *M. haemolytica* LPS with anhydrous hydrazine followed by strong alkali afforded water-soluble, deacylated LPS oligosaccharides. The deacylated LPS sample was representative of the intact backbone oligosaccharide of the native material containing core and lipid A oligosaccharide moieties. This was confirmed by electrospray ionization ESI-MS which gave molecular ions corresponding to Hex$_3$Hep$_5$Kdo$_1$HexN$_2$(H$_2$PO$_3$)$_3$ as the major oligosaccharide component (see Experimental section).

From the proton spectrum (FIG. 1) and HMQC and COSY spectra (FIG. 2), 10 anomeric $^1$H NMR resonances were observed, as well as methylene proton resonances. The anomeric resonances were labelled a-j in decreasing order of their $^1$H NMR chemical shifts and k3$_{eq}$ and k3$_{ax}$ assigned to the methylene protons of Kdo. The integral for the b1 and de1 and j1 anomeric peaks were 40% less than those for the other anomeric resonances confirming heterogeneity in the sample. There was also some heterogeneity at h1 with the appearance of a downfield doublet at 4.91 ppm near h1.

Standard homo- and hetero-nuclear 2D-NMR analyses were undertaken. From the COSY spectrum in FIG. 2, the H-2 resonances could be located. It was realized that for residues b, d, e, f, and g, J$_{1,2}$ was small, typical of manno-heptoses, and that a 2D-TOCSY could not be used to transfer magnetization from H-1 past H-2. From the HMQC spectrum in FIG. 3, the H-2 of the heptose residues overlapped with other resonances making 2D-TOCSY difficult to analyze for these residues. The 2D-NOESY spectrum also showed an unusually high number of NOEs especially for the b1, de1 resonances. Also, there was overlap of several resonances in the anomeric region. Hence, due to the complexity of the spectra and heterogeneity of the sample, 1D selective methods were used to extract spectral parameters that could not be obtained using standard 2D methods, thus permitting the resolution of the structure and conformational analysis. HMQCTOCSY and HMBC experiments were also very important in determining the complete assignments, especially for the heptose units. Using this approach, the complete assignment for the $^1$H and $^{13}$C NMR chemical shifts for the major backbone oligosaccharide (A1) was possible (Example 1, Table 1).

The Kdo-GlcN$_{II}$-GlcN$_I$ sequence and partial assignments are known from previous studies and are consistent with the assignments made here. The 1D-TOCSYs for residues a and h permitted assignment of the resonances and measurement of proton coupling constants (FIG. 4a, 4b). Location of phosphate groups was confirmed from a $^{31}$P HMQC experiment as done previously. Assignment of the $^{13}$C NMR chemical shifts was then made from HMQC, HMQC-TOCSY, and HMBC spectra. This information led to the definition of residues a and h as the α-D-GlcN and β-D-GlcN pyranosyl units of the lipid A moiety. Most of the proton, $_{31}$P and $_{13}$C NMR chemical shifts were similar to those previously reported in a similar structural element. In the 1D-TOCSY for h1, the h'5 peak at 3.62 ppm is due to hydrolysis of the Kdo-(2-6)-β-D-GlcN$_{II}$ glycosidic linkage. After several months in solution, the linkage was completely hydrolyzed with h'6 and h'6 appearing at 3.82 and 3.92 ppm, respectively. The sharp anomeric signal at 3.91 ppm was also found to be due to h'1 of this disaccharide.

For Kdo, the H-4 and H-5 resonances were assigned from 1D-TOCSY experiments with selective excitation of H-3$_{eq}$ or H-3$_{ax}$. The H-4 resonance is shifted downfield due to a phosphate group at C-4, confirmed by a $^{31}$P HMQC. A small J$_{5,6}$<1 Hz impeded the TOCSY transfer past H-5 (FIG. 4c). However, a strong NOE is observed between k4 and k6 in FIG. 2c in accord with the X-ray structure of Kdo. 1D NOESY-TOCSY (k4, k6) was used to complete the assignment (FIG. 4d). As shown later, for the HepI-(1-5)-Kdo linkage, the d1-k7 NOE was also observed, typical of a substitution at C-5 of Kdo. Using this NOE, the Kdo resonances detected from the 1D-NOESY-TOCSY (de1, k7) (FIG. 4e) had the same chemical shifts and similar multiplet patterns as those found in the previous experiment, thus confirming the Kdo $^1$H NMR assignments. The $^{13}$C NMR assignments for Kdo where then obtained from the HMQC spectrum and confirmed from the HMQC-TOCSY spectrum.

Residue i was determined to be 6-substituted β-D-glucose denoted as Glc$_I$. The anomeric resonance for residue i overlapped with the H-4 resonance of Kdo. In the 1D-TOCSY for these two overlapping resonances, it was possible to distinguish the resonances for residue i because of the small J$_{5,6}$ coupling constant for Kdo (FIG. 4c). All resonances up to H-6s could be detected and coupling constants of the multiplets could be measured. Due to its B-D configuration the i1-i3 and i1-i5 NOE were also observed in the NOESY spectrum (FIG. 2 and FIG. 5f). $^{13}$C NMR assignments for Glc$_I$ were then obtained from the HMQC spectrum and confirmed with the HMQC-TOCSY spectrum. From a comparison with chemical shifts of terminal glucose, a glycosidation downfield shift of 3.7 ppm was observed for the C-6 resonance, indicating its substitution at that position. A substantial shift of −2.2 ppm was also observed for C-5. The rotamer distribution about the C-5—C-6 bond could be determined from the H-5 multiplet observed for the i1-i5 NOE in FIG. 5f. It was apparent that both J$_{5,6}$ and J$_{5,6}$ had small values <2 Hz since the H-5 multiple appeared as a doublet dominated by the large J$_{4,5}$ coupling of 10 Hz. This showed that both H-6 and H-6' were gauche to H-5 with the O6-C$_6$-C5-O5=−60° rotamer being preferred in solution.

Residue c was determined to be a terminal α-D-glucose denoted as Glc$_{II}$. From the 1D-TOCSY for c1 (FIG. 4f) resonances up to H-5 were detected, indicating that residue c was an α-glucose based on the measured proton coupling constants. From the HMQC spectra and comparison with chemical shifts of terminal glucose model compounds, all the $^1$H and $^{13}$C NMR assignments could be completed.

The terminal galactose, residue j, denoted as Gal, was identified from the 1D-TOCSY of j 1 and resonances up to H-4 were observed (FIG. 4j). To get past the small J$_{4,5}$ coupling constants and identify H-5, the 1D-TOCSY-NOESY (1, j4) was done (FIG. 4h). From the HMQC spectra and comparison with chemical shifts of terminal galactose model compounds, all the $^1$H and $^{13}$C NMR assignments were completed.

To assign the heptose residues, model compounds were synthesized to obtain accurate $^1$H and $^{13}$C NMR chemical shifts and JH,H values. These were crucial in assigning the terminal heptose units by chemical shifts comparisons. Also, upon glycosidation, the $^{13}$C NMR resonance of the substituted carbon experiences a substantial down-field glycosidation shift. The proton spectra for D-D-heptose and D-L-heptose are shown in FIG. 6. In solution both the α and β forms are present for each compound. Their $^1$H NMR spectra were assigned using 1D-TOCSY experiments. To obtain accurate coupling constants and chemical shifts, spin simulations of the proton spectra were done. The simulated spectra are shown in FIG. 6. The simulated spectra reproduced exactly the observed spectra, especially the strong coupling for H-3-H— in D-α-L-heptose (FIG. 6b). $^{13}$C NMR chemical shifts were assigned using HMQC. The NMR data for the heptose monosaccharides are given in Example 1, Table 2. The chemical shifts for L-D-heptose are the same as those of D-L-heptose since they are enantiomers of each other.

Residues b, d, e, f, and g in A1 were identified as heptoses from their narrow anomeric resonance due to the small J1,2 coupling and lack of transfer of magnetization beyond H-2 from H-1 in a TOCSY experiment. All the heptoses in A1 had the α-D configuration since the only intra-residue NOE from H-1 was to H-2 (FIG. 2). 1D-TOCSY-TOCSY (H-1, H-2) was used to assign all the heptose residues. The first TOCSY step from H-1 transfers the magnetization to H-2 and further transfer is impeded due to the small J$_{1,2}$ value of 1.8 Hz. However, the second step at H-2 will transfer the magnetization further to higher spins due to the larger J$_{2,3}$ value of 3 Hz. However, for L-D-heptose, transfer of magnetization stops at H-5 due to the small J$_{5,6}$ value of 1.6 Hz. For D-D-heptose, transfer of magnetization is less impeded due to a large J$_{5,6}$ value of 3.2 Hz. However, relaxation effects can also impede transfer of magnetization and one cannot use a lack of transfer beyond H-5 as proof of L-D-heptose identification.

Residue b was determined to be the 2-substituted L-α-D-heptose denoted as Hep$_{II}$. The 1D-TOCSY-TOCSY (b1, b2) identified resonances at 3.64 ppm and 3.9 ppm (FIG. 7a). The multiplet pattern at 3.64 ppm was indicative of a H-5 resonance while those at 3.9 ppm were similar to the strongly coupled H-3 and H-4 resonances observed in the monosaccharide (FIG. 6b). To identify H-6 a 1D-TOCSYNOESY (b2, b5) was done (FIG. 7b). In the first TOCSY step for b2, the a6 resonance was also irradiated but the second step only selected the b5 resonance. NOEs from b2 were observed on b3 and b6 along with an inter-residue NOE on d2. Once b6 was located, the HMQC-TOCSY from the C-7-H-7s-C-6-H-6 was used to assign the H-7 and H-7' resonances (FIG. 3b). Assignments for the other resonances were then obtained from the HMQC spectrum and confirmed from the HMQC-TOCSY and HMBC spectra (FIG. 3). Comparison of chemical shifts with those of L-α-D-heptose indicated a 9 ppm down-field shift for C-2 and an up-field shift of –0.8 ppm for C-3 indicative of a substitution at C-2. The C-4 to C-7 chemical shifts were within 0.6 ppm of those of the monosaccharide.

Residue e was determined to be a terminal L-α-D-heptose denoted as Hep$_{III}$. Although the d1 and e1 resonances overlap, this is of no concern since their H-2 resonances did not overlap. The 1D-TOCSY-TOCSY (de1, e2) identified the e3, e4, and e5 spins (FIG. 7c). From the b1 NOE in FIG. 5a, the e5 resonance was also observed. The high digital resolution of the 1D selective experiments permits accurate matching of resonances between different experiments due to the observation of their multiplet pattern. In FIG. 5a, the b1-e7 and b1-e7' NOEs were also observed. As seen later, these NOEs are due to the close proximity of b 1 proton to the e5 and the e7 and e7' protons. The H-6 resonance was located in the HMQC-TOCSY from C-7-H-7s-C-6-H-6. $^1$H and $^{13}$C NMR assignments were completed with HMQC and HMQC-TOCSY. $^1$H and $^{13}$C NMR chemical shifts of residue e were similar to those of L-α-D-heptose.

Residue d was identified as a 3,4,6-trisubstituted L-α-D-heptose denoted as Hep$_I$. The 1D-TOCSY-TOCSY (de1, d2) identified a narrow multiplet at 4.17 and a broader one at 4.01 ppm (FIG. 7d). The multiplets at 4.01 ppm and 4.17 ppm (d2) were also observed in the 1D-NOESY for b1 (FIG. 5a). The resonance at 4.17 ppm was also observed in the 1D-NOESY for i1 (FIG. 5f). In the HMQC spectrum two narrow crosspeaks at (δc, δh) (74.9, 4.17), (72.5, 4.17) and a broader one at (75.3, 4.01) were identified. HMQC-TOCSY correlations were also observed between these crosspeaks. From a comparison of the $^{13}$C NMR chemical shifts with those of the α-D-heptopyranoses in Example 1, Table 2, it was obvious that the crosspeaks at (74.9, 4.17) and (75.3, 4.01) were subject to a $^{13}$C NMR down-field glycosidation shift. Since these three crosspeaks are from d3, d4, or d5, only the d5 crosspeak will not experience a large glycosidation shift since substitutions on heptose cannot occur at C-5. Hence, the crosspeak at (72.5, 4.17) was assigned to (C-5, H-5). The crosspeak at (75.3, 4.01) was assigned to (C-3, H-3) based on the HMBC (d3, d1) and (d3, b1) correlations. The crosspeak at (74.9, 4.01) was thus assigned as (d4, d1), consistent with the observation of the HMBC (d4, i1) correlation and (i1, d4) NOE (FIG. 3 and FIG. 5f). The d6 resonance was assigned from the 1D-NOESY from i1, since for the GlcI-(1-4)-HepI linkage, a strong NOE to H-6 is also expected only if residue d is L-D-heptose. The d6 resonance was also observed for the 1D-NOESY for c1 (FIG. 5b). The H-7 and H-7.' resonances were located from the HMQCTOCSY (C-7, H-6) crosspeak (FIG. 3) and from 1DNOESY-TOCSY (i1, d6) (not shown). Comparison of chemical shifts with those of L-α-D-heptose indicated a 3.9, 7.9, and 11.6 ppm down-field glycosidation shift for C-3, C-4, and C-6, respectively.

As shown below, there should be a 4,6-disubstituted L-α-D-heptose (d') present due to heterogeneity on the branching heptose (FIG. 1). From the HMQC and COSY spectra for the anomeric region, no separate signal could be observed either for the H-1 or H-2 due to overlap with other resonances. It is suspected that the proton chemical shifts of d'1 were the same as the one for d1, and that d'2 had a similar chemical shift to e2.

Residue g was determined to be a 6-substituted D-α-D-heptose denoted as Hep$_{IV}$. The 1D-TOCSY-TOCSY (g1, g2) identified the g3, g4, and g5 spins (FIG. 7e). The multiplet pattern at 3.94 was indicative of a H-5 resonance. To identify H-6, a 1D-TOCSY-NOESY (g2, g5) was acquired (FIG. 7f). NOEs from g2 were observed on g3 and g6 along with a putative inter-residue NOE on i6. Once g6 was located, the HMQC-TOCSY from the C-7-H-7s-C-6-H-6 (FIG. 3b) and 1D-NOESY-TOCSY (f1, g6) (FIG. 7g) were used to assign the H-7 and H-7.' resonances. Assignments for the other resonances were then obtained from the HMQC spectrum and confirmed with the HMQC-TOCSY spectrum (FIG. 3). In the 1D-NOESY (f1), the g6 and g5 resonances were observed (FIG. 5d). The NOE f1-g5 NOE can only be possible if residue g is a D-D-heptose from molecular modeling studies (see below). Comparison of chemical shifts with those of D-α-D-heptose indicated a 4.3 ppm down-field shift for C-6.

Residue f was determined to be a 7-substituted D-α-D-heptose and denoted as HepV. The 1D-TOCSY-TOCSY (f1, f2) identified spins up to f6 indicating that residue f was a D-D-heptose. The f5 multiplet pattern was quite clear. From a 1D-TOCSY starting on f6, the f7, and f7' resonances were identified. The $^{13}$C NMR assignments were then obtained from the HMQC spectrum and confirmed with the HMQC-TOCSY spectrum. Comparison of chemical shifts with those of α-D-D-heptose indicated a 8.8 ppm down-field shift for C-7. A terminal D-α-D-heptose, denoted f', was only detected due to heterogeneity at this linkage site. As seen in the 1D-TOCSY-TOCSY (f1, f2), the f'5 and f'6 resonance can be detected, along with crosspeaks in the HMQC and HMQC-TOCSY spectra which correspond to those of a terminal D-α-D-heptose similar to those for D-α-D-heptose in Example 1, Table 2.

The sequence of the core octosaccharide was established from the 1D-NOESY spectrum for the anomeric resonances presented in FIG. 5 and from the HMBC spectrum of the anomeric proton resonances (FIG. 3c). Inter-residue NOEs were also observed in 1D-TOCSY-NOESY experiments in FIGS. 7b and 7f. The results are tabulated in Example 1, Table 3 and the structure shown in FIG. 1. From integration of the anomeric resonances and appearance of new resonances with time, the linkage sites where heterogeneity occurs were determined. The k(2-6)h linkage and the b(1-3)d linkage hydrolyzed over a period of months in solution at pH 3, while the j(1-7)f linkage was stable.

An unusually large number of long-range NOEs were observed spanning up to five sequential residues. For an α-D sugar, the H-1-H-2 intra-residue NOE is expected. For a β-D-sugar, the H-1-H-3 and H-1-H-5 intra-residue NOEs are expected. The H-1-C-1-O-1-C-x-H-x interglycosidic NOEs are expected for (1-x) linkage. Inter-residue anomeric NOEs between two linked sugars on the H-x±1 and H-x±2 can also occur. Other inter-residue NOEs, not in the vicinity of the glycosidic linkage, are deemed to be long-range NOEs as listed in Example 1, Table 3.

To explain the large number of long-range NOEs, conformational analysis was done using the Metropolis Monte Carlo (MMC) method to vary the glycosidic linkage angles and sample the multiple conformations of the molecule. Using this method for the inner core oligosaccharide with Kdo at the reducing end, it was found that all the observed long-range NOEs could be explained by the close proximity of the e-b branch to the g-i branch. These long range NOEs were possible due to restriction of the inner core residues brought about by the three branching points on $Hep_I$.

A minimum energy conformer obtained from the calculation is shown in FIG. 8. The various interproton distances measured from these coordinates are given in Example 1, Table 3. As can be observed the occurrence of most NOEs can be explained by the short inter-proton distances. The long-range NOEs for g1-b2 and g1-b3 are not consistent with distances obtained from the molecular model drawn in FIG. 8. Although there is restriction due to the (3,4,6)-$Hep_I$ substitution pattern, there is flexibility about the glycosidic linkage and this must be taken into account. As shown in FIG. 9 for the g1-b2 and g1-b3 distances, multiple conformations having short inter-proton distances are sampled consistent with the observed NOEs. The same situation was applicable for all the other long-range and inter-residue NOEs. The long-range NOEs for g1-b2 and g1-b3 and e1-i4 span four residues with mobility about the three glycosidic ($\phi$, $\psi$) angles for a total of 6 df. The long-range NOEs between e1-g2 and e1-g3 that span five residues (e-b-d-i-g) vary even more due to 8 df about the glycosidic angles, not counting possible flexibility about the C-5-C-6 bond for the g(1-6)i linkage. The b1-e5, b1-e7, and b1-e7.' are dependent on mobility about the e(1-2)b glycosidic bond and rotation about C-6-C-7 of residue e. In all cases, the occurrence of multiple conformations that have short inter-proton distances is consistent with the observed inter-residue and long-range NOEs.

In the present study it was established that the lipid A region of the *M. haemolytica* A1 LPS molecule contains a bis-4,4'-phosphorylated $\beta$-1,6 linked D-glucosamine disaccharide moiety. The nature and substitution patterns of the fatty acyl groups attached to this disaccharide have not been reported. The fully acylated LPS molecule makes up the outer most leaflet of the bacterial membrane and is essential for maintaining membrane integrity. The glycose portion of the molecule typically extends out and away from the plane defined by the bacterial membrane. The LPS oligosaccharide portion is important in virulence and is involved in eliciting host immune responses. To gain a perspective of the relative sizes and orientation of the core oligosaccharide and membrane-anchoring lipid A regions of this LPS molecule, a molecular model was constructed using the lipid A fatty acid substitution pattern found in a related organism, *Haemophilus influenzae*. This is shown in FIG. 10. The *H. influenzae* lipid A has been reported to have six fatty acyl groups in which the amide group (C-2) and C-3 hydroxyl groups of the reducing glucosamine residue are acylated by 3-hydroxytetradecanoic acid while the C-2.' amide and C-3' hydroxyl groups of the non-reducing residue are acylated by 3-tetradecanoyloxytetradecanoic acid. As observed in FIG. 10, due to the inner core which provides a fairly rigid structure, the glycose portion projects out from the lipid A moiety which defines the bacterial membrane. More mobility was observed for the terminal residues, especially for the terminal Gal residue. In the NOESY spectrum in FIG. 2, no NOEs for the anomeric resonance were observed consistent with increased mobility of this residue.

The core structures of several LPS have been found to be highly branched and this can result in well-defined conformations for the inner core. In a previous study, the LPS of *Moraxella catharrhalis* was found to adopt an unusual conformation in which a very rare anti conformer was observed. For a highly branched 3,4,6-trisubstituted D-glucose residue in this LPS molecule, a dihedral angle (C-1'-O-1'-C-4-H-4) near 180° was detected for $\beta$-D-Glcp-(1-4)-DGlcp linkage to the branched glucose unit.

The results of the present study have provided a detailed picture of the structure of the LPS core oligosaccharide region of *M. haemolytica* serotype A1. We have previously shown that the oligosaccharide region of *M. haemolytica* LPS is immunogenic in mice, sheep, and cattle and that eight of the 12 *M. haemolytica* serotypes (i.e., serotypes A1, A5, A6, A7, A8, A12, A14, and A16) share common core oligosaccharide determinants. The core oligosaccharides from serotypes A1 and A8 show almost identical $^1$H NMR spectra establishing the presence of a common basal structure. Based on the results of the present study it is apparent that the O-chain deficient LPS elaborated by *M. haemolytica* serotype A8 lacks the terminal Gal unit in the core oligosaccharide, a residue which possibly provides a site for O-chain attachment. An understanding of LPS structural differences among *M. haemolytica* serotypes could provide the basis for a vaccine against *M. haemolytica* bovine pasturellosis. Serotype A1 is the principal microorganism responsible for this disease, accounting for 30% of total cattle deaths globally. The use of a less virulent serotype or antigens thereof in a vaccine formulation could provide an effective disease management strategy.

Experimental for Example 1

Preparation of LPS from *M. haemolytica*

*Pasteurella* (*Mannheimia*) *haemolytica* serotype A1 (NRCC 4212) was obtained from the Veterinary Infectious Diseases Organization (VIDO), Saskatoon, SK, Canada. LPS was extracted and purified from fermenter-grown bacteria culture by the hot aqueous phenol method as previously described in Severn et al. Carbohydr. Res. 240, 277 (1993).

Deacylation of LPS to give Backbone Oligosaccharides

Backbone oligosaccharide was prepared as previously described in Severn et al. J. Bacteriol. 178, 1731 (1996) by modification of the deacylation procedure of Holst et al. Ester-bound fatty acids were removed from the lipid A of the LPS by treatment of a sample (400 mg) with anhydrous hydrazine at ambient temperature (20 mL, 37° C., 30 min). Excess hydrazine was destroyed by addition of acetone (three volumes) to the cooled reaction mixture (0° C.). The precipitated O-deacylated LPS product was isolated by centrifugation (5000 rpm, 10 min), washed with acetone, and lyophilized from water. Removal of N-acyl groups was achieved by heating the O-deacylated sample (200 mg) in aq KOH (4 M, 10 mL) at 100° C. for 20 h. The reaction mixture was cooled (0° C.), neutralized with 4 M HCl, and the precipitated fatty acids removed by centrifugation (12000×g, 30 min). The supernatants were filtered in an Amicon concentration cell with a 500-molecular-weight-cutoff membrane (Amicon; YC05) and washed with deionized water until the eluant was free of chloride ions (as determined with aq $AgNO_3$). The dialyzed material was lyophilized to give deacylated LPS (ca. 80 mg). The oligosaccharide was purified by anion-exchange chromatography on DEAE A-25. The backbone oligosaccharide fraction (ca. 50 mg) showed a doubly charged ion at m/z 1124.8 in the positive ion ESI-MS as the major ion which corresponded to a composition of $Hex_3Hep_5Kdo$ $HexN_2$ $(H_2PO_3)_3$ (M, 2246.9). MS-MS of the doubly charged ion gave characteristic fragments at m/z 500 ($HexN_2(H_2PO_3)_2$) and 801 ($KdoHexN_2(H_2PO_3)_2$) corresponding to deacylated lipid A and the Kdo-P substituted units, respectively.

D-glycero-L-manno-Heptose

The heptose was prepared by the condensation of D-galactose with nitromethane in alkaline methanol. The crystalline 1-deoxy-1-nitro-D-glycero-L-manno-heptitol obtained from the aqueous solution of the deionized products (mp 158° C., 21% yield) was converted to its sodium salt. On treatment with dilute sulphuric acid (35° C.), followed by deionization with Rexyn 101(H⁺) and Amberlite A4(OH⁻) ion-exchange resins, the solution was lyophilized to give the heptose as a syrup (80% yield). The product was fractionated by cellulose column chromatography using butan-1-ol-water (1:10 v/v) as the eluant. Fractions containing the heptose were concentrated to dryness under reduced pressure. The D-glycero-L-manno-heptose having $[\alpha]_D$ −14° (c 0.2, water) was pure by paper chromatography and its reduced ($NaBH_4$) and acetylated product on GLC gave a single peak corresponding in retention time with that of authentic hepta-O-acetyl-D-glycero-L-manno-heptitol, establishing its purity.

D-glycero-D-manno-Heptose

The heptose was prepared from D-altrose via its condensation with nitromethane to yield 1-deoxy-1-nitro-D-glycero-Dmanno-heptitol (mp 109° C., $[\alpha]_D$ −7.0° (c 1.1, EtOH), 27% yield)) whose aqueous sodium salt solution on slow dropwise addition to stirred 20% (v/v) sulfuric acid maintained at 0° C. was converted to D-glycero-D-manno-heptose. The reaction mixture was neutralized with sat. $Ba(OH)_2$ solution, filtered, passed through Rexyn 101(H⁺) and Duolite A4(OH⁻) ion-exchange resins to remove residual ionic material, and was concentrated to a syrup (92% yield). The heptose product, as indicated by paper chromatography, was contaminated with altrose and unchanged 1-deoxy-1-nitro-D-glycero-D-manno-heptitol (ca. 2 to 3%). The product was purified by cellulose column chromatography using butan-1-ol-water (1:10 v/v) as the mobile phase. The D-glycero-D-mannomannose had $[\alpha]D$ +22° (c 2, MeOH). A reduced ($NaBH_4$) and acetylated sample on GLC gave a single peak corresponding to authentic hepta-O-acetyl-D-glycero-D-manno-Dheptitol indicating the identity and purity of the synthesized heptose.

Electrospray Mass Spectrometry

Samples were analyzed on a VG Quattro triple quadrupole mass spectrometer (Micromass, Manchester, U.K.) fitted with an electrospray ion source. Backbone oligosaccharide was dissolved in acetonitrile-water (approx. 1:2 v/v) containing 0.5% acetic acid. Injection volumes were 10 μL and the flow rate was set at 4 mL min⁻¹. The electrospray tip voltage was typically 2.7 kV and the mass spectrometer was scanned from m/z 50 to 2500 with a scan time of 10 s. For MS-MS experiments, precursor ions were selected using the first quadrupole and fragment ions formed by collisional activation with argon in the RF-only quadrupole cell, were mass analyzed by scanning the third quadrupole. Collision energies were typically 60 ev (laboratory frame of reference).

Nuclear Magnetic Resonance

NMR spectra were performed on a Bruker AMX 600, AMX 500, or a Varian Inova 600 spectrometer using standard software. All measurements were made at 300 K and at pH 3, containing 10 mg of sample dissolved in 0.6 mL of $D_2O$. Measurements were done at pH 3 to improve resolution of the proton spectrum as done previously (Cox, 1996). Acetone was used as an internal or external reference at 2.225 ppm for $^1H$ spectra and 31.07 ppm for $^{13}C$ spectra. Standard homo- and heteronuclear correlated 2D techniques were used for general assignments of the core oligosaccharide: COSY, TOCSY, NOESY, triple quantum homonuclear correlated experiment, HMQC, HMQC-TOCSY, and HMBC and $^{31}P$ HMQC. Spin simulations for the heptose monosaccharides were performed with standard Varian software. Accurate chemical shifts and coupling constants were obtained from the parameters used to perform the spin simulation and not from the peak listing of the spectra.

Selective 1D-TOCSY, 1D-NOESY, 1D-TOCSY-TOCSY, 1D-TOCSY-NOESY, and 1D-NOESY-TOCSY experiments were performed for complete residue assignment and for determination f inter-residue $^1H$—$^1H$ nuclear Overhauser enhancements. The nomenclature used to describe the use of the 1D selective sequences will be 1D EXP (spin, mixing time) and 1D EXP1-EPX2 (spin1, mixing time; spin2, mixing time), where EXP, EXP1, and EXP2 stand for either TOCSY or NOESY. Also, in the figures, the selected resonances are underlined. A doubly underlined resonance means that this resonance was selected as the second selection step. As shown in FIG. 1, all the residues are labelled by letters and the spins are labelled by the atom number, so that a1 refers to the H-1 resonance of residue a.

On the AMX spectrometers, selective excitation was achieved by means of half-Gaussian pulses. The mixing time used for a TOCSY depended on the spin system. Usually a range of mixing times (spin lock times) from 30 to 180 ms was used to assign the spin system. The mixing time for a 1D-NOESY depended on the correlation time of the molecule and internal motion about the glycosidic linkage. NOESY mixing times were in the range from 150 to 400 ms. To detect inter-residue NOEs for the terminal Gal residue, a 1D-ROESY experiment was done with a mixing time of 500 ms. For the doubly selective experiments, the selective pulses were kept as short as possible to avoid loss of signal intensity due to relaxation effects. Each part was optimized one at a time. The 1D-TOCSY could be carried out in a matter of minutes. The 1D-NOESY took from minutes to hours depending on the magnitude of the NOE. Some doubly selective experiments took up to 12 h. The 1D-TOCSYTOCSY and 1D-TOCSY-NOESY were the most efficient. As the sample degraded with time, some experiments were also performed on an Inova 600 spectrometer making use of pulse field gradients.

Molecular Modeling

The conformational analysis was done using the Metropolis Monte Carlo method as previously described (Peters et al. Carbohydr. Res. 238, 49 (1993)). The PFOS potential was used. Minimized coordinates for the monosaccharides were obtained using MM3 available from the Quantum Chemistry Program Exchange (QCPE). The minimum energy conformation for each disaccharide was used as the starting conformation. Starting from the Kdo at the reducing end, calculations were performed for various oligosaccharides up to the complete structure. For the inner core octasaccharide, $5\times10^4$ macro moves were used with a step length of 5° for the glycosidic linkage and a temperature of $1\times10^3$ K resulting in an acceptance ratio of 0.36. The molecular model for the inner core octasaccharide was generated using the minimum energy conformer. Distances were extracted from the saved coordinates at each macro move. The complete LPS with lipid A was generated using the lipid A structure and the minimum energy conformer for the Kdo linkage. Molecular drawings were done using Schaka197 from E. Keeler, University of Freiburg, Germany.

TABLE 1

NMR chemical shifts (ppm) of the core oligosaccharide component from *Mannheimia (Pasteurella) haemolytica* serotype A1 LPS.

| Residue | $\delta_C$ $\delta_H$ | C-1 H-1 | C-2 H-2 | C-3 H-3 H-3' | C-4 H-4 | C-5 H-5 | C-6 H-6 H-6' | C-7 H-7 H-7' | C-8 H-8 H-8' |
|---|---|---|---|---|---|---|---|---|---|
| Hep$_I$ D | | 100.3 5.17 | 71.1 4.13 | 75.3 4.01 | 74.9 4.17 | 72.5 4.17 | 81.2 4.11 | 63.5 4.02 3.89 | |
| Hep$_{II}$ B | | 100.7 5.57 | 80.5 4.26 | 70.6 3.89 | 67.6 3.90 | 72.2 3.64 | 69.6 4.05 | 64.1 3.70 3.60 | |
| Hep$_{III}$ E | | 102.5 5.16 | 71.5 4.01 | 71.5 3.87 | 67.0 3.83 | 72.4 3.78 | 70.2 4.04 | 64.5 3.83 3.68 | |
| Hep$_{IV}$ G | | 99.8 4.95 | 70.5 4.08 | 71.7 3.81 | 67.9 3.78 | 71.8 3.94 | 77.0 4.14 | 61.2 3.91 3.80 | |
| Hep$_V$ F | | 99.0 5.04 | 70.8 3.93 | 71.5 3.85 | 68.1 3.82 | 73.7 3.99 | 71.7 4.22 | 71.6 4.16 3.85 | |
| Hep$_V$ f | | 99.0 5.04 | 70.8 3.93 | 71.5 3.85 | 68.3 3.77 | 73.7 3.97 | 72.8 4.05 | 62.9 3.79 3.73 | |
| Glc$_I$ I | | 104.0 4.64 | 74.2 3.51 | 77.7 3.45 | 70.2 3.64 | 74.6 3.54 | 65.5 4.06 3.69 | | |
| Glc$_{II}$ C | | 102.4 5.22 | 72.9 3.58 | 73.9 3.83 | 69.3 3.58 | 72.4 3.95 | 60.3 3.96 3.76 | | |
| Gal J | | 104.3 4.46 | 71.7 3.56 | 73.5 3.67 | 69.5 3.93 | 76.0 3.71 | 61.8 3.80 3.76 | | |
| GlcN$_I$ A | | 92.6 5.75 | 54.8 3.45 | 70.2 3.93 | 70.5 3.51 | 73.4 4.13 | 69.7 4.28 3.89 | | |
| GlcN$_{II}$ H | | 99.7 4.88 | 56.3 3.17 | 72.2 3.90 | 75.0 3.94 | 74.6 3.78 | 63.4 3.81 3.64 | | |
| Kdo K | | | 99.7 | 34.5 2.37 2.13 | 70.8 4.61 | 72.7 4.32 | 73.2 3.87 | 69.9 3.78 | 64.2 3.94 3.73 |

Note:

Measured at 600 MHz ($^1$H) in D$_2$O, 25° C. and pH 3 from HMQC and HMBC data with the CH$_3$ signal of external acetone set at 2.225 ppm for $^1$H NMR and 31.07 ppm for $^{13}$C NMR. Average error of ±0.2 ppm for $\delta_C$ and ±0.02 ppm for $\delta_H$. The minor component for f due to heterogeneity is indicated by f. The CH$_2$ spin systems, (H, H'), are in decreasing order of chemical shifts. For Kdo, H-3 and H-3' are assigned to H-3$_{sq}$ and H-3$_{sx}$.

TABLE 2

NMR data for D-L-heptose and D-D heptose monosaccharides.

| Heptose | $\delta_C$ $\delta_H$ $J_{H,H}$ | C-1 H-1 $J_{1,2}$ | C-2 H-2 $J_{2,3}$ | C-3 H-3 $J_{3,4}$ | C-4 H-4 $J_{4,5}$ | C-5 H-5 $J_{5,6}$ | C-6 H-6 $J_{6,7}$ | C-7 H-7 $J_{6,7'}$ | H-7' $J_{7,7'}$ |
|---|---|---|---|---|---|---|---|---|---|
| D-α-L- | | 95.00$^a$ 5.166 1.8 | 71.45 3.914 3.1 | 71.36 3.838 10.0 | 67.05 3.845 9.7 | 71.81 3.749 1.6 | 69.63 4.024 7.3 | 63.84 3.689 5.5 | 3.652 −11.7 |
| D-β-L- | | 94.74$^b$ 4.866 1.0 | 72.02 3.927 3.2 | 74.09 3.649 10.0 | 66.69 3.788 9.8 | 75.43 3.329 1.8 | 69.53 3.98 7.5 | 63.57 3.713 5.8 | 3.695 −11.7 |
| D-α-D- | | 94.86$^a$ 5.151 1.8 | 71.32 3.905 3.4 | 71.38 3.812 9.4 | 68.35 3.756 10.1 | 73.42 3.865 3.2 | 72.72 4.018 3.3 | 62.75 3.797 7.6 | 3.708 −12.0 |
| D-β-D- | | 94.79$^b$ 4.851 1.1 | 71.84 3.921 3.3 | 74.11 3.622 9.5 | 68.16 3.682 9.9 | 77.22 3.423 3.3 | 72.623 4.025 3.4 | 62.58 3.788 7.4 | 3.725 −12.0 |

Note:

Measured at 600 MHz ($^1$H) in D$_2$O at 25° C. from $^1$H spin simulations and from the $^{13}$C spectra (150 MHz) with the CH$_3$ signal of acetone set at 2.225 ppm for $^1$H NMR and 31.07 ppm for $^{13}$C NMR. $\delta_C$ and $\delta_H$ are in ppm with an average error of ±0.005 ppm for $\delta_C$ and ±0.003 ppm for $\delta_H$. $J_{H,H}$ values are in Hz with an average error of ±0.2 Hz. H-7 and H-7' are in decreasing g order of chemical shifts.

$^a$$J_{C1,H1}$ = 171 ± 1 Hz.

$^b$$J_{C1,H1}$ = 160 ± 1 Hz measured from the undecoupled $^{13}$C NMR spectrum.

TABLE 3

HMBC and NOE data for A1 and distances from a minimum energy conformer of the core heptasaccharide shown in FIG. 8.

| Linkage | HMBC H-1-C-x | Intra-residue NOE | r (Å) | Inter-residue NOE | r (Å) | Long range NOE | r (Å) |
|---|---|---|---|---|---|---|---|
| b(1-3)d | b1-d3 | b1-b2 | 2.6 | b1-d3 | 2.6 | b1-e5 | 3.3 |
|  |  | b5-b3 | 2.5 | b1-d4 | 3.7 | b1-e7 | 2.9 |
|  |  | b5-b6 | 2.4 | b5-d2 | 2.3 | b1-e7' | 2.6 |
|  |  |  |  | k3ax-d5 | 3.2 | b1-i2 | 2.2 |
| c(1-6)d | c1-d6 | c1-c2 | 2.4 | c1-d6 | 2.0 | c1-i1 | 2.4 |
| d(1-5)k |  | d1-d2 | 2.6 | d1-k5 | 2.2 |  |  |
|  |  |  |  | d1-k7 | 2.9 |  |  |
| e(1-2)b | e1-b2 | e1-e2 | 2.6 | e1-b2 | 2.1 | e1-g2 | 4.2 |
|  |  |  |  | e1-b1 | 2.8 | e1-g3 | 2.3 |
|  |  |  |  |  |  | e1-i4 | 2.0 |
| f(1-6)g[a] | f1-g6 | f1-f2 | 2.6 | f1-g6 | 2.5 |  |  |
|  |  |  |  | f1-g5 | 2.6 |  |  |
| g(1-6)i | g1-i6 | g1-g2 | 2.6 | g1-i6 | 2.6 | g1-b2 | 4.2 |
|  |  | g5-g3 | 2.6 | g1-i6' | 2.6 | g1-b3 | 4.9 |
|  |  | g5-g6 | 2.5 | g5-i6 | 3.0 |  |  |
| i(1-4)d | i1-d4 | i1-i3 | 2.6 | i1-d4 | 2.8 | i1-c1 | 2.4 |
|  |  | i1-i5 | 2.4 | i1-d6 | 2.1 |  |  |
| j(1-7)f[a] | j1-f7 | j1-j2 | 3.1 | j1-f7 | 2.7 |  |  |
|  |  | j1-j3 | 2.7 | j1-f7' | 2.5 |  |  |
|  |  | j1-j5 | 2.4 |  |  |  |  |

[a]For the j and f residues in the Gal-(1-7)-Hep$_{IV}$-(1-6)-Hep$_{IV}$ sequence (j-f-g), the average distances from MMC calculations are given.

Example 2

This Example forms the basis of a publication in Carbohydr. Res. 339: 1973 (2004). Investigation of *A. pleuropneumoniae* Serotypes 5a, b, 2 and 1.

Sugar analysis of the column-fractionated LPS revealed glucose (Glc), galactose (Gal), N-acetyl-glucosamine (GlcNAc), D-glycero-D-manno-heptose (DD-Hep), and L-glycero-D-manno-heptose (LD-Hep) in the approximate ratio of 2:1.5:1:2:3 respectively. The core OS was purified following gel filtration chromatography fractionation of the acid hydrolysate as described in the materials and methods and a fraction enriched in core OS and relatively free from O-antigen was obtained and subjected to sugar analysis which revealed; Glc, Gal, DD-Hep, and LD-Hep in the ratio of 2:1:2:3 respectively. As the capsular polysaccharide of serotype 5b contains N-acetyl-D-glucosamine and a ketose residue we suspected that the LPS had some capsule (CPS) contamination and that the fractionated core OS sample was devoid of CPS due to the sensitivity of the ketosidic bond in the CPS to the acid hydrolysis conditions employed to obtain the core OS. Additionally the relatively low amount of galactose, the only O-antigen residue, suggested that the fraction examined was primarily core OS without significant O-antigen extension.

LPS-OH was prepared and fractionated by gel filtration chromatography. A fraction eluting at a volume consistent with containing a low proportion of O-antigen was analysed by CE-ES-MS (Example 2, Table 1). A simple mass spectrum was observed corresponding to a molecule of 2537 amu consistent with a composition of 2Hex, 5Hep, Kdo, P, Lipid A-OH. CE-MS/MS analysis (data not shown) on the doubly charged ion, m/z 1268, gave two singly charged peaks at m/z 951 and 1584, confirming the size of the O-deacylated lipid A as 952 amu and the core OS as 1584. The O-deacylated lipid A species (952 amu) consists of a disaccharide of N-acylated (3-OH C 14:0) glucosamine residues, each residue being substituted with a phosphate molecule. ES-MS and CE-ES-MS analyses of the fractionated OS sample revealed a mass of 1505 Da, consistent with a composition of 2Hex, 5Hep, Kdo (Ex. 2, Table 1) (FIG. 11). The CE-ES-MS spectrum of a later eluting core OS fraction had a mass of 1562, 57 amu higher than the major glycoform (Ex. 2, Table 1). This mass corresponds to the amino acid glycine as has been recently observed in the LPS of *Neisseria meningitidis* and *Haemophilus influenzae*. CE-ES-MS/MS analyses located this glycine residue on the second heptose residue (Hep II) from the Kdo molecule (data not shown).

Methylation analysis was performed on the core OS in order to determine the linkage pattern of the molecule. Analysis on a fraction corresponding to core OS alone revealed the presence of approximately equimolar amounts of terminal Glc, 6-substituted Glc, terminal DD-Hep, terminal LD-Hep, 6-substituted DD-Hep, 2-substituted LD-Hep and 3,4,6-trisubstituted LD-Hep. Analysis of an earlier fraction of the OS, containing predominantly O-antigen, revealed the presence of 6-substituted Gal (the O-antigenic component) confirming the linkage pattern of the O-antigen.

In order to elucidate the exact locations and linkage patterns of the OS, NMR studies were performed on the OS fraction enriched for the absence of O-antigen (FIG. 12a). The assignment of $^1$H resonances of the OS was achieved by COSY and TOCSY experiments. FIG. 13 shows a series of selective 1D-TOCSY experiments from the anomeric $^1$H-resonance of each residue in the OS. In the course of the NMR analysis it became apparent that the Ap 5a OS was structurally related to the structure of *Mannheimia haemolytica* core OS and assignment of the Ap 5a OS spectra was aided by reference to this $^1$H NMR data (Example 2, Table 2).

In the selective spectra of the Ap 5a OS, spin systems arising from heptose residues (Hep I, (FIG. 13a), Hep II, (FIG. 13b), Hep III, (FIG. 13c), Hep IV (FIG. 13d) and Hep V, (FIG. 13e),) were readily identified from their anomeric $^1$H resonances at 5.11 (Hep I), 5.70 (Hep II), 5.17 (Hep III), 4.96 (Hep IV) and 5.03 (Hep V) ppm coupled with the appearance of their spin systems which pointed to manno-pyranosyl ring systems. The heterogeneity observed for the anomeric protons of Hep I and Hep II (FIG. 12a) was due to rearrangements of the Kdo residue on acid hydrolysis. The remaining residue in the α-anomeric region at 5.21 ppm (Glc II) was determined to be gluco-pyranose sugar, based upon the appearance of its spin system (FIG. 13f). The remainder of the anomeric resonances in the low field region (4.45-6.00 ppm) of the spectrum were all attributable to β-linked residues by virtue of their anomeric $^1$H resonances and in the case of resolved residues their high $J_{1,2}$ (~8 Hz) coupling constants. One of the resonances at 4.66 ppm (Glc I) was assigned to the gluco-configuration from the appearance of the spin system (FIG. 13g). The remaining resonance in the low-field region at 4.49 (Gal I) ppm was assigned to a galacto-pyranosyl residue from the appearance of the characteristic spin system to the H-4 resonance in a TOCSY experiment (FIG. 13h). The Kdo spin system was also accessed in this experiment as the H-6 $^1$H resonance of Kdo at 4.48 ppm was also irradiated and revealed the H-4 and H-5 $^1$H resonances at 4.10 and 4.21 ppm respectively. However the spin system of Kdo was difficult to completely determine due to rearrangements of the Kdo residue on core hydrolysis and the very low intensity levels of the methylene H-3 protons probably due to deuterium exchange. However, the spin system was further assigned in another 1-D TOCSY experiment from the H-3 axial proton at 1.92 ppm, revealing $^1$H resonances for the equatorial proton at 2.08 ppm and the H-4 proton at 4.10 ppm (data not shown).

The sequence of the glycosyl residues in the OS was determined from the inter-residue $^1$H-1H NOE measurements between anomeric and aglyconic protons on adjacent glycosyl residues and confirmed and extended the methylation analysis data. The linkage pattern for the Ap 5a OS was determined in this way (FIG. 14) (Example 2, Table 2). Thus the occurrence of intense transglycosidic NOE connectivities between the proton pairs Hep III H-1 and Hep II H-2 (FIG. 14a) and Hep II H-1 and Hep I H-3 (FIG. 14b) established the sequence and points of attachment of the three LD-heptose residues. This linkage pattern is commonly encountered in the inner core OS from M. haemolytica and H. influenzae. Furthermore, inter-residue NOE's between the anomeric protons Hep III H-1 and Hep II H-1 provided confirmation of the 1,2-linkage. Examination of NOE connectivities from H-1 of Glc I illustrated that this glucose residue was connected to Hep I at the 4-position by virtue of inter-residue NOE's to Hep I H-4 and Hep I H-6 (FIG. 14c). The appearance of an inter-residue NOE to H-6 is a common occurrence for 4-substituted heptose residues. The occurrence of a long range NOE connectivity between H-1 of Glc I and H-1 of Glc II suggested that the α-configured glucose residue (Glc II) was substituting Hep I at the 6-position as has been observed previously for the OS from M. haemolytica. Examination of NOE connectivities from H-1 of Glc II confirmed that this glucose residue was connected to Hep I at the 6-position by virtue of inter-residue NOE's to Hep I H-6 (FIG. 14d). Similarly to Glc I a long-range NOE connectivity was observed between the anomeric $^1$H resonances of Glc I and Glc II. The linkage positions of the remaining heptose residues (Hep IV and Hep V) were deduced as follows. Examination of NOE connectivities from H-1 of Hep IV revealed that this heptose residue was connected to Glc I at the 6-position by virtue of inter-residue NOE's to Glc I H-6 and H-6' (FIG. 14e). Finally, Hep V was determined to be substituting Hep IV at the 6-position by virtue of a NOE connectivity from Hep V H-1 to Hep IV H-6 (FIG. 14f). Additionally, NMR analysis of OS from serotype 5a enabled the point of attachment of the O-chain galactose residue to be identified. A fraction that contained just one galactose residue was utilised for this purpose. NOE connectivities from the anomeric $^1$H-resonance included intra-connectivities to H-3 and H-5 at 3.68 and 3.93 ppm and an inter-connectivity to 3.93 ppm (FIG. 15a). Selective 1-D experiments were then utilised to identify the spin-system of the proton resonance at 3.93 ppm. A 1D NOESY-TOCSY experiment from the H-1 proton of Gal I in the NOESY step followed by selective excitation of the resonance at 3.93 ppm in the TOCSY step confirmed the connectivity of the resonance at 3.93 ppm to a resonance at 4.06 ppm (FIG. 15b). A 1-D TOCSY experiment from the anomeric proton resonance of the Hep III residue at 5.16 ppm utilising a 150 ms mixing time revealed the H-4 and H-5 proton resonances of this spin-system at 3.82 ppm (FIG. 13c). This resonance was then selectively irradiated in a NOESY step that revealed the Hep III H-6 resonance at 4.06 ppm thus confirming the 7-position of the Hep III residue as the point of attachment of the O-chain (FIG. 15c). Confirmatory data was obtained from a $^{13}$C-1H HMBC experiment which identified a cross-peak from the anomeric 1H-resonance of the O-chain galactose residue at 4.48 ppm that correlated with a $^{13}$C-resonance at 70.3 ppm (FIG. 15d), which in a $^{13}$C—$^1$H HSQC experiment was found to correlate to the proton resonance at 3.93 ppm (FIG. 15e), which appeared as positive peak in a $^{13}$C—$^1$H HSQC spectrum indicative of a —CH$_2$— group, confirming the 7-position of a heptose residue as the point of O-chain attachment. This conclusion was confirmed by methylation analysis on a fraction that contained just one galactose residue that indicated the presence of a 7-substituted LD-Hep residue; this permethylated alditol acetate derivate was not observed following methylation analysis of a core OS fraction devoid of O-chain.

Investigation of A. pleuropneumoniae Serotype 5b

All analyses of LPS, LPS-OH and OS from serotype 5b were identical or very similar to the previous analyses described for serotype 5a (Example 2, Tables 1 and 2; FIG. 12b).

Investigation of A. pleuropneumoniae Serotype 2

Sugar analysis of the intact LPS revealed the presence of Glc, DD-Hep, LD-Hep, Rha, Gal, GlcNAc and GalNAc in the approximate ratio 8:2:2:1:2:1:2 consistent with the presence of O-antigen and capsular polysaccharide in this material. Sugar analysis of the fractionated acid hydrolysate revealed the presence of Glc, Rha, Gal and GalNAc in an early eluting fraction, in the approximate ratio 2:1:1:1 consistent with a fraction enriched for O-antigen. A later fraction enriched for the absence of O-antigen revealed the presence of only Glc, DD-Hep and LD-Hep in the approximate ratio of 3:2:3 consistent with the absence of O-antigen from this core OS fraction.

LPS-OH was prepared and fractionated by gel filtration chromatography. A fraction eluting at a volume consistent with containing a low proportion of O-antigen was analysed by CE-ES-MS in the negative ion mode (Example 2, Table 1). A simple mass spectrum was observed corresponding to a molecule of 2700 amu consistent with a composition of 3Hex, 5Hep, Kdo, P, Lipid A-OH with minor amounts of a second molecule indicated with a mass of 80 amu lower, consistent with the absence of a phosphate residue. CE-MS/MS analysis (data not shown) on the triply charged ion m/z 899 gave a singly charged peak at m/z 951 confirming the size of the O-deacylated lipid A as 952 amu for the major molecule of mass 2700 amu. CE-ES-MS analyses of the fractionated core OS sample enriched for absence of the O-antigen revealed a mass of 1667 Da, consistent with a composition of 3Hex, 5Hep, Kdo (Example 2, Table 1). Mass spectrometric analyses therefore indicated that the core OS of serotype 2 contained an additional glucose residue than the core OS from serotypes 5a and 5b.

Methylation analysis of the core OS fraction enriched for absence of O-antigen revealed the presence of terminal Glc, 6-substituted Glc, terminal DD-Hep, terminal LD-Hep, 2-substituted DD-Hep, 2-substituted LD-Hep, 4,6-di-substituted DD-Hep, and 3,4,6-tri-substituted LD-Hep in the approximate ratio 6:3:3:2:1:2:3:2. The main discrepancy between the methylation data for the serotype 2 and 5b OS was the replacement of the mono-6-substituted DD-Hep with a 4,6-di-substituted DD-Hep tentatively identifying the 4-position of the internal DD-Hep residue as the point of attachment of the additional glucose residue. The ratio of terminal glucose residues, identified by methylation analyses, between serotypes 2 and 5b is also consistent with the presence of an additional terminal glucose residue in the core OS of serotype 2.

$^1$H-NMR data (Example 2, Table 2, (FIG. 12c)) corroborated the mass spectrometric and methylation analyses data, confirming that the core OS of serotype 2 was identical to that found for serotype 5b but with the identification of an additional terminal α-configured glucose residue (Glc III). NOE data defined the point of attachment of the Glc III residue at the 4-position of Hep IV by virtue of an inter NOE connectivity from the $^1$H resonance of the anomeric proton of Glc III at 4.53 ppm to the $^1$H resonance of the 4 position of Hep IV at 3.96 ppm (data not shown). A NOE connectivity was also observed to the 6-position of Hep IV as has been observed previously for 4-substituted heptose residues.

Investigation of *A. pleuropneumoniae* Serotype 1

Sugar analysis of the column-fractionated LPS revealed the presence of Rha, Glc, Gal, GlcNAc, DD-Hep and LD-Hep in an approximate ratio of 1:3:1:0.5:1:3. The identification of Rha and GlcNAc suggested some O-antigenic components were still present in this fraction. Sugar analysis of a core OS fraction enriched for absence of O-antigen revealed Glc, Gal, DD-Hep, and LD-Hep in the ratio 2:1.5:1:3. Sugar analysis on earlier fractions containing full length O-antigen revealed Rha, Glc and GlcNAc in an approximate ratio of 2:1:1 consistent with the published structure for the O-antigen of this serotype.

LPS-OH was prepared and fractionated by gel filtration chromatography. A fraction eluting at a volume consistent with containing a low proportion of O-antigen was analysed by ES-MS and CE-ES-MS in the negative ion mode (Example 2, Table 1). A simple mass spectrum was observed corresponding to a molecule of 2874 amu consistent with a composition of 4Hex, HexNAc, 4Hep, Kdo, P, Lipid A-OH with minor amounts of a second molecule indicated with a mass of 123 amu higher, consistent with the presence of an additional phosphoethanolamine residue and a third molecule with a mass of 80 amu lower, consistent with the absence of a phosphate residue. CE-MS/MS analysis (data not shown) on the triply charged ion m/z 957 gave a singly charged peak at m/z 951 confirming the size of the O-deacylated lipid A as 952 amu for the major molecule of mass 2874 amu and a doubly charged ion at m/z 959 corresponding to the core OS. ES-MS and CE-ES-MS analyses on several core OS fractions enriched for absence of the O-antigen revealed a mass of 1840 Da, consistent with a composition of 4Hex, HexNAc, 4Hep, Kdo (Example 2, Table 1). CE-MS/MS analysis in positive ion mode on the doubly charged ion at m/z 930 revealed singly charged ions consistent with the presence of the following groups of residues in serotype 1 core OS including, HexNAc m/z 204, Hex-Hex-HexNAc m/z 528, Hep-Hex-Hex-HexNAc m/z 720 (FIG. 16). Mass spectrometric analyses therefore indicated that the core OS of serotype 1 contained one DD-Hep residue less than the core OS from serotypes 5a and 5b, but contained and an additional 2 Hex's and a HexNAc residue. However the absence of evidence for HexNAc in sugar analysis of core OS enriched for the absence of O-antigen was initially confusing.

Methylation analysis on a core OS fraction enriched for absence of O-antigen revealed the presence of terminal Glc, 6-substituted Glc, 3-substituted Gal, terminal LD-Hep, 4,6-disubstituted Gal, 4-substituted DD-Hep, 2-substituted LD-Hep and 3,4,6-trisubstituted LD-Hep in approximately equimolar amounts. Once again the absence of any evidence for a HexNAc residue was perplexing.

The mass spectrometric, sugar and methylation analyses data were therefore consistent with the inner core structure observed for serotypes 2, 5a and 5b and $^1$H NMR data corroborated these inferences (FIG. 12d) (Example 2, Table 2). $^1$H NMR data also enabled identification of the additional core OS residues not present in the core OS from serotypes 2, 5a and 5b. An α-configured galactose residue (Gal II) was assigned at 5.18 ppm by virtue of a characteristic spin system to the H-4 $^1$H resonance in a TOCSY experiment. A β-configured galactose residue (Gal I) was identified at 4.55 ppm by virtue of the $^1$H resonance of its anomeric proton and from the appearance of its characteristic spin system. An α-configured N-acetyl hexosamine residue (HexNAc) was assigned at 4.88 ppm by virtue of the $^1$H resonance of its H-2 proton at 4.34 ppm correlating to a $^{13}$C chemical shift of 52.6 ppm in a $^{13}$C—$^1$H HSQC experiment (FIG. 17a). The $^{13}$C chemical shift being consistent with a nitrogen substituted carbon atom. However it was very difficult to access the spin system of this HexNAc residue beyond the H-2 proton, and the chemical shift of the H-2 proton seemed to be of considerably low-field. Inter-residue NOE connectivities established the linkage pattern between the anomeric proton of the Gal I residue at 4.55 ppm and the 4-position of Hep IV at 3.94 ppm. In a similar way a NOE connectivity between the anomeric proton of the Gal II at 5.18 ppm and the 3-position of the Gal I residue at 3.79 ppm established this linkage. However, inter-residue NOE connectivities between the anomeric proton of the HexNAc residue at 4.88 ppm and the 4-position of the Gal II residue at 4.25 ppm and the 6-position of this residue at 4.12 and 4.01 ppm suggested that the HexNAc residue was substituting the Gal II residue at both the 4 and 6-positions, consistent with the methylation analysis data but nonetheless confusing (FIG. 17c). FAB-MS of the methylated OS gave further insight in to the sequence of the sugars of this portion of the OS. The m/z of the A-type primary glycosyl oxonium ions and secondary ions (loss of methanol) observed were as follows, 464→432 (Hex, HexNAc)$^+$, 668→636 (Hex$_2$, Hex-NAc)$^+$, 916→884 (Hex$_2$, HexNAc, Hep)$^+$, 1120→1088 (Hex$_3$, HexNAc, Hep)$^+$, 1368 (Hex$_3$, HexNAc, Hep$_2$)$^+$, 1572→1540 (Hex$_4$, HexNAc, Hep$_2$)$^+$, and 1865→1833 (Hex$_3$, HexNAc, Hep$_4$)$^+$. This FAB data was consistent with the NOE and positive ion CE-ES-MS/MS data, but the lack of evidence for a terminal HexNAc residue was confusing but in agreement with the sugar analysis and methylation analysis data. The lack of definitive data for the HexNAc residue therefore prompted more sophisticated NMR studies to attempt to identify the nature of the presumed HexNAc residue and confirm the linkage pattern for this region of the core OS from serotype 1.

A series of selective 1D experiments from the H-1 $^1$H-resonance of the HexNAc residue at 4.88 ppm with mixing times ranging from 30-150 ms revealed the H-2 $^1$H-resonance at 4.34 ppm and weak signals assigned to H-3 at 4.13 ppm and H-4 at 3.36 ppm. To confirm these inferences and complete assignment of this HexNAc residue further selective experiments were performed. A 1-D TOCSY experiment was obtained from the H-4 $^1$H-resonance at 3.36 ppm, which confirmed the H-2 and H-3 assignments and identified the H-5 and H-6, 6' resonances at 3.93, 3.66 and 3.64 ppm respectively (FIG. 17d). A 1-D NOESY experiment was obtained from the H-2 $^1$H-resonance at 4.34 ppm, which confirmed the H-3 and H-4 assignments (FIG. 17e). A 1-D NOESY experiment was obtained from the H-4 $^1$H-resonance at 3.36 ppm, which confirmed the H-2, H-3, H-5 and H-6, 6' assignments (FIG. 17f). The coupling constants were determined from these experiments and found to be $J_{1,2}$ 4.8 Hz, $J_{2,3}$ 1.0 Hz, $J_{3,4}$ 9.7 Hz, $J_{4,5}$ 1.4 Hz, $J_{5,6}$ 6.5 Hz, $J_{5,6}$ 6.5 Hz and $J_{6,6}$ –12 Hz. A 2D-$^{13}$C—$^1$H-HSQC NMR spectrum was performed (FIG. 17e) which identified the $^{13}$C chemical shifts for the C-1 to C-6 positions on the HexNAc molecule as 101.1 ppm, 52.6 ppm, 68.5 ppm, 70.0 ppm, 70.7 ppm and 64.1 ppm respectively. This data was initially confusing, however a search of an in-house carbohydrate database identified a similar set of data for an open-chain N-acetyl galactosamine residue found in the core OS from *Proteus* species. The identification of an open-chain residue although surprising, was consistent with the sugar, methylation and FAB analysis data as such a residue would be sensitive to the hydrolysis conditions employed for the sugar and methylation analyses and the formation of a glycosyl oxonium ion for the terminal residue, in FAB analysis, would be precluded by the open-chain configuration of this residue.

Structural analysis of the core OS's from the 1, 2, 5a and 5b serotypes was therefore complete and had identified a conserved inner core structure in all strains with different decoration beyond this conserved structure as illustrated in FIG. 18.

Structural analysis of core oligosaccharides from serotypes 1, 2, 5a and 5b representing core types I, II, II and II, revealed a relatively conserved structure. The inner core OS was identical for each strain consisting of a trisaccharide of L-glycero-D-manno-heptose residues linked to a Kdo residue. In each serotype the proximal heptose residue (Hep I) was substituted at the 3-position by the second L-glycero-D-manno-heptose residue (Hep II) of the L-glycero-D-manno-heptose trisaccharide, at the 4-position by a β-glucose residue (Glc I) and at the 6-position by an α-glucose residue (Glc II). A D-glycero-D-manno-heptose residue (Hep IV) was found at the 6-position of the Glc I residue in each strain. A second D-glycero-D-manno-heptose residue (Hep V) substitutes Hep IV at the 6-position in serotypes 2, 5a and 5b. The only difference between serotypes 2 and 5a, 5b was an additional glucose residue linked to the 4-position of the Hep IV residue in serotype 2. There was a striking similarity between these OS structures and that found previously for the OS from *M. haemolytica* serotype A1. The only difference between the 5b, 5a OS structures and *M. haemolytica* serotype A1 core OS was the absence of the additional terminal galactose residue at Hep V found in *M. haemolytica* A1 OS. In serotype 1 there is no Hep V residue, Hep IV is alternatively substituted at the 4-position by a trisaccharide of α-GaloNAc-(1-4,6)-α-Gal-(1-3)-β-Gal-, wherein the HexNAc residue was of the rarely encountered open-chain configuration. The structural arrangement identified as the initial trisaccharide extension from Hep I in serotype 1 is identical to that previously found for *Haemophilus ducreyi* strain 2665 LPS, however the serotype 1 LPS has a different extension beyond the Gal I residue when compared to the DD-Hep interrupted lacto-N-neotetraose structure found in *H. ducreyi*.

A structural explanation has therefore been attained for the SDS-PAGE observation of two core types in Ap LPS. Serotypes 2, 5a and 5b of core type II have very similar LPS structures differing only by an additional glucose residue in serotype 2. However serotype 1 of core type I has lost a DD-Hep residue, but gained two hexoses and a novel open chain HexNAc residue. To investigate if this novel open chain HexNAc residue was found in other core type I serotypes LPS from serotypes 6, 9 and 11 were examined. Evidence for the open chain HexNAc was seen by both MS and NMR studies (data not shown) in serotypes 9 and 11 but not in serotype 6. Closer examination of SDS-PAGE profiles that had been used to categorise core types revealed that serotype 6 had both LPS migration patterns of the two core types and therefore it is possible that the serotype 6 strain we examined only had a core type II profile.

Few data are available on the genetic control of LPS biosynthesis in Ap. A recent paper by Galarneau et al identified three genes following transposon mutagenesis that appeared to be involved in the biosynthesis of the core OS region of Ap serotype 1 LPS. These genes were tentatively identified as glycosyltransferases based on homology to other glycosyltransferases. The three genes were postulated to be lbgB, an α-1,6-DD-heptosyltransferase, lbgA a β-1,4-galactosyltransferase and a hexose or N-acetyl-hexosamine transferase. The former two genes, lbgAB, are consistent with the structure identified here in serotype 1 core OS, and have the same locus arrangement as found in *H. ducreyi* LPS. Another paper by Rioux et al identified a gene galU, the structural gene for UTP-α-D-glucose-1-phosphate uridyltransferase. SDS-PAGE of LPS isolated from a serotype 1 Ap galU mutant strain had an altered migration pattern of the core-lipid A region, and this mutant strain was less adherent to pig tracheal cells and was less virulent in pigs, suggesting that an alteration in the nature or presentation of the core OS region could have an effect on the virulence of this animal pathogen.

The identification of a novel open chain HexNAc residue was of interest. This structure has only previously been identified in two *Proteus* species and recently in *Shewanella oneidensis* and its significance is unknown. As found in the existing literature, the open chain residue identified here was found to concurrently di-substitute the neighbouring residue at the 4- and 6-positions, so this could be a common arrangement for such residues.

The identification of a DD-Hep residue in the oligosaccharide extension from Hep I has been observed before for several strains including *M. haemolytica, H. ducreyi* and nontypable *H. influenzae*. In *M. haemolytica* two DD-Hep residues were observed, whereas in *H. ducreyi* and *H. influenzae* only one DD-Hep residue was found. In Ap both scenarios exist, with serotypes 2 and 5a, 5b having two DD-Hep residues and serotype 1 having just one DD-Hep residue in the oligosaccharide extension from Hep I. The tri-LD-heptosyl inner core group has also been observed previously in *M. haemolytica, H. ducreyi* and *H. influenzae*. The 3,4,6-trisubstituted Hep I residue found here for all strains of App studied has been observed before in *M. haemolytica* LPS, however *H. ducreyi* LPS only elaborates the 3,4-di-substituted Hep I residue as also found in *H. influenzae*.

The identification of the 7-position of the Hep III residue as the point of attachment of the O-antigen galactose residue in serotype 5a was of interest and consistent with the observation that three variously truncated core oligosaccharide mutants in serotype 1 still elaborated an O-antigen, as the anticipated function of the three mutated gene products would not interfere with the biosynthesis of the inner core LD-heptosyl trisaccharide unit and therefore the acceptor for O-antigen attachment would still be present in the mutant LPS core oligosaccharide.

This study has structurally characterised the core oligosaccharide region of several strains of Ap, representative of the two core types, identifying a conserved inner-core structure and a novel outer-core constituent. This region is known to be involved in adherence of Ap and is therefore implicated in virulence. This study will therefore better enable future studies on the relevance of the structure of the core oligosaccharide region of Ap LPS to the potential virulence of this organism.

Materials and Methods—Example 2

Media and Growth Conditions

Ap serotypes 1 (strain 4074), 2 (strain 4226), 5a (strain K17) and 5b (strain L20) were initially grown overnight on chocolate agar plates at 37° C. and growths were used to inoculate 1 L of brain-heart infusion (BHI) medium supplemented with β NAD (Sigma N-7004) to a final concentration of 5 ug/ml, haemin (Sigma H-2250) to a final concentration of 5 ug/ml and 1% glucose (10 g). Cultures were then incubated at 37° C. at 200 rpm for 6 hours and used to inoculate 23 L BHI medium (supplemented as above) in a 28 L NBS fermenter. The cultures were then grown at 37° C., with 24 $lmin^{-1}$ aeration and stirring at 200 rpm for 18 hours. Cells were killed (2% phenol w/v, for 4 hours) and harvested by using a Sharples continuous centrifuge (~40 g wet weight).

Isolation and Purification of Lipopolysaccharide

The lipopolysaccharide (LPS) was isolated from the dried cell mass by the hot water/phenol method, following washing of the dried cell mass with organic solvents for serotypes 5a and 5b. The aqueous phase was dialyzed against water and lyophilised and in the case of serotype 2 the LPS was isolated from the extensively dialysed phenol phase. The dried sample was dissolved in water to give a 1-2% solution (w/v) and treated with deoxyribonuclease I (DNase) (0.01 mg/ml) and ribonuclease (RNase) (0.01 mg/ml) for 3 hrs at 37° C., then treated with proteinase K (0.01 mg/ml) for 3 hrs. The dialysed, dried sample was dissolved in water to make a 1% solution and ultracentrifuged (5 hrs, 100,000 g). The LPS pellet was redissolved in water and lyophilised, purified by gel-filtration on a column of Bio-Gel P-2 (1 cm×100 cm) with water as eluent and fractions containing sugar were pooled and lyophilised. Purified LPS was treated with anhydrous hydrazine with stirring at 37° C. for 1 hr to prepare O-deacylated LPS (LPS-OH). The reaction was cooled in an ice bath and gradually cold acetone (−70° C., 5 vols.) was added to destroy excess hydrazine and the precipitated LPS-OH was isolated by centrifugation. The sample was then purified down a Bio-Gel P-2 column as described above. The core oligosaccharide (OS) was isolated by treating the purified LPS with 1% acetic acid (10 mgml$^{-1}$, 100° C., 1.5 hr) with subsequent removal of the insoluble lipid A by centrifugation (5000 g). The lyophilised OS was further purified down a Bio-Gel P-2 column with individual fractions lyophilised.

Analytical Methods

Sugars were determined as their alditol acetate derivatives by GLC-MS. Samples were hydrolysed for 4 hrs using 4 M trifluoroacetic acid at 100° C. The hydrolysate was reduced (NaBD$_4$) overnight in H$_2$O and acetylated with acetic anhydride at 100° C. for 2 h using residual sodium acetate as catalyst. The GLC-MS was equipped with a 30 M DB-17 capillary column (180° C. to 260° C. at 3.5° C./min) and MS was performed in the electron impact mode on a Varian Saturn II mass spectrometer. Methylation analysis was carried out by the NaOH/DMSO/methyl iodide procedure and analysed by GLC-MS as above.

Mass Spectrometry

ESI-MS was performed in the negative ion mode on a VG Quattro Mass Spectrometer (Micromass, Manchester, U.K.) by direct infusion of samples in 25% aqueous acetonitrile containing 0.5% acetic acid. Capillary electrophoresis (CE)-ESI-MS was performed on a crystal Model 310 (CE) instrument (AYI Unicam) coupled to an API 3000 mass spectrometer (Perkin-Elmer/Sciex) via a microIonspray interface. A sheath solution (isopropanol-methanol, 2:1) was delivered at a flow rate of 1 μL/min to a low dead volume tee (250 μm i.d., Chromatographic Specialties). All aqueous solutions were filtered through a 0.45-μm filter (Millipore) before use. An electrospray stainless steel needle (27 gauge) was butted against the low dead volume tee and enabled the delivery of the sheath solution to the end of the capillary column. The separations were obtained on about 90 cm length bare fused-silica capillary using 10 mM ammonium acetate/ammonium hydroxide in deionized water, pH 9.0, containing 5% methanol. A voltage of 20 kV was typically applied at the injection. The outlet of the capillary was tapered to ca. 15 μm i.d. using a laser puller (Sutter Instruments). Mass spectra were acquired with dwell times of 3.0 ms per step of 1 m/z unit in full-mass scan mode. The MS/MS data were acquired with dwell times of 1.0 ms per step of 1 m/z unit. Fragment ions formed by collision activation of selected precursor ions with nitrogen in the RF-only quadrupole collision cell, were mass analyzed by scanning the third quadrupole.

Nuclear Magnetic Resonance

NMR experiments were acquired on Varian Inova 400, 500 and 600 MHz spectrometers using a 5 mm or 3 mm triple resonance (1H, $^{13}$C, $^{31}$P) probe. The lyophilised sugar sample was dissolved in 600 μL (5 mm) or 140 μL (3 mm) of 99% D$_2$O. The experiments were performed at 25° C. with suppression of the HOD (deuterated H$_2$O) signal at 4.78 ppm. The methyl resonance of acetone was used as an internal reference at 2.225 ppm for $^1$H spectra and 31.07 ppm for $^{13}$C spectra. Standard homo and heteronuclear correlated 2D pulse sequences from Varian, COSY, TOCSY, NOESY, $^{13}$C-$^1$H HSQC, $^{13}$C—$^1$H HSQC-TOCSY and $^{13}$C—$^1$H HMBC, were used for general assignments. Selective 1D-TOCSY with a Z-filter and 1D-NOESY experiments and 1-D analogues of 3-D NOESY-TOCSY and TOCSY-NOESY experiments were performed for complete residue assignment and for the determination of $^1$H—$^1$H nuclear Overhauser enhancements. The pulse width of the selective pulses was 30-80 Hz. Mixing times of 30-150 ms were used for the 1D-TOCSY experiments. Mixing times of 400-800 ms were used for the 1D-NOESY experiments.

TABLE 1

Negative ion ES-MS and CE-ES-MS data and proposed compositions of O-deacylated LPS and core oligosaccharides from *A. pleuropneumoniae* serotypes 1, 2, 5a and 5b. Average mass units were used for calculation of molecular weight based on proposed composition as follows: Hex, 162.15; HexNAc, 203.19; Hep, 192.17; Kdo, 220.18; P, 79.98; PEtn, 123.05; Gly, 57.05. O-deacylated lipid A (Lipid A-OH) is 952.00.

| | Observed Ions (m/z) | | Molecular Mass (Da) | | |
|---|---|---|---|---|---|
| Serotype | $(M - 2H)^{2-}$ | $(M - 3H)^{3-}$ | Observed | Calculated | Proposed Composition |
| 1 | 1396 | 930 | 2794 | 2792.7 | HexNAc, 4Hex, 4Hep, Kdo, Lipid A-OH |
| O-deac | 1436 | 957 | 2874 | 2872.6 | HexNAc, 4Hex, 4Hep, Kdo, P, Lipid A-OH |
| | 1497 | 998 | 2997 | 2995.7 | HexNAc, 4Hex, 4Hep, Kdo, P, PEtn, Lipid A-OH |
| Core OS | 919 | — | 1840 | 1840.7 | HexNAc, 4Hex, 4Hep, aKdo$^a$ |
| | 928 | | 1858 | 1858.7 | HexNAc, 4Hex, 4Hep, Kdo |
| 2 | 1309 | 872 | 2620 | 2620.5 | 3Hex, 5Hep, Kdo, Lipid A-OH |
| O-deac | 1349 | 899 | 2700 | 2699.5 | 3Hex, 5Hep, Kdo, P, Lipid A-OH |
| Core OS | 832 | — | 1667 | 1667.5 | 3Hex, 5Hep, Kdo |
| 5a O-deac | 1268 | 845 | 2537 | 2537.4 | 2Hex, 5Hep, Kdo, P, Lipid A-OH |

TABLE 1-continued

Negative ion ES-MS and CE-ES-MS data and proposed compositions of O-deacylated LPS and core oligosaccharides from *A. pleuropneumoniae* serotypes 1, 2, 5a and 5b. Average mass units were used for calculation of molecular weight based on proposed composition as follows: Hex, 162.15; HexNAc, 203.19; Hep, 192.17; Kdo, 220.18; P, 79.98; PEtn, 123.05; Gly, 57.05.
O-deacylated lipid A (Lipid A-OH) is 952.00.

| Serotype | Observed Ions (m/z) $(M - 2H)^{2-}$ | $(M - 3H)^{3-}$ | Molecular Mass (Da) Observed | Calculated | Proposed Composition |
|---|---|---|---|---|---|
| Core OS | 752 | | 1505 | 1505.3 | 2Hex, 5Hep, Kdo |
| | 780 | | 1562 | 1562.3 | 2Hex, 5Hep, Kdo, Gly |
| 5b O-deac | 1268 | 845 | 2537 | 2537.4 | 2Hex, 5Hep, Kdo, P, Lipid A-OH |
| Core OS | 752 | — | 1505 | 1505.3 | 2Hex, 5Hep, Kdo |
| | 780 | | 1562 | 1562.3 | 2Hex, 5Hep, Kdo, Gly |

[a] The major ion corresponded to the molecular ion - 18 (loss of $H_2O$).

TABLE 2

$^1$H- and $^{13}$C-NMR chemical shifts for the core OS from *Actinobacillus pleuropneumoniae* serotypes 1, 2, 5a and 5b.

| | H-1 | H-2 | H-3 | H-4 | H-5 | H-6 | H-7 | NOE's Inter | Intra | Long Range |
|---|---|---|---|---|---|---|---|---|---|---|
| Inner Core[a] Serotypes 1, 2, 5a, 5b | | | | | | | | | | |
| Kdo (k) | — | — | 2.08 1.92 | 4.10 | 4.21 | 4.48 | nd | | | |
| Hep-I (a) | 5.11 (98.9) | 4.01 (71.2) | 3.97 (73.7) | 4.21 (74.7) | 3.79 (72.6) | 4.13 (80.3) | 3.88 3.73 (62.9) | 4.20 Kdo H-5 | 4.01 H-2 | |
| Hep-I (A) | 5.37 (101.3) | 4.08 (71.2) | 3.95 (73.5) | 4.22 (74.6) | 3.78 (72.6) | 4.13 (80.3) | 3.88 3.73 (62.9) | nd | 4.00 H-2 | |
| Hep-II (b) | 5.70 (100.2) | 4.19 (80.5) | 3.87 (70.7) | 3.89 (67.5) | 3.55 (72.7) | 4.04 (70.3) | 3.76 3.74 (64.2) | 5.15 Hep III H-1 3.97 Hep I H-3 | 4.19 H-2 3.87 H-3 | 3.79 Hep I H-5 3.82 Hep III H-5 3.77 Hep III H-7a 3.56 Glc I H-2 |
| Hep-III[b] (c) | 5.17 (102.3) | 4.00 (71.5) | 3.88 (71.6) | 3.82 (67.1) | 3.82 (72.4) | 4.06 (70.2) | 3.93 3.93 (70.3) | 5.70 Hep II H-1 4.19 Hep II H-2 | 4.00 H-2 | 4.08 Hep IV H-2 3.80 Hep IV H-3 3.63 Glc I H-4 |
| Hep-III[c] (c) | 5.17 (102.3) | 4.00 (71.5) | 3.88 (71.6) | 3.82 (67.1) | 3.82 (72.4) | 4.04 (70.2) | 3.77 3.62 (64.6) | 5.70 Hep II H-1 4.19 Hep II H-2 | 4.00 H-2 | 4.08 Hep IV H-2 3.80 Hep IV H-3 3.63 Glc I H-4 |
| β-Glc (Glc-I) (d) | 4.66 (104.0) | 3.56 (74.1) | 3.43 (77.8) | 3.63 (70.3) | 3.54 (74.5) | 4.06 3.70 (65.5) | — | 4.21 Hep I H-4 4.13 Hep I H-6 | 3.54 H-5 3.43 H-3 | 5.21 Glc II H-1 |
| α-Glc (Glc-II) (e) | 5.21 (102.6) | 3.58 (72.8) | 3.81 (73.8) | 3.59 (69.3) | 3.92 (72.4) | 3.96 3.76 (60.2) | — | 4.13 Hep I H-6 | 3.58 H-2 | 4.66 Glc I H-1 |
| Outer Core Serotypes 5a, 5b | | | | | | | | | | |
| Hep-IV (f) | 4.96 (99.8) | 4.08 (70.5) | 3.80 (71.7) | 3.78 (68.1) | 3.93 (71.9) | 4.13 (77.0) | 3.90 3.80 (61.2) | 4.06 Glc I H-6a 3.70 Glc I H-6b | 4.08 H-2 | |
| Hep-V (g) | 5.03 (99.0) | 3.92 (70.8) | 3.84 (71.5) | 3.79 (68.2) | 3.97 (73.7) | 4.02 (73.1) | 3.79 3.74 (63.0) | 4.13 Hep IV H-6 3.93 Hep IV H-5 | 3.92 H-2 3.97 H-5 | 4.19 Hep II H-2 4.04 Hep II H-6 3.93 Hep IV H-5 |
| β-Gal (Gal-I) (h) | 4.49 (104.2) | 3.55 (71.6) | 3.68 (73.4) | 3.97 (69.5) | 3.93 (74.5) | 3.75 3.61 (65.7) | — | 3.93 Hep III H-7a 3.93 Hep III H-7b | 3.68 H-3 3.93 H-5 | |
| Serotype 2 | | | | | | | | | | |
| Hep-IV | 4.96 (99.5) | 4.13 (70.3) | 3.90 (70.6) | 3.96 (78.0) | 4.05 (70.3) | 4.30 (75.4) | 3.97 3.82 (60.9) | 4.06 Glc I H-6a 3.70 Glc I H-6b | 4.14 H-2 | |
| Hep-V | 5.02 (98.6) | 3.88 (70.7) | 3.82 (71.5) | 3.78 (68.1) | 3.97 (73.9) | 4.00 (73.0) | 3.80 3.74 (62.8) | 4.30 Hep IV H-6 4.05 Hep IV H-5 | 3.88 H-2 | |

TABLE 2-continued $^1$H- and $^{13}$C-NMR chemical shifts for the core OS from
*Actinobacillus pleuropneumoniae* serotypes 1, 2, 5a and 5b.

| | H-1 | H-2 | H-3 | H-4 | H-5 | H-6 | H-7 | NOE's Inter | Intra | Long Range |
|---|---|---|---|---|---|---|---|---|---|---|
| β-Glc (Glc III) | 4.53 (103.4) | 3.33 (74.0) | 3.51 (76.4) | 3.41 (70.4) | 3.51 (77.0) | 3.95 3.74 (61.6) | — | 3.96 Hep IV H-4 4.30 Hep IV H-6 4.05 Hep IV H-5 | 3.51 H-3 3.52 H-5 | |
| Serotype 1 | | | | | | | | | | |
| Hep-IV$^d$ | 4.95 (99.7) | 4.13 (70.2) | 3.94 (70.7) | 3.94 (79.5) | 3.94 (72.9) | 4.17 (66.9) | 3.83 3.80 (61.9) | 4.15 Glc I H-6a 3.74 Glc I H-6b | 4.13 H-2 | |
| β-Gal (Gal-I) | 4.55 (103.9) | 3.67 (70.3) | 3.79 (78.4) | 4.17 (65.9) | 4.17 (71.6) | 3.87 3.75 (62.4) | — | 3.94 Hep IV H-4 | 3.79 H-3 4.17 H-5 | |
| α-Gal (Gal-II) (j) | 5.18 (97.3) | 3.97 (68.8) | 4.06 (68.7) | 4.25 (76.7) | 4.13 (64.2) | 4.12 4.01 (69.5) | — | 3.79 Gal I H-3 | 3.97 H-2 | |
| α-GalNAc Open chain (i) | 4.88 (101.1) | 4.34 (52.6) | 4.13 (68.5) | 3.36 (70.0) | 3.93 (70.7) | 3.66 3.64 (64.1) | — | 4.25 Gal II H-4 4.12 Gal II H-6a 4.01 Gal II H-6b | 4.34 H-2 | |

$^a$Inner core data derived from serotype 5a; letter designation of residues as indicated in parentheses. Chemical shifts from other serotypes inner core residues were virtually identical
$^b$Data for substituted Hep III residue in serotypes 5a and 5b
$^c$Data for terminal Hep III residue of serotypes 1 and 2
$^d$For serotype 1 $^1$H-resonances, Glc I H-6a and H-6b are 4.15 and 3.74 ppm respectively.

Example 3

This Example forms the basis of a publication in Glycobiology. 15: 323 (2005). Investigation of *P. multocida* strain Pm70

Sugar analysis of the purified LPS revealed glucose (Glc), galactose (Gal) and L-glycero-D-manno-heptose (LD-Hep) in the approximate ratio of 4:2:3 respectively. Small amounts of N-acetyl-glucosamine (GlcNAc) and N-acetyl-galactosamine (GalNAc) were also identified and in contrast to other veterinary pathogens recently studied no D-glycero-D-manno-heptose (DD-Hep) was identified (Brisson, et al, 2002; St. Michael et al, 2004). GLC analysis of the core oligosaccharide (OS) derived butyl-glycosides revealed Glc, Gal and GalNAc residues to be present as their D-isomers.

O-deacylated LPS (LPS-OH) was prepared and fractionated by gel filtration chromatography and analysed by CE-MS (Example 3, Table 1). A simple mass spectrum was observed with one major triply charged ion of m/z 1173.8 corresponding to a molecule of 3525 amu consistent with a composition of HexNAc2, Hep4, Hex6, PEtn, Kdo, P, Lipid A-OH with low amounts of ions consistent with the loss or gain of one PEtn residue from the major species indicated by m/z 1132.9$^{3-}$ and 1215.2$^{3-}$. CE-MS/MS analysis (data not shown) on the triply charged ion m/z 1173.8 gave a singly charged peak of m/z 951 and a doubly charged ion of m/z 1236.5, confirming the size of the O-deacylated lipid A as 952 amu and the core OS as 2475 amu. The O-deacylated lipid A basal species (952 amu) consists of a disaccharide of N-acylated (3-OH C 14:0) glucosamine residues, each residue being substituted with a phosphate molecule. Interestingly, small amounts of glycoforms that would correspond to the losses of a hexose and phosphate molecules with the concomitant gain of a Kdo molecule were indicated by m/z 1125.7$^{3-}$ and 1166.7$^{3-}$, suggesting the presence of two distinct arrangements of the Kdo region of the molecule with either a Kdo-P or a Kdo-Kdo arrangement (Example 3, Table 1). A similar mixture of one and two Kdo residue-containing glycoforms were observed in the CE-MS spectrum of KOH treated LPS (Example 3, Table 1). ES-MS and CE-MS analyses of the fractionated core OS sample revealed a mass of 2492 Da, consistent with a composition of HexNAc2, Hep4, Hex6, PEtn, Kdo (Example 3, Table 1) (FIG. 19). CE-MS/MS analyses in positive ion mode was performed on the core OS in order to obtain information as to the location of some of the functional groups in the OS molecule. MS/MS analysis on the doubly charged ion at m/z 1246.5$^{2+}$ revealed several product ions (FIG. 20). Dominant were the singly charged ions corresponding to a HexNAc residue at 203.5$^+$, and two HexNAc residues at 407.5$^+$. Other product ions were also identified and correspond to the compositions indicated in FIG. 20. Following precursor ion scanning for an ion with m/z 316 (which corresponds to a Hep-PEtn group) the PEtn moiety of the core OS was localized to a heptose residue (Hep) of the inner core by virtue of the identification of hydrated doubly charged ions of m/z 817.5$^{2+}$ (Hex3, Hep4, Kdo, PEtn), 898.5$^{2+}$ (Hex4, Hep4, Kdo, PEtn), 979.5$^{2+}$ (Hex5, Hep4, Kdo, PEtn), 1059.5$^{2+}$ (Hex6, Hep4, Kdo, PEtn) and 1263.5$^{2+}$ (HexNAc2, Hex6, Hep4, Kdo, PEtn) (FIG. 21). Precursor ion scanning for an ion with m/z 407 (which corresponds to a HexNAc-HexNAc group) revealed a singly charged ion of 893$^+$ that corresponds to a composition of Hex3, HexNAc2 (data not shown). These two precursor ion experiments therefore suggested an inner core composition of Hex3, Hep4, Kdo, PEtn with an outer core extension of 3Hex and 2HexNAc residues.

Methylation analysis was performed on the core OS in order to determine the linkage pattern of the molecule revealing the presence of terminal Glc, 6-substituted Glc, 4-substituted Glc, 4-substituted Gal, 3-substituted Gal, terminal LD-Hep and 4,6-disubstituted LD-Hep, in the approximate molar ratio of 2:1:1:1:1:1:1 with lesser amounts of terminal Gal, 2-substituted LD-Hep, 3,4-disubstituted LD-Hep and 3,4,6-trisubstituted LD-Hep also observed. Additionally, by comparison to the permethylated alditol acetates from *Actinobacillus pleuropneumoniae* (Ap) serotype 2, the retention time for a 4,6 di-substituted LD-Hep residue resolves from a 4,6 di-substituted DD-Hep residue, confirming the assignment and consistent with the absence of DD-Hep in the LPS of Pm.

In order to elucidate the exact locations and linkage patterns of the OS, NMR studies were performed on the OS fraction that gave the most resolved and homogeneous spectrum and the fully deacylated (KOH treated) material (FIG. 22). The assignment of $^1$H resonances of the OS and KOH treated LPS was achieved by COSY and TOCSY (FIG. 5a) experiments with reference to the structurally related core OS from *Mannheimia haemolytica* (Mh) and Ap (Brisson, et al, 2002; St. Michael et al, 2004) (Example 3, Table 2).

In the $^1$H-NMR spectrum of the Pm70 OS and KOH treated LPS, spin systems arising from heptose residues (Hep I (E), Hep II (F), Hep III (G) and Hep IV (J)) were readily identified from their anomeric $^1$H resonances at $5.10_{OS}$ (OS sample)/$5.19_{KOH}$ (KOH treated sample) (Hep I, E), $5.87_{OS}/5.74_{KOH}$ (Hep II, F), $5.23_{OS\&KOH}$ (Hep III, G) and $5.12_{OS\&KOH}$ (Hep IV, J) ppm coupled with the appearance of their spin systems which pointed to manno-pyranosyl ring systems. Heterogeneity was observed for the anomeric protons of Hep I in the OS sample due to the presence of various rearrangement products of the neighbouring Kdo molecule following acid hydrolysis (assignments from the major Hep I signal in the OS sample are detailed). The α-configurations were evident for the heptosyl residues from the occurrence of intra-residue NOE's between the H1 and H2 resonances only. Two of the remaining residues in the α-anomeric region at $5.22_{OS\&KOH}$ ppm (Glc II, H) and $5.09_{OS}/5.53_{KOH}$ ppm (GalNAc II/GalN II, P) were determined to be gluco- and galacto-pyranose sugars respectively, based upon the appearance of their spin systems. The galacto-configured residue at $5.09_{OS}/5.53_{KOH}$ ppm was determined to be an amino sugar by virtue of its 1H resonance of its H-2 proton at $4.24_{OS}/3.65_{KOH}$ ppm correlating to a $^{13}$C chemical shift of $50.4_{OS}/51.5_{KOH}$ ppm in $^{13}$C—$^1$H HSQC experiments. The $^{13}$C chemical shift being consistent with a nitrogen substituted carbon atom. The remaining residue in the o-anomeric region at $4.95^{OS}/4.99_{KOH}$ ppm (Gal II, N) was determined to be a galacto-pyranose sugars, based upon the appearance of its characteristic spin system to the H-4 resonance in a TOCSY experiment (FIG. 23). The remainder of the anomeric resonances in the low field region (4.45-6.00 ppm) of the spectrum were all attributable to P-linked residues by virtue of the chemical shifts of their anomeric $^1$H resonances and in the case of resolved residues their high $J_{1,2}$ (~8 Hz) coupling constants. Resonances at $4.65_{OS\&KOH}$ ppm (Glc I, I), $4.70_{OS\&KOH}$ ppm (Glc III, K) and $4.69_{OS\&KOH}$ ppm (Glc IV, L) were assigned to the gluco-configuration from the appearance of their spin systems. The remaining resonances in the low-field region at $4.53_{OS\&KOH}$ ppm (Gal I, M) and $4.73_{OS}/5.01_{KOH}$ ppm (GalNAc I/GalN I, O) were assigned to galacto-pyranosyl residues from the appearance of characteristic spin systems to the H-4 resonances in a TOCSY experiment. The galacto-configured residue at $4.73_{OS}/5.01_{KOH}$ ppm was determined to be an amino sugar by virtue of its $^1$H resonance of its H-2 proton at 4.12/3.53 ppm correlating to a $^{13}$C chemical shift of $51.9_{OS}/53.1_{KOH}$ ppm in $^{13}$C-$^1$H HSQC experiments. The $^{13}$C chemical shift being consistent with a nitrogen substituted carbon atom. Signals for the CH$_2$ protons of the PEtn moiety were observed in the OS sample at 3.27 and 4.16 ppm that correlated to characteristic $^{13}$C chemical shifts of 40.1 and 62.2 ppm respectively in a $^{13}$C—$^1$H HSQC experiment. Additionally characteristic signals for acetyl groups of the amino sugars were observed in the OS sample at 2.06 and 2.04 ppm that correlated to $^{13}$C chemical shifts of 22.4 and 22.1 ppm respectively in a $^{13}$C—$^1$H HSQC experiment.

The sequence of the glycosyl residues in the OS was determined from the inter-residue $^1$H—$^1$H NOE measurements between anomeric and aglyconic protons on adjacent glycosyl residues and confirmed and extended the methylation analysis data. The linkage pattern for the Pm70 deacylated oligosaccharide was determined in this way (FIG. 24) (Example 3, Table 2). Thus, the occurrence of intense transglycosidic NOE connectivities between the proton pairs Hep III (G) H-1 and Hep II (F) H-2, Hep II (F) H-1 and Hep I (E) H-3 and Hep I (E) H-1 and Kdo (C)H-5 established the sequence and points of attachment of these three LD-heptose residues as the frequently observed tri-heptosyl moiety, this linkage pattern is commonly encountered in the inner core OS from *Haemophilus influenzae* (Hi) and Mh (Cox et al, 2001a; Brisson et al, 2002). Furthermore, inter-residue NOE's between the anomeric protons Hep III (G) H-1 and Hep II (F) H-1 provided confirmation of the 1,2-linkage (Romanowska et al, 1988). Examination of NOE connectivities from H-1 of Glc I (1) illustrated that this glucose residue was connected to Hep I (E) at the 4-position by virtue of inter-residue NOE's to Hep I (E) H-4 and Hep I (E) H-6. The appearance of an inter-residue NOE to H-6 is a common occurrence for 4-substituted heptose residues (Backman et al, 1988). The occurrence of a long range NOE connectivity between H-1 of Glc I (1) and H-1 of Glc II (H) suggested that the α-configured glucose residue (Glc II (H)) was substituting Hep I at the 6-position as has been observed previously for the OS from both MA and Ap (Brisson, et al, 2002; St. Michael et al, 2004). Examination of NOE connectivities from H-1 of Glc II (H) confirmed that this glucose residue was connected to Hep I (E) at the 6-position by virtue of inter-residue NOE's to Hep I (E) H-6. Similarly to Glc I (I) a long-range NOE connectivity was observed between the anomeric $^1$H resonances of Glc I (I) and Glc II (H). Examination of NOE connectivities from H-1 of Hep IV (J) revealed that this heptose residue was connected to Glc I (I) at the 6-position by virtue of inter-residue NOE's to Glc I (1) H-6a and H-6b. This inner core glycose structure has been observed previously for both Mh and Ap, however in both these cases the HepIV residue (J) was of the D-glycero-D-manno configuration, whereas here the HepIV residue (J) is of the L-glycero-D-manno configuration as this was the only configuration of heptose residue identified in sugar analysis. The linkage pattern of the outer core residues was deduced from NOE connectivities and $^{13}$C—$^1$H-HMBC evidence, in conjunction with the methylation analysis data. The two gluco-configured residues (K & L) with their anomeric proton resonances at $4.70_{OS\&KOH}/4.69_{OS\&KOH}$ ppm showed inter-NOE connectivities to the H-4 and H-6 proton resonances of the Hep IV residue (J) at $4.15_{OS\&KOH}$ and $4.31_{OS\&KOH}$ ppm, consistent with the 4,6-disubstituted LD-heptose residue observed in methylation analysis and similar to the arrangement of the DD-HepIV previously observed in Ap serotype 2 (St. Michael et al, 2004). By virtue of a $^1$H—$^{13}$C HMBC experiment (FIG. 25) it could be determined that Glc III (K) was linked to HepIV (J) at the 4-position and Glc IV (L) was linked to HepIV (J) at the 6-position. An inter-NOE connectivity from the anomeric proton resonance of Gal I (M) at $4.53_{OS\&KOH}$ ppm to the H-4 proton resonance of Glc IV (L) suggested that Gal I (M) substituted Glc IV (L) at the 4-position. An inter-NOE connectivity from the anomeric proton resonance of Gal II (N) to the H-4 proton resonance of Gal I (M) suggested that Gal II (N) substituted Gal I (M) at the 4-position, consistent with methylation analysis data that had resolved two 4-linked hexose residues i.e. a 4-linked glucose and a 4-linked galactose residue. An inter-NOE connectivity from the anomeric proton resonance of GalNAc I/GalN I (O) to the H-3 proton resonance of Gal II (N) suggested that GalNAc I/GalN I (O) substituted Gal II (N) at the 3-position, confirmed by methylation analysis that had identified a 3-linked hexose residue. Finally, an inter-NOE connectivity from the anomeric proton resonance of GalNAc II/GalN II (P) to the H-3 proton resonance of GalNAc I/GalN I (O) suggested that GalNAc II/GalN II (P) substituted Gal-NAc I/GalN I (O) at the 3-position, consistent with MS/MS identification of a HexNAc-HexNAc disaccharide. Confirmation of the 3-position of Hep II (F) as the location of PEtn substitution was obtained from $^{31}$P—$^{1}$H-HSQC and $^{31}$P—$^{1}$H-HSQC-TOCSY experiments on the OS sample. The HSQC experiment identified a cross-peak from the phosphorus signal to the proton resonance at 4.41 ppm which had been assigned to the 3-position of the Hep II residue (F) and this was confirmed and extended in the HSQC-TOCSY experiment which revealed the H-2 and H-1 proton resonances of Hep n (F) at 4.31 and 5.87 ppm respectively (data not shown).

The linkages of the Hep I-Kdo-Lipid A region (E-C-B-A) were confirmed from analyses on the KOH treated LPS as L-α-D-Hep I-(1-5)-α-Kdo4P-(2-6)-β-GlcN4P-(1-6)-α-GlcN1P (Example 3, Table 2). A two Kdo containing fraction was isolated by chromatography and identified by MS, but insufficient amounts were available for NMR analysis.

The availability of the genome sequence for the Pm70 strain (May et al, 2001) along with a thorough knowledge of the OS structure, coupled with information about the glycosyltransferases that put similar OS structures together in the structurally and taxonomically related species enabled several candidate glycosyltransferases for the biosynthesis of the Pm70 OS to be identified (FIG. 26). Several accepted heptosyltransferases were identified in the Pm70 genome sequence and included a Hep III Tase PM1294, a Hep II Tase PM1844, two Hep I Tases PM1302 and PM1843 and a Hep IV Tase PM1144. The best homologue of each of these genes in the databases are detailed in Example 3, Table 3 and the high degree of homology suggests that the candidate PM gene would have the indicated function. Previously our group and collaborators showed that PM1294 was the Hep III Tase in another Pm strain VP161 (Harper et al, 2004). The gene that adds the α-glucose (H) to the 6-position of Hep I (E) is not known but there is a good homologue PM1306 to the β-glucosyltransferase that substitutes Hep I (E) at the 4-position. The Kdo transferase was readily identified as PM1305 due to an extensive number of excellent homologues, however only one Kdo transferase homologue has been identified in the Pm genome. Interestingly, several genes involved in the biosynthesis of the Kdo (C), Hep I (E), Glc I (I) region are clustered in this region of the chromosome. Putative glycosyltransferases for the outer core region also appear to be clustered in a region of the chromosome ranging from PM1138 to PM1144. This clustering of glycosyltransferase genes is not always observed in this genus and indeed the glycosyltransferase for Hi OS are liberally scattered throughout the genome. Another locus of putative glycosyltransferases can be found in another region of the Pm genome from PM0506 to PM0512. This locus lines up very well with the so-called lsg locus from both Hi and *Haemophilus ducreyi* (Hd). The role of this locus in the biosynthesis of Hi OS has been the matter of some discussion in the literature without any clearcut role being assigned (Phillips et al, 1996, 2000; Cox et al, 2001b). However in the midst of this Pm70 locus is one sialyltransferase homologue (PM0508) of the three sialyltransferase homologues in the Pm70 genome (also PM0188 and PM1174) and structural studies are ongoing in our laboratory to see if Pm70 LPS can be sialylated under the appropriate growth conditions. Candidate genes for the formation of the activated nucleotide sugar donors are also detailed in Example 3, Table 3.

Discussion

Structural analysis of the oligosaccharide of the Pm70 genome strain of Pm has revealed a structure with similarities to the previously determined LPS core oligosaccharide structures for the related species Mh (Brisson et al, 2000), Ap (St. Michael et al, 2004), Hd (Schweda et al, 1994) and Hi (Cox et al, 2001a). In each case the core OS contains an identically linked tri-heptosyl unit that is attached to a Kdo residue. Interestingly in Pm the 3-position of the HepII residue is substituted in the majority of cases with a PEtn residue, whereas Ap, Hd and Mh do not contain a PEtn residue and Hi elaborates a PEtn residue at the 6-position of Hep II. The substitution pattern at the Hep I residue of Pm is identical to that found for the veterinary pathogens Ap and Mh with two glucose residues at the 4- and 6-positions, whereas the Hep I residue in Hi and Hd is only substituted at the 4-position. Additionally the glucose residue at the 4-position of Hep I is consistently substituted at the 6-position with a heptose residue in the three veterinary pathogens, Hd and in some strains of Hi. However in Pm (and in some strains of Hi) the heptose residue substituting the glucose residue is L-glycero-D-manno configured compared to a D-glycero-D-manno configured heptose residue in Ap, Hd, Mh and some strains of Hi. The substitution pattern of this heptose residue is considerably varied amongst these strains and it is at this point of the OS structure that the conserved inner core structural similarities between the various strains end. In Pm the heptose residue is di-substituted with two glucose residues at the 4- and 6-positions, similar to Ap serotype 2 in which this heptose residue is di-substituted at the same locations, but with another heptose residue at the 4-position rather than a glucose residue. Mh also has a further D,D-heptose residue at the 4-position whereas Ap serotype 1, Hd and Hi also have further hexose extensions from this fourth heptose residue, but none have the extension observed here which terminates in the novel GalNAc-GalNAc disaccharide unit.

Based on the Pm70 OS structure homologues to glycosyltransferases with similar specificities were identified in the Pm70 genome. Considering the novel finding of two LPS populations depending upon the presence of one or two Kdo residues it was interesting to note that only one homologue to Kdo transferases was identified in the Pm genome. This is not surprising since the pleiotropic nature of Kdo transferases is well documented, i.e. the same Kdo transferase can transfer a Kdo residue to lipid A and a second Kdo residue to the initial Kdo residue. The novel feature of Pm LPS though, is that populations with both one and two Kdo residues have been identified, that has to our knowledge not been observed previously. However, it was observed that there were two good homologues in the Pm70 genome for Hep I (E) to Kdo (C) (α-1,5 heptosyltransferase) transferases. One transferase had the highest homology to HI 0261 (OpsX) of Hi wherein the LPS structure contains one Kdo residue; and the second transferase had the highest homology to WaaC from *Escherichia coli* and *Klebsiella pneumoniae* that have two Kdo residues in their LPS structures. The identification of two Hep I transferases is therefore consistent with the presence of two structural arrangements in the Kdo region of the Pm70 LPS, and it will be intriguing to understand the regulation of the Kdo transferase from this organism.

This study has structurally characterised the core OS region of the genome strain of Pm and identified putative glycosyltransferases for the complete biosynthesis of the core OS.

Materials and Methods

Media and Growth Conditions

Pm strain Pm70 (NRCC # 6232) was initially grown overnight on chocolate agar plates at 37° C. and growths were used to inoculate 1 L of brain-heart infusion (BHI) medium supplemented with β NAD (Sigma N-7004) to a final concentration of 5 ug/ml, haemin (Sigma H-2250) to a final concentration of 5 ug/ml and 1% glucose (10 g). Cultures were then incubated at 37° C. at 200 rpm for 6 hours and used to inoculate 24 L BHI medium (supplemented as above) in a 28 L NBS fermenter. The cultures were then grown at 37° C., with 24 $lmin^{-1}$ aeration and stirring at 200 rpm for 18 hours with 20% $O_2$ saturation. Following treatment with hyaluronidase (1 g, Sigma,) cells were killed (2% phenol w/v, for 4 hours) and harvested by using a Sharples continuous centrifuge (~240 g wet weight).

Isolation and Purification of Lipopolysaccharide

Following washing of the lyophilised cell mass (~70 g) with organic solvents yielding ~50 g, the lipopolysaccharide (LPS) was isolated from 10 g of the washed, lyophilised cell mass by the hot water/phenol method (Westphal and Jann, 1965). The aqueous phase was dialysed against water and lyophilised. The dried sample was dissolved in water to give a 1-2% solution (w/v) and treated with deoxyribonuclease I (DNase) (0.01 mg/ml) and ribonuclease (RNase) (0.01 mg/ml) for 3 hrs at 37° C., then treated with proteinase K (0.01 mg/ml) for 3 hrs. The dialysed, dried sample was dissolved in water to make a 1% solution and ultra-centrifuged at 45 K following a low speed spin at 8K to remove any insoluble material (124 mg). The LPS pellet from the 45K spin was redissolved in water and lyophilised (180 mg). Purified LPS (75 mg) was treated with anhydrous hydrazine with stirring at 37° C. for 1 hr to prepare O-deacylated LPS (LPS-OH). The reaction was cooled in an ice bath and gradually cold acetone (−70° C., 5 vols.) was added to destroy excess hydrazine and the precipitated LPS-OH was isolated by centrifugation (60 mg). The sample was then purified down a Bio-Gel P-2 column as described above. The core oligosaccharide (OS) was isolated by treating the purified LPS (100 mg) with 1% acetic acid (10 $mgml^{-}$, 100° C., 1.5 hr) with subsequent removal of the insoluble lipid A by centrifugation (5000 g). The lyophilised OS (50 mg) was further purified down a Bio-Gel P-2 column with individual fractions lyophilised. Fully deacylated LPS was isolated by treatment of LPS-OH (20 mg) with 4N KOH at 125° C. for 16 h and following neutralisation were fractionated by anion-exchange liquid chromatography as described previously (Vinogradov, E and Bock, K. 1999).

Analytical Methods

Sugars were determined as their alditol acetate derivatives by GLC-MS (Sawardeker et al, 1965). Samples were hydrolysed for 4 hrs using 4 M trifluoroacetic acid at 100° C., then reduced ($NaBD_4$) overnight in $H_2O$ and acetylated with acetic anhydride at 100° C. for 2 h using residual sodium acetate as catalyst. The GLC-MS was equipped with a 30 M DB-17 capillary column (180° C. to 260° C. at 3.5° C./min) and MS was performed in the electron impact mode on a Varian Saturn II mass spectrometer. Methylation analysis was carried out by the NaOH/DMSO/methyl iodide procedure (Ciucanu and Kerek, 1994) and analysed by GLC-MS as above. Absolute configurations were determined by GLC analysis of butyl glycoside derivatives (St. Michael et al, 2004).

Mass Spectrometry

ESI-MS was performed in the negative ion mode on a VG Quattro Mass Spectrometer (Micromass, Manchester, U.K.) by direct infusion of samples in 25% aqueous acetonitrile containing 0.5% acetic acid. Capillary electrophoresis (CE)-MS was performed on a Prince CE system (Prince Technologies, The Netherlands) coupled to an API 3000 mass spectrometer (Applied Biosystem/Sciex, Concord, Canada) via a microspray interface. A sheath solution (isopropanol-methanol, 2:1) was delivered at a flow rate of 1 μL/min to a low dead volume tee (250 μm i.d., Chromatographic Specialties). All aqueous solutions were filtered through a 0.45-μm filter (Millipore) before use. An electrospray stainless steel needle (27 gauge) was butted against the low dead volume tee and enabled the delivery of the sheath solution to the end of the capillary column. The separations were obtained on about 90 cm length bare fused-silica capillary using 10 mM ammonium acetate/ammonium hydroxide in deionised water, pH 9.0, containing 5% methanol. A voltage of 20 kV was typically applied at the injection site. The outlet of the capillary was tapered to ca. 15 μm i.d. using a laser puller (Sutter Instruments). Mass spectra were acquired with dwell times of 3.0 ms per step of 1 m/z unit in fall-mass scan mode. The MS/MS data were acquired with dwell times of 1.0 ms per step of 1 m/z unit. Fragment ions formed by collision activation of selected precursor ions with nitrogen in the RF-only quadrupole collision cell, were mass analyzed by scanning the third quadrupole.

Nuclear Magnetic Resonance

NMR experiments were acquired on Varian Inova 400, 500 and 600 MHz spectrometers using a 5 mm or 3 mm triple resonance ($^1H$, $^{13}C$, $^{31}P$) probe. The lyophilised sugar sample was dissolved in 600 μL (5 mm) or 140 μL (3 mm) of 99% $D_2O$. The experiments were performed at 25° C. with suppression of the HOD (deuterated $H_2O$) signal at 4.78 ppm. The methyl resonance of acetone was used as an internal reference at 2.225 ppm for $^1H$ spectra and 31.07 ppm for $^{13}C$ spectra. Standard homo and heteronuclear correlated 2D pulse sequences from Varian, COSY, TOCSY, NOESY, $^{13}C$—$^1H$ HSQC, $^{13}C$—$^1H$ HSQC-TOCSY and $^{13}C$—$^1H$ HMBC, were used for general assignments. The 2D $^1H$-$^{31}P$ HSQC experiment was acquired on a Varian Inova 400 spectrometer for 6 h. The coupling constant was optimised at 12 Hz by performing an array of 1D-HSQC experiments. The sweep width in the F2 ($^1H$) dimension was 6.0 ppm and in the F1 ($^{31}P$) dimension was 16.2 ppm. Water presaturation during the relaxation delay was 1.5 s, acquisition time in $t_2$ was 0.21 s, and 32 increments with 180 (HMQC) scans per increment were obtained. The 2D $^1H$—$^{31}P$ HSQC-TOCSY experiment was acquired on a Varian Inova 400 spectrometer for 8 h using the same parameters as the HSQC experiment with a TOCSY mixing time of 80 ms

TABLE 1

Negative ion CE-MS data and proposed compositions of core OS, O-deacylated and KOH treated LPS from *P. multocida* strain Pm70. Average mass units were used for calculation of molecular weight based on proposed composition as follows: Hex, 162.15; Hep, 192.17; Kdo, 220.18; HexNAc, 203.19; HexN, 161.15; PEtn, 123.05.

| Strain | $[M-3H]^{3-}$ | $[M-2H]^{2-}$ | Observed Molecular Ion | Calculated Molecular Ion | Relative Intensity | Proposed Composition |
|---|---|---|---|---|---|---|
| Pm70 |  | 1111.2 | 2224.4 | 2224.0 | 0.1 | 2HexNAc, 4Hep, 5Hex, Kdo |
| Core OS | — | 1173.1 | 2348.2 | 2347.0 | 0.2 | 2HexNAc, 4Hep, 5Hex, PEtn, Kdo |
|  | 829.8 | 1245.3 | 2492.5 | 2491.2 | 1.0 | 2HexNAc, 4Hep, 6Hex, PEtn, aKdo |
| Pm70 | 1125.7 | 1689.3 | 3380.3 | 3378.2 | 0.1 | 2HexNAc, 4Hep, 5Hex, 2Kdo, Lipid A-OH |
| O-deac | 1132.9 | 1700.7 | 3402.5 | 3400.1 | 0.3 | 2HexNAc, 4Hep, 6Hex, Kdo, P, Lipid A-OH |
|  | 1166.7 | 1750.4 | 3502.9 | 3501.2 | 0.2 | 2HexNAc, 4Hep, 5Hex, PEtn, 2Kdo, Lipid A-OH |
|  | 1173.8 | 1761.4 | 3524.6 | 3523.1 | 1.0 | 2HexNAc, 4Hep, 6Hex, PEtn, Kdo, P, Lipid A-OH |
|  | 1215.2 | — | 3648.6 | 3646.2 | 0.2 | 2HexNAc, 4Hep, 6Hex, 2PEtn, Kdo, P, Lipid A-OH |
| Pm70 | 980.3 | 1471.3 | 2944.3 | 2944.2 | 1.0 | 6Hex, 4HexN, 4Hep, Kdo, 4P |
| KOH | 973.3 | — | 2922.9 | 2922.8 | 0.2 | 5Hex, 4HexN, 4Hep, 2Kdo, 3P |

TABLE 2

$^{1}$H- and $^{13}$C-NMR chemical shifts for the fully deacylated (KOH treated) LPS[a] and core OS[b] from *Pasteurella multocida* Pm70.

|  | H-1 | H-2 | H-3 | H-4 | H-5 | H-6 | H-7 | H-8 | NOE's Inter | Intra | Long Range |
|---|---|---|---|---|---|---|---|---|---|---|---|
| α-GlcN[a] (A) | 5.74 (92.5) | 3.46 (55.0) | 3.93 (70.3) | 3.52 (70.6) | 4.14 (73.4) | 4.31 3.89 (70.1) |  |  | — | 3.46 H-2 |  |
| β-GlcN[a] (B) | 4.89 (99.9) | 3.17 (56.4) | 3.91 (72.6) | 3.92 (75.2) | 3.78 (74.7) | 3.72 3.57 (63.2) |  |  | 4.31 α-GlcN H-6 3.89 α-GlcN H-6 | 3.91 H-3 3.78 H-5 |  |
| Kdo[a] (C) | — | — | 2.37 2.03 (35.0) | 4.62 (71.1) | 4.28 (72.7) | 3.83 (73.0) | 3.77 (70.1) | 3.97 3.72 (64.5) | 3.72 β-GlcN H-6 3.57 β-GlcN H-6 |  |  |
| Hep I[a] (E) | 5.19 (100.1) | 4.15 (71.0) | 4.03 (74.1) | 4.20 (75.0) | 4.20 (72.4) | 4.08 (81.4) | 4.08 3.92 (63.7) |  | 4.28 Kdo H-5 3.77 Kdo H-7 | 4.15 H-2 |  |
| Hep I[b] (E) | 5.10 (99.4) | 4.02 (70.6) | 3.99 (nd) | 4.22 (73.9) | nd (nd) | 4.11 (79.5) | 3.86 3.73 (62.1) |  | nd nd | 4.02 H-2 |  |
| Hep II[a] (F) | 5.74 (99.8) | 4.34 (79.8) | 4.47 (75.3) | 4.09 (66.6) | 3.67 (72.8) | 4.09 (69.4) | 3.71 3.62 (64.1) |  | 5.23 Hep III H-1 4.03 Hep I H-3 | 4.34 H-2 |  |
| Hep II[b] (F) | 5.87 (99.4) | 4.31 (80.6) | 4.41 (76.3) | 4.09 (66.2) | 3.67 (72.3) | 4.09 (69.7) | nd nd (nd) |  | 5.23 Hep III H-1 3.99 Hep I H-3 | 4.31 H-2 |  |
| Hep III[ab] (G) | 5.23 (102.0) | 4.06 (71.7) | 3.90 (71.8) | 3.87 (67.2) | 3.88 (72.7) | 4.06 (70.6) | 3.80 3.76 (64.6) |  | 5.87 Hep II H-1 4.31 Hep II H-2 | 4.06 H-2 |  |
| β-Glc(Glc I)[ab] (I) | 4.65[c] (104.2) | 3.56 (74.4) | 3.41 (78.2) | 3.63 (70.6) | 3.53 (74.9) | 4.11 3.75 (65.8) |  |  | 4.22 Hep I H-4 4.11 Hep I H-6 | 3.53 H-5 3.41 H-3 | 5.22 Glc II H-1 |
| α-Glc(Glc II)[ab] (H) | 5.22 (101.9) | 3.60 (72.3) | 3.83 (73.1) | 3.61 (68.7) | 3.93 (71.7) | 3.97 3.77 (60.6) |  |  | 4.11 Hep I H-6 | 3.60 H-2 | 4.65 Glc I H-1 |
| Hep IV[ab] (J) | 5.12 (100.2) | 4.01[d] (70.1) | 4.00 (69.8) | 4.15 (78.0) | 3.94 (71.1) | 4.31 (80.1) | nd nd (nd) |  | 4.11 Glc I H-6 3.75 Glc I H-6 | 4.01 H-2 |  |
| β-Glc(GlcIII)[ab] (K) | 4.70 (103.5) | 3.36 (74.3) | 3.55 (76.6) | 3.44 (70.6) | 3.58 (76.9) | 3.96 3.76 (61.7) |  |  | 4.15 Hep IV H-4 | 3.55 H-3 3.58 H-5 |  |
| β-Glc(Glc IV)[ab] (L) | 4.69 (104.4) | 3.46 (74.1) | 3.71 (75.2) | 3.71 (79.8) | 3.70 (75.7) | 4.02 3.84 (61.1) |  |  | 4.31 Hep IV H-6 4.15 Hep IV H-4 | 3.71 H-3 3.70 H-5 |  |
| β-Gal (Gal I)[ab] (M) | 4.53 (104.3) | 3.61 (71.8) | 3.77 (73.2) | 4.07 (78.4) | 3.81 (76.4) | 3.93 3.86 (61.4) |  |  | 3.71 Glc IV H-4 | 3.77 H-3 3.81 H-5 |  |
| α-Gal (Gal II)[a] (N) | 4.99 (101.2) | 4.07 (68.8) | 4.17 (79.9) | 4.32 (69.9) | 4.42 (71.4) | 3.72 3.72 (61.2) |  |  | 4.07 Gal I H-4 | 4.07 H-2 | 3.81 Gal I H-5 |

TABLE 2-continued $^1$H- and $^{13}$C-NMR chemical shifts for the fully deacylated (KOH treated) LPS$^a$ and core OS$^b$ from *Pasteurella multocida* Pm70.

|  | H-1 | H-2 | H-3 | H-4 | H-5 | H-6 | H-7 | H-8 | NOE's Inter | Intra | Long Range |
|---|---|---|---|---|---|---|---|---|---|---|---|
| α-Gal (Gal II)$^b$ (N) | 4.95 (101.4) | 3.93 (68.7) | 4.02 (79.9) | 4.29 (69.9) | 4.41 (71.3) | 3.71 3.71 (61.4) | | | 4.07 Gal I H-4 | 3.93 H-2 | 3.81 Gal I H-5 |
| β-GalN I$^a$ (O) | 5.01 (101.3) | 3.53 (53.1) | 4.20 (74.3) | 4.40 (63.9) | 3.80 (76.2) | nd nd (nd) | | | 4.17 Gal II H-3 | 4.20 H-3 3.80 H-5 | |
| β-GalNAc I$^b$ (O) | 4.73 (103.7) | 4.12 (51.9) | 3.84 (75.7) | 4.13 (64.7) | 3.67 (75.9) | nd nd (nd) | | | 4.02 Gal II H-3 | 3.84 H-3 3.67 H-5 | |
| α-GalN II$^a$ (P) | 5.53 (92.6) | 3.65 (51.5) | 4.23 (67.0) | 4.07 (68.8) | 4.01 (73.4) | 3.82 3.82 (62.1) | | | 4.20 GalNAc I H-3 | 3.65 H-2 | |
| α-GalNAc II$^b$ (P) | 5.09 (94.5) | 4.24 (50.4) | 3.82 (68.7) | 4.03 (69.3) | 3.89 (72.5) | 3.82 3.82 (61.8) | | | 3.84 GalNAc I H-3 | 4.24 H-2 | 4.12 GalNAc I H-2 |
| PEtn$^b$ | 3.26 (40.1) | 4.16 (62.2) | | | | | | | | | |
| CH$_3$C=O$^b$ | 2.06 (22.4) | | | | | | | | | | |
| CH$_3$C=O$^b$ | 2.04 (22.1) | | | | | | | | | | |

$^a$Data from KOH treated LPS;
$^b$Data from core OS sample;
$^{ab}$Data from both KOH treated LPS and core OS, assignments identical; except
$^c$H-1 chemical shift of residue I from KOH treated LPS is 4.60 ppm and
$^d$H-2 chemical shift of residue J from KOH treated LPS is 4.11 ppm.

TABLE 3

Putative glycosyltransferases for the LPS core biosynthesis in *Pasteurella multocida* genome strain Pm70.

| . *multocida* gene | Putative function | Best homologues | e-value |
|---|---|---|---|
| M 1305 | Kdo to lipid A a-2,6 Kdo transferase | KdtA Hi (HI0652) KdtA Hd (HD0454) | $e^{-152}$ $e^{-120}$ |
| M 1843 | Hep I to Kdo α-1,5 heptosyltransferase | WaaC Kp WaaC Ec | $e^{-96}$ $e^{-94}$ |
| M 1302 | Hep I to Kdo α-1,5 heptosyltransferase | OpsX Hi (HI 0261) | $e^{-149}$ |
| M 1844 | Hep II to Hep I α-1,3 heptosyltransferase | RfaF Hi (HI 1105) RfaF Hd | $e^{-164}$ $e^{-139}$ |
| M 1294 | Hep III to Hep II α-1,2 heptosyltransferase | OrfH Hi (HI 0523) | $e^{-127}$ |
| M 0223 | PEtn to Hep II | Lpt3 Nm (NMB 2010) | $e^{-154}$ |
| M 1306 | Glc I to Hep I β-1,4 glucosyltransferase | LgtF Hi (HI 0653) | $e^{-108}$ |
| M 1144 | Hep IV to Glc I α-1,6 heptosyltransferase | LbgB App LbgB Hd (HD 1720) | $e^{-93}$ $e^{-87}$ |
| M 1143 | Glc IV to Hep IV β-1,6 glucosyltransferase | LbgA Hd (HD 1721) LbgA App | $e^{-74}$ $e^{-73}$ |
| M 1141 | Gal I to Glc IV β-1,4 galactosyltransferase | Lic2a Hi (HI 0550) | $e^{-38}$ |
| M 1139 | Gal II to Gal I α-1,4 galactosyltransferase | LgtC Hi (HI 0258) LgtC Nm | $e^{-62}$ $e^{-59}$ |
| M 1140 | GalNAc I to Gal II α-1,3 N-acetylgalactosaminyltransferase | LgtD Hi (HI 1578) | $e^{-83}$ |
| M 1138 | GalNAc II to GalNAc I β-1,3 N-acetylgalactosaminyltransferase | GTase App | $e^{-62}$ |
| M 0858 | CMP-Kdo synthetase | HI0058 | $e^{-103}$ |
| M 0884 | ADP-Hep pyrophosphorylase | HI1526 | 0 |
| M 1289 | UDP-Glc pyrophosphorylase (galU) | HI0812 | $e^{-145}$ |
| M 0286 | UDP-Glc-4-epimerase (galE) | HI0351 | $e^{-173}$ |
| M 1030 | UDP-N-acetylglucosamine epimerase | HI0873 | $e^{-122}$ |

Example 4

This Example forms the basis of a publication in Carbohydrate Research 340, 59 (2005). Structural analysis of the lipopolysaccharide of *Pasteurella multocida* strain VP161.

In this example the structure of the lipopolysaccharide from the *Pasteurella multocida* strain VP161 was elucidated. The lipopolysaccharide was subjected to a variety of degradative procedures. The structures of the purified products were established by monosaccharide and methylation analyses, NMR spectroscopy and mass spectrometry. The following structures for the lipopolysaccharides were determined on the basis of the combined data from these experiments,

```
                            PCho
                             |
                             3
        PCho              β-D-Gal II                    (e)
         |                   |(h)                    α-D-Glc II           P...PEtn
         3                   6                          6                    4
    β-D-Gal I-(1 ——→ 4)-L-α-D-Hep IV-(1 ——→ 6)-β-D-Glc I-(1 ——→ 4)-L-α-D-Hep I-(1 ——→ 5)-α-Kdo-Lipid A
        (g)                 (f)                       (d)             (a)  3
                                                                           ↑
                                                                           |
                                                                           1
                                                                      L-α-D-Hep II
                                                                       (b)  2
                                                                            ↑
                                                                            |
                                                                            1
                                                                      L-α-D-Hep III
                                                                         (c)

PCho
                             |
                             3
        PCho              β-D-Gal II                                     α-Kdo
         |                   |(h)                                          2
         3                   6                                             4
    β-D-Gal I-(1 ——→ 4)-L-α-D-Hep IV-(1 ——→ 6)-β-D-Glc I-(1 ——→ 4)-L-α-D-Hep I-(1 ——→ 5)-α-Kdo-Lipid A
        (g)                 (f)                       (d)             (a)  3
                                                                           ↑
                                                                           |
                                                                           1
                                                                      L-α-D-Hep II
                                                                       (b)  2
                                                                            ↑
                                                                            |
                                                                            1
                                                                      L-α-D-Hep III
                                                                         (c)
``` where based on the NMR data all sugars were found in pyranose ring forms and Kdo is 2-keto-3-deoxy-octulosonic acid, L-α-D-Hep is L-glycero-D-manno-heptose, PPEtn is pyrophosphoethanolamine and PCho is phosphocholine. Intriguingly, when the O- and fully deacylated LPS was examined it was evident that there was variability in the arrangement of the Kdo region of the molecule. Glycoforms were found with a Kdo-P moiety as well as glycoforms elaborating a Kdo-Kdo group. Furthermore the Glc II residue was not attached to Hep I when two Kdo residues were present but was when the Kdo-P arrangement was elaborated, suggesting a biosynthetic incompatibility due to either steric hindrance or an inappropriate acceptor conformation. This variation in the Kdo region of the LPS was also observed in several other *Pasteurella multocida* strains investigated including the genome strain Pm70.

*Pasteurella multocida* (Pm) is a Gram-negative bacterium and multi-species pathogen that causes serious diseases in food animals and humans. This bacterium is the causative agent of fowl cholera in chickens and turkeys, hemorrhagic septicaemia in cattle, atrophic rhinitis in pigs, and dog and cat bite infections in humans. Several Pm virulence factors have previously been identified, including the capsule in serogroups A and B, and LPS. However, there are conflicting reports as to the endotoxic properties of LPS isolated from Pm. LPS isolated from a serotype B:2 strain was shown to be endotoxic and intravenously administered LPS could reproduce clinical signs of hemorrhagic septicemia in buffalo. However, turkey poults were found to be relatively resistant to the lethal effects of LPS isolated from serogroup A strains of Pm, although the inflammatory response and microscopic hepatic lesions were similar to those observed in mammalian hosts. In contrast, chicken embryos and mice were found to be highly susceptible to the toxic effects of Pm LPS.

Pm strains are classified into Heddleston serotypes based on the antibody responses to LPS, whilst antibodies raised against heat-killed Pm vaccines are primarily directed against LPS and protect the host against strains within the same serotype. Early studies demonstrated that LPS purified using the hot phenol/water method and injected into mice and rabbits resulted in a poor antibody response and no protection against Pm infection, however the same LPS when injected into chickens induced a good antibody response that passively protected recipients against disease. Monoclonal antibodies raised against the LPS from a serotype A strain were shown to be bactericidal and to completely protect mice against homologous challenge. In addition, an opsonic monoclonal antibody against a serotype B strain of Pm LPS was shown to partially protect mice against Pm infection.

A modified LPS structure clearly affects the viability of Pm in vivo. Recently three strongly attenuated mutants of Pm strain VP161 were identified that each had a single transposon insertion in the gene pm1294 (designated $waaQ_{PM}$). This gene was subsequently shown to encode a heptosyltransferase, mutation of which resulted in a highly truncated LPS structure. Furthermore, a Pm galE mutant has been constructed previously and was attenuated in mice although no structural analysis of the LPS was reported. Pm isolates may be grouped serologically based on their capsular antigens into 5 serogroups A, B, D-F using a passive haemaglutination test with erythrocytes sensitised with capsular antigen. Structural information is available for the capsules of serogroups A (hyaluronic acid), D (heparin) and F (chondroitin) each being an example of the well-studied glycosaminoglycans. Somatic (LPS) typing can also be used for the identification of strains and there have been two main systems reported. The Namioka system is based on a tube agglutination test and is able to recognise 11 serotypes, whereas the Heddleston system using a gel diffusion precipitation test and can recognise 16 serotypes and is currently the preferred method.

In 1981 a standard system for the identification of *P. multocida* serotypes was recommended that utilized both the Carter capsular typing identified by the letters A, B, D, E and F, and the Heddleston somatic typing system identified by numbers. Pm expresses LPS molecules that do not have the polymeric O-antigen, so-called rough LPS. Recently we analysed the LPS structure of the genome strain Pm70 that exhibited a rough LPS structure. The latter study also suggested that the LPS contain variation in the Kdo region of the molecule. This study was carried out on another strain of Pm, VP161, a highly virulent serotype A: 1 strain, in order to gain further insight into Pm LPS structure and to examine if the variability in the Kdo region was also present in this strain. We had previously characterised the core OS of a heptosyltransferase mutant in VP161 and here we report the complete structure for the LPS including the novel arrangement in the Kdo region of the LPS molecule.

Experimental

Media and Growth Conditions

*P. multocida* strain VP161 was initially grown for 16 h on a chocolate agar plate at 37° C. and growth was used to inoculate 1 L of brain-heart infusion (BHI) medium supplemented with β NAD (Sigma N-7004) to a final concentration of 5 ug/ml, haemin (Sigma H-2250) to a final concentration of 5 ug/ml and 1% glucose (10 g). Cultures were then incubated at 37° C. at 200 rpm for 6 h and used to inoculate the fermenter. *P. multocida* strain VP161 was then grown in a 28 L fermenter in 24 L of BHI broth for 18 h at 37° C. with 20% DO saturation. The cells were killed by addition of phenol to 2%, and 3 h post-phenol 1 g of hyaluronidase (Roche Chemicals) was added and stirred for 1 h before harvesting cells by using a Sharples continuous flow centrifuge (~210 g).

Isolation, Purification and Degradation of Lipopolysaccharide

*P. multocida* cells (~210 g wet wt.) were freeze-dried, yielding ~56 g. Freeze-dried cells were washed with organic solvents (1× ethanol, 2× acetone, 2× light petroleum ether) to remove lipids and other lipophilic components to enhance the efficiency of the LPS extraction. Washed cells (10 g from ~42 g) were extracted by the hot phenol/water method and the aqueous phases combined and dialysed against running water for 48 h. The retentate was freeze-dried yielding ~1.6 g, made up to a 2% solution in water and treated with DNase and RNase at 37° C. for 4 h followed by proteinase K treatment at 37° C. for 4 h. Small peptides were removed by dialysis. After freeze-drying, the retentate (~0.2 g) was made up to a 2% solution in water, centrifuged at 8,000 g for 15 min (yielding an 8K pellet of ~85 mg) followed by further centrifugation of the supernatant at 100,000 g for 5 h. The pellet, containing purified LPS, was redissolved and freeze-dried (yielding ~17 mg). 8K pellet material (~40 mg) was treated with anhydrous hydrazine with stirring at 37° C. for 1 h to prepare O-deacylated LPS (LPS-OH). The reaction was cooled in an ice bath and gradually, cold acetone (−70° C., 5 vols.) was added to destroy excess hydrazine and the precipitated LPS-OH was isolated by centrifugation and lyophilisation of the redissolved pellet (~35 mg). The sample was then purified down a Bio-Gel P-2 column with individual fractions lyophilised. The core oligosaccharide (OS) was isolated by treating separately the 8K pellet material (~45 mg) and the LPS (~17 mg) with 1% acetic acid (10 mg/ml, 100° C., 1.5 h) with subsequent removal of the insoluble lipid A by centrifugation (5,000×g). The lyophilised OS sample from the 8K pellet was subsequently further purified down a Bio-Gel P-2 column as above. Fully deacylated LPS was isolated by treatment of LPS-OH (~12 mg) with 4N KOH at 125° C. for 16 h and following neutralisation were fractionated by anion-exchange liquid chromatography.

Analytical Methods

Sugars were determined as their alditol acetate derivatives by GLC-MS. Samples were hydrolysed for 4 h using 4 M trifluoroacetic acid at 100° C. The hydrolysate was reduced ($NaBD_4$) for 16 h in $H_2O$ and acetylated with acetic anhydride at 100° C. for 2 h using residual sodium acetate as catalyst. The GLC-MS was equipped with a 30 M DB-17 capillary column (180° C. to 260° C. at 3.5° C./min) and MS was performed in the electron impact mode on a Varian Saturn II mass spectrometer. Methylation analysis was carried out by the NaOH/DMSO/methyl iodide procedure and analysed by GLC-MS. Absolute configurations were determined by GLC analysis of butyl glycoside derivatives.

Mass Spectrometry

ESIMS was performed in the negative ion mode on a VG Quattro Mass Spectrometer (Micromass, Manchester, U.K.) by direct infusion of samples in 25% aqueous acetonitrile containing 0.5% acetic acid. Capillary electrophoresis (CE)-MS was performed on a Prince CE system (Prince Technologies, The Netherlands) coupled to an API 3000 mass spectrometer (Applied Biosystem/Sciex, Concord, Canada) via a microspray interface. A sheath solution (isopropanol-methanol, 2:1) was delivered at a flow rate of 1 μL/min to a low dead volume tee (250 μm i.d., Chromatographic Specialties). All aqueous solutions were filtered through a 0.45-μm filter (Millipore) before use. An electrospray stainless steel needle (27 gauge) was butted against the low dead volume tee and enabled the delivery of the sheath solution to the end of the capillary column. The separations were obtained on about 90 cm length bare fused-silica capillary using 10 mM ammonium acetate/ammonium hydroxide in deionized water, pH 9.0, containing 5% methanol. A voltage of 20 kV was typically applied at the injection. The outlet of the capillary was tapered to ca. 15 μm i.d. using a laser puller (Sutter Instruments). Mass spectra were acquired with dwell times of 3.0 ms per step of 1 m/z unit in full-mass scan mode. The MS/MS data were acquired with dwell times of 1.0 ms per step of 1 m/z unit. Fragment ions formed by collision activation of selected precursor ions with nitrogen in the RF-only quadrupole collision cell, were mass analyzed by scanning the third quadrupole.

Nuclear Magnetic Resonance

NMR experiments were acquired on Varian Inova 400, 500 and 600 MHz spectrometers using a 5 mm or 3 mm triple resonance ($^1$H, $^{13}$C, $^{31}$P) probe. The lyophilised sugar sample was dissolved in 600 μL (5 mm) or 140 μL (3 mm) of 99% $D_2O$. The experiments were performed at 25° C. with suppression of the HOD (deuterated $H_2O$) signal at 4.78 ppm. The methyl resonance of acetone was used as an internal reference at 2.225 ppm for $^1$H spectra and 31.07 ppm for $^{13}$C spectra. Standard homo and heteronuclear correlated 2D pulse sequences from Varian, COSY, TOCSY, NOESY, $^{13}$C—$^1$H HSQC, $^{13}$C—$^1$H HSQC-TOCSY and $^{13}$C—$^1$H HMBC, were used for general assignments. The 1D $^{31}$P experiment was carried out on a Varian Inova 200 spectrometer with a sweep width of 40 ppm, 20000 transients and acquisition time of 1.6 s. The 2D $^1$H—$^{31}$P HSQC experiment was acquired on a Varian Inova 400 spectrometer for 6 h. The coupling constant was optimised at 10 Hz by performing an array of 1D-HSQC experiments. The sweep width in the F2 (1H) dimension was 6.0 ppm and in the F1 ($^{31}$P) dimension was 16.2 ppm. Water presaturation during the relaxation delay was 1.5 s, acquisition time in $t_2$ was 0.21 s, and 32 increments with 180 (HMQC) scans per increment were obtained. The 2D $^1$H—$^{31}$P HSQC-TOCSY experiment was acquired on a Varian Inova 400 spectrometer for 8 h using the same parameters as the HSQC experiment with a TOCSY mixing time of 150 ms.

Results & Analysis

Investigation of *P. multocida* Strain VP161

Sugar analysis of the purified LPS and 8K pellet material revealed glucose (Glc), galactose (Gal) and L-glycero-D-manno-heptose (LD-Hep) in the approximate ratio of 2:1:4 respectively. A small amount of N-acetyl-glucosamine (GlcNAc) was also identified. GLC analysis of the core oligosaccharide (OS) derived butyl-glycosides revealed Glc and Gal to be D-isomers.

Figure 27A:
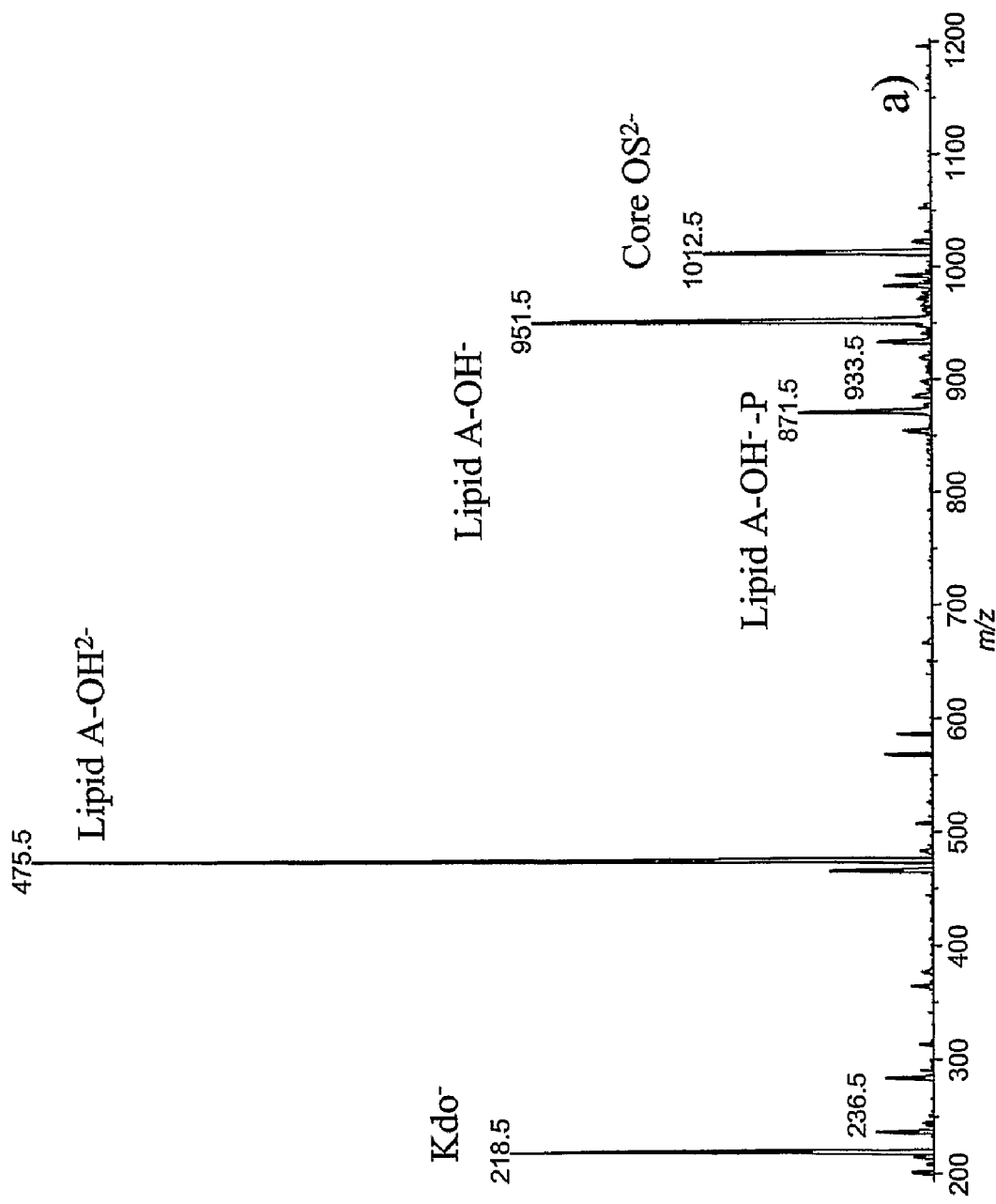
Figure 27B:
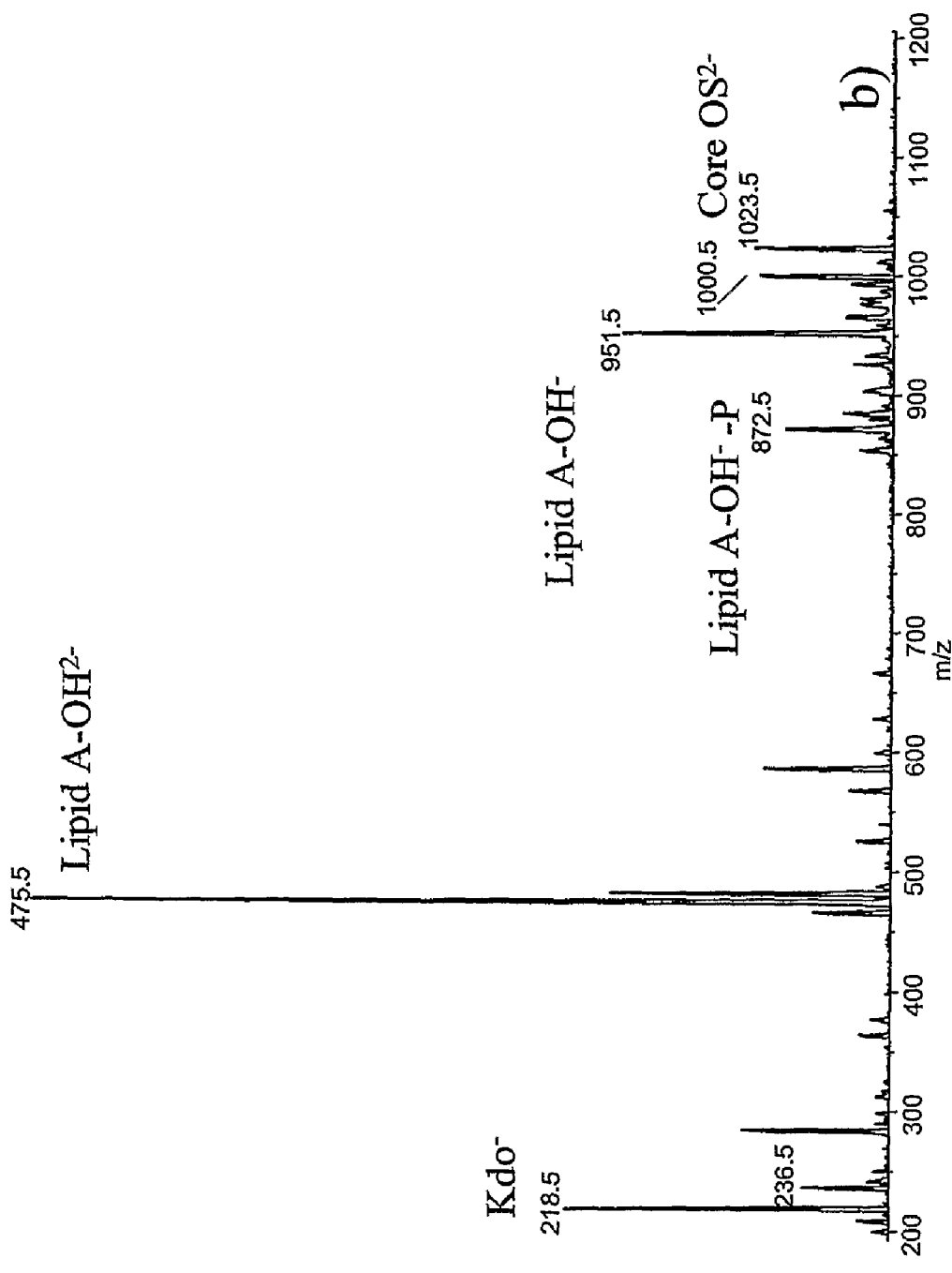
Figure 27C:
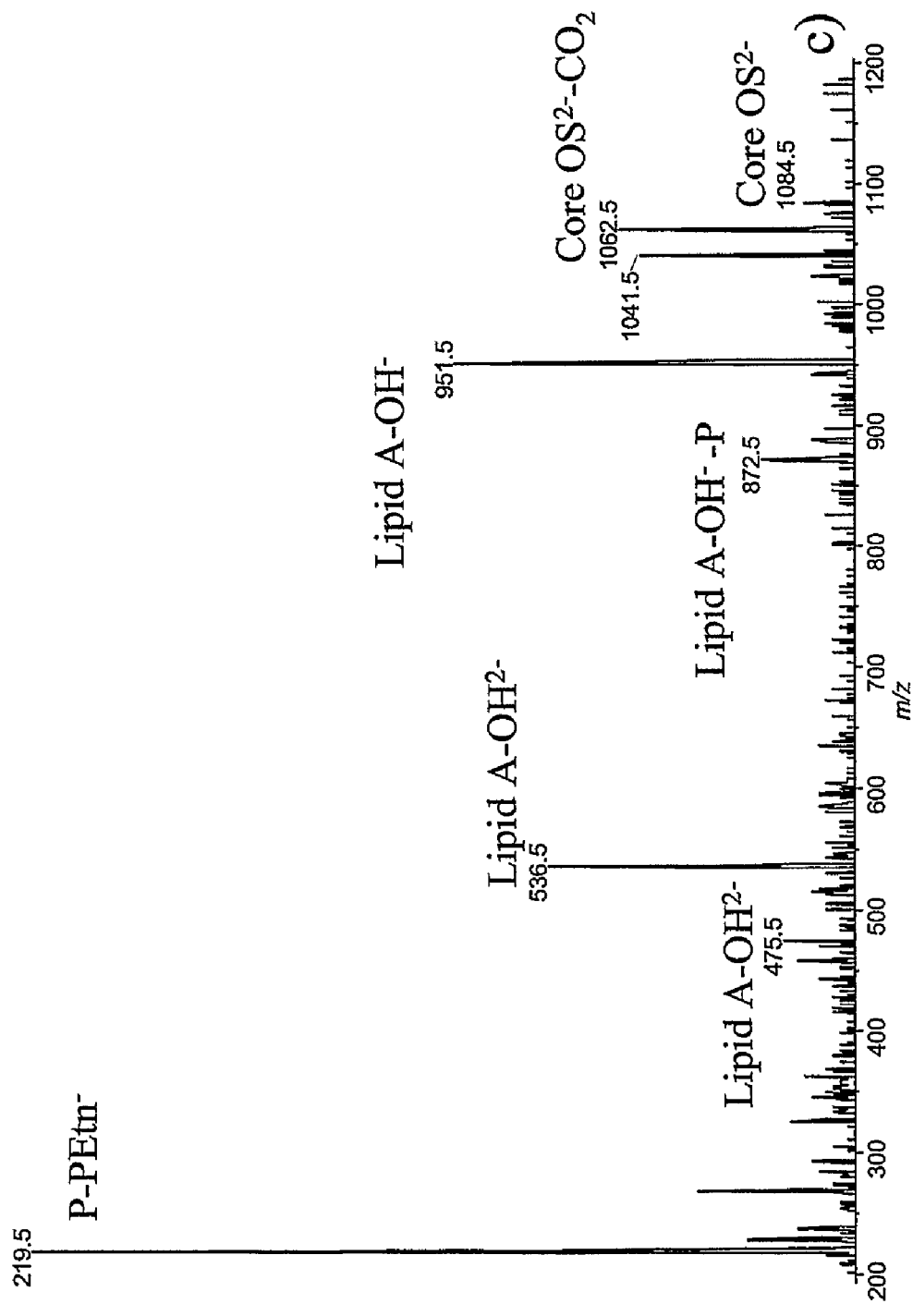

LPS-OH was prepared from LPS of fermenter-grown cells and analysed by CE-MS (Example 4 Table 1). Triply charged ions were observed at m/z 992.0, 999.0 and 1040.0 corresponding to a composition of 2PCho, 4Hep, 3Hex, 2 Kdo, Lipid A-OH for the smallest molecule. As shown below the larger glycoforms corresponded to molecules with a phosphate molecule in place of the second Kdo residue, one more hexose residue in the core oligosaccharide and for the largest glycoform (m/z 1040.0) an additional PEtn residue on the Kdo-P. Following growth on chocolate agar plates additional glycoforms were indicated from triply charged ions of m/z 1033.0 and 1081.0 (Example 4 Table 1). MS/MS analysis revealed that two different lipid A-OH species were found in the mixture of glycoforms, a basal species with a molecular mass of 952 amu as indicated by doubly and singly charged ions of m/z 475.5 and 951.5 following MS/MS and a species containing an additional PEtn residue by virtue of a doubly charged ion of m/z 536.5 observed following MS/MS (FIG. 27c). The O-deacylated lipid A basal species (952 amu) consists of a disaccharide of N-acylated (3-OH C 14:0) glucosamine residues, each residue being substituted with a phosphate molecule. The larger lipid A species was only observed from plate grown cells for the triply charged ions m/z 1033.0, 1040.0 and 1081.0. Additionally, evidence for the moiety P-PEtn was observed following MS/MS on glycoforms corresponding to the triply charged ions m/z 1040.0 and 1081.0 by virtue of a singly charged ion with m/z 219.5 (FIG. 27c). This ion was not observed following MS/MS on the triply charged ions of m/z 992.0, 999.0 and 1033.0. Furthermore MS/MS experiments revealed the size of the core OS molecules. For the triply charged ion at m/z 992.0 the core OS was 2027 amu as indicated by a doubly charged ion of m/z 1012.5 (FIG. 27a). This corresponds to a composition of 2 Kdo, 2PCho, 4Hep, 3Hex. For the triply charged ion at m/z 999.0 the core OS was 2049 amu as indicated by a doubly charged ion of m/z 1023.5 (FIG. 27b). This corresponds to a composition of Kdo, P, 2PCho, 4Hep, 4Hex. For the triply charged ion at m/z 1040.0 the core OS was observed at 2172 amu as indicated by a doubly charged ion of m/z 1084.5 or inferred to be 2049 amu as indicated by a doubly charged ion of m/z 536.5 that corresponds to a basal lipid A species with an additional PEtn residue (FIG. 27c). This ion at m/z 1040.0 therefore corresponds to isomeric glycoforms which have either the P-PEtn moiety on Kdo or the additional PEtn on-lipid A as evidenced by the two diagnostic doubly charged ions for the two lipid A species at m/z 475.5 and 536.5. As is often the case, evidence for the loss of $CO_2$ from Kdo on MS/MS analysis was also observed.

Figure 28A:
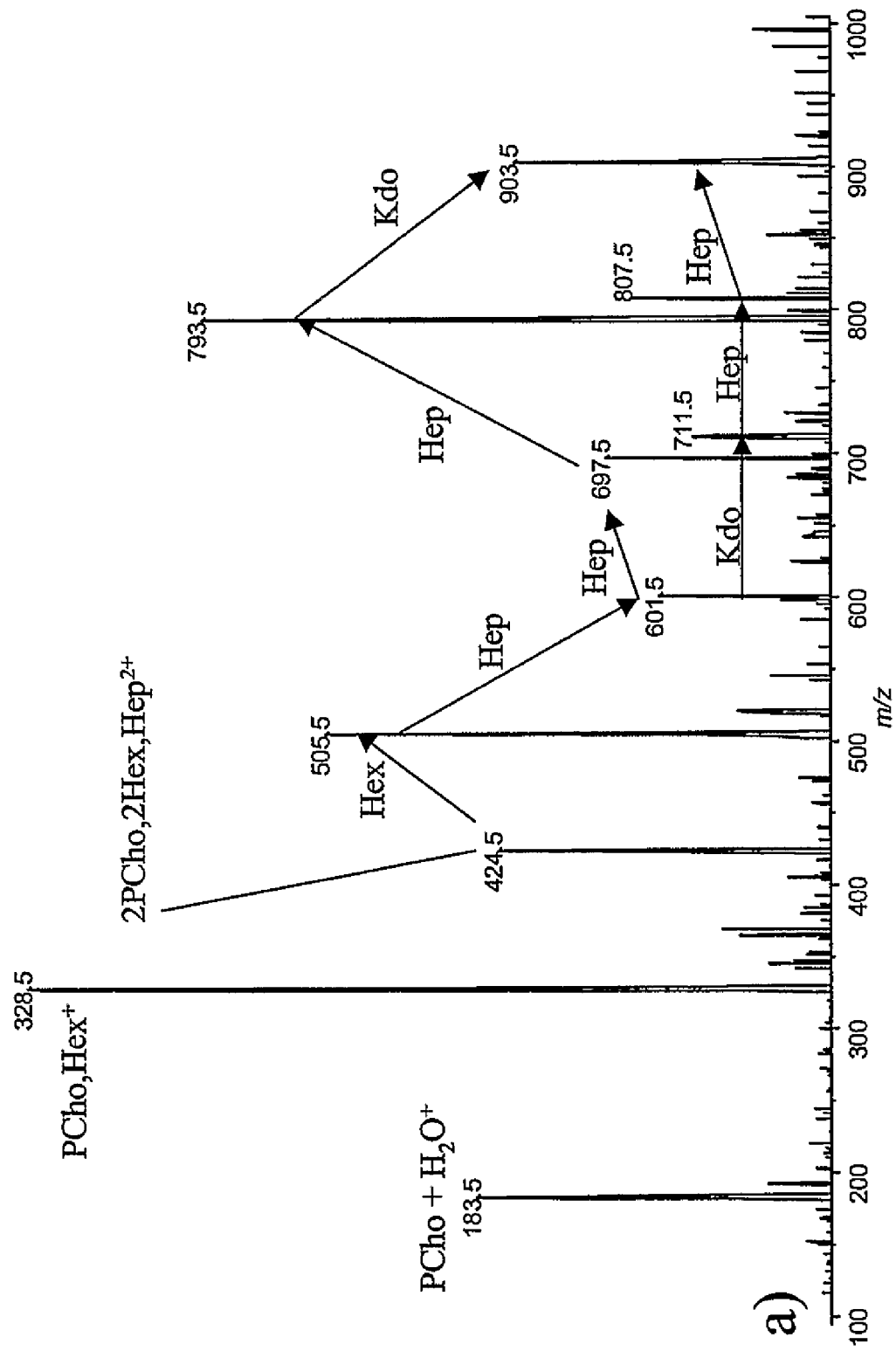
Figure 28B:
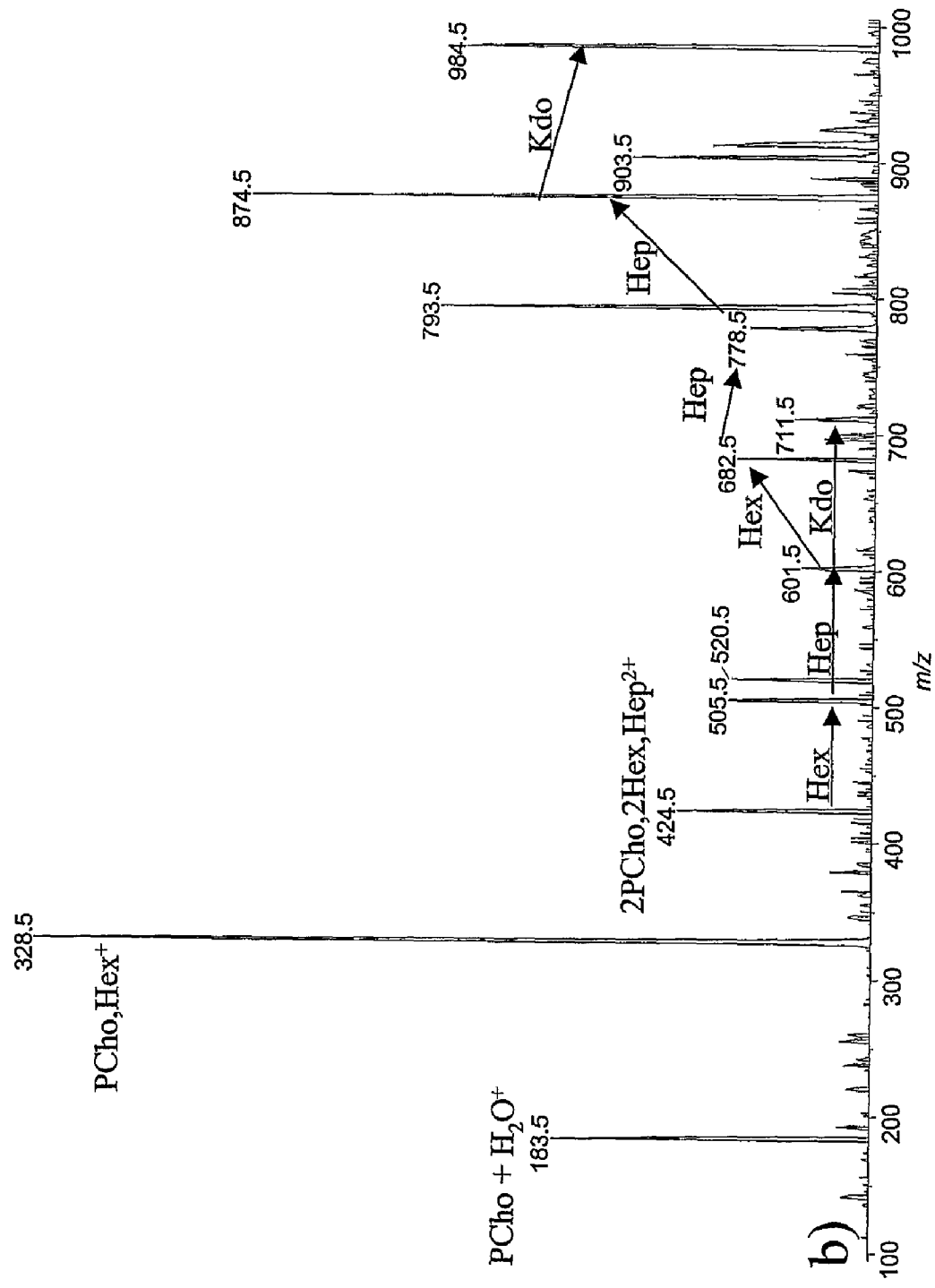
Figure 28C:
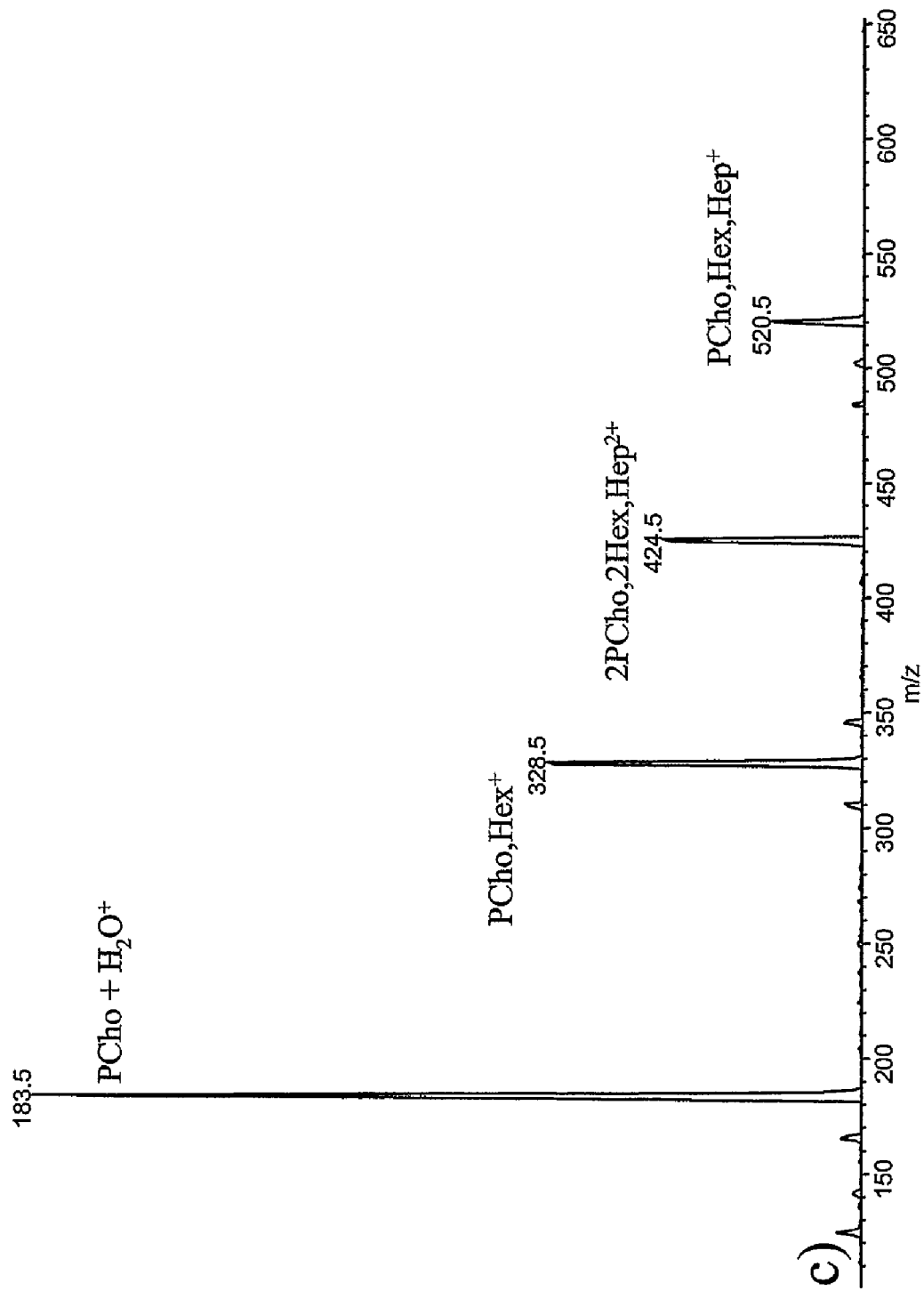

MS analysis on the core oligosaccharides alone (derived from both LPS and 8K pellet material; giving the same spectra), revealed different fragmentation patterns from the doubly charged positive ions at m/z 903.0 and 984.0, that correspond to the doubly charged negative ions at m/z 902.0 and 983.0 in Example 4 Table 1, consistent with the presence or absence of a hexose residue at the proximal heptose residue (Hep I) to Kdo. MS/MS on the doubly charged ion of m/z 903 (FIG. 28a) revealed a fragmentation pattern consistent with the absence of a Hex residue at Hep I. MS/MS on the doubly charged ion of m/z 984 (FIG. 28b) revealed that the larger OS had an additional hexose residue when compared to the former and this hexose residue was located on the Hep I residue by the presence of a doubly charged ion at m/z 682.0 and the absence of this signal but the presence of the doubly charged ion m/z 697.0 following MS/MS of m/z 903.0 (FIG. 28a). Taken together this data suggests a novel mixture of glycoforms produced by VP161 LPS some of which contain one Kdo species with a phosphate or pyrophosphoethanolamine moieties attached and another population that contains two Kdo molecules. In the species that contain two Kdo molecules a hexose residue was not present at the proximal heptose residue of the core OS suggesting that biosynthesis of this arrangement is not possible. The location of the PCho residues was also determined from these MS/MS experiments in positive ion mode. A doubly charged ion of m/z 424.5 was found to correspond to a composition of 2PCho, 2Hex, Hep and subsequent MS/MS/MS on this doubly charged ion revealed singly charged ions of m/z 328.5 and 520.5 corresponding to PCho-Hex and PCho-Hex-Hep respectively, suggesting that two PCho-Hex moieties were attached to a Hep residue (FIG. 28c).

Methylation analysis was performed on the O-deacylated LPS (LPS-OH) in order to determine the linkage pattern of the molecule revealing the presence of terminal Glc, 6-substituted Glc, terminal LD-Hep, 2-substituted LD-Hep and 4,6-disubstituted LD-Hep in the approximate molar ratio of 1:1:1:1:1, with lesser amounts of terminal Gal, 3,4-disubstituted LD-Hep and 3,4,6-trisubstituted LD-Hep being observed. Following HF treatment to remove phosphate residues that preclude optimal release of phosphorylated sugars on hydrolysis, methylation analysis was repeated which revealed the same sugars in the same ratio apart from the t-Gal residue which was now double the amount of the other components suggesting that the PCho residues had been substituting Gal sugars.

In order to elucidate the exact locations and linkage patterns of the OS, NMR studies were performed on the OS fraction that gave the most resolved and homogeneous spectra. The assignment of $^1$H resonances of the OS sample was achieved by COSY and TOCSY experiments with reference to the structurally related core OS from *Pasteurella multocida* strain Pm70 and from the related species Mannheimia haemolytica and *Actinobacillus pleuropneumoniae* (Example 4 Table 2). The inner core residues (to Hep IV (f/f')) were linked identically to the inner-core from the recently published *Pasteurella multocida* strain Pm70 and the assignments listed in Example 4 Table 2 were consistent with that. However there was no PEtn residue at the 3-position of Hep II (b) in the VP161 core OS. Interestingly for the core OS sample, the presence or absence of the Glc II residue (e) at Hep I (a) led to the identification of two sets of signals for the remaining inner core residues (FIG. 29). The two signals for Glc I at 4.64 (d) and 4.51 (d') ppm were identified by NOE contact to the 4- and 6-positions of Hep I (a) as has been described previously, however the absence of an inter-NOE contact between the anomeric proton resonances of Glc II (e) and the Glc I residue (d') at 4.51 ppm identified the spin system for this Glc I residue (d') when Glc II was absent. Conversely the presence of an inter-NOE contact between the anomeric proton resonances of Glc II (e) and the Glc I residue at 4.64 ppm (d) identified the spin system for this Glc I residue (d) when Glc II (e) was present (FIG. 29), this inter-anomeric NOE contact having been observed previously in the LPS of Pm70 and the related species Mannheimia haemolytica and *Actinobacillus pleuropneumoniae*. In such a way it was possible to assign the remaining inner core residues based upon the presence or absence of Glc II (e). The location and identification of the hexose residues at Hep IV (f/f') remained to be elucidated. MS analysis had indicated that both hexose residues were substituted with PCho residues and were both substituting Hep IV (f/f'). The increased amount of t-Gal identified in methylation analysis following HF treatment concurred with this and suggested that the hexose residues bearing PCho were both Gal sugars. Two P-configured Gal residues, Gal I and Gal II, were identified in the core OS sample at 4.70 (g) and 4.66 (h) ppm respectively, by virtue of their coupling constants and characteristic spin systems to H-4. The linkage positions of Gal I (g) and Gal II (h) at Hep IV (f/f') were inferred from a NOESY experiment which indicated that the Gal I residue (g) was linked to the 4-position of Hep IV (f) and the Gal II residue was linked to the 6-position of Hep IV (f/f') (FIG. 29). These inferences were confirmed from a $^{13}$C—$^1$H-HMBC experiment that also confirmed the other linkages in the core OS (FIG. 30). In order to identify the locations of the two PCho residues $^{31}$P—$^1$H-HSQC and $^{31}$P—$^1$H-HSQC-TOCSY experiments were performed that identified the previously assigned 3-positions of each Gal sugar as the point of attachment of each PCho residue (FIG. 31). This was confirmed by a $^{13}$C—$^1$H-HMQC experiment, which identified the chemical shifts of the C-3 atoms of each Gal residue at low-field values (~78 ppm) consistent with phosphorylation.

In order to explore further the novel arrangements in the Kdo region of the molecule deacylated samples were examined following KOH treatment. It was possible to separate fully deacylated LPS fractions that contained one and two Kdo residues (FIGS. 32a & b). The presence of one and two Kdo residue containing glycoforms is clearly illustrated in FIG. 32, as only one equatorial and one axial signal are visible for the H-3 protons of Kdo in FIG. 32a ($z_{3e}$ and $z_{3a}$), compared to two sets of signals for the equatorial and axial protons in FIG. 32b ($z_{3e}$, $z_{3a}$ and $z'_{3e}$ and $z'_{3a}$). Complete assignment was possible for the one Kdo containing sample and partial assignment was only possible for the two Kdo residue containing sample due to smaller amounts of this glycoform being available, resulting in a less intense spectrum. However, a rudimentary examination of the anomeric regions of the two spectra plainly shows the presence of a signal for the Glc II residue (e) in FIG. 32a (where only one Kdo residue is present) and the absence of such a signal in FIG. 32b (where two Kdo residues are present). As indicated by the core OS data, the presence or absence of the Glc II residue has an effect on the chemical shifts of several of the other anomeric proton resonances, particularly the Hep I (a), Hep II (b) and Glc I (d) signals, consistent with an effect on the conformation of the inner core molecule. Assignments for the one Kdo containing glycoform are detailed in Example 4 Table 2, which confirmed the assignments based on the core OS sample and extended this to include the Kdo-Lipid A region for the one Kdo containing glycoform.

Structural analysis of the oligosaccharide of the VP161 strain of *Pasteurella multocida* (Pm) has revealed a structure with similarities to and differences from the previously determined LPS core oligosaccharide structures for the genome strain Pm70 of Pm and the related species *Mannheimia haemolytica* (Mh), *Actinobacillus pleuropneumoniae* (App). In each case the core OS contains an identically linked tri-heptosyl unit that is attached to a Kdo residue. Interestingly in Pm70 the 3-position of the HepII residue is substituted in the majority of cases with a PEtn residue, whereas in strain VP161, and in the related species App and Mh no inner core PEtn residues were observed. Apart from this variation in the substitution of Hep II with PEtn, both Pm strains and the related veterinary species Mh and App share a relatively conserved inner core structure. The only other differences in the inner core structure of Pm are the identification of a L-glycero-D-manno configured heptose residue in the extension from the Glc I residue at Hep I compared to the D-glycero-D-manno configured heptose residues encountered in App and Mh, and the variable presence of the Glc II residue in the Pm inner core, apparently due to the variability of the Kdo region of the molecule. This Glc II residue was stoichiometrically found in the inner core LPS of App and Mh. A different extension beyond this conserved inner core region was observed in strain VP161, whereby the Hep IV residue was di-substituted with two PCho-Gal moieties at the 4- and 6-positions. To our knowledge this structural arrangement has not been observed previously. It is rare to encounter two PCho residues in the same LPS molecule; non-typable Hi carriage strains 11 and 16 are the only documented examples of such an arrangement. The presence of PCho residues could be implicated in the virulence of the Pm organism, as a role for PCho in adherence and colonisation in the respiratory tract has been documented. It was also found that a mutant of strain VP161 that presented a truncated LPS structure lacking the two PCho residues was attenuated in both a mouse model and in chickens. A previous study by other authors had also observed a decrease in virulence of a galE mutant serotype D strain of Pm that could be due to alteration of the LPS structure. The most intriguing aspect of the VP161 LPS structure however is the variation observed in the Kdo region; where both one Kdo and two Kdo containing glycoforms have been observed. Additionally the impact on the inner core structure, i.e. the presence or absence of Glc II at Hep I, caused by the variability of the Kdo region arrangement is interesting. The α-1,6glucosyltransferase responsible for the transfer of Glc II to the Hep I residue is not known. It was interesting to note that only one homologue to Kdo transferases was identified in the Pm genome of strain Pm70 whose LPS also contained populations with both one Kdo and two Kdo containing species. It would also be of interest to compare the sequence of the Kdo transferase genes from Pm, App and Mh in order to investigate any sequence differences that could be attributed to the "bi-functional" nature of the Pm transferase or if other regulatory factors are involved in this variability. This study has identified the LPS structure of a second Pm strain, both strains share a similar inner core structure but a variable outer core decoration, and both exhibit an interesting variation in the Kdo region of the molecule, the significance of which remains to be investigated.

TABLE 1

Negative ion CE-MS data and proposed compositions of O-deacylated LPS (LPS-OH) and core OS from *P. multocida* strain VP161.
Average mass units were used for calculation of molecular mass based on proposed composition as follows:
Hex, 162.15; Hep, 192.17; Kdo, 220.18; PEtn, 123.05; Lipid A-OH, 952.00.

| Strain | $[M-3H]^{3-}$ | $[M-4H]^{4-}$ | Observed Molecular Ion | Calculated Molecular Ion | Lipid A size | Core OS size | Proposed Composition |
|---|---|---|---|---|---|---|---|
| VP161 | 992.0 | 744.0 | 2979.5 | 2977.6 | 952 | 2025.6 | 2PCho, 3Hex, 4Hep, 2Kdo, Lipid A-OH |
| LPS-OH | 999.0 | 749.0 | 2999.5 | 2999.5 | 952 | 2047.5 | 2PCho, 4Hex, 4Hep, Kdo-P, Lipid A-OH |
|  | 1033.0 | 774.0 | 3101.0 | 3100.7 | 1075 | 2025.7 | 2PCho, 3Hex, 4Hep, 2Kdo, Lipid A-OH |
|  | 1040.0 | 780.0 | 3123.5 | 3122.6 | 952 | 2170.6 | 2PCho, 4Hex, 4Hep, Kdo-P-PEtn, Lipid A-OH |
|  | 1040.0 | 780.0 | 3123.5 | 3122.6 | 1075 | 2047.6 | 2PCho, 4Hex, 4Hep, Kdo-P, Lipid A-OH |
|  | 1081.0 | 810.0 | 3245.0 | 3245.6 | 1075 | 2170.6 | 2PCho, 4Hex, 4Hep, Kdo-P-PEtn, Lipid A-OH |
|  | $[M+2H]^{2+}$ | | | | | | |
| VP161 | 901.8 | | 1805.6 | 1805.4 | — | | 2PCho, 3Hex, 4Hep, Kdo |
| Core OS | 982.9 | | 1967.8 | 1967.6 | — | | 2PCho, 4Hex, 4Hep, Kdo |

TABLE 2

$^1$H- and $^{13}$C-NMR chemical shifts for the core OS and fully deacylated (KOH treated) LPS from *Pasteurella multocida* VP161

|  | H-1 | H-2 | H-3 | H-4 | H-5 | H-6 | H-7 | H-8 | Inter (NOE's) | Intra | Long Range |
|---|---|---|---|---|---|---|---|---|---|---|---|
| α-GlcN$^a$ (x) | 5.75 (92.7) | 3.47 (55.1) | 3.93 (70.5) | 3.53 (70.7) | 4.13 (73.7) | 4.31 3.90 (70.2) | | | | | |
| β-GlcN$^a$ (y) | 4.88 (100.0) | 3.17 (56.6) | 3.92 (72.8) | 3.94 (75.3) | 3.78 (74.9) | 3.75 3.59 (63.4) | | | | | |
| Kdo$^a$ (z) | — | — | 2.37 2.06 (35.0) | 4.62 (71.2) | 4.29 (72.9) | 3.84 (nd) | 3.77 (70.3) | 3.96 3.72 (64.6) | | | |
| Hep-I$^a$ (a) | 5.18 (100.4) | 4.13 (71.3) | 4.01 (75.2) | 4.19 (75.2) | 4.19 (72.8) | 4.11 (81.5) | nd nd (nd) | | 4.29 Kdo H-5 | 4.09 H-2 | |
| Hep-I$^b$ (a) | 5.07 (101.9) | 4.09 (71.3) | 3.96 (73.9) | 4.20 (74.7) | 3.78 (72.9) | 4.13 (80.3) | 3.88 3.75 (62.9) | | nd | 4.09 H-2 | |
| Hep-I$^b$ (a') | 5.01 (101.4) | 4.15 (71.3) | 4.04 (73.9) | 4.26 (74.2) | nd (nd) | 4.05 (nd) | nd (64.2) | | nd | 4.15 H-2 | |
| Hep-II$^a$ (b) | 5.62 (100.7) | 4.26 (80.8) | 3.90 (70.9) | 3.90 (67.8) | 3.63 (72.4) | 4.07 (69.7) | 3.72 3.62 (64.6) | | 5.14 Hep III H-1 3.96 Hep I H-3 | 4.19 H-2 | 3.75 Hep I H-5 |
| Hep-II$^b$ (b) | 5.70 (100.1) | 4.19 (80.5) | 3.86 (70.7) | 3.84 (67.6) | 3.55 (72.8) | 4.05 (70.3) | 3.76 3.65 (64.5) | | 5.14 Hep III H-1 3.96 Hep I H-3 | 4.19 H-2 | 3.75 Hep I H-5 |
| Hep-II$^b$ (b') | 5.76 (99.7) | 4.17 (80.5) | 3.85 (70.7) | 3.83 (67.6) | 3.60 (72.8) | 4.05 (70.3) | 3.76 3.65 (64.5) | | 5.11 Hep III H-1 4.04 Hep I H-3 | 4.17 H-2 | 3.76 Hep I H-5 |
| Hep-III$^{ab}$ (c) | 5.11 (102.4) | 4.01 (71.4) | 3.87 (70.8) | 3.83 (67.0) | 3.78 (71.6) | 4.05 (70.3) | 3.77 3.65 (64.9) | | 5.76 Hep II H-1 4.17 Hep II H-2 | 4.01 H-2 | 3.94 Hep IV H-3 3.59 Glc I H-4 |

TABLE 2-continued $^1$H- and $^{13}$C-NMR chemical shifts for the core OS and fully deacylated (KOH treated) LPS from *Pasteurella multocida* VP161

| | H-1 | H-2 | H-3 | H-4 | H-5 | H-6 | H-7 | H-8 | NOE's Inter | Intra | Long Range |
|---|---|---|---|---|---|---|---|---|---|---|---|
| Hep-III$^b$ (c') | 5.14 (102.4) | 4.02 (71.4) | 3.87 (70.8) | 3.83 (67.0) | 3.78 (71.6) | 4.05 (70.3) | 3.77 3.65 (64.9) | | 5.70 Hep II H-1 4.19 Hep II H-2 | 4.02 H-2 | 3.94 Hep IV H-3 3.57 Glc I H-4 |
| β-Glc-I$^{ab}$ (d) | 4.64 (104.3) | 3.54 (74.2) | 3.40 (77.6) | 3.59 (70.5) | 3.51 (74.6) | 4.09 3.76 (65.8) | — | | 4.20 Hep I H-4 4.13 Hep I H-6 | 3.51 H-5 3.40 H-3 | 5.20 Glc II H-1 |
| β-Glc-I$^b$ (d') | 4.51 (104.2) | 3.53 (74.2) | 3.42 (77.7) | 3.57 (70.5) | 3.57 (74.7) | 4.05 3.83 (65.6) | — | | 4.26 Hep I H-4 4.05 Hep I H-6 | 3.57 H-5 3.42 H-3 | |
| α-Glc-II$^{ab}$ (e) | 5.20 (102.6) | 3.58 (72.8) | 3.81 (73.8) | 3.58 (69.4) | 3.91 (72.4) | 3.93 3.74 (60.4) | — | | 4.13 Hep I H-6 | 3.58 H-2 | 4.64 Glc I H-1 |
| Hep-IV$^{ab}$ (f) | 4.95 (99.9) | 4.17 (70.1) | 3.93 (71.0) | 4.19 (77.2) | 3.91 (70.3) | 4.32 (79.9) | 3.97 3.75 (64.0) | | 4.09 Glc I H-6 3.77 Glc I H-6 | 4.17 H-2 | |
| Hep-IV$^b$ (f') | 4.93 (99.9) | 4.16 (70.1) | 3.93 (71.0) | 4.19 (77.2) | 3.91 (70.3) | 4.32 (79.9) | 3.97 3.75 (64.0) | | 4.04 Glc I H-6 3.83 Glc I H-6 | 4.16 H-2 | |
| β-Gal-I$^b$ (g) | 4.70 (103.2) | 3.69 (71.0) | 4.19 (78.5) | 4.12 (68.6) | 3.80 (75.7) | nd nd (nd) | — | | 4.19 Hep IV H-4 | 4.19 H-3 3.80 H-5 | |
| β-Gal-II$^b$ (h) | 4.66 (104.5) | 3.73 (71.0) | 4.18 (78.5) | 4.11 (68.6) | 3.76 (75.5) | nd nd (nd) | — | | 4.32 Hep IV H-6 | 4.18 H-3 3.76 H-5 | |
| PCho-I | 4.38 (60.4) | 3.68 (66.8) | 3.22 (54.7) | | | | | | | | |
| PCho-II | 4.38 (60.4) | 3.68 (66.8) | 3.21 (54.7) | | | | | | | | |

$^a$Data from KOH treated LPS is from the Kdo residue containing glycoform;
$^b$Data from core OS sample;
$^{ab}$Data from both KOH treated LPS and core OS, assignments identical. Data from Gal-I and Gal-II for the KOH treated LPS is not included due to considerable heterogeneity introduced by hydrolysis and migration of PCho residues.

Example 5

This Example forms the basis of a publication in Carbohydrate Research 340, 1253 (2005). Structural analysis of the core oligosaccharide from *Pasteurella multocida* strain X73.

In this example the structure of the core oligosaccharide region of the lipopolysaccharide from the *Pasteurella multocida* strain X73 was elucidated. The lipopolysaccharide was subjected to a variety of degradative procedures. The structure of the purified oligosaccharide was established by monosaccharide and methylation analyses, NMR spectroscopy and mass spectrometry. The following structure illustrates a similar structure to the recently identified oligosaccharide from another *P. multocida* strain VP161, but with additional symmetrical substitution of the terminal galactose residues with phosphoethanolamine moieties, where based on the NMR data all sugars were found in pyranose ring forms and Kdo is 2-keto-3-deoxy-octulosonic acid, L,D-α-Hep is L-glycero-D-manno-heptose, PEtn is phosphoethanolamine and PCho is phosphocholine.

*Pasteurella multocida* (Pm) is a Gram-negative bacterium and multi-species pathogen that causes serious diseases in food animals and humans. Structural analyses on the lipopolysaccharide (LPS) of the genome strain Pm70 and a virulent serotype A: 1 strain VP161 have revealed a conserved inner core oligosaccharide (OS) structure with variable outer core OS structures. This study was carried out on another virulent serotype A strain X73 and structural analysis of the purified LPS products revealed a similar OS structure to that found for strain VP161 but with an additional symmetrical phosphorylation pattern to the outer core OS. Sugar analysis of the purified LPS and 8K pellet material from strain X73

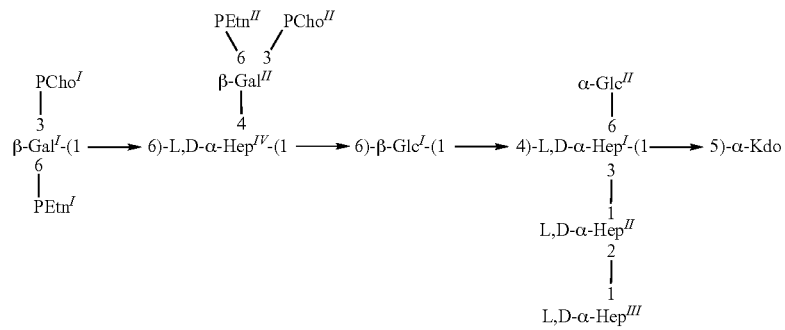

revealed a similar profile to strain VP161 containing the sugars glucose (Glc), galactose (Gal) and L-glycero-D-manno-heptose (LD-Hep) in the approximate ratio of 2:1:4 respectively. O-deacylated LPS (LPS-OH) was prepared from fermenter-grown cells and analysed by CE-MS (Example 5 Table 1). A similar mass profile to that observed for strain VP161 was observed but with the major species now being a triply charged ion of m/z 1081.0, which would correspond to two additional PEtn residues compared to the most prominent species (m/z 999.0) from VP161 LPS-OH. MS/MS analyses revealed that all lipid A molecules were the basal species consisting of a disaccharide of N-acylated (3-OH C 14:0) glucosamine residues, each residue being substituted with a phosphate molecule with a molecular weight of 952 amu as indicated by doubly and singly charged ions of m/z 475.5 and 951.5. This MS/MS analysis therefore indicated that the additional PEtn residues in strain X73 reside in the core OS region of the LPS molecule, and the expected mass of the core OS molecules is indicated in Example 5 Table 1.

MS analysis on the core oligosaccharides alone, revealed a series of ions consistent with the compositions inferred from the LPS-OH data, indicating the presence of additional PEtn residues when compared to strain VP161. The location of the PEtn residues was determined from MS/MS experiments in positive ion mode. Fragmentation of the doubly charged ion of m/z 1108 corresponding to the largest glycoform produced several product ions including m/z $183.5^+$ (PCho), $450.5^+$ (PCho-Hex-PEtn), $547.5^{2+}$ (2PCho, 2PEtn, 2Hex, Hep) and $916.5^{2+}$ (M-Kdo-Hex). The doubly charged ion at m/z $547.5^{2+}$ was of particular interest when compared to the doubly charged ion observed at m/z $424^{2+}$ in strain VP161, as it would indicate a glycoform with a mass 246 amu higher consistent with the presence of two PEtn residues. MS/MS/MS analysis on the doubly charged ion at m/z $916.5^{2+}$ revealed the product ion spectrum shown in FIG. 33a. The fragmentation pattern indicated in FIG. 33a enabled the PEtn residues to be localized to the terminal Hex-PCho moieties on the $Hep^{IV}$ residue, and a subsequent MS/MS/MS experiment (FIG. 33b) fragmenting the ion m/z 450.5 confirmed that this ion corresponded to the PCho-Hex-PEtn moiety as originally inferred.

In order to confirm and extend these inferences NMR experiments were performed on the fractionated core OS sample that contained both PEtn residues (as determined by MS—data not shown). Apart from the two terminal galactose residues all assignments were identical to those obtained on the core OS from strain VP161. Chemical shifts for the H-1 and H-2 resonances of the galactose residues were as observed for the VP161 sample, but the H-3 and H-4 resonances were shifted slightly downfield from 4.17 and 4.12 to 4.21 and 4.17 ppm respectively. Inter-NOE contacts from the galactose residues were as observed previously although the intra-NOE contact to the H-5 residue was now observed at 3.94 ppm as opposed to 3.80 and 3.76 ppm for strain VP161 (Example 5 Table 2). In order to identify the locations of the two PEtn residues a $^{31}P$—$^{1}H$-HSQC experiment was performed that identified a resonance at 4.07 ppm as the point of attachment of each PEtn residue, a subsequent $^{31}P$—$^{1}H$-HSQC-TOCSY experiment identified the H-5 resonance of the galactose residues at 3.94 ppm (FIG. 34). The assignment of 4.07 ppm as the H-6 resonance of the galactose residues was confirmed by a $^{13}C$—$^{1}H$-HMQC experiment, which identified as a characteristic positive peak for a —$CH_2$ moiety, the downfield chemical shift of the C-6 atoms of each Gal residue at low-field values (~65 ppm) consistent with phosphorylation. Finally a $^{13}C$—$^{1}H$-HMQC-TOCSY experiment identified cross-peaks between the C-6 and H-5 resonances and vice-versa, confirming the 6-positions of the two galactose residues as the points of attachments of the additional two PEtn moieties found in the strain X73 core OS (FIG. 35).

This study has therefore identified a similar core OS structure from the LPS of a second serotype A strain. Further studies will extend LPS structural analyses to other serotypes to examine if this novel terminal structure is present in other serotypes. The identification of PEtn at the 6-position of a six-carbon sugar is somewhat unusual. PEtn is commonly found at the 6-position of heptose residues in both *Neisseria meningitidis* and *Haemophlilus influenzae*. Recent studies in our laboratory have identified PEtn at the 6-position of a terminal GalNAc residue in several *Haemophilus influenzae* strains and a recent poster also found a PEtn residue at the 6-position of a 3-linked galactose molecule in *Citrobacter* sp. PCM1443 (serotype O39) with similar chemical shifts to those observed here.

1. Experimental 1.1 Growth of Bacteria, Isolation and Fractionation of LPS

*P. multocida* strain X73 (NRCC#6235) was grown and isolated. Briefly, *P. multocida* cells (~210 g wet wt.) were freeze-dried, yielding ~56 g. Freeze-dried cells were washed with organic solvents (1× ethanol, 2× acetone, 2× light petroleum ether) to remove lipids and other lipophilic components to enhance the efficiency of the LPS extraction. Washed cells (10 g from ~42 g) were extracted by the hot phenol/water method and the aqueous phases combined and dialysed against running water for 48 h. The retentate was freeze-dried yielding ~0.57 g, made up to a 2% solution in water and treated with DNase and RNase at 37° C. for 4 h followed by proteinase K treatment at 37° C. for 4 h. Small peptides were removed by dialysis. After freeze-drying, the retentate (~0.42 g) was made up to a 2% solution in water, centrifuged at 8,000 g for 15 min (yielding an "8K pellet" of ~265 mg) followed by further centrifugation of the supernatant at 100,000 g for 5 h. The pellet, containing purified LPS, was redissolved and freeze-dried (yielding ~3 mg). LPS-OH and core OS were isolated and fractionated. Briefly, 8K pellet material (~15 mg) and LPS (~3 mg) were treated with anhydrous hydrazine with stirring at 37° C. for 1 h to prepare LPS-OH yielding ~10 mg from the 8K preparation and ~1 mg from the LPS. The core OS was isolated by treating the 8K pellet material (~115 mg) with 1% acetic acid (10 mg/ml, 100° C., 1.5 h) with subsequent removal of the insoluble lipid A by centrifugation (5,000×g). The lyophilised supernatant was subsequently further purified down a Bio-Gel P-2 column with separate fractions lyophilised yielding ~40 mg.

1.2 Analytical Methods

Sugars were determined as their alditol acetate derivatives by GLC-MS. Methylation analysis was carried out by the NaOH/DMSO/methyl iodide procedure and analysed by GLC-MS.

1.3 Mass Spectrometry and NMR Spectroscopy

All mass spectrometry and NMR experiments were performed as described above.

TABLE 1

Negative ion CE-MS data and proposed compositions of O-deacylated LPS (LPS-OH) and core OS from *P. multocida* strain X73. Average mass units were used for calculation of molecular weight based on proposed composition as follows: Hex, 162.15; Hep, 192.17; Kdo, 220.18; PEtn, 123.05; PCho, 165.05; Lipid A-OH, 952.00. Relative intensity is expressed as relative to the largest triply charged ion in the spectrum for the LPS-OH molecule.

| Strain | $[M - 3H]^{3-}$ | $[M - 4H]^{4-}$ | Observed Molecular Ion | Calculated Molecular Ion | Relative Intensity | Lipid A size | Core OS size | Proposed Composition |
|---|---|---|---|---|---|---|---|---|
| X73 LPS-OH | 992.0 | 744.0 | 2979.5 | 2977.6 | 0.1 | 952 | 2025.6 | 2PCho, 3Hex, 4Hep, 2Kdo, Lipid A-OH |
| | 999.0 | 749.0 | 2999.5 | 2999.5 | 0.2 | 952 | 2047.5 | 2PCho, 4Hex, 4Hep, Kdo-P, Lipid A-OH |
| | 1033.0 | 774.0 | 3101.0 | 3100.7 | 0.2 | 952 | 2148.7 | PEtn, 2PCho, 3Hex, 4Hep, 2Kdo, Lipid A-OH |
| | 1040.0 | 780.0 | 3123.5 | 3122.6 | 0.4 | 952 | 2170.6 | PEtn, 2PCho, 4Hex, 4Hep, Kdo-P, Lipid A-OH |
| | 1074.0 | 805.0 | 3224.1 | 3223.7 | 0.3 | 952 | 2271.7 | 2PEtn, 2PCho, 3Hex, 4Hep, 2Kdo, Lipid A-OH |
| | 1081.0 | 810.0 | 3245.0 | 3245.6 | 1.0 | 952 | 2293.7 | 2PEtn, 2PCho, 4Hex, 4Hep, Kdo-P, Lipid A-OH |
| | 1122.0 | 841.0 | 3368.5 | 3368.7 | 0.2 | 952 | 2416.7 | 3PEtn, 2PCho, 4Hex, 4Hep, Kdo-P, Lipid A-OH |
| | $[M - 2H]^{2-}$ | | | | | | | |
| X73 Core OS | — | 901.3 | 1804.6 | 1805.2 | | — | — | 2PCho, 3Hex, 4Hep, Kdo |
| | — | 962.8 | 1927.6 | 1928.2 | | — | — | PEtn, 2PCho, 3Hex, 4Hep, Kdo |
| | — | 982.8 | 1967.6 | 1967.6 | | — | — | 2PCho, 4Hex, 4Hep, Kdo |
| | — | 1024.3 | 2050.3 | 2051.3 | | — | — | 2PEtn, 2PCho, 3Hex, 4Hep, Kdo |
| | — | 1044.3 | 2090.6 | 2090.6 | | — | — | PEtn, 2PCho, 4Hex, 4Hep, Kdo |
| | 736.8 | 1106.3 | 2214.0 | 2213.7 | | — | — | 2PEtn, 2PCho, 4Hex, 4Hep, Kdo |

TABLE 2

$^1$H- and $^{13}$C-NMR chemical shifts for the terminal region of the core OS from *Pasteurella multocida* strain X73: All other residues have identical chemical shifts to strain VP161.

| Residue | H-1 | H-2 | H-3 | H-4 | H-5 | H-6 | H-7 | NOE connectivities Inter | Intra |
|---|---|---|---|---|---|---|---|---|---|
| Hep$^{IV}$ | 4.95 (99.9) | 4.18 (70.0) | 3.96 (70.9) | 4.18 (77.4) | 3.93 (70.2) | 4.32 (79.9) | 3.97 3.75 (63.5) | 4.09 Glc$^J$ H-6 3.77 Glc$^J$ H-6 | 4.18 H-2 |
| β-Gal$^I$ | 4.72 (103.4) | 3.70 (70.7) | 4.20 (78.2) | 4.17 (68.2) | 3.94 (74.0) | 4.07 4.07 (65.4) | — | 4.18 Hep$^{IV}$ H-4 | 4.20 H-3 3.93 H-5 |
| β-Gal$^{II}$ | 4.70 (104.5) | 3.73 (70.7) | 4.21 (78.1) | 4.17 (68.2) | 3.94 (74.0) | 4.07 4.07 (65.4) | — | 4.32 Hep$^{IV}$ H-6 | 4.21 H-3 3.93 H-5 |
| PEtn$^I$ | 4.13 (62.7) | 3.31 (40.8) | | | | | | | |
| PEtn$^{II}$ | 4.13 (62.7) | 3.31 (40.8) | | | | | | | |
| PCho$^I$ | 4.38 (60.4) | 3.68 (66.8) | 3.22 (54.7) | | | | | | |
| PCho$^{II}$ | 4.38 (60.4) | 3.68 (66.8) | 3.21 (54.7) | | | | | | |

Example 6

This example forms the basis of a publication in Infect. Immun. 72: 3436 (2004). A heptosyltransferase mutant of *Pasteurella multocida* produces a truncated lipopolysaccharide structure and its virulence is attenuated Analysis of the *P. multocida* VP161 wild type LPS indicated a "rough" LPS, similar to the LPS or lipooligosaccharide isolated from gram-negative mucosal pathogens such as *Haemophilus influenzae.*, *H. ducreyi*, *Neisseria meningitides*, and *N. gonorrhoeae*, with only a short non-repeating polysaccharide unit attached to the lipid A. The inner-core structure of *P. multocida* LPS is similar to that described for *H. influenzae*, *Mannheimia haemolytica*, and *H. ducreyi* with a tri-heptose unit liked via a KDO residue to lipid A (FIG. 30). In the AL251 mutant, inactivation of waaQ$_{PM}$ resulted in the expression of a highly truncated LPS that lacked the third heptose molecule (Hep III) in the inner-core region. The most abundant glycoforms of LPS in the mutant also lacked all sugars distal to the first heptose, suggesting that the inactivation of waaQ$_{PM}$ prevented further sugar additions. It is therefore probable that conformational changes in the LPS intermediates due to the lack of the third heptose largely prevented the action of subsequent transferases.

Materials and Methods

Bacterial strains, plasmids, media and growth conditions. The bacterial strains and plasmids used in this study are shown in Example 6, Table 1. *Escherichia coli* was grown routinely in Luria-Bertani broth. *P. multocida* strains were grown in either brain heart infusion (BHI) or nutrient broth (NB) supplemented with yeast extract (3%) (Oxoid, Basingstoke, United Kingdom). Solid media were obtained with the addition of 1.5% agar. When required, the media were supplemented with tetracycline at 2.5 µg/ml. For structural studies,

*P. multocida* strains VP161 and AL251 were grown in a 28 L fermenter in 24 L of BHI broth for 18 h at 37° C. with 20% DO saturation. The cells were killed by addition of phenol to 2%, and 3 h post-phenol 1 g of hyaluronidase (Roche Chemicals) was added and stirred for 1 h before harvesting cells by using a Sharples continuous flow centrifuge.

Transposon stability studies. *P. multocida* AL251 was grown in 10 ml of NB, shaken at 37° C. After approximately 10, 34 and 58 generations, samples of the culture were taken, diluted appropriately, and plated onto NB agar. After overnight incubation 100 colonies were patched onto NB with tetracycline and incubated overnight at 37° C. Transposon loss was expressed as the percentage of tetracycline sensitive colonies.

SDS-PAGE and silver staining. Analysis of LPS was performed with a Bio-Rad mini protein gel apparatus using SDS-PAGE as described in Laemmli, Nature 227, 680 (1970). LPS was then visualized by silver staining.

DNA manipulations. Restriction digests, ligations and polymerase reactions were performed according to the manufacturers' instructions using enzymes obtained from NEB (Beverley, Mass.) or Roche Diagnostics GmbH (Mannheim, Germany). Plasmid DNA was prepared using alkaline lysis and purified using Qiagen columns (QIAGEN GmbH, Germany) or by PEG precipitation (Ausubel, 1995). Genomic DNA was prepared using the CTAB method. PCR amplification of DNA was performed using Taq DNA polymerase or Expand High Fidelity PCR System (Roche Diagnostics) and purified using the Qiagen PCR Purification Kit. The oligonucleotides used in this study are listed in Example 6, Table 1. The DNA Sequence was determined on a Model 373A DNA Sequencing System (Applied Biosystems) and analyzed with Sequencher Version 3.1.1 (GenCodes, Ann Arbor, Mich.).

In trans complementation of $waaQ_{PM}$. The complete $waaQ_{PM}$ gene was amplified from *P. multocida* VP161 genomic DNA using oligonucleotides BAP2146 and BAP2147 (Example 6, Table 1). The amplified 1.1 kb DNA fragment was ligated to SalI and BamHI-digested vector pAL99 (Example 6, Table 1), such that transcription was driven by the *P. multocida* tpiA promoter. *E. coli* transformants were screened for the presence of the correct plasmid and one, designated pAL170, was used to transform *P. multocida* AL251, generating the strain AL298. As a control, the vector pAL99 was transformed separately into AL251 generating strain AL438 (Example 6, Table 1).

Competitive growth assays. Competitive growth assays were performed as described in Harper (2003) and were used to quantify the relative growth rates of the *P. multocida* LPS mutant AL251 and the complemented mutant AL298. The competitive index (CI) was determined by dividing the percentage of tetracycline resistant colonies obtained from the output culture (in vitro or in vivo) by the percentage of tetracycline colonies obtained from the input culture. The relative competitive index (rCI), which measures the difference between growth in vivo and growth in vitro, was determined by dividing the in vivo CI by the in vitro CI. Mutants were identified as attenuated if the rCI value was significantly less than 1.0 as determined by statistical analysis using the one sided z-test ($p<0.05$).

Virulence trials. Groups of ten commercially obtained Leghorn-cross chickens aged 12 weeks were infected with *P. multocida* VP161 or AL251 at two different doses by injection of 100 µl into breast muscle. Blood samples were obtained at various time points after infection with AL251, and the birds deemed incapable of survival were euthanized in accordance with animal ethics requirements. Blood samples were diluted two-fold in BHI containing heparin and plated onto BHI plates. *P. multocida* colonies isolated from the blood were patched onto NB agar and NB agar with tetracycline.

Serum sensitivity assays. The sensitivity of *P. multocida* and *E. coli* to fresh chicken serum was determined as described in Chung et al. Infect. Immun. 69, 2487 (2001).

Purification of LPS. *P. multocida* cells (210 g, VP161; 254 g of AL251) were freeze-dried, yielding 56 g of VP161 and 52 g of AL251. Freeze-dried cells were washed with organic solvents to remove lipids and other lipophilic components to enhance the efficiency of the LPS extraction. Washed cells (42 g, VP161; 50 g, AL251) were extracted by the hot-phenol/water method and the aqueous phases combined and dialysed against running water for 48 h. The retentate was freeze-dried, made up to a 2% solution in water and treated with DNase and RNase at 37° C. for 4 h followed by proteinase K treatment at 37° C. for 4 h. Small peptides were removed by dialysis. After freeze-drying, the retentate was made up to a 2% solution in water, centrifuged at 8,000 g for 15 min followed by further centrifugation of the supernatant at 100,000 g for 5 h. The pellet, containing purified LPS, was redissolved and freeze-dried. The core oligosaccharide (OS) was isolated by treating the purified LPS with 1% acetic acid (10 mg/ml, 100° C., 1.5 h) with subsequent removal of the insoluble lipid A by centrifugation (5,000×g).

Analytical methods. Sugars were determined by their alditol acetate derivatives by GLC-MS. LPS was hydrolyzed for 4 h using 4 M trifluoroacetic acid at 100° C., reduced overnight with $NaBD_4$ in $H_2O$ and then acetylated with acetic anhydride at 100° C. for 2 h using residual sodium acetate as catalyst. The GLC-MS was equipped with a 30 M DB-17 capillary column (180° C. to 260° C. at 3.5° C./min) and MS was performed in the electron impact mode on a Varian Saturn II mass spectrometer. Methylation analysis was carried out by the NaOH/DMSO/methyl iodide procedure and analyzed by GLC-MS as above.

MS analysis. Capillary electrophoresis electrospray ionization MS (CE-ESI-MS) was performed on a crystal Model 310 capillary electrophoresis (CE) instrument (AYI Unicam) coupled to an API 3000 mass spectrometer (Perkin-Elmer/Sciex) via a microIonspray interface. A sheath solution (isopropanol-methanol, 2:1) was delivered at a flow rate of 1 µL/min to a low dead volume tee (250 µm i.d., Chromatographic Specialties). All aqueous solutions were filtered through a 0.45-µm filter (Millipore) before use.

Nuclear Magnetic Resonance. NMR spectra were acquired on a Varian Inova 500 MHz spectrometer using a 3 mm triple resonance ($^1H$, $^{13}C$, $^{31}P$) probe. The lyophilized sugar sample was dissolved in 140 µL (3 mm) of 99% $D_2O$. The experiments were performed at 25° C. with suppression of the HOD (deuterated $H_2O$) signal at 4.78 ppm. The methyl resonance of acetone was used as an internal or external reference at 2.225 ppm for $^1H$ spectra and 31.07 ppm for $^{13}C$ spectra. Standard homo and heteronuclear correlated 2D pulse sequences from Varian, COSY, TOCSY, NOESY, $^{13}C$—$^1H$ HSQC, $^{13}C$—$^1H$ HSQC-TOCSY and $^{13}C$—$^1H$ HMBC, were used for general assignments.

Results

An attenuated *P. multocida* STM mutant produces a truncated LPS that is restored to full-length LPS by complementation with a functional $waaQ_{PM}$ gene. Signature-tagged mutagenesis (STM) was used to identify mutants attenuated for growth in mice and chickens. During this previous analysis a mutant was identified (designated AL251) that was attenuated in both chickens and mice. Sequence analysis of the mutant revealed a single transposon insertion within the gene waaQ$_{PM}$ that is predicted to encode a putative heptosyl-transferase, a glycosyltransferase responsible for the addition of heptose to LPS.

We compared the LPS profile of AL251 with that of its wild-type parent VP161, and the complemented mutant AL298, using polyacrylamide gel electrophoresis followed by silver staining. The LPS from AL251 migrated further within the gel compared to wild-type LPS indicating that the LPS produced by the mutant was significantly truncated (FIG. 36a). Furthermore, the LPS profile of the complemented mutant AL298, was identical to that observed for the wild-type indicating that complementation of the mutant AL251 with an intact waaQ$_{PM}$ gene was able to restore the synthesis of wild-type LPS (FIG. 36a).

Complementation of AL251 with waaQ$_{PM}$ also restores in vivo growth to wild-type levels. As complementation of AL251 with waaQ$_{PM}$ restored production of wild-type LPS we wanted to determine if complementing the inactivated waaQ$_{PM}$ also restored the mutant AL251 to wild-type levels of growth in vivo. Initial studies with the complemented mutant AL298 indicated that there was significant loss of the complementing plasmid pAL170 once antibiotic selection for the plasmid was removed (44% retention after 6 h). For this reason, mice were chosen for the competitive growth assay instead of chickens, as previous studies had demonstrated that the infection time required to harvest bacteria from mice was only 6 h compared with more than 12 h for infections in chickens. Three mice were injected with an equal mix of VP161 and the complemented strain AL298. As controls, two mice were injected with an equal mix of wild-type VP161, and the control strain AL438 (AL251 with vector pAL99). The complemented mutant AL298 was able to compete equally with wild-type VP161 with an average rCI value of 1.0 while the control strain AL438 had an average rCI value of 0.57 (p=0.03), similar to the rCI values previously reported for AL251 in mice. These results demonstrate that waaQ$_{PM}$ is required for both production of full-length LPS and for normal growth during infection.

The *P. multocida* waaQ$_{PM}$ mutant is unable to cause disease in chickens. Strain AL251 displayed a profoundly reduced growth rate in chickens. It was desired to determine whether the mutant was still capable of causing disease in these hosts. Chickens were challenged with either VP161 or AL251 at two different doses (Example 6, Table 2). All of the chickens challenged with wild-type VP161 died within 20 h. In contrast, most chickens challenged with AL251 remained well over the first twenty hours but within 4 days all of the chickens inoculated with AL251, irrespective of dose, succumbed to fowl cholera infection. *P. multocida* was isolated from the blood of AL251-infected chickens in the late or terminal stages of the disease and it was found that all of the isolated *P. multocida* colonies were tetracycline sensitive indicating that the transposon was no longer present in the bacteria. Sequence analysis of waaQ$_{PM}$ from the recovered colonies indicated that in all cases the transposon had excised, thereby reconstituting a functional waaQ$_{PM}$ gene. Interestingly, for all but one isolate, the sequence analysis also revealed the presence of nucleotide substitutions at the point of transposon excision resulting in two amino acid changes within waaQ$_{PM}$ (amino acids 88,89; Ser to Leu, and Asp to Cys respectively). These amino acid changes did not affect the function of waaQ$_{PM}$, as the LPS profiles of the *P. multocida* isolates recovered from the chickens challenged with AL251 were all identical to wild type (FIG. 36b). Taken together, these results indicate that the later onset of fowl cholera observed in the chickens inoculated with AL251 was due entirely to wild-type revertants of AL251 and therefore strains with an inactivated waaQ$_{PM}$ gene are therefore incapable of causing disease.

Attenuation of the waaQ$_{PM}$ mutant in chickens is not due to increased sensitivity to chicken serum. To determine the relative sensitivity of the wild-type *P. multocida* strain VP161 and the LPS mutant AL251 to complement-mediated killing, mid-log phase cells of each strain and a control strain, *E. coli* DH5α, were incubated in either normal or heat-treated chicken serum for 3 h. Wild-type *P. multocida*, strain VP161 was able to grow at the same rate in either the heated or unheated serum, indicating that it is fully serum resistant as previously reported for other *P. multocida* serotype A strains. The bactericidal activity of the chicken serum was confirmed using the *E. coli* control strain, which multiplied 19-fold in heat-treated serum, whilst in untreated serum its viability was reduced approximately 9-fold. Interestingly, for the mutant AL251, there was no difference in growth observed between the heat-treated and normal serum with approximately 160-fold increase in growth in the heat-treated serum and an identical growth rate in the normal serum. These results indicate that the attenuation observed for the LPS mutant in chickens was not due to increased sensitivity to complement.

Structural analysis of the LPS from *P. multocida* VP161 and AL251. Sugar analysis of the LPS from the parent strain VP161 revealed glucose (Glc), galactose (Gal), N-acetyl glucosamine (GlcNAc) and L-glycero-D-manno-heptose (LD-Hep) in the ratio of 2:1:1:3 respectively. In contrast, the LPS from mutant strain AL251 revealed only Glc and LD-Hep in the ratio of 1:3 with traces of Gal and GlcNAc. It is possible that the presence of GlcNAc could be contributed from residual amounts of the hyaluronic acid capsule known for this serogroup in addition to the anticipated two residues in the lipid A region of each LPS molecule. CE-ES-MS analyses of the core OS sample derived from the parent VP161 LPS revealed a simple mass spectrum (FIG. 37*a*) corresponding to two glycoforms of mass 1805 and 1967 Da, the smaller glycoform being consistent with a composition of 2PCho, 3Hex, 4Hep, Kdo, where Kdo is the unique LPS sugar 2-keto-3-deoxy-octulosonic acid and PCho is the phosphate moiety phosphocholine. The larger glycoform contains an additional hexose species (Example 6, Table 3 and FIG. 37*a*). Consistent with SDS-PAGE analysis of the mutant AL251 LPS, CE-ES-MS analyses of the core OS sample derived from the mutant AL251 LPS revealed a simple mass spectrum of a highly truncated molecule of mass 605 Da (Example 6, Table 3, FIG. 37*b*). This mass corresponds to a composition of 2Hep, Kdo. A larger glycoform was observed consistent with the presence of an additional hexose residue (767 Da). Trace amounts of a more extended glycoform of 1448 Da (PCho, 3Hep, 3Hex, Kdo) were observed, but no glycoforms were observed that contained the full parental complement of 4 Hep residues (Example 6, Table 3). To characterise completely the nature of the truncation in the core OS of the mutant strain, $^1$H-NMR experiments were performed on the parent and mutant derived core OS. As MS data had suggested that a Hep residue was missing in the mutant OS and amino acid homology comparisons had suggested that $WaaQ_{PM}$ was a heptosyltransferase, close attention was paid to the resonances from the heptose residues of the molecule. Examination of the $^1$H-NMR spectra revealed some heterogeneity for the heptose residues closest to Kdo as is often observed for core oligosaccharides due to rearrangement of the Kdo residue under the acidic hydrolysis conditions employed to obtain the core OS (FIG. 38). For the core OS derived from the parent strain, chemical shifts for the Hep II anomeric proton were identified at ~5.7 ppm, consistent with 2-substitution of this residue (FIG. 38*a*). However, in the AL251 mutant OS $^1$H-NMR spectrum (FIG. 38*b*) the anomeric resonance for the Hep II residue had shifted up-field about 0.5 ppm, consistent with this residue no longer being 2-substituted. The Hep II residue is now a terminal moiety as it was observed previously for a *H. somnus* strain, and the chemical shifts to the H-4 resonance were consistent with this assignment. Definitive evidence for the structural nature of the mutation was obtained from 2D NOESY experiments (FIG. 39). Characteristic NOEs were observed for VP161 core OS between the Hep III and Hep II anomeric protons that are diagnostic for the α-1-2 linkage between the Hep III and Hep II residues (FIG. 39). The NOESY spectrum of the AL251 mutant core OS confirmed the lack of 2-substitution of Hep II as the characteristic NOEs described above were absent, confirming that the Hep III residue is no longer present in the mutant OS. Chemical shift and NOE data for the Hep II and Hep III residues for the parent OS and Hep II residue for the mutant OS are summarised in Example 6, Table 4. Structural techniques have therefore demonstrated that the effect on the LPS structure of mutating gene waaQ$_{PM}$ is to preclude addition of Hep III to Hep II (FIG. 40), and this function is consistent with strong similarity of the encoded protein to known heptosyltransferases.

Discussion

The *P. multocida* LPS mutant AL251, first identified using STM in mice and chickens, was shown to have a transposon insertion in a predicted heptosyltransferase gene waaQ$_{PM}$ and was significantly attenuated in chickens and mice. Silver stained polyacrylamide gels of cell lysates from wild-type VP161 and AL251 showed that the LPS from the mutant was significantly truncated (FIG. 36A), consistent with waaQ$_{PM}$ encoding a heptosyltransferase responsible for the addition of a heptose molecule in the core region of the LPS structure.

Analysis of the *P. multocida* Pm70 genome revealed that the gene waaQ$_{PM}$ was probably transcribed independently and therefore the truncated LPS structure and reduced growth in vivo in chickens and mice was due directly to the inactivation of waaQ$_{PM}$ and not due to polar effects on downstream genes. This was confirmed by complementation, as introduction of a wild-type waaQ$_{PM}$ gene in trans restored both the LPS structure (FIG. 36A) and wild-type levels of growth in mice.

Virulence trials in chickens using the LPS mutant AL251 resulted in a delayed onset of fowl cholera symptoms (Example 6, Table 2) and *P. multocida* isolated from chickens with disease symptoms were tetracycline sensitive, indicating that they no longer carried the transposon. Nucleotide sequence data obtained from *P. multocida* DNA isolated from infected birds confirmed that the gene waa$Q_{PM}$ was intact and in most cases, had nucleotide base changes at the point where the transposon had previously been inserted, resulting in two amino acid changes. The LPS from the *P. multocida* isolates recovered from the chickens challenged with AL251 showed that they produced wild-type LPS confirming that the waa$Q_{PM}$ gene was functional despite the amino acid changes (FIG. 36B). Taken together, these data indicate that the infection observed in chickens inoculated with AL251 was due only to revertant strains that had lost the transposon insertion. The wild-type *P. multocida* strain VP161 is a highly virulent organism, with less than 50 bacteria causing fowl cholera in chickens. Our observations measured the transposon excision rate from AL251 cells at 1% after the first ten generations (overnight in vitro growth) rising to 4% after 58 generations (data not shown). This rate of excision would result in the generation and selection of wild-type revertants in chickens at a rate sufficient to cause lethal fowl cholera infection during the course of the trial. Thus, a stable inactivation of waa$Q_{PM}$ would result in a *P. multocida* strain incapable of causing fowl cholera. However, a reliable method of constructing defined mutants in *P. multocida* has not yet been established.

Analysis of the *P. multocida* VP161 wild-type LPS indicated a "rough" LPS, similar to the LPS or lipooligosaccharide (LOS) isolated from Gram-negative mucosal pathogens such as *H influenzae, H. ducreyi, N. meningitidis* and *N. gonorrhoeae*, with only a short non-repeating polysaccharide unit attached to the core. The inner core structure of *P. multocida* LPS is similar to that described for *H. influenzae, M. haemolytica* and *H. ducreyi*, with a tri-heptose unit linked via a Kdo residue to lipid A (FIG. 39). In the AL251 mutant, inactivation of waa$Q_{PM}$ resulted in expression of a highly truncated LPS that lacked the third heptose molecule (Hep III) in the inner core region (FIG. 37*b*). The most abundant glycoforms of LPS in the mutant also lacked all sugars distal to the first heptose, suggesting that the inactivation of waa$Q_{PM}$ prevented further sugar additions (Example 6, Table 3). It is therefore probable that conformational changes in the LPS intermediates due to the lack of the third heptose for the most part prevented the action of subsequent transferases.

The loss of a full length LPS molecule clearly affects the ability of the mutant AL251 to grow in mice and to cause disease in chickens. The specific reasons for this attenuation are not clear. However, in wild-type *P. multocida* VP161 LPS, two PCho groups were identified while the mutant AL251 contained only a single PCho group in a very minor glycoform (Example 6, Table 3). The presence of more than one PCho residue in the VP161 LPS is unusual; bacteria with PCho-decorated LPS usually have only a single residue attached, although the position of attachment onto the LPS structure varies. Only one other bacterium, a non-typable *H. influenzae* strain, is known to have two PCho residues attached to the LPS. Interestingly, there are no PCho groups on the LPS of the serotype A turkey isolate, PM70, and this strain is not virulent for chickens.

PCho groups are frequently attached to various bacterial structures on the surface of mucosal pathogens such as *H. influenzae, Actinobacillus actinomycetemcomitans, Streptococcus pneumoniae* and *Neisseria* spp., and play a key role in adhesion and invasion of epithelial and endothelial host cells by binding to the platelet-activating receptor (PAF). Non-typable *H. influenzae* that has PCho positive glycoforms of LPS can attach and invade human bronchial epithelial cells via a series of signalling events. However, in both *H. influenzae* and *Neisseria* spp., although expression of PCho on LPS was required for adhesion and invasion of human epithelial cells, its presence reduced survival in some host niches, as strains expressing PCho were more serum sensitive, mediated by binding of PCho to C-reactive protein and subsequent activation of the complement system. Interestingly, the present studies have demonstrated that the LPS mutant AL251 is still highly resistant to the bactericidal action of complement in chicken serum, indicating that a complete wild-type LPS structure is not required for the bacteria to have full serum resistance. This is not surprising, as the capsule of *P. multocida* serotype A strains confers serum resistance.

In conclusion, a *P. multocida* waa$Q_{PM}$ mutant that expresses a severely truncated LPS. Additionally the inner core structure for both the wild-type *P. multocida* LPS molecule and the waa$Q_{PM}$ mutant molecule was determined and it was demonstrated that a functional waa$Q_{PM}$ gene is required for the addition of the third heptose residue to the inner core of the LPS. Thus waa$Q_{PM}$ has been identified as a heptosyltransferase III and through virulence trials it has been demonstrated that its activity is required for bacterial virulence in chickens, the natural host for this *P. multocida* strain. The inactivation of waa$Q_{PM}$ leads to the complete absence of the third heptose in the inner core and, as a result, the fall wild-type glycoforms. The majority of glycoforms identified from the mutant LPS lack PCho residues that in LPS of other Gram negative mucosal pathogens play a key role in bacterial virulence.

TABLE 1

Bacterial strains, plasmids and oligonucleotides (oligo) used in this study.

| Strain, plasmid or oligo | Relevant description | Source or reference |
|---|---|---|
| Strains | | |
| *P. multocida* | | |
| VP161 | Serotype A: 1, Vietnamese isolate from chickens. | Wilkie et al. Vet. Microbiol. 72, 57 (2000). |
| AL251 | VP161 Tn916EΔC waaQ$_{PM}$ mutant | Harper et al. Infect. Immun. 71, 5440 (2003). |
| AL298 | AL251 with plasmid pAL170 | This study |
| AL438 | AL251 with plasmid pAL99 | This study |
| *E. coli* | | |
| DH5α | deoR, endA1, gyrA96, hsdR17($r_k^-$ $m_k^+$), recA1, relA1, supE44, thi-1, (lacZYA-argFV169), Φ80lacZ ΔM15, F- | Bethesda Research Laboratories |
| Plasmids | | |
| pPBA1100 | *P. multocida*/*E. coli* shuttle vector. | Homchampa et al. Vaccine 15, 203 (1997). |
| pAL99 | 240 bp EcoR1 fragment containing *P. multocida* tpiA promoter region cloned into pPBA1100 EcoR1 site. | This study |
| pAL170 | pAL99 containing waaQ$_{PM}$ gene. | This study |
| Oligonucleotides | | |
| BAP2146 | Forward primer for waaQ$_{PM}$ amplification; has BamHI site for cloning. GAGTAGGATCCTGAAACATGTTCCC (SEQ ID No. 1) | This study |
| BAP2147 | Reverse primer for waaQ$_{PM}$ amplification, has SalI site for cloning. GGTTGGGTCGACCAAGCCACATTACTG (SEQ ID No. 2) | This study |

TABLE 2

Virulence of VP161 and AL251 in groups of 10 chickens.

| Strain | Dose (CFU) | Mean time to death (h) | Range (h) |
|---|---|---|---|
| VP161 | $1.5 \times 10^2$ | <20 | ND |
|  | $1.5 \times 10^3$ | <20 | ND |
| AL251 | 70 | 65 | 33-120 |
|  | $7 \times 10^2$ | 30 | 23-42 |

CFU = colony forming units,
h = hours,
N.D = not determined.

TABLE 3

Negative ion CE-MS data and proposed compositions for core OS from *P. multocida* strains VP161 (parent) and AL251 (mutant). Average mass units were used for calculation of molecular weight based on proposed composition as follows: Hex, 162.15; Hep, 192.17; Kdo, 220.18; PCho, 165.05. Relative intensity is expressed as relative height of either doubly or singly charged ions.

| Strain | [M − H]$^-$ | [M − 2H]$^{2-}$ | Observed Molecular Ion | Calculated Molecular Ion | Relative Intensity | Proposed Composition[a] |
|---|---|---|---|---|---|---|
| VP161 | 1804.4 | 901.8 | 1805.6 | 1805.4 | 0.2 | 2PCho, 4Hep, 3Hex, aKdo[b] |
| Core OS | 1822.4 | 910.9 | 1823.1 | 1823.4 | 1.0 | 2PCho, 4Hep, 3Hex, Kdo |
|  | — | 921.8 | 1845.1 | 1845.4 | 0.3 | 2PCho, 4Hep, 3Hex, Kdo, Na |
|  | 1966.3 | 982.9 | 1967.8 | 1967.6 | 0.9 | 2PCho, 4Hep, 4Hex, aKdo |
|  | 1988.4 | 993.9 | 1989.1 | 1989.6 | 0.3 | 2PCho, 4Hep, 4Hex, aKdo, Na |

TABLE 3-continued

Negative ion CE-MS data and proposed compositions for core OS from
P. multocida strains VP161 (parent) and AL251 (mutant). Average mass units were
used for calculation of molecular weight based on proposed composition as follows:
Hex, 162.15; Hep, 192.17; Kdo, 220.18; PCho, 165.05. Relative intensity is
expressed as relative height of either doubly or singly charged ions.

| Strain | $[M - H]^-$ | $[M - 2H]^{2-}$ | Observed Molecular Ion | Calculated Molecular Ion | Relative Intensity | Proposed Composition[a] |
|---|---|---|---|---|---|---|
| AL251 | 603.5 | — | 604.5 | 604.5 | 1.0 | 2Hep, aKdo |
| Core OS | 621.5 | — | 622.5 | 622.5 | 0.9 | 2Hep, Kdo |
|  | 765.5 | — | 766.5 | 766.7 | 0.8 | Hex, 2Hep, aKdo |
|  | 1447.5 | — | 1448.5 | 1448.2 | 0.1 | PCho, 3Hep, 3Hex, aKdo |

[a]PCho, phosphocholine; Hep, heptose; Hex, hexose; Kdo, 2-keto-3-deoxyoctulosonic acid.
[b]aKdo refers to anhydro-Kdo derivative

TABLE 4

$^1$H-NMR chemical shifts for the Hep II and Hep III residues from the core OS derived
from strains of P. multocida VP161 (parent) and AL251 (mutant). Recorded
at 25° C., in D$_2$O. Chemical shifts referenced to internal acetone at
2.225 ppm. nd, not determined. Two resonances were observed for each residue
due to heterogeneity of Kdo molecule following core hydrolysis.

| | H-1 | H-2 | H-3 | H-4 | H-5 | H-6 | H-7 | NOEs Inter | Intra |
|---|---|---|---|---|---|---|---|---|---|
| VP161 | | | | | | | | | |
| Hep-II | 5.76 | 4.17 | 3.85 | 3.83 | 3.60 | 4.05 | 3.76 3.65 | 5.11 Hep III H-1 4.04 Hep I H-3 | 4.17 H-2 |
| Hep-II | 5.70 | 4.19 | 3.86 | 3.84 | 3.55 | 4.05 | 3.76 3.65 | 5.14 Hep III H-1 3.96 Hep I H-3 | 4.19 H-2 |
| Hep-III | 5.14 | 4.02 | 3.87 | 3.83 | 3.78 | 4.05 | 3.77 3.65 | 5.70 Hep II H-1 4.19 Hep II H-2 | 4.02 H-2 |
| Hep-III | 5.11 | 4.01 | 3.87 | 3.83 | 3.78 | 4.05 | 3.77 3.65 | 5.76 Hep II H-1 4.17 Hep II H-2 | 4.01 H-2 |
| AL251 | | | | | | | | | |
| Hep II | 5.22 | 4.07 | 3.89 | 3.72 | nd | nd | nd | 4.03 Hep I H-3 | |
| Hep II | 5.17 | 4.06 | 3.88 | 3.65 | nd | nd | nd | nd | |

Example 7

Production of a D-glycero-D-manno-heptosyltransferase Mutant of *Mannheimia haemolytica* Displaying a Veterinary Pathogen Specific Conserved LPS Structure and Development and Cross-Reactivity of Antibodies to this LPS Structure Previous structural studies of the lipopolysaccharides from the veterinary pathogens *Mannheimia haemolytica, Actinobacillus pleuropneumoniae* and *Pasteurella multocida* had identified a conserved inner core oligosaccharide structure that was present in all strains investigated. In order to examine the potential of this inner core structure as a vaccine, a mutagenesis strategy was adopted to interrupt a D-glycero-D-manno-heptosyltransferase gene (losB) of *Mannheimia haemolytica*. This gene encodes the enzyme responsible for the addition of a D-glycero-D-manno-heptose residue, the first residue beyond the conserved inner core, and its inactivation exposed the conserved inner core structure as a terminal unit on the mutant LPS molecule. Subsequent analyses determined the structure of the mutant LPS as the following, and complementation with losB in trans confirmed that the losB gene encodes an α-1,6-D-glycero-D-manno-heptosyltransferase.

```
                                              α-Glc
                                                |
                                                6
D,D-α-Hep-(1-6)-β-Glc-(1-4)-L,D-α-Hep-1-5-α-Kdo
                                                3
                                                |
                                                1
                                            L,D-α-Hep
                                                2
                                                |
                                                1
                                            L,D-α-Hep
```

Polyclonal and monoclonal antibodies were raised in mice to this LPS structure and were found to recognise LPS and whole-cells of all three species, *Mannheimia haemolytica, Actinobacillus pleuropneumoniae* and *Pasteurella multocida*.

Bacterins or crudely modified live strains are the traditional vaccines of practice, however, field trials and experimental studies have repeatedly shown that bacterins are not effective and indeed often cause adverse effects. This work seeks to address the need for effective, defined sub-unit vaccines. Antigens that could be considered as vaccine candidates would almost certainly have to be displayed on the surface of the bacteria in its natural state in order for the immune response to the vaccine antigen to subsequently target the live organism.

In this context, the veterinary organisms contain surface exposed carbohydrate moieties that could be utilised as vaccine candidates. The carbohydrate moieties are lipopolysaccharides (LPS) and capsular polysaccharides. Capsular polysaccharides are repeating units of several carbohydrate residues directly linked to the bacterial surface whereas LPS consists of three regions, a lipid A region that links the LPS molecule to the bacterial surface via fatty acid residues, a relatively conserved core oligosaccharide region which links the lipid A region to the third region, the variable polysaccharide antigen (O-antigen). Strain heterogeneity in capsular and O-antigenic polysaccharides would preclude these structures as economically viable vaccine candidates due to their ability to provide coverage only to the homologous strain or to strains producing an identical structure. Alternatively, if a conserved core LPS structure could be identified, this may have a utility as a vaccine candidate that would provide broad coverage to all strains.

Previous and ongoing structural analysis of the LPS structures of these three species in our laboratories had identified a conserved inner core LPS structure in all strains so far investigated, App, Pm and Mh. In order to examine the potential of this conserved inner core unit, it is necessary to expose this structure as a terminal residue by adopting a mutagenesis strategy in which the gene(s) encoding the glycosyltransferases responsible for outer core biosynthesis are disrupted. As a consequence of this mutation the conserved inner core structure is thus exposed.

This study describes the identification, cloning and mutagenesis of a heptosyltransferase gene from *Mannheimia haemolytica* responsible for the first biosynthetic step in outer core decoration. Subsequent structural analysis of the LPS from the mutant strain confirmed that the LPS was truncated appropriately. The mutant strain was then used to produce antibodies to the conserved LPS structure and those antibodies tested for cross-reactivity amongst strains of the three target species.

Experimental

Bacterial Strains and Growth Conditions.

Mh strains A1 Sh1217 (S. Highlander, Baylor College of Medicine, Houston Tex.) and A1 strain O1A ADRI (Perry Fleming, IBS) were routinely cultured on BHI plates or BHI broth at 37° C. *E. coli* DH10B (Invitrogen, Carlsbad Calif.) was used for cloning and propagation of recombinant plasmids and was grown on LB medium supplemented with the appropriate antibiotics (ampicillin 100 μg/ml, chloramphenicol 25 μg/ml). When required *M. haemolytica* strains were cultured in BHI media supplemented with ampicillin (50 μg/ml) and chloramphenicol (5 μg/ml).

Construction of Recombinant Plasmids Containing Insertion into the losB Gene.

The losB gene was amplified by PCR from chromosomal DNA of strain O1A using flanking primers. The primers that were used were losB-kpn 5' ATATGGTACCTATCAGCGG-TAGAGATTC TAAC and losB-xba 5' TGCTC TAGAC-CGAACCTGCACCAAAAAGATTTAACGC. These primers amplified a 2 Kb fragment, which was then cloned into pBluescript following Kpn/Xba restriction enzyme digestion and electroporated into *E. coli* DH10B. Inverse PCR using this plasmid as template was then performed with the following primers 5'CCGCTGCGAGAGATAAGTGGATACTT-TATC-3' and 5'GACATTGGGATCTTTATTTA-GATTTCAAACCGAC-3' that correspond to sequence within the losB structural gene and the product excised from an agarose gel and purified using a Qiagen gel extraction kit. The modified chloramphenicol acetyl transferase (Cat) cassette (plpCat) was amplified by PCR from pNFplpcat and the product was blunt end ligated to the PCR product above to produce pSK losB::cat. Restriction enzyme mapping and sequencing of the recombinant plasmid confirmed that the Cat cassette was inserted into the losB structural gene in the same orientation as the losB gene.

Selection of losB Strains.

Plasmid pSK losB::cat was introduced into Mh cells by electroporation. Briefly, following electroporation cells were transferred immediately to 1 ml of pre-warmed BHI broth and incubated at 37° C. for 1.5 h. Transformants were selected by plating onto BHI agar containing 5 mg/ml chloramphenicol. To confirm that the transformants no longer harboured pSK losB::cat plasmid colonies were replica plated onto BHI/Amp plates and ampicillin-sensitive colonies were examined by PCR. Insertional inactivation of the losB gene following double recombination was confirmed by PCR. Primers specific to sequences upstream and downstream of losB-Kpn and losB-Xba that had been used in the initial cloning experiments confirmed the insertion of the Cat cassette into the chromosomal copy of the losB gene.

Complementation of losB Mutant with losB Gene in Trans.

The wild type copy of the losB gene from pSK losB (see above) was excised by restriction enzyme digest using Xba and Kpn and cloned into the shuttle plasmid pNF2176 to create pNF2176AalosB. This plasmid was then electroporated into the Mh losB mutant and transformants selected on Amp/Cat.

Mutant LPS Characterisation

LPS was isolated from killed cells by standard techniques. Sugar analysis and partially methylated alditol acetates were prepared as described previously. Core OS and O-deacylated LPS (LPS-OH) were purified. Completely deacylated LPS was purified. Mass spectrometry and nuclear magnetic resonance spectroscopy were performed.

Antibody Production 5 female BALB/c mice were immunised intraperitoneally (ip) on days (D) 0, 14 and 35 with $10^8$ cells of formalin killed, PBS washed Mh losB in 0.5 ml. A trial bleed was performed on D42 removing a small amount of blood from the facial vein of each mouse and the derived sera was examined by ELISA for cross-reactivity to Mh losB and Mh wt LPS. On D54 each mouse received the repeat ip immunisation and mouse # 2 also received an intra-venous (iv) injection of $4 \times 10^7$ cells in 0.2 ml. On D57 the spleen from this mouse was removed and fused to a myeloma cell line. Initial screening antigens for this fusion were purified LPS from Mh losB and Ah wt. Both mouse # 3 and # 5 were boosted on D90 with an ip immunisation of Mh losB whole cells (~$10^8$). Mouse # 3 was boosted both ip and iv with Mh losB cells on D131 in preparation for spleen cell fusion on D134, and mouse # 5 was boosted with ip and iv injections of formalin killed whole cells from Pm strain VP161 on D152 and the spleen cells fused on D155. Initial screening antigens for mice # 3 and # 5 fusions were purified LPS from App serotype 5a and Pm strain VP161. Ascitic fluid of monoclonal antibodies was prepared.

LPS ELISA

Purified and well-characterized wild-type and mutant LPS were used in a solid-phase indirect ELISA to determine the binding specificities of the mAbs.

Whole-Cell ELISA

Phenol-killed cells were used.

Results

Identification of Candidate Glycosyltransferases.

The LPS from the 3 species of interest (Mh, App and Pm) elaborate the same inner core structure (Example 7, Table 1). In order to examine the potential of this conserved inner core structure as a useful vaccine candidate it is necessary to remove the outer core decoration beyond this region. To facilitate this, the approach taken was to identify and mutate the glycosyltransferase gene responsible for the first glycose addition of the outer core decoration. Mh was selected for mutagenesis studies as the amount of O-antigen present in this organism is low compared to App and therefore should not interfere with subsequent immunological studies. Genome sequencing is complete for Pm strain Pm70 [24] and is in progress for Pm (strain P-3480), App (serotypes 1 and 5b) and Mh (A1 strain). As illustrated in FIG. 41 candidate glycosyltransferases were identified in both App serotype 1 and Mh strain A1. Galarneau et al had identified the lbgA gene in App located between two genes that were found to be involved in core oligosaccharide biosynthesis by mini-Tn10 transposon mutagenesis. The adjacent gene lbgB showed considerable homology to a D-glycero-D-manno-heptosyltransferase from *Haemophilus ducreyi*. Blast analysis of the Mh genome sequence (Baylor College, Houston) with the lbgB gene sequence from App, revealed two adjacent homologues to the D-glycero-D-manno-heptosyltransferase. The best lbgB homologue identified was postulated to be the D-glycero-D-manno-heptosyltransferase responsible for the addition of the first D-glycero-D-manno-heptose residue in the extension from the first L-glycero-D-manno-heptose residue, and we therefore postulated that the second homologue, which we termed losB, was the D-glycero-D-manno-heptosyltransferase responsible for the addition of the second D-glycero-D-manno-heptose residue.

Mutagenesis of losB in Mh

Plasmid pSK losB::cat cannot replicate in Mh and so functions as a suicide plasmid. Following electroporation (5 ug plasmid DNA) into Mh, 136 cat$^R$ transformants were obtained of which 104 were amp$^S$. Two of these were randomly selected for further studies. Both mutants were confirmed to have undergone a double crossover event by PCR using primers that bracketed the insertion site (data not shown). To ensure that the effect observed on LPS structure (see below) was due to inactivation of the losB gene we complemented the mutant strain with a wild type copy of losB gene in trans on the shuttle vector pNF2176.

Characterisation of the LPS from the losB Mutant

LPS was isolated by standard methods. Sugar analysis of the purified LPS revealed glucose (Glc), D-glycero-D-manno-heptose (DD-Hep), and L-glycero-D-manno-heptose (LD-Hep) in the approximate ratio of 2:1:3 respectively with trace amounts of N-acetyl-glucosamine (GlcNAc) also being observed. This sugar composition is consistent with the anticipated structure of the mutant LPS and moreover suggests that the losB gene mutated is, as predicted from homology data, the specific heptosyltransferase and not a gene involved in heptose biosynthesis as four other heptose residues remain in the mutant LPS. O-deacylated LPS (LPS-OH) was prepared by standard methods and analysed by CE-MS (Example 7, Table 2). A simple MS spectrum was observed (FIG. 42*a*) with doubly (1172.3$^2$), triply (781.3$^{3-}$) and quadruply (585.8$^{4-}$) charged ions being observed consistent with the expected composition of Hex2, Hep4, Kdo-P, Lipid A-OH. Minor charged ions were also observed; doubly (1065.3$^{2-}$), triply (709.8$^{3-}$) and quadruply (532.3$^{4-}$) that correspond to the presence of an additional Kdo residue with the concomitant loss of a hexose, heptose and phosphate moieties. This behaviour has been observed before in the related veterinary pathogen *Pasteurella multocida*. Core oligosaccharide (OS) was purified and similarly examined by CE-MS (Example 7, Table 2) giving a spectrum of singly (1312$^-$) and doubly (655.6$^{2-}$) charged ions consistent with the expected composition of Hex4, Hep2, Kdo. In order to prove the linkage pattern of the mutant LPS was unchanged by the mutagenesis, methylation analysis was performed on the core OS revealing the presence of terminal Glc, 6-substituted Glc, terminal LD-Hep, terminal DD-Hep, 2-substituted LD-Hep and 3,4,6-trisubstituted LD-Hep in approximate equimolar ratio, once again consistent with the anticipated mutant LPS structure. Final confirmation of the core OS structure of the mutant LPS was obtained from NMR experiments on the completely deacylated LPS and by comparison to the wild-type LPS spectrum (FIG. 43) it was clear that the terminal Gal-Hep disaccharide was absent in the mutant LPS. Assignment of the chemical shifts revealed (Example 7, Table 3) that all the linkages of the conserved core OS were identical to those from the wild type LPS and thus the desired structure had been obtained. LPS-OH was obtained from the complemented mutant strain and CE-ES-MS analysis confirmed a wt LPS phenotype with small amounts of glycoforms with the additional Kdo residue (Example 7, Table 2, FIG. 42*b*).

Antibody Production

Sera from the five mice were examined for the ability to recognise Mh losB and Mh wt LPS following a prime and a boost immunisation (FIG. 44). As mouse # 2 gave the highest IgG titre against the wt strain this mouse was chosen for the first fusion experiment to generate mAbs. Nine stable hybridomas that recognised Mh losB were produced and examined for their ability to cross react with the wt LPS from Mh, App and Pm (FIG. 45). However, none of the mAbs were capable of recognising App and Pm LPS and only four of the mAbs were able to recognise Mh wt LPS. Examination of the polyclonal sera from D42 revealed that antibodies were present that could recognise purified LPS from App serotype 5a, Pm strains VP161 and X73 but not App serotype 1 (FIG. 46). Therefore a fusion was performed on mouse # 3 but no hybridomas were identified that were capable of recognising the purified LPS from App serotype 5a and Pm strain VP161. Finally a fusion was performed on mouse # 5 following a final boost with killed whole cells from Pm strain VP161 as examination of the polyclonal sera at D152 had revealed cross reactivity to LPS from Mh losB and wt, App serotypes 1 and 5a and Pm strains VP161 and X73 (FIG. 47). Fourteen hybridomas were obtained, eleven that were capable of recognising the purified LPS from Pm strain VP161 only, and three that could recognise the purified LPS from both App serotype 5a and Pm strain VP161. Subsequently these three cross-reactive hybridomas were also found to be able to recognise purified LPS from App serotype 1, Pm strain X73 and Mh losB and wt strains and the eleven Pm VP161 recognising hybridomas could only also recognise the related Pm strain X73 (FIG. 48, Example 7, Table 4).

There is currently no effective vaccine to combat the diseases caused by the veterinary pathogens Mh, Pm and App. Vaccine approaches to combat diseases caused by Mh are still mainly based on bacterins and live attenuated strains. More recent versions of live vaccines incorporate secreted or extracted Mh antigens such as neuraminidase, leukotoxin, sialoglycoprotease, outer membrane and uncharacterised proteins. Leukotoxin has traditionally been the main sub-unit vaccine candidate, although immunisation with a mutant strain expressing non-toxic leukotoxin was still partially virulent in a calf challenge model and leukotoxin in combination with capsular polysaccharide was unable to produce a protective immune response. In contrast, LPS has been shown to stabilise leukolytic activity and so a conjugate vaccine based on LPS and detoxified leukotoxin may offer promise.

Current vaccine approaches to combat diseases caused by App are based on live attenuated strains as they contain the highly labile Apx toxins, which induce neutralizing antibodies required for protection. These Apx toxins form the basis for the major sub-unit vaccine against App but only seem to induce partial clinical protection. Adhesins including the core OS of LPS have been proposed as improved vaccine candidates.

Current vaccines to prevent Pm disease in pigs consist of toxoids and somatic antigens such as capsules and outer membrane proteins. Pm was first shown by Pasteur to induce fowl cholera in chickens and current strategies for protection against this disease utilise an attenuated Pm strain. In general however, this strategy is severely limited as the immune response remains serotype-restricted and fails to provide cross-protection against other serotypes. The LPS of Pm has however been shown to play a partial role in the immunity to infection.

Considerable evidence has accumulated recently indicating that LPS from each of these organisms may be a good candidate for subunit vaccine design. LPS has been shown to be both visible and a major antigenic determinant on the surface of Mh and mAbs raised to A1 LPS facilitated phagocytosis but not complement mediated killing in vitro.

In Pm ribosome-LPS vaccines protected chickens against fowl cholera disease from homologous Pm strains. Additionally, immunisation with a LPS-protein complex provided 100% protection to mice when challenged with a homologous strain yet when separated the individual components of the complex afforded no protection. mAbs raised to LPS from Pm only afforded partial protection in a mouse model and although they were opsonophagocytic, were not bactericidal in the presence of complement. However in another study a mAb to Pm LPS completely protected mice against homologous challenge and was bactericidal. An anti-idiotype vaccine mimicking LPS from type A was protective in a mouse model when challenge was with homologous organisms.

In App, the LPS and more specifically the core region of the LPS has been implicated in the adhesive abilities of the bacterium. A conjugate vaccine of BSA linked to App serotype 1 LPS was protective against mice following homologous but not heterologous challenge, and conjugates of both smooth and rough App LPS from serotype 5 and 1 suggested that the carbohydrate portion of the cell wall of App plays a significant role in the porcine immune response.

As a consequence we undertook this study to produce a conserved truncated core LPS which is common to all three organisms. LPS has been shown to play a role in the immunity to each of these veterinary pathogens and if a conserved LPS antigen can be identified the protective response to homologous strains could possibly be extended to heterologous strains and indeed species. Coupling this with the structural analysis data suggesting that all these veterinary pathogens shared a common and conserved inner core OS structure it was decided to explore the potential of a LPS-based vaccine. A first step in this process is the construction of a mutant strain expressing exclusively the conserved inner core OS epitope as a terminally exposed structure.

This study has generated a mutant in the α-1,6-D-glycero-D-manno-heptosyltransferase gene from Mh strain A1 in order to present the conserved inner core epitope as a terminally exposed moiety. Mutagenesis strategies are far from straightforward in Mh. A limited number of previous studies have made mutants in the aroA gene, the lpp locus, the capsular nmaAB locus, and the leukotoxin lktCABD gene cluster. While electroporation is an efficient means of introducing foreign DNA into Mh cells, the incorporation of foreign DNA into the chromosome through homologous recombination is difficult and occurs at low frequency with a large preponderance of single crossover events occurring resulting in the presence of both a mutant and functional copy of the targeted gene. Plasmids that are unstable in Mh (suicide plasmids) have been used for this approach by several authors, and have been successfully used in this current study. The structural analysis of the LPS from the mutant strain confirmed the expected LPS phenotype and complementation experiments confirmed that the effect observed was indeed due to the inactivation of this gene. Re-introduction of an intact copy of the losB gene in trans returned the LPS structure to that of wild type confirming that the losB gene is an α-1,6-D-glycero-D-manno-heptosyltransferase. MAbs and pAbs were raised to this truncated LPS structure in order to examine the degree of conservation and accessibility of this structure across a range of strains of these veterinary pathogens. Three mAbs were obtained that were capable of cross-reacting with all of the strains of interest from App, Pm and Mh thus establishing the potential of a conserved cross-reactive LPS epitope shared between these three significant veterinary pathogens.

TABLE 1

Structure of conserved and variable regions in the core oligosaccharides of the LPS from the veterinary pathogens
*Mannheimia haemolytica*, *Actinobacillus pleuropneumoniae* and *Pasteurella multocida*.

R′ → 6 (Hep IV); α-Glc II-(1 → 6 (Hep I)

R-4)-D-α-D-Hep IV-(1-6)-β-Glc I-(1-4)-L-α-D-Hep I-(1-5)-α-Kdo

R″ → 3 (Hep II); Hep II-(1 → 3 (Hep I)

L-α-D-Hep III-(1-2)-L-α-D-Hep II-(1

| Species | Strain/ Serotype | R | R' | R" |
|---|---|---|---|---|
| *Mannheimia* | A1 | H | β-D-Galp-(1-7)-D-α-D-Hepp-(1- | H |
| *haemolytica* | A8 | H | D-α-D-Hepp-(1- | H |
| | SH1217 | H | β-D-Galp-(1-7)-D-α-D-Hepp-(1- | H |
| *Actinobacillus* | 1 | (1S)-GalaNAc-(1-4,6)-α-D-Gal-(1-3)-β-D-Gal-(1- | H | H |
| *pleuropneumoniae* | 2 | β-D-Glc-(1- | D-α-D-Hep V-(1- | □ |
| | 5a | H | D-α-D-Hep V-(1- | H |
| | 5b | H | D-α-D-Hep V-(1- | H |

TABLE 1-continued Structure of conserved and variable regions in the core oligosaccharides of the LPS from the veterinary pathogens
*Mannheimia haemolytica*, *Actinobacillus pleuropneumoniae* and *Pasteurella multocida*.

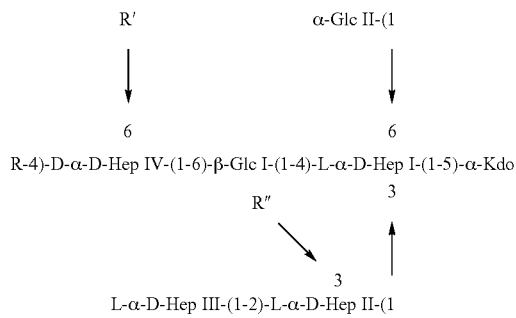

R-4)-D-α-D-Hep IV-(1-6)-β-Glc I-(1-4)-L-α-D-Hep I-(1-5)-α-Kdo

L-α-D-Hep III-(1-2)-L-α-D-Hep II-(1

| Species | Strain/ Serotype | R | R' | R'' |
|---|---|---|---|---|
| *Pasteurella multocida** | Pm70 | β-D-Glc-(1- | α-D-GalpNAc-(1-3)-β-D-GalpNAc-(1-3)-α-D-Gal-(1-4)-β-D-Gal-(1-4)-β-D-Glc-(1- | PEtn |
| | VP161 | PCho-3-β-D-Gal-(1- | PCho-3-β-D-Gal-(1- | H |
| | X73 | (PEtn-6)-PCho-3-β-D-Gal-(1- | (PEtn-6)-PCho-3-β-D-Gal-(1- | H |

For *Pasteurella multocida* the heptose residue, Hep IV, is of the L-□-D configuration and the glucose residue, □-Glc II, is absent in a minority of glycoforms.

TABLE 2

Negative ion CE-ESI-MS data and proposed compositions of O-deacylated LPS and core oligosaccharides from *M. haemolytica* losB mutant and the complemented mutant. Average mass units were used for calculation of molecular weight based on proposed composition as follows: Hex, 162.15Hep, 192.17; Kdo, 220.18; P, 79.98. O-deacylated lipid A (Lipid A-OH) is 952.00.

| Strain | Observed Ions (m/z) | | | | Molecular Mass (Da) | | Proposed Composition |
|---|---|---|---|---|---|---|---|
| | $(M - H)^-$ | $(M - 2H)^{2-}$ | $(M - 3H)^{3-}$ | $(M - 4H)^{4-}$ | Observed | Calculated | |
| O-deac | | | | | | | |
| losB | — | 1172.3 | 781.3 | 585.8 | 2347.0 | 2345.1 | 2Hex, 4Hep, Kdo-P, Lipid A-OH |
| | — | 1065.3 | 709.8 | 532.3 | 2133.0 | 2131.0 | Hex, 3Hep, 2Kdo, Lipid A-OH |
| losB (comp) | — | 1349.3 | 899.3 | 674.3 | 2701.0 | 2699.4 | 3Hex, 5Hep, Kdo-P, Lipid A-OH |
| | — | 1242.3 | 827.8 | 620.8 | 2486.5 | 2485.3 | 2Hex, 4Hep, 2Kdo, Lipid A-OH |
| Core OS | | | | | | | |
| losB | 1312.4 | 655.6 | — | — | 1313.3 | 1313.2 | 2Hex, 4Hep, Kdo |
| losB (comp) | — | 832.8 | — | — | 1667.6 | 1667.5 | 3Hex, 5Hep, Kdo |

TABLE 3

$^1$H- and $^{13}$C-NMR chemical shifts for KOH treated LPS from *Mannheimia haemolytica* losB mutant.

| | H-1 | H-2 | H-3 | H-4 | H-5 | H-6 | H-7 | H-8 | NOE's Inter | Intra | Long Range |
|---|---|---|---|---|---|---|---|---|---|---|---|
| α-GlcN (x) | 5.41 (94.3) | 3.89 (54.6) | 3.93 (70.5) | 3.53 (70.7) | 4.13 (73.7) | 4.14 3.87 (68.9) | | | | | |
| β-GlcN (y) | 4.60 (102.2) | 3.80 (55.9) | 3.92 (73.1) | 3.94 (75.4) | 3.78 (74.9) | 3.75 3.59 (64.0) | | | | | |
| Kdo (z) | — | — | 2.35 2.02 (35.0) | 4.59 (71.1) | 4.27 (72.9) | — (nd) | (70.3) | 3.96 3.72 (64.4) | | | |
| Hep-I (a) | 5.18 (100.4) | 4.13 (71.1) | 4.03 (75.0) | 4.17 (75.0) | — (72.8) | 4.11 (81.0) | nd nd (nd) | | 4.27 Kdo H-5 | 4.13 H-2 | |

TABLE 3-continued

¹H- and ¹³C-NMR chemical shifts for KOH treated LPS from *Mannheimia haemolytica* losB mutant.

| | H-1 | H-2 | H-3 | H-4 | H-5 | H-6 | H-7 | H-8 | NOE's Inter | Intra | Long Range |
|---|---|---|---|---|---|---|---|---|---|---|---|
| Hep-II (b) | 5.60 | 4.24 | 4.01 | — | — | — | 3.72 | | 5.16 Hep III H-1 | 4.24 H-2 | 3.80 Hep I H-5 |
| | (100.5) | (80.5) | (70.9) | (67.8) | (72.4) | (69.7) | 3.62 | | 4.03 Hep I H-3 | | |
| | | | | | | | (64.6) | | | | |
| Hep-III (c) | 5.16 | 4.00 | 3.86 | 3.81 | — | — | — | | 5.60 Hep II H-1 | 4.01 H-2 | 3.80 Hep IV H-3 |
| | (102.4) | (71.4) | (70.8) | (67.0) | (71.6) | (70.3) | | | 4.24 Hep II H-2 | | 3.62 Glc I H-4 |
| | | | | | | | | (64.9) | | | |
| β-Glc-I (d) | 4.61 | 3.50 | 3.43 | 3.62 | 3.51 | 4.13 | — | | 4.17 Hep I H-4 | 3.52 H-5 | 5.22 Glc II H-1 |
| | (103.9) | (74.3) | (77.5) | (70.6) | (74.6) | 3.72 | | | 4.11 Hep I H-6 | 3.43 H-3 | |
| | | | | | | (65.6) | | | | | |
| α-Glc-II (e) | 5.22 | 3.56 | 3.84 | 3.54 | 3.96 | — | — | | 4.11 Hep I H-6 | 3.56 H-2 | 4.62 Glc I H-1 |
| | (102.2) | (73.0) | (73.8) | (69.5) | (72.4) | — | | | | | |
| | | | | | | (60.4) | | | | | |
| Hep-IV (f) | 4.94 | 4.08 | 3.80 | 3.76 | — | — | — | | 4.13 Glc I H-6 | 4.08 H-2 | |
| | (100.0) | (70.5) | (71.0) | (68.3) | (70.3) | (79.9) | | | 3.72 Glc I H-6 | 3.80 H-3 | |
| | | | | | | | (64.0) | | | | |

TABLE 4

Summary of mAbs produced from mouse # 5 fusion

| MAb Mh3- | IgG subclass | Working dilution 1: |
|---|---|---|
| 1 | G3k | 500 |
| 2 | G2ak | 200 |
| 3* | G2aλ | undiluted |
| 4* | G2aλ | undiluted |
| 5. | G2aλ | undiluted |
| 6 | G3k | 800 |
| 7 | G3 | 200 |
| 8 | G3k | 800 |
| 9 | G3k | 1000 |
| 10 | G3k | 1600 |
| 11 | G3 | 1000 |
| 12 | G3k | 1000 |
| 13 | G3k | 2000 |
| 14 | G3k | 1000 |
| 15⁻ | G2bλ | undiluted |
| 16⁻ | G2bλ | undiluted |

*⁻mAbs 3-3 and 3-4, and mAbs 3-15 and 3-16 were subsequently shown to be from the same clones.

Example 8

Candidacy of LPS-Based Glycoconjugates to Prevent Disease Caused by the Veterinary Pathogens *Mannheimia haemolytica*, *Actinobacillus pleuropneumoniae* and *Pasteurella multocida*: Conjugation Chemistry and Investigation of Immunological Responses Following Immunization of Mice In order to prepare the glycoconjugate the LPS was derivatised as follows. Both LPS (145 mg) and 8K material (104.5 mg) from the Mh losB mutant strain that elaborates the target structure were de-acylated by dissolving in 4N KOH (~10 mg/ml.) and stirring at 125° C. for 30 h. The solution was cooled to room temperature and neutralised with acetic anhydride, which served to re-N-acetylate the amino groups created by this procedure. Precipitated salt was removed by centrifugation (9 k, 15 min.) and the supernatant was applied to a Sephadex G-25 column and eluted with water as eluent. Carbohydrate-positive fractions were pooled and freeze-dried resulting in ~20-25% yield of KOH'd LPS (25 mg 8K, 33.3 mg LPS). The resulting material was de-O-acetylated by treatment in 0.1M NaOH (10 mg/ml) at room temperature for 2 h and purified on a Sephadex G-25 column in water, and lyophilised, resulting in ~20% yield (20 mg 8K, 30 mg LPS) of KOH'd LPS.

Quality control was performed by ¹H-NMR spectroscopy and ES-MS analysis. MS analysis revealed some heterogeneity in the KOH-treated LPS material consistent with the variable loss of the terminal heptose and glucose residues (FIG. 49).

De-phosphorylation

The resulting material derived from LPS or 8K material was combined and de-phosphorylated by dissolving (~10 mg/ml.) in 0.1M $NH_4HCO_3$ buffer, pH 8.0 with recombinant alkaline phosphatase (Roche) (~140 units/mg units alk.P/mg KOH'd LPS) and stirred at 37° C. for ~4 h. The solution was heated to 100° C. for 5 min., cooled and centrifuged at 14K for 10 min. The supernatant was freeze-dried.

The resulting material was de-salted on a Sephadex G-25 column in water, and lyophilised, resulting in ~20% yield (48 mg) of KOH'd alk. P'd LPS. Quality control was performed by ¹H-NMR and CE-ES-MS analysis confirming de-phosphorylation of the KOH treated LPS.

Amination

The resulting aldehydro functional group was aminated by dissolving the dried carbohydrate 48 mg) in 600 ul of DMSO and adding 4800 ul of 2M $NH_4OAc$ in MeOH and 120 mg of $NaCNBH_3$ dissolved in 1200 ul of MeOH at pH 8.3 at 50° C. for 72 h. The MeOH was evaporated under $N_2$ and the product lyophilised and purified on a Sephadex G-25 column in water, and lyophilised, resulting in ~10% 32 mg yield of KOH'd alk. P'd aminated LPS. Quality control was performed by ¹H-NMR analysis confirming amination of the KOH treated LPS.

Attachment of Linker Molecule

A linker molecule (squarate) was attached to the resulting amino group by dissolving the dried carbohydrate (32 mg) in 4000 ul of $H_2O$ and adding 4000 ul of MeOH and 100 ul of squarate at pH 8.2 (adjust with triethylamine (4 ul)) for 2 h at room temperature, monitoring the pH every 15 min. The MeOH was evaporated under $N_2$ and the product lyophilised and purified on a Sephadex G-25 column in water, and lyophilised, resulting in ~12% yield (30 mg) of KOH'd alk. P'd aminated squarated LPS. Quality control was performed by $^1$H— and $^{13}$C—$^1$H-NMR and CE-ES-MS analysis confirming attachment of the squarate linker. However MS analysis suggested that only ~50% of the material carried the squarate linker.

Conjugation to Protein Carrier

~20 mg of HSA was linked to a 25× molar excess of the squarate linked carbohydrate (30 mg) in 1 ml of 0.02M sodium borate buffer by stirring at room temperature for 24 h at pH 9.2, carbohydrate was added at initiation of the reaction and after ~6 h. After 24 h an aliquot was removed and examined by MALDI-MS and SDS-PAGE with Western blotting with a carbohydrate specific monoclonal antibody G8 (FIG. 50). The final reaction mixture was purified down a Sepharose 6B column with PBS (50 mM sodium phosphate, 100 mM NaCl, 10 mM Na citrate pH 7.5) to achieve separation of free from conjugated carbohydrate. The fractions corresponding to the product peak were concentrated in an Amicon ultra-15 10K cutoff spin column. The final volume of conjugate was quantified for protein by the BCA assay and for carbohydrate by the PhOH/$H_2SO_4$ method, to give the molar ratio of carbohydrate to protein of 4.5:1. The final conjugate was also compared to the carrier protein HSA by nano-electro-spray mass spectrometry in 1% AcOH which revealed the expected molecular weight for HSA (FIG. 51a) and a series of peaks consistent with variable glycosylation of the carrier protein (FIG. 51b).

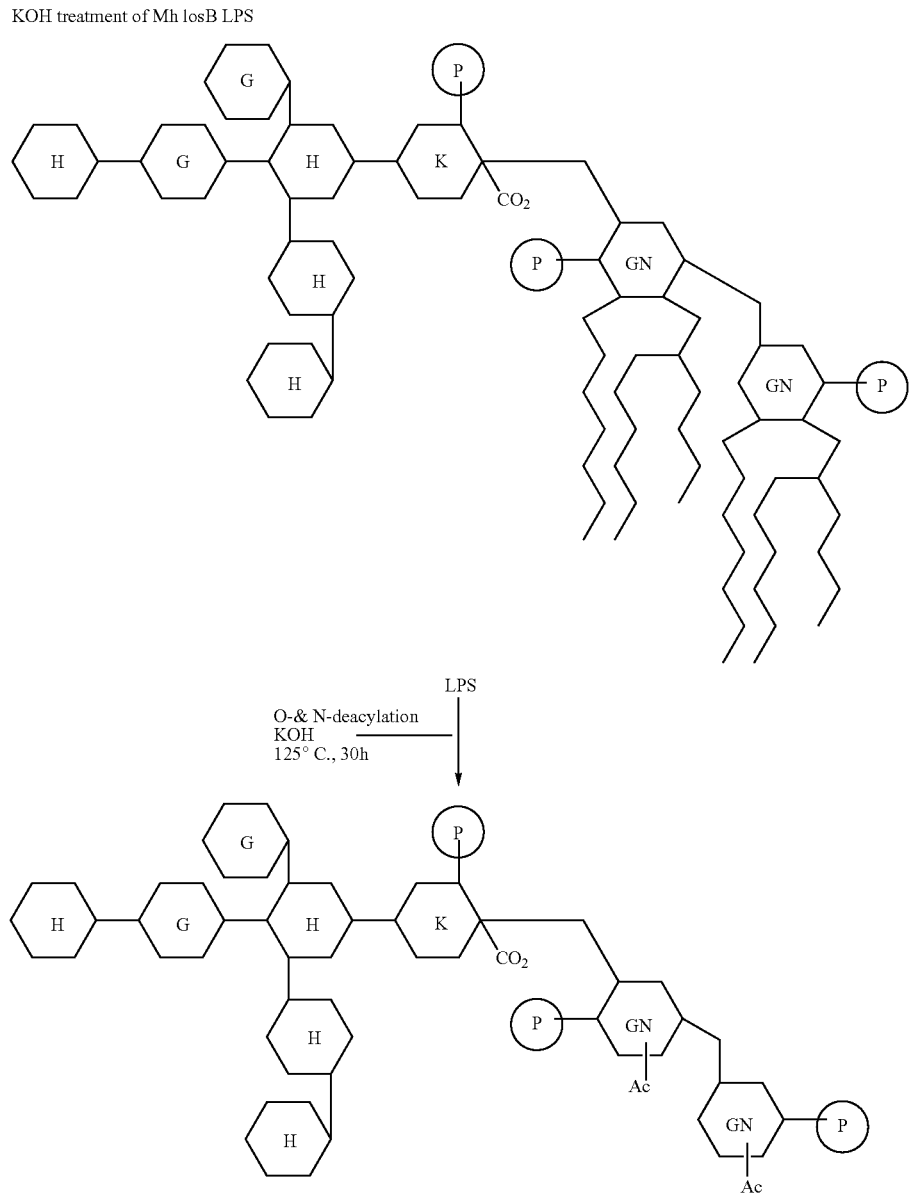

Step 2
alkP treatment of Mh losB KOH' dLPS
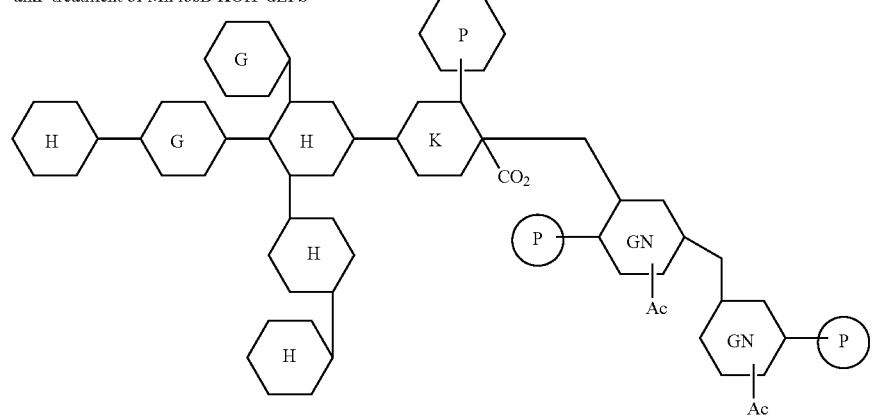
alkP
0.1M NH₄HCO₃
54° C., 4h
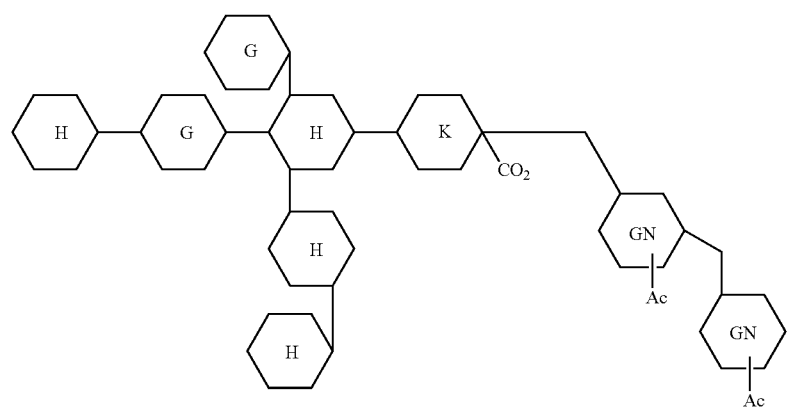
Step 3
Amination reaction of alkP treated of Mh losB KOH'd LPS
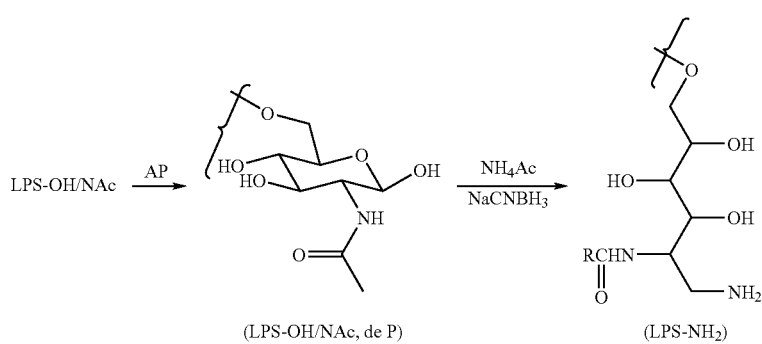

-continued
Step 4
Squarate reaction of KOH'd alkP'd aminated Mh losB LPS
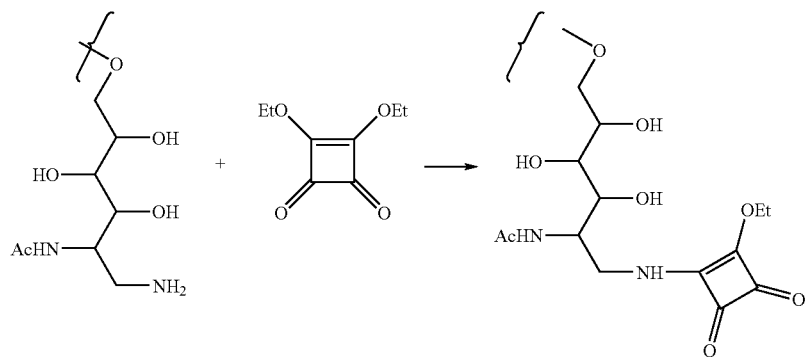
Step 5
Conjugation reaction of KOH'd alkP'd aminated squarated Mh losB LPS
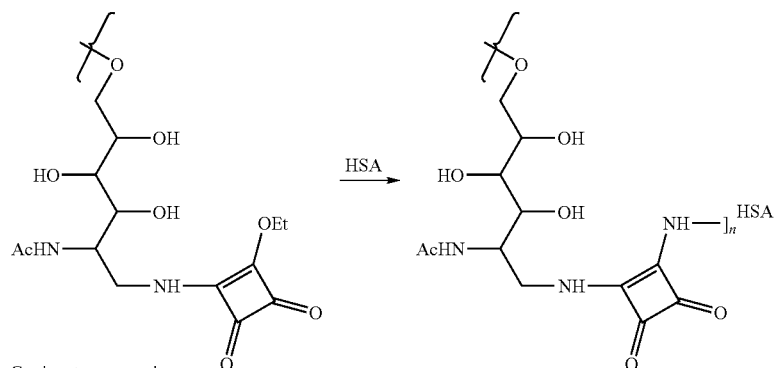
Conjugate prepared:
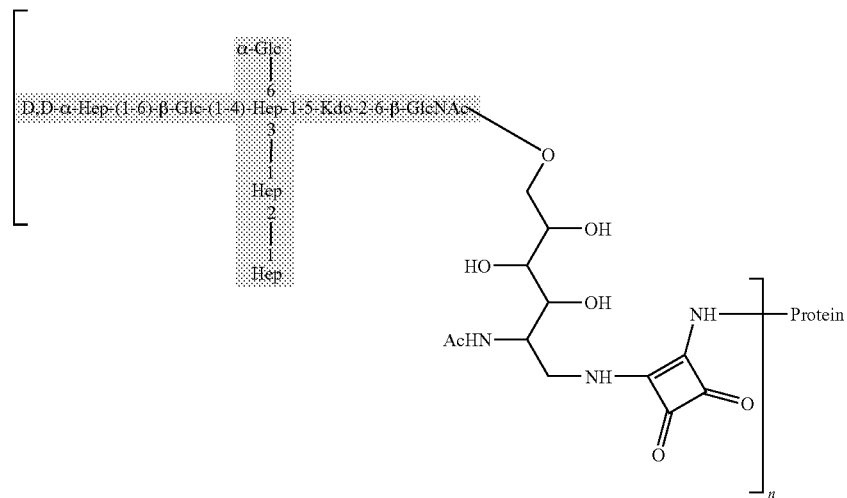
Mh losB-HSA (~4 CHO/CRM), into m Immunisation 6 BALB/c mice, 6-8 weeks old were immunised with conjugate, 3 female BALB/c mice, 6-8 weeks old were immunised as controls with admixed carbohydrate and HSA. All vaccines were in sterile PBS solution and 10 µg carbohydrate per 0.1 ml sc injection in Ribi adjuvant was administered.

The mice were immunised according to the following schedule:—

| | |
|---|---|
| D 0 | pre-bleed & prime injection |
| D 14 | $1^{st}$ boost |
| D 23 | trial bleeds |
| D 35 | $2^{nd}$ boost |
| D 45 | bleed out mice |

Trial bleed at D23 and final bleed at D45 revealed that one mouse #V2 had given an IgG response to the carbohydrate antigen, as revealed by LPS ELISA against Mh losB LPS (FIGS. 52 and 53). Polyclonal sera from mouse #V2 following three immunisations was examined for its ability to cross-react with the three species of interest. Both LPS and whole cells of Ap, Mh and Pm were recognised by this polyclonal sera (FIGS. 54 and 55). However LPS and whole cells from *Neisseria meningitidis* strains L3galE and L2 galE were also recognised in LPS and whole cell ELISA respectively. This behaviour was attributed to the partial degradation of the carbohydrate antigen during KOH treatment for preparation of the conjugate, which caused variable losses of the terminal heptose and hexose residues (see FIG. 49). This would result in a portion of this carbohydrate antigen in the final conjugate containing epitopes, which would mimic regions of the meningococcal LPS used in testing the polyclonal sera V2, causing this observed cross-reactivity. Nevertheless, sera raised from immunisation with this conjugate sera was capable of recognising both LPS and whole cells from the veterinary pathogens Ap, Pm and Mh.

Example 9

Bactericidal Assay Using Monoclonal Antibodies Specific for the Conserved Inner Core Lipopolysaccharide Polyclonal sera from mouse #1 D140, which recognises whole cells of Mh (FIG. 56) and contains antibodies specific for the inner core LPS of Mh (FIG. 57), and ascites fluid from mAbs G3, G8, 3-5 and 3-16 (FIGS. 58-61), along with control ascites fluid L2-16 were used as the source of sera for the bactericidal assay. The assay was performed according to the method of Sutherland A.D. 1988. Vet. Microbiol. 16: 263-271. Briefly, Mh cells were grown to a growth level of ~$5 \times 10^3$ cfu/ml in 100 ml BHI broth. 10 ml of culture was used and the cells were pelleted at 5000×g, 4° C. and washed twice in D-PBS (containing Ca and Mg [Gibco # 14040-[33]). The final cell pellet was resuspended in 10 ml D-PBS. Test sera and ascites samples were heat-inactivated at 56° C. for 30 min. to destroy endogenous complement. Assays were set-up in triplicate in 96-well, tissue culture grade, flat-bottomed micro-titre plates (NUNC). 20 ul of the appropriate dilution of antisera in D-PBS was added to each well followed by the bacterial suspension (100 ul) and the plate incubated for 15 min at RT. Complement (80 ul, baby rabbit, #CL3441-S, Cedarlane) was added to each well, and incubated covered at 37° C. for 30 min. The reaction was terminated by placing the plate on ice, and triplicate samples (50 ul) from each well were plated on BHI agar plates and incubated at 37° C. overnight. Control wells containing bacterial suspension alone, bacterial suspension with complement, and bacterial suspension with appropriate dilution of antibody were also included in each assay.

The bacterial growth was counted and the percentage killing relative to the control wells calculated.

As can be seen in the Tables below and in FIGS. 62-64, mAbs G3 and G8 and the polyclonal sera all facilitated complement-mediated lysis of the Mh A1 wt cells. The failure of ascites fluid from mAb 3-5 and 3-16 was attributed to the very low titres of these sera (working dilution 1:50 compared to $1:10^6$).

TABLE 1

Bactericidal activity of mAbs G3 and G8 on Mh A1 cells

| Assay conditions | Mean CFU of Mh cells in 50 µl assay vol. (+/− SE) | | | | | | | |
|---|---|---|---|---|---|---|---|---|
| | control | 1:10,000 | 1:20,000 | 1:40,000 | $1 \times 10^{-5}$ | $1 \times 10^{-6}$ | $1 \times 10^{-7}$ | $1 \times 10^{-8}$ |
| Mh cells alone | 65 +/− 2.7 | NA | NA | NA | NA | NA | NA | NA |
| Mh cells + complement | 55 +/− 4.6 | NA | NA | NA | NA | NA | NA | NA |
| Mh cells + complement + G3 | — | 11 +/− 2.8 | 7 +/− 2.8 | 3 +/− 2.3 | 0 | 0 | 4 +/− 0.8 | 48 +/− 3.8 |
| Mh cells + G3 | — | 83 +/− 9.5 | 82 +/− 9 | 61 +/− 7.5 | 75 +/− 5.2 | 75 +/− 0.88 | 78 +/− 0.88 | 71 +/− 3 |
| Mh cells + complement + G8 | — | 27 +/− 3 | 8 +/− 0.88 | 3 +/− 2.5 | 0 | 0 | 2 +/− 0.88 | 52 +/− 2.3 |
| Mh cells + G8 | — | 69 +/− 12 | 62 +/− 11 | 86 +/− 4.9 | 18 +/− 10 | 68 +/− 2.9 | 75 +/− 6 | 82 +/− 11 |

SE = SD/√n where n = sample size

TABLE 2

Bactericidal activity of polyclonal sera Mh #1 D140 on Mh A1 cells.

| Assay conditions | Mean CFU of Mh cells in 50 µl assay vol. (+/− SE) | | | |
|---|---|---|---|---|
| | Control | 1:640 | 1:1280 | 1:1256 |
| Mh cells Alone | 87 +/− 2.3 | NA | NA | NA |
| Mh cells + complement | 80 +/− 6 | NA | NA | NA |
| Mh cells + Mh #1 D140 | NA | 110 +/− 0.6 | 150 +/− 25 | 126 +/− 12 |
| Mh cells + complement + Mh #1 D140 | NA | 2 +/− 0.7 | 2 +/− 0.6 | 0 |

SE = SD/√n where n = sample size

The bactericidal activity exhibited by mAbs G3 and G8 and polyclonal sera illustrates that antibodies specific for a conserved inner core LPS epitope in Mh can recognise and are functionally active against live Mh whole cells.

Example 10

Passive Protection Experiment Using Monoclonal Antibodies Specific for the Conserved Inner Core Lipopolysaccharide The experiment was performed according to the method of Lopez et al. 1982. Can. J. Comp. Med. 46: 314-316 with methods and modifications as described below.

Mice and Reagents:

IgG from ascitic fluid of mAbs was purified on a protein A column and sterile filtered (FIG. 65) for use in the passive protection experiment.

Experimental mAbs G3 and G8. G8, IgG2b, 3.8 mg/ml; G3, IgG2a, 4.7 mg/ml.

Control mAb: L2-16, IgG2b, 1.9 mg/ml.

Balb/c mice: 40 female, 6-8 weeks of age, CRL. 5 mice/group.

*M. haemolytica* A1: $7.5 \times 10^7$ cfu/mouse.

Experimental Plan and Groups:

| Group | Treatment with | Treatment at |
|---|---|---|
| A | — | — |
| B | Control MAb | In vitro incubation |
| C | G3 | In vitro incubation |
| D | G8 | In vitro incubation |
| E | Control MAb | −1 h in vivo |
| F | G3 | −1 h in vivo |
| G | G8 | −1 h in vivo |

| | |
|---|---|
| D-1 | Purification and quantitation of mAbs G3, G8 and L2-16 |
| D-1 | Put up plates of Mh A1 on BHI agar |
| D0 | Inoculate BHI broth with Mh |
| | Harvest Mh at OD ~1.2 or higher for inoculation |
| | Confirm the inoculum by viable count |
| | IP mAb administration to Groups E-G mice |
| | IN administration of ~$10^8$ Mh to Groups A and E-G mice |
| | In vitro incubation of mAb s with Mh for 30 min |
| | IN administration of ~$10^8$ pre-incubated Mh to Groups B-D mice |
| D1 | Observe mice daily and record clinical signs until the end of experiment |
| D3 | Termination of experiment and collect Gross lung pathology Remove the lung for histology |

| Group | Clinical signs[i] Day 2 | Clinical signs[i] Day 3 | Macroscopic changes[ii] | Histological changes[iii] |
|---|---|---|---|---|
| A | ++++[iv] | +++ | +++[v] | +++[vi] |
| B | ++++ | ++ | +++ | +++ |
| C | ++ (2)[vii] | − | ++ | ++ |
| D | ++ (2) | − | ++ | ++ |
| E | ++++ | ++ (4) | ++ | +++ |
| F | +++ | − (4) | ++ | + to ++ |
| G | +++ | + to ++ (4) | ++ | + to ++ |

[i]All mice showed various degrees of clinical signs such as rough coat, dehydration and reluctance to move on DPI 2. However, Groups C and D mice were generally healthy and Groups F and G mice remained active although with a rough coat. On DPI 3, groups A and B mice were severely dehydrated and had loss of weight and Group G mice were also moderately sick.
[ii]All mice showed various degrees of lung consolidation and no attempt has been made to quantify the area involved.
[iii]The major difference among the groups was that Groups A, B and E mice overall appeared to have more neutrophils in their lungs than the other groups of mice. However, all mice, regardless of treatments, showed some degrees of pneumonia.
[iv]++++: rough coat, moderate to severe loss of weight and dehydration, and reluctant to move; +++: rough coat, slight to moderate loss of weight and dehydration, but remain active; ++: rough coat and slight loss of weight; +: slightly rough coat.
[v]+++: moderate areas of consolidation, ++: small areas of consolidation.
[vi]+++: moderate degree of bronchopneumonia with the presence of medium to large numbers of neutrophils and marked infiltration of lymphoid cells in the perivascular and peribronchial areas. ++: mild to moderate degree of bronchopneumonia with the presence of small numbers of neutrophils and infiltration of lymphoid cells in the perivascular and peribronchial areas. +: mild degree of bronchopneumonia with the occasional presence of neutrophils and mild infiltration of lymphoid cells in the perivascular and peribronchial areas.
[vii]The number of mice showed clinical symptoms.

Based on this pilot experiment, it appears that the mAb treatment, particularly by in vitro pre-incubation with *M. haemolytica*, showed a moderate effect on the clinical symptoms and histopathology of the infected mice.

FIG. 66 shows the presence of a moderate number of neutrophils in the lumen of a medium-sized bronchus from control mouse B, consistent with pathogenesis, whereas FIG. 67 shows the lung from a Group C mouse killed at the same time as FIG. 66, showing the resolution of bronchopneumonia with the presence of small numbers of lymphoid cells in some areas, consistent with some degree of protection afforded by in vitro pre-mixing of mAb G3 with the Mh cells.

Biological Deposits

A deposit of *Mannheimia haemolytica* strain A1 losB was made on May 4, 2005 at IDAC. The deposit number is IDAC 040505-01.

The invention claimed is:

1. An isolated lipopolysaccharide moiety comprising a conserved di-glucosyl-tri-heptosyl inner-core moiety of formula Ib:

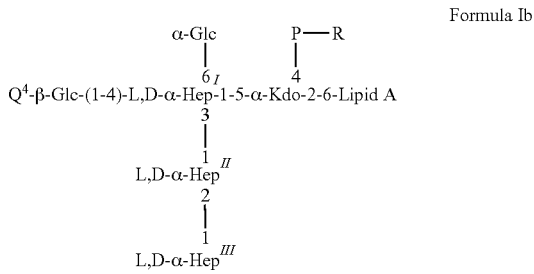

Formula Ib wherein Glc is glucose; Hep is heptose; Kdo is 3-deoxy-D-manno-2-octulosonic acid; Lipid A is detoxified; P is phosphate; R is H or phosphoethanolamine; and $Q^4$ is D,D-α-Hep-, L,D-α-Hep - or H.

2. An isolated lipopolysaccharide moiety according to claim 1 comprising a conserved di-glucosyl-tetra-heptosyl inner-core moiety of formula Ic:

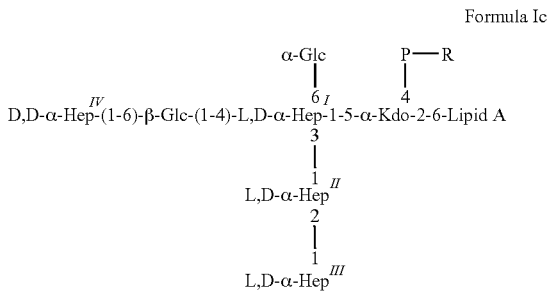

Formula Ic wherein Glc is glucose; Hep is heptose, P is phosphate; Kdo is 3-deoxy-D-manno-2-octulosonic acid; R is H or phosphoethanolamine and Lipid A is detoxified.

3. An isolated lipopolysaccharide moiety according to claim 1 comprising a conserved di-glucosyl-tetra-heptosyl inner-core moiety of formula Id:

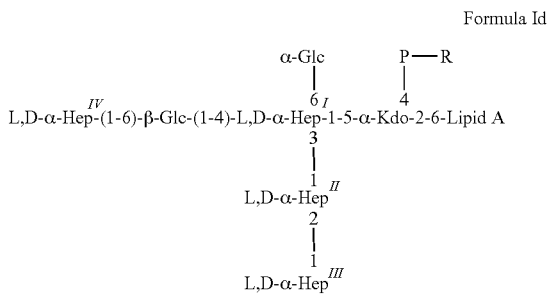

Formula Id wherein Glc is glucose; Hep is heptose, P is phosphate; Kdo is 3-deoxy-D-manno-2-octulosonic acid; R is H or phosphoethanolamine and Lipid A is detoxified.

4. An immunogenic composition comprising the lipopolysaccharide moiety of claim 1 together with a pharmaceutically acceptable carrier.

5. The immunogenic composition of claim 4, wherein the pharmaceutically acceptable carrier is immunogenic.

6. A method for producing and harvesting a functional cross-reactive antibody against *Mannheimia haemolytica*, *Actinobacillus pleuropneumoniae* or *Pasteurella multocida* which method comprises:
 (a) generating antibodies to the lipopolysaccharide moiety of claim 1;
 (b) testing antibodies resulting from step (a) against a plurality of *Mannheimia haemolytica*, *Actinobadilus pleuropneumoniae* and *Pasteurella multocida* strains; and
 (c) selecting antibodies that are cross-reactive with all of *Mannheimia haemolytica*, *Actinobadilus pleuropneumoniae* and *Pasteurella multocida*.

7. A method of producing a medicament for treating a disease caused by infection with bacteria from the family Pasteurellaceae, which bacteria have said inner-core moiety which method comprises combining the lipopolysaccharide moiety of claim 1 with a pharmaceutically acceptable carrier.

8. A method of producing a medicament for treating a disease caused by infection with bacteria from the genus *Mannheimia*, *Actinobacillus* or *Pasteurella*, which bacteria have the inner-core moiety defined in claim 1, which method comprises combining the lipopolysaccharide moiety of claim 1 with a pharmaceutically acceptable carrier.

9. A method of producing a medicament for treating a disease caused by infection with bacteria from the species *Mannheimia haemolytica*, *Actinobadilus pleuropneumoniae* or *Pasteurella multocida*, which bacteria have the inner-core moiety defined in claim 1, which method comprises combining the lipopolysaccharide moiety of claim 1 with a pharmaceutically acceptable carrier.

10. The method according to claim 7, wherein the disease is selected from the group consisting of porcine fibrinohemorrhagic necrotizing pleuropneumonia, avian fowl cholera, bovine hemorrhagic septicaemia, porcine atrophic rhinitis, ovine and bovine pneumonic pasteurellosis (shipping fever) and ovine septicaemia.

11. A process for preparing a lipopolysaccharide moiety comprising a conserved di-glucosyl-tri-heptosyl inner-core moiety of formula Ib:

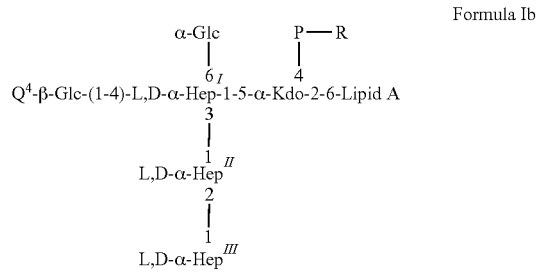

Formula Ib wherein Glc is glucose; Hep is heptose, P is phosphate; Kdo is 3-deoxy-D-manno-2-octulosonic acid; R is H or phosphoethanolamine; $Q^4$ is D,D-α-Hep-, L,D-α-Hep- or H; and Lipid A is detoxified; said process comprising:
 (a) isolating a mutant strain from the species *Mannheimia haemolytica* (Mh), *Actinobadilus pleuropneumoniae* (Ap), or *Pasteurella multocida* (Pm) with an inactivated glycosyltransferase gene (α-1,6-DD-heptosyltransferase lbgB in Mh; α-1,6-D D-heptosyltransferase lbgB in Ap; α-1,6-heptosyltransferase PM1144 in Pm ) in order to present the lipopolysaccharide moiety as a terminal unit;

(b) culturing the *Mannheimia haemolytica, Actinobacillus pleuropneumoniae* or *Pasteurella multocida* mutant bacterial strain resulting from step (a) under conditions suitable for expressing the lipopolysaccharide moiety;

(c) isolating and characterizing the resulting lipopolysaccharide moiety; and (d) detoxifying the Lipid A portion of the lipopolysaccharide moiety.

12. A process for preparing a lipopolysaccharide moiety comprising a conserved di-glucosyl-tetra-heptosyl inner-core moiety as defined in claim 11 of formula lc:

Formula Ic 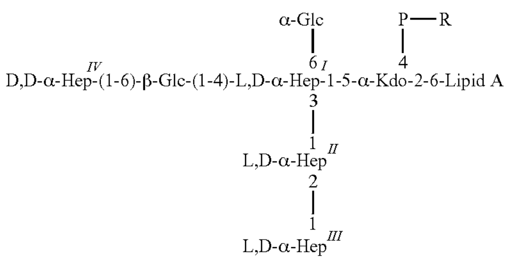 wherein Glc is glucose; Hep is heptose, P is phosphate; Kdo is 3-deoxy-D-manno-2 -octulosonic acid; R is H or phosphoethanolamine and Lipid A is detoxified; said process comprising:

(a) isolating a mutant strain from the species *Mannheimia haemolytica* with an inactivated glycosyltransferase gene (D-glycero-D-manno-heptosyltransferase losB) in order to present structure lc as a terminal unit;

(b) culturing the *Mannheimia haemolytica* mutant bacterial strain resulting from step (a) under conditions suitable for expressing the lipopolysaccharide moiety;

(c) isolating and characterizing the resulting lipopolysaccharide moiety; and (d) detoxifying the Lipid A portion of the lipopolysaccharide moiety.

13. A process for preparing a lipopolysaccharide moiety comprising a conserved di-glucosyl-tetra-heptosyl inner-core moiety as defined in claim 11 of formula Id:

Formula Id 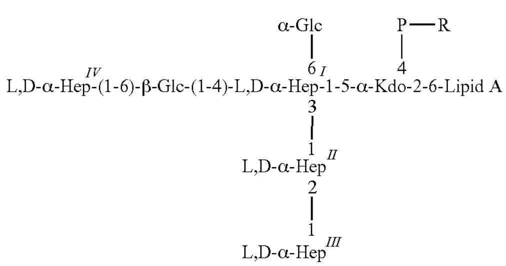 wherein Glc is glucose; Hep is heptose, P is phosphate; Kdo is 3-deoxy-D-manno-2 -octulosonic acid; R is H or phosphoethanolamine and Lipid A is detoxified; said process comprising:

(a) isolating a mutant strain from the species *Pasteurella multocida* with a glycosyltransferase gene (β-1,6-/β-1,4-glucosyltransferase PM1143) inactivated in order to present structure Id as a terminal unit;

(b) culturing the *Pasteurella multocida* mutant bacterial strain resulting from step (a) under conditions suitable for expressing the lipopolysaccharide moiety;

(c) isolating and characterizing the resulting lipopolysaccharide moiety; and (d) detoxifying the Lipid A portion of the lipopolysaccharide moiety.

14. A process for preparing a lipopolysaccharide moiety comprising a conserved di-glucosyl-tetra-heptosyl inner-core moiety as defined in claim 11 of formula Ic:

Formula Ic 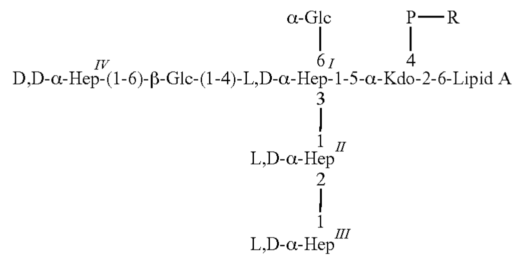 wherein Glc is glucose; Hep is heptose, P is phosphate; Kdo is 3-deoxy-D-manno-2 -octulosonic acid; R is H or phosphoethanolamine and Lipid A is detoxified; said process comprising:

(a) isolating a mutant strain from the species *Actinobacillus pleuropneumoniae* with an inactivated glycosyltransferase gene (β-1,4-galactosyltransferase lbgA) in order to present structure lc as a terminal unit;

(b) culturing the *Actinobacillus pleuropneumoniae* mutant bacterial strain resulting from step (a) under conditions suitable for expressing the lipopolysaccharide moiety;

(c) isolating and characterizing the resulting lipopolysaccharide moiety; and (d) detoxifying the Lipid A portion of the lipopolysaccharide moiety.

15. The process of claim 11 further comprising identifying the lipopolysaccharide moiety by contacting the lipopolysaccharide moiety with a monoclonal antibody specific for an epitope contained within said inner core lipopolysaccharide moiety.

16. A glycoconjugate comprising the lipopolysaccharide moiety as defined in claim 1 linked to an immunogenic carrier.

17. The glycoconjugate according to claim 16 wherein the lipopolysaccharide moiety and the immunogenic carrier are linked through a linker molecule.

18. The glycoconjugate of claim 17 wherein the linker molecule is selected from the group consisting of squarate, cystamine, adipic acid dihydrazide, ϵ-aminohexanoic acid, chlorohexanol dimethyl acetal, D-glucuronolactone and p-nitrophenylamine.

19. The glycoconjugate of claim 16 wherein the immunogenic carrier is selected from the group consisting of detoxified *P. aeruginosa* toxin A, cholera toxin/toxoid, pertussis toxin/toxoid, *Clostridium perfringens* exotoxins/toxoid, hepatitis B surface antigen, hepatitis B core antigen, rotavirus VP 7 protein, respiratory syncytial virus F and G proteins, diphtheria toxoid $CRM_{197}$, tetanus toxoid TT, human serum albumin (HSA), *Mannheimia haemolytica* leukotoxin toxoid, *Mannheimia haemolytica* PlpE lipoprotein, *Actinobacillus pleuropneumoniae* OmlA, *Mannheimia haemolytica* or *Actinobadilus pleuropneumoniae* TbpA & B (transferring binding proteins), *Mannheimia haemolytica* sialoglycoprotease,

*Actinobacillus pleuropneumoniae* Apx exotoxoids selected from the group consisting of Apx I to IV, *Actinobacillus pleuropneumoniae* or *Pasteurella multocida* Plp-40 lipoprotein, *Pasteurella multocida* Omp28 major outer membrane protein, *Pasteurella multocida* 39kDa capsular protein and *Pasteurella multocida* PlpB (39kDa cross-protective lipoprotein).

20. An immunogenic composition comprising the glycoconjugate of claim 16 and an adjuvant.

21. The immunogenic composition of claim 20 wherein the vaccine is formulated as a liposome, archaeosome or from an archaeolipid.

22. The immunogenic composition of claim 20 which elicits antisera that is cross-reactive to whole cells of bacteria from the family Pasteurellaceae following immunization of a mammal.

23. A multivalent immunogenic composition comprising a mixture of glycoconjugates as defined in claim 16 and an adjuvant.

24. The isolated lipopolysaccharide moiety of claim 1, wherein $Q^4$ is H.

* * * * *